US006998256B2

(12) United States Patent
Arslanian

(10) Patent No.: US 6,998,256 B2
(45) Date of Patent: Feb. 14, 2006

(54) METHODS OF OBTAINING EPOTHILONE D USING CRYSTALLIZATION AND /OR BY THE CULTURE OF CELLS IN THE PRESENCE OF METHYL OLEATE

(75) Inventor: Robert L. Arslanian, Pacifica, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 387 days.

(21) Appl. No.: 09/957,483

(22) Filed: Sep. 19, 2001

(65) Prior Publication Data

US 2003/0073205 A1 Apr. 17, 2003

Related U.S. Application Data

(63) Continuation-in-part of application No. PCT/US01/13793, filed on Apr. 26, 2001, which is a continuation-in-part of application No. 09/825,856, filed on Apr. 3, 2001, and a continuation-in-part of application No. 09/825,857, filed on Apr. 3, 2001, and a continuation-in-part of application No. 09/560,367, filed on Apr. 28, 2000.

(60) Provisional application No. 60/269,020, filed on Feb. 13, 2001, provisional application No. 60/257,517, filed on Dec. 21, 2000, and provisional application No. 60/232,696, filed on Sep. 14, 2000.

(51) Int. Cl.
*C12P 19/62* (2006.01)

(52) U.S. Cl. .......................................... 435/76; 548/204

(58) Field of Classification Search ................... 435/76; 548/204

See application file for complete search history.

(56) References Cited

U.S. PATENT DOCUMENTS

| | | | | |
|---|---|---|---|---|
| 5,783,431 | A | 7/1998 | Peterson et al. | 435/172.3 |
| 6,121,029 | A | 9/2000 | Schupp et al. | 435/183 |
| 6,303,342 | B1 | 10/2001 | Julien et al. | 435/76 |
| 6,346,404 | B1 | 2/2002 | Schupp et al. | 435/183 |
| 6,355,457 | B1 | 3/2002 | Schupp et al. | 435/183 |
| 6,355,458 | B1 | 3/2002 | Schupp et al. | 435/183 |
| 6,355,459 | B1 | 3/2002 | Schupp et al. | 435/183 |
| 6,358,719 | B1 | 3/2002 | Schupp et al. | 435/189 |
| 6,383,787 | B1 | 5/2002 | Schupp et al. | 435/183 |
| 6,410,301 | B1 | 6/2002 | Julien et al. | |
| 6,489,314 | B1 | 12/2002 | Ashley et al. | |
| 6,562,795 | B2 * | 5/2003 | Ashley et al. | 514/29 |
| 6,583,290 | B1 | 6/2003 | Julien et al. | |
| 6,589,968 | B2 | 7/2003 | Arslanian et al. | |
| 2003/0045711 | A1 | 3/2003 | Ashley et al. | |
| 2003/0096381 | A1 | 5/2003 | Julien et al. | |

FOREIGN PATENT DOCUMENTS

| | | |
|---|---|---|
| WO | WO 98/22461 | 5/1998 |
| WO | WO 99/42602 | * 8/1999 |
| WO | WO 99/66028 | 12/1999 |
| WO | WO 00/22139 | 4/2000 |
| WO | WO 00/31247 | 6/2000 |
| WO | WO 01/083800 | 11/2001 |
| WO | WO 02/080846 | 10/2002 |

OTHER PUBLICATIONS

Reichenbach et al. Biologically active secondary metabolites from myxobacteria. Biotechnol. Adv (1993) 11(2):219–277.*

Hardt et al. New Natural Epothilones from Sorangium cellulosum, Strains So ce90/B2 and So ce/90/D13: Isolation, Structure Elucidation, and SAR Studies. J. Natural Products (Jun., 2001) 64(7): 847–856.*

Arslanian et al. Large–Scale Isolation and Crystallization of Epothilone D from Myxococcus xanthus Cultures. J. Natural Products (2002) 65:570–572.*

Lau et al. Optimizing the Heterologous Production of Epothilone D in Myxococcus xanthus. Biotechnol Bioeng. (2002) 78(3):280–8.*

Beyer et al., Biochimica et Biophysica Acta (1999) 1445:185–195.

Chou et al., Proc. Natl. Acad. Sci. USA (1998) 95(16):9642–9647.

Molnar et al., Chemistry and Biology (2000) 7(2):97–109.

Oliynyk et al., Chemistry and Biology (1996) 3:833–839.

Paitan et al., J. Molecular Biology (1999) 286:465–474.

Tang et al., Science (2000) 287:640–642.

Varon et al., Antimicrobial Agents and Chemotherapy (1992) 36(10):2316–2321.

* cited by examiner

*Primary Examiner*—Kathleen Kerr
(74) *Attorney, Agent, or Firm*—Townsend and Townsend and Crew LLP

(57) ABSTRACT

Methods are provided for purification of epothilone D and epothilone D analogs from epothilone producing cells such as, for example, *Sorangium cellulosum* and *Myxococcus xanthus* (recombinant). Epothilone can be purified from fermentation broth, for example by using resins, chromatography, and crystallization. Epothilone D can be crystallized from a binary solvent system in which water is the forcing solvent.

7 Claims, 10 Drawing Sheets

```
                         SEQUENCE LISTING


<160> NUMBER OF SEQ ID NOS: 62

<210> SEQ ID NO 1
<211> LENGTH: 30
<212> TYPE: DNA
<213> ORGANISM: Artificial Sequence
<220> FEATURE:
<223> OTHER INFORMATION: Primer Seq1

<400> SEQUENCE: 1

agcggataac aatttcacac aggaaacagc                                        30


<210> SEQ ID NO 2
<211> LENGTH: 29
<212> TYPE: DNA
<213> ORGANISM: Artificial Sequence
<220> FEATURE:
<223> OTHER INFORMATION: Primer Mxpil1

<400> SEQUENCE: 2

ttaattaaga gaaggttgca acgggggc                                          29


<210> SEQ ID NO 3
<211> LENGTH: 848
<212> TYPE: DNA
<213> ORGANISM: Artificial Sequence
<220> FEATURE:
<223> OTHER INFORMATION: Sequence of the pilA promoter

<400> SEQUENCE: 3

cgacgcaggt gaagctgctt cgtgtgctcc aggagcggaa ggtgaagccg gtcggcagcg      60

ccgcggagat tcccttccag gcgcgtgtca tcgcggcaac gaaccggcgg ctcgaagccg     120

aagtaaaggc cggacgcttt cgtgaggacc tcttctaccg gctcaacgtc atcacgttgg     180

agctgcctcc actgcgcgag cgttccggcg acgtgtcgtt gctggcgaac tacttcctgt     240

ccagactgtc ggaggagttg gggcgacccg gtctgcgttt ctcccccgag acactggggc     300

tattggagcg ctatcccttc ccaggcaacg tgcggcagct gcagaacatg gtggagcggg     360

ccgcgaccct gtcggattca gacctcctgg ggccctccac gcttccaccc gcagtgcggg     420

gcgatacaga ccccgccgtg cgtcccgtgg agggcagtga gccagggctg gtggcgggct     480

tcaacctgga gcggcatctc gacgacagcg agcggcgcta tctcgtcgcg gcgatgaagc     540

aggccggggg cgtgaagacc cgtgctgcgg agttgctggg cctttcgttc cgttcattcc     600

gctaccggtt ggccaagcat gggctgacgg atgacttgga gcccgggagc gcttcggatg     660

cgtaggctga tcgacagtta tcgtcagcgt cactgccgaa ttttgtcagc cctggaccca     720

tcctcgccga ggggattgtt ccaagccttg agaattgggg ggcttggagt gcgcacctgg     780

gttggcatgc gtagtgctaa tcccatccgc gggcgcagtg ccccccgttg caaccttctc     840

ttaattaa                                                              848
```

-continued

<210> SEQ ID NO 4
<211> LENGTH: 31
<212> TYPE: DNA
<213> ORGANISM: Artificial Sequence
<220> FEATURE:
<223> OTHER INFORMATION: Primer 111-44.1

<400> SEQUENCE: 4
aaaagcttcg gggcacctcc tggctgtcgg c 31

<210> SEQ ID NO 5
<211> LENGTH: 34
<212> TYPE: DNA
<213> ORGANISM: Artificial Sequence
<220> FEATURE:
<223> OTHER INFORMATION: Primer 111-44.4

<400> SEQUENCE: 5
ggttaattaa tcaccctcct cccaccccgg gcat 34

<210> SEQ ID NO 6
<211> LENGTH: 33
<212> TYPE: DNA
<213> ORGANISM: Artificial Sequence
<220> FEATURE:
<223> OTHER INFORMATION: Primer 90-66.1

<400> SEQUENCE: 6
gcgggaagct ttcacggcgc aggccctcgt ggg 33

<210> SEQ ID NO 7
<211> LENGTH: 31
<212> TYPE: DNA
<213> ORGANISM: Artificial Sequence
<220> FEATURE:
<223> OTHER INFORMATION: Insert 90-67

<400> SEQUENCE: 7
gcggtacctt caacaggcag gccgtctcat g 31

<210> SEQ ID NO 8
<211> LENGTH: 32
<212> TYPE: DNA
<213> ORGANISM: Artificial Sequence
<220> FEATURE:
<223> OTHER INFORMATION: Insert 111-44.3

<400> SEQUENCE: 8
aaaagcttag gcggtattgc tttcgttgca ct 32

<210> SEQ ID NO 9
<211> LENGTH: 34
<212> TYPE: DNA
<213> ORGANISM: Artificial Sequence
<220> FEATURE:
<223> OTHER INFORMATION: Insert 111-44.5

<400> SEQUENCE: 9
ggttaattaa ggtcagcaca cggtccgtgt gcat 34

<210> SEQ ID NO 10
<211> LENGTH: 26
<212> TYPE: DNA
<213> ORGANISM: Artificial Sequence
<220> FEATURE:
<223> OTHER INFORMATION: Primer 111-44.8

-continued

<400> SEQUENCE: 10
aaagatctct cccgatgcgg gaaggc 26

<210> SEQ ID NO 11
<211> LENGTH: 31
<212> TYPE: DNA
<213> ORGANISM: Artificial Sequence
<220> FEATURE:
<223> OTHER INFORMATION: Primer 111-44.9

<400> SEQUENCE: 11
ggggatccaa tggaagggga tgtccgcgga a 31

<210> SEQ ID NO 12
<211> LENGTH: 34
<212> TYPE: DNA
<213> ORGANISM: Artificial Sequence
<220> FEATURE:
<223> OTHER INFORMATION: Insert 111-44.6

<400> SEQUENCE: 12
ggttaattaa catcgcgcta tcagcagcgc tgag 34

<210> SEQ ID NO 13
<211> LENGTH: 34
<212> TYPE: DNA
<213> ORGANISM: Artificial Sequence
<220> FEATURE:
<223> OTHER INFORMATION: Insert 111-44.7

<400> SEQUENCE: 13
ggttaattaa tcctcagcgg ctgacccgct cgcg 34

<210> SEQ ID NO 14
<211> LENGTH: 31
<212> TYPE: DNA
<213> ORGANISM: Artificial Sequence
<220> FEATURE:
<223> OTHER INFORMATION: Primer 90-103

<400> SEQUENCE: 14
aaaaaatgca tctacctcgc tcgtggcggt t 31

<210> SEQ ID NO 15
<211> LENGTH: 32
<212> TYPE: DNA
<213> ORGANISM: Artificial Sequence
<220> FEATURE:
<223> OTHER INFORMATION: Primer 90-107.1

<400> SEQUENCE: 15
ccccctctag aataggtcgg cagcggtacc cg 32

<210> SEQ ID NO 16
<211> LENGTH: 34
<212> TYPE: DNA
<213> ORGANISM: Artificial Sequence
<220> FEATURE:
<223> OTHER INFORMATION: Primer 90-105

<400> SEQUENCE: 16
tttttatgca tgcggcagtt tgaacggaga tgct 34

<210> SEQ ID NO 17

-continued

<211> LENGTH: 32
<212> TYPE: DNA
<213> ORGANISM: Artificial Sequence
<220> FEATURE:
<223> OTHER INFORMATION: Primer 90-106

<400> SEQUENCE: 17
cccccgaatt ctcccggaag gcacacggag ac 32

<210> SEQ ID NO 18
<211> LENGTH: 26
<212> TYPE: DNA
<213> ORGANISM: Artificial Sequence
<220> FEATURE:
<223> OTHER INFORMATION: Primer TL3

<400> SEQUENCE: 18
atgaattcat gatggcccga gcagcg 26

<210> SEQ ID NO 19
<211> LENGTH: 29
<212> TYPE: DNA
<213> ORGANISM: Artificial Sequence
<220> FEATURE:
<223> OTHER INFORMATION: Primer TL4

<400> SEQUENCE: 19
atctgcagcc agtaccgctg ccgctgcca 29

<210> SEQ ID NO 20
<211> LENGTH: 30
<212> TYPE: DNA
<213> ORGANISM: Artificial Sequence
<220> FEATURE:
<223> OTHER INFORMATION: Primer TL5

<400> SEQUENCE: 20
gctctagaac ccggaactgg cgtggcctgt 30

<210> SEQ ID NO 21
<211> LENGTH: 29
<212> TYPE: DNA
<213> ORGANISM: Artificial Sequence
<220> FEATURE:
<223> OTHER INFORMATION: Primer TL6

<400> SEQUENCE: 21
gcagatctac cgcgtgagga cacggcctt 29

<210> SEQ ID NO 22
<211> LENGTH: 50
<212> TYPE: DNA
<213> ORGANISM: Artificial Sequence
<220> FEATURE:
<223> OTHER INFORMATION: Primer TL23

<400> SEQUENCE: 22
ggcgccggcc aagagcgccg cgccggtcgg cgggccagcc ggggacgggt 50

<210> SEQ ID NO 23
<211> LENGTH: 58
<212> TYPE: DNA
<213> ORGANISM: Artificial Sequence
<220> FEATURE:
<223> OTHER INFORMATION: Primer TL24

<400> SEQUENCE: 23

-continued ctagacccgt ccccggctgg cccgccgacc ggcgcggcgc tcttggccgg cgcctgca 58

<210> SEQ ID NO 24
<211> LENGTH: 29
<212> TYPE: DNA
<213> ORGANISM: Artificial Sequence
<220> FEATURE:
<223> OTHER INFORMATION: Primer TL33

<400> SEQUENCE: 24
ggatgcatgc gccggccgaa gggctcgga 29

<210> SEQ ID NO 25
<211> LENGTH: 30
<212> TYPE: DNA
<213> ORGANISM: Artificial Sequence
<220> FEATURE:
<223> OTHER INFORMATION: Primer TL34

<400> SEQUENCE: 25
tcactagtca gcgacaccgg cgctgcgttt 30

<210> SEQ ID NO 26
<211> LENGTH: 24
<212> TYPE: DNA
<213> ORGANISM: Artificial Sequence
<220> FEATURE:
<223> OTHER INFORMATION: Primer TL7

<400> SEQUENCE: 26
gcgctcgaga gcgcgggtat cgct 24

<210> SEQ ID NO 27
<211> LENGTH: 26
<212> TYPE: DNA
<213> ORGANISM: Artificial Sequence
<220> FEATURE:
<223> OTHER INFORMATION: Primer TL8

<400> SEQUENCE: 27
gagatgcatc caatggcgct cacgct 26

<210> SEQ ID NO 28
<211> LENGTH: 28
<212> TYPE: DNA
<213> ORGANISM: Artificial Sequence
<220> FEATURE:
<223> OTHER INFORMATION: Primer TL9

<400> SEQUENCE: 28
gctctagagc cgcgcgcctt ggggcgct 28

<210> SEQ ID NO 29
<211> LENGTH: 27
<212> TYPE: DNA
<213> ORGANISM: Artificial Sequence
<220> FEATURE:
<223> OTHER INFORMATION: Primer TL10

<400> SEQUENCE: 29
gcagatcttg gggcgctgcc tgtggaa 27

<210> SEQ ID NO 30
<211> LENGTH: 28
<212> TYPE: DNA

-continued

```
<213> ORGANISM: Artificial Sequence
<220> FEATURE:
<223> OTHER INFORMATION: Primer TL31

<400> SEQUENCE: 30

ggctgcagac ccagaccgcg ggcgacgc                                          28


<210> SEQ ID NO 31
<211> LENGTH: 29
<212> TYPE: DNA
<213> ORGANISM: Artificial Sequence
<220> FEATURE:
<223> OTHER INFORMATION: Primer TL32

<400> SEQUENCE: 31

gctctagagg tggcgccggc cgcccggcg                                         29


<210> SEQ ID NO 32
<211> LENGTH: 552
<212> TYPE: DNA
<213> ORGANISM: Artificial sequence
<220> FEATURE:
<223> OTHER INFORMATION: KR domain of extender module 6 of the
      epothilone PKS
<221> NAME/KEY: CDS
<222> LOCATION: (1)...(552)

<400> SEQUENCE: 32

gac ggc acc tac ctc gtg acc ggc ggt ctg ggt ggg ctc ggt ctg agc        48
Asp Gly Thr Tyr Leu Val Thr Gly Gly Leu Gly Gly Leu Gly Leu Ser
 1               5                  10                  15

gtg gct gga tgg ctg gcc gag cag ggg gct ggg cat ctg gtg ctg gtg        96
Val Ala Gly Trp Leu Ala Glu Gln Gly Ala Gly His Leu Val Leu Val
            20                  25                  30

ggc cgc tcc ggt gcg gtg agc gcg gag cag cag acg gct gtc gcc gcg       144
Gly Arg Ser Gly Ala Val Ser Ala Glu Gln Gln Thr Ala Val Ala Ala
        35                  40                  45

ctc gag gcg cac ggc gcg cgt gtc acg gta gcg agg gca gac gtc gcc       192
Leu Glu Ala His Gly Ala Arg Val Thr Val Ala Arg Ala Asp Val Ala
    50                  55                  60

gat cgg gcg cag atc gag cgg atc ctc cgc gag gtt acc gcg tcg ggg       240
Asp Arg Ala Gln Ile Glu Arg Ile Leu Arg Glu Val Thr Ala Ser Gly
 65                  70                  75                  80

atg ccg ctc cgc ggc gtc gtt cat gcg gcc ggt atc ctg gac gac ggg       288
Met Pro Leu Arg Gly Val Val His Ala Ala Gly Ile Leu Asp Asp Gly
                 85                  90                  95

ctg ctg atg cag caa acc ccc gcg cgg ttc cgc gcg gtc atg gcg ccc       336
Leu Leu Met Gln Gln Thr Pro Ala Arg Phe Arg Ala Val Met Ala Pro
            100                 105                 110

aag gtc cga ggg gcc ttg cac ctg cat gcg ttg aca cgc gaa gcg ccg       384
Lys Val Arg Gly Ala Leu His Leu His Ala Leu Thr Arg Glu Ala Pro
        115                 120                 125

ctc tcc ttc ttc gtg ctg tac gct tcg gga gca ggg ctc ttg ggc tcg       432
Leu Ser Phe Phe Val Leu Tyr Ala Ser Gly Ala Gly Leu Leu Gly Ser
    130                 135                 140

ccg ggc cag ggc aac tac gcc gcg gcc aac acg ttc ctc gac gct ctg       480
Pro Gly Gln Gly Asn Tyr Ala Ala Ala Asn Thr Phe Leu Asp Ala Leu
145                 150                 155                 160

gca cac cac cgg agg gcg cag ggg ctg cca gca ttg agc atc gac tgg       528
Ala His His Arg Arg Ala Gln Gly Leu Pro Ala Leu Ser Ile Asp Trp
                165                 170                 175

ggc ctg ttc gcg gac gtg ggt ttg                                       552
Gly Leu Phe Ala Asp Val Gly Leu
```

-continued

180

<210> SEQ ID NO 33
<211> LENGTH: 184
<212> TYPE: PRT
<213> ORGANISM: Artificial Sequence
<220> FEATURE:
<223> OTHER INFORMATION: KR domain of extender module 6 of the epothilone PKS

<400> SEQUENCE: 33

```
Asp Gly Thr Tyr Leu Val Thr Gly Gly Leu Gly Gly Leu Gly Leu Ser
 1               5                  10                  15

Val Ala Gly Trp Leu Ala Glu Gln Gly Ala Gly His Leu Val Leu Val
            20                  25                  30

Gly Arg Ser Gly Ala Val Ser Ala Glu Gln Gln Thr Ala Val Ala Ala
        35                  40                  45

Leu Glu Ala His Gly Ala Arg Val Thr Val Ala Arg Ala Asp Val Ala
    50                  55                  60

Asp Arg Ala Gln Ile Glu Arg Ile Leu Arg Glu Val Thr Ala Ser Gly
65                  70                  75                  80

Met Pro Leu Arg Gly Val Val His Ala Ala Gly Ile Leu Asp Asp Gly
                85                  90                  95

Leu Leu Met Gln Gln Thr Pro Ala Arg Phe Arg Ala Val Met Ala Pro
            100                 105                 110

Lys Val Arg Gly Ala Leu His Leu His Ala Leu Thr Arg Glu Ala Pro
        115                 120                 125

Leu Ser Phe Phe Val Leu Tyr Ala Ser Gly Ala Gly Leu Leu Gly Ser
    130                 135                 140

Pro Gly Gln Gly Asn Tyr Ala Ala Ala Asn Thr Phe Leu Asp Ala Leu
145                 150                 155                 160

Ala His His Arg Arg Ala Gln Gly Leu Pro Ala Leu Ser Ile Asp Trp
                165                 170                 175

Gly Leu Phe Ala Asp Val Gly Leu
            180
```

<210> SEQ ID NO 34
<211> LENGTH: 552
<212> TYPE: DNA
<213> ORGANISM: Artificial Sequence
<220> FEATURE:
<223> OTHER INFORMATION: Mutated and inactive KR domain of extender module 6 of the novel 9-keto- epothilone PKS
<221> NAME/KEY: CDS
<222> LOCATION: (1)...(552)

<400> SEQUENCE: 34

```
gac ggc acc tac ctc gtg acc ggc gct ctg ggt ggg ctc ggt ctg agc       48
Asp Gly Thr Tyr Leu Val Thr Gly Ala Leu Gly Gly Leu Gly Leu Ser
 1               5                  10                  15

gtg gct gga tgg ctg gcc gag cag ggg gct ggg cat ctg gtg ctg gtg       96
Val Ala Gly Trp Leu Ala Glu Gln Gly Ala Gly His Leu Val Leu Val
            20                  25                  30

ggc cgc tcc ggt gcg gtg agc gcg gag cag cag acg gct gtc gcc gcg      144
Gly Arg Ser Gly Ala Val Ser Ala Glu Gln Gln Thr Ala Val Ala Ala
        35                  40                  45

ctc gag gcg cac ggc gcg cgt gtc acg gta gcg agg gca gac gtc gcc      192
Leu Glu Ala His Gly Ala Arg Val Thr Val Ala Arg Ala Asp Val Ala
    50                  55                  60

gat cgg gcg cag atc gag cgg atc ctc cgc gag gtt acc gcg tcg ggg      240
```

-continued

```
Asp Arg Ala Gln Ile Glu Arg Ile Leu Arg Glu Val Thr Ala Ser Gly
 65                  70                  75                  80

atg ccg ctc cgc ggc gtc gtt cat gcg gcc ggt atc ctg gac gac ggg      288
Met Pro Leu Arg Gly Val Val His Ala Ala Gly Ile Leu Asp Asp Gly
                 85                  90                  95

ctg ctg atg cag caa acc ccc gcg cgg ttc cgc gcg gtc atg gcg ccc      336
Leu Leu Met Gln Gln Thr Pro Ala Arg Phe Arg Ala Val Met Ala Pro
            100                 105                 110

aag gtc cga ggg gcc ttg cac ctg cat gcg ttg aca cgc gaa gcg ccg      384
Lys Val Arg Gly Ala Leu His Leu His Ala Leu Thr Arg Glu Ala Pro
        115                 120                 125

ctc tcc ttc ttc gtg ctg tac gct tcg gga gca ggg ctc ttg ggc tcg      432
Leu Ser Phe Phe Val Leu Tyr Ala Ser Gly Ala Gly Leu Leu Gly Ser
    130                 135                 140

ccg ggc cag ggc aac ttc gcc acg gcc aac acg ttc ctc gac gct ctg      480
Pro Gly Gln Gly Asn Phe Ala Thr Ala Asn Thr Phe Leu Asp Ala Leu
145                 150                 155                 160

gca cac cac cgg agg gcg cag ggg ctg cca gca ttg agc atc gac tgg      528
Ala His His Arg Arg Ala Gln Gly Leu Pro Ala Leu Ser Ile Asp Trp
                165                 170                 175

ggc ctg ttc gcg gac gtg ggt ttg                                      552
Gly Leu Phe Ala Asp Val Gly Leu
            180


<210> SEQ ID NO 35
<211> LENGTH: 184
<212> TYPE: PRT
<213> ORGANISM: Artificial Sequence
<220> FEATURE:
<223> OTHER INFORMATION: Mutated and inactive KR domain of extender
      module 6 of the novel 9-keto- epothilone PKS

<400> SEQUENCE: 35

Asp Gly Thr Tyr Leu Val Thr Gly Ala Leu Gly Gly Leu Gly Leu Ser
 1               5                  10                  15

Val Ala Gly Trp Leu Ala Glu Gln Gly Ala Gly His Leu Val Leu Val
            20                  25                  30

Gly Arg Ser Gly Ala Val Ser Ala Glu Gln Gln Thr Ala Val Ala Ala
        35                  40                  45

Leu Glu Ala His Gly Ala Arg Val Thr Val Ala Arg Ala Asp Val Ala
    50                  55                  60

Asp Arg Ala Gln Ile Glu Arg Ile Leu Arg Glu Val Thr Ala Ser Gly
65                  70                  75                  80

Met Pro Leu Arg Gly Val Val His Ala Ala Gly Ile Leu Asp Asp Gly
                85                  90                  95

Leu Leu Met Gln Gln Thr Pro Ala Arg Phe Arg Ala Val Met Ala Pro
            100                 105                 110

Lys Val Arg Gly Ala Leu His Leu His Ala Leu Thr Arg Glu Ala Pro
        115                 120                 125

Leu Ser Phe Phe Val Leu Tyr Ala Ser Gly Ala Gly Leu Leu Gly Ser
    130                 135                 140

Pro Gly Gln Gly Asn Phe Ala Thr Ala Asn Thr Phe Leu Asp Ala Leu
145                 150                 155                 160

Ala His His Arg Arg Ala Gln Gly Leu Pro Ala Leu Ser Ile Asp Trp
                165                 170                 175

Gly Leu Phe Ala Asp Val Gly Leu
            180
```

-continued

<210> SEQ ID NO 36
<211> LENGTH: 26
<212> TYPE: DNA
<213> ORGANISM: Artificial Sequence
<220> FEATURE:
<223> OTHER INFORMATION: Primer TLII-1

<400> SEQUENCE: 36
acaagcttgc gaaaaagaac gcgtct 26

<210> SEQ ID NO 37
<211> LENGTH: 30
<212> TYPE: DNA
<213> ORGANISM: Artificial Sequence
<220> FEATURE:
<223> OTHER INFORMATION: Primer TLII-2

<400> SEQUENCE: 37
cgagatctgc cgggcgagga agcggccctg 30

<210> SEQ ID NO 38
<211> LENGTH: 26
<212> TYPE: DNA
<213> ORGANISM: Artificial Sequence
<220> FEATURE:
<223> OTHER INFORMATION: Primer TLII-3B

<400> SEQUENCE: 38
gcatgcatgc gccggtcgat ggtgag 26

<210> SEQ ID NO 39
<211> LENGTH: 30
<212> TYPE: DNA
<213> ORGANISM: Artificial Sequence
<220> FEATURE:
<223> OTHER INFORMATION: Primer TLII-4

<400> SEQUENCE: 39
agactagtca ccggctggcc caccacaagg 30

<210> SEQ ID NO 40
<211> LENGTH: 28
<212> TYPE: DNA
<213> ORGANISM: Artificial Sequence
<220> FEATURE:
<223> OTHER INFORMATION: Primer TLII-20

<400> SEQUENCE: 40
gcatgcatcc agtagcggtc acggcgga 28

<210> SEQ ID NO 41
<211> LENGTH: 29
<212> TYPE: DNA
<213> ORGANISM: Artificial Sequence
<220> FEATURE:
<223> OTHER INFORMATION: Primer TLII-21

<400> SEQUENCE: 41
cgagatctgt gttcgcgttc cccgggcag 29

<210> SEQ ID NO 42
<211> LENGTH: 30
<212> TYPE: DNA
<213> ORGANISM: Artificial Sequence
<220> FEATURE:
<223> OTHER INFORMATION: Primer TLII-13

-continued

<400> SEQUENCE: 42
gcatgcatcc agtagcgctg ccgctggaat 30

<210> SEQ ID NO 43
<211> LENGTH: 28
<212> TYPE: DNA
<213> ORGANISM: Artificial Sequence
<220> FEATURE:
<223> OTHER INFORMATION: Primer TLII-14

<400> SEQUENCE: 43
gcagatctgt gttcgtgttc cccggcca 28

<210> SEQ ID NO 44
<211> LENGTH: 26
<212> TYPE: DNA
<213> ORGANISM: Artificial Sequence
<220> FEATURE:
<223> OTHER INFORMATION: Primer TLII-17

<400> SEQUENCE: 44
gcatgcatcc agtaccgctc gcgctg 26

<210> SEQ ID NO 45
<211> LENGTH: 29
<212> TYPE: DNA
<213> ORGANISM: Artificial Sequence
<220> FEATURE:
<223> OTHER INFORMATION: Primer TLII-18

<400> SEQUENCE: 45
cgagatctgt cttcgtcttt cccggccag 29

<210> SEQ ID NO 46
<211> LENGTH: 28
<212> TYPE: DNA
<213> ORGANISM: Artificial Sequence
<220> FEATURE:
<223> OTHER INFORMATION: Primer TLII-5

<400> SEQUENCE: 46
ggatgcatgt cgagcctgac gcccgccg 28

<210> SEQ ID NO 47
<211> LENGTH: 35
<212> TYPE: DNA
<213> ORGANISM: Artificial Sequence
<220> FEATURE:
<223> OTHER INFORMATION: Primer TLII-6

<400> SEQUENCE: 47
gcactagtga tggcgatctc gtcatccgcc gccac 35

<210> SEQ ID NO 48
<211> LENGTH: 27
<212> TYPE: DNA
<213> ORGANISM: Artificial Sequence
<220> FEATURE:
<223> OTHER INFORMATION: Primer TL16

<400> SEQUENCE: 48
acagatctcg gcgcgctgcc gccggag 27

<210> SEQ ID NO 49
<211> LENGTH: 28

-continued

<212> TYPE: DNA
<213> ORGANISM: Artificial Sequence
<220> FEATURE:
<223> OTHER INFORMATION: Primer TL15

<400> SEQUENCE: 49
ggtctagact cgaacggctc gccaccgc 28

<210> SEQ ID NO 50
<211> LENGTH: 28
<212> TYPE: DNA
<213> ORGANISM: Artificial Sequence
<220> FEATURE:
<223> OTHER INFORMATION: Primer TLII-11

<400> SEQUENCE: 50
gtatgcatcc agtagcggac ccgctcga 28

<210> SEQ ID NO 51
<211> LENGTH: 28
<212> TYPE: DNA
<213> ORGANISM: Artificial Sequence
<220> FEATURE:
<223> OTHER INFORMATION: Primer TLII-12

<400> SEQUENCE: 51
gcagatctgt gtggctcttc tccggaca 28

<210> SEQ ID NO 52
<211> LENGTH: 30
<212> TYPE: DNA
<213> ORGANISM: Artificial Sequence
<220> FEATURE:
<223> OTHER INFORMATION: Primer TLII-15

<400> SEQUENCE: 52
gcatgcatcc agtagcgctg ccgctggaac 30

<210> SEQ ID NO 53
<211> LENGTH: 28
<212> TYPE: DNA
<213> ORGANISM: Artificial Sequence
<220> FEATURE:
<223> OTHER INFORMATION: Primer TLII-16

<400> SEQUENCE: 53
ggagatctgc ggtgctgttc acggggca 28

<210> SEQ ID NO 54
<211> LENGTH: 28
<212> TYPE: DNA
<213> ORGANISM: Artificial Sequence
<220> FEATURE:
<223> OTHER INFORMATION: Primer TLII-19

<400> SEQUENCE: 54
gtagatctgc tttcctgttc accggaca 28

<210> SEQ ID NO 55
<211> LENGTH: 24
<212> TYPE: DNA
<213> ORGANISM: Artificial Sequence
<220> FEATURE:
<223> OTHER INFORMATION: Primer TL11

<400> SEQUENCE: 55

-continued

```
ggatgcatct caccccgcga agcg                                           24


<210> SEQ ID NO 56
<211> LENGTH: 25
<212> TYPE: DNA
<213> ORGANISM: Artificial Sequence
<220> FEATURE:
<223> OTHER INFORMATION: Primer TL12

<400> SEQUENCE: 56

gtactagtca agggcgctgc ggagg                                          25


<210> SEQ ID NO 57
<211> LENGTH: 29
<212> TYPE: DNA
<213> ORGANISM: Artificial Sequence
<220> FEATURE:
<223> OTHER INFORMATION: Primer TLII-7

<400> SEQUENCE: 57

gcagatctgc cgcgcgagga gctcgcgat                                      29


<210> SEQ ID NO 58
<211> LENGTH: 27
<212> TYPE: DNA
<213> ORGANISM: Artificial Sequence
<220> FEATURE:
<223> OTHER INFORMATION: Primer TLII-8

<400> SEQUENCE: 58

catctagagc cgctcctgtg gagtcac                                        27


<210> SEQ ID NO 59
<211> LENGTH: 30
<212> TYPE: DNA
<213> ORGANISM: Artificial Sequence
<220> FEATURE:
<223> OTHER INFORMATION: Primer TLII-9B

<400> SEQUENCE: 59

ggatgcatgc gccggccgaa gggctcggag                                     30


<210> SEQ ID NO 60
<211> LENGTH: 32
<212> TYPE: DNA
<213> ORGANISM: Artificial Sequence
<220> FEATURE:
<223> OTHER INFORMATION: Primer TLII-10

<400> SEQUENCE: 60

gcactagtga tggcgatcgg gtcctctgtc gc                                  32


<210> SEQ ID NO 61
<211> LENGTH: 37
<212> TYPE: DNA
<213> ORGANISM: Artificial Sequence
<220> FEATURE:
<223> OTHER INFORMATION: Primer TLII-22

<400> SEQUENCE: 61

tgatccatgc tgcggccgct agcgtgggca tggccgc                             37


<210> SEQ ID NO 62
<211> LENGTH: 37
<212> TYPE: DNA
<213> ORGANISM: Artificial Sequence
```

-continued

```
<220> FEATURE:
<223> OTHER INFORMATION: Primer TLII-23

<400> SEQUENCE: 62

gcggccatgc ccacgctagc ggccgcagca tggatca                          37
```

METHODS OF OBTAINING EPOTHILONE D USING CRYSTALLIZATION AND /OR BY THE CULTURE OF CELLS IN THE PRESENCE OF METHYL OLEATE

This patent application claims priorty as a continuation-in-part (CIP) to PCT patent application US01/13793, filed 26 Apr. 2001; which claims priority as a CIP to U.S. patent applications Ser. No. 09/560,367, filed 28 Apr. 2000; U.S. Ser. No. 09/825,856, filed 3 Apr. 2001; and U.S. Ser. No. 09/825,876, tiled 3 Apr. 2001; and which also claims the benefit of the filing date of U.S. Provisional Application Ser. Nos 60/232,696, filed 14 Sep. 2000, 60/257,517, filed 21 Dec. 2000, and 60/269,020 , filed 13 Feb. 2001.

FIELD OF THE INVENTION

The present invention provides recombinant methods and materials for producing polyketides in recombinant host cells; recombinant host cells that produce polyketides; novel polyketides related in structure to the epothilones; methods for purifying epothilones; and crystalline forms of epothilone D. In a preferred embodiment, the recombinant host cells of the invention are from the suborder Cystobacterineae, preferably from the genera *Myxococcus* and *Stigmatella*, which have been transformed with recombinant DNA expression vectors of the invention that encode modular or iterative polyketide synthase (PKS) genes. The recombinant host cells produce known and novel polyketides, including but not limited to epothilone and epothilone derivatives. The invention relates to the fields of agriculture, chemistry, medicinal chemistry, medicine, molecular biology, and pharmacology.

BACKGROUND OF THE INVENTION

Polyketides constitute a class of structurally diverse compounds synthesized, at least in part, from two carbon unit building block compounds through a series of Claisen type condensations and subsequent modifications. Polyketides include antibiotics such as tetracycline and erythromycin, anticancer agents such as the epothilones and daunomycin, and immunosuppressants such as FK506, FK520, and rapamycin. Polyketides occur naturally in many types of organisms, including fungi and mycelial bacteria. Polyketides are synthesized in vivo by polyketide synthase enzymes commonly referred to as PKS enzymes. Two major types of PKS are known that differ in their structure and the manner in which they synthesize polyketides. These two types are commonly referred to as Type I or modular and Type II or iterative (aromatic) PKS enzymes.

The present invention provides methods and recombinant expression vectors and host cells for the production of modular and iterative PKS enzymes and the polyketides produced by those enzymes. Modular PKS enzymes are typically multi-protein complexes in which each protein contains multiple active sites, each of which is used only once during carbon chain assembly and modification. Iterative PKS enzymes are typically multi-protein complexes in which each protein contains only one or at most two active sites, each of which is used multiple times during carbon chain assembly and modification. As described in more detail below, a large number of the genes for both modular and aromatic PKS enzymes have been cloned.

Modular PKS genes are composed of coding sequences organized to encode a loading module, a number of extender modules, and a releasing domain. As described more fully below, each of these domains and modules corresponds to a polypeptide with one or more specific functions. Generally, the loading module is responsible for binding the first building block used to synthesize the polyketide and transferring it to the first extender module. The building blocks used to form complex polyketides are typically acylthioesters, most commonly acetyl, propionyl, malonyl, methylmalonyl, hydroxymalonyl, methoxymalonyl, and ethylmalonyl CoA. Other building blocks include amino acid and amino acid-like acylthioesters. PKSs catalyze the biosynthesis of polyketides through repeated, decarboxylative Claisen condensations between the acylthioester building blocks. Each module is responsible for binding a building block, performing one or more functions on that building block, and transferring the resulting compound to the next module. The next module, in turn, is responsible for attaching the next building block and transferring the growing compound to the next module until synthesis is complete. At that point, the releasing domain, often an enzymatic thioesterase (TE) activity, cleaves the polyketide from the PKS.

The polyketide known as 6-deoxyerythronolide B (6-dEB) is synthesized by a prototypical modular PKS enzyme. The genes, known as eryAI, eryAII, and eryAIII, that code for the multi-subunit protein known as deoxyerythronolide B synthase or DEBS (each subunit is known as DEBS1, DEBS2, or DEBS3) that synthesizes 6-dEB are described in U.S. Pat. Nos. 5,672,491, 5,712,146 and 5,824,513, each of which is incorporated herein by reference.

The loading module of the DEBS PKS consists of an acyltransferase (AT) and an acyl carrier protein (ACP). The AT of the DEBS loading module recognizes propionyl CoA (other loading module ATs can recognize other acyl-CoAs, such as acetyl, malonyl, methylmalonyl, or butyryl CoA) and transfers it as a thioester to the ACP of the loading module. Concurrently, the AT on each of the six extender modules of DEBS recognizes a methylmalonyl CoA (other extender module ATs can recognize other CoAs, such as malonyl or alpha-substituted malonyl CoAs, i.e., malonyl, ethylmalonyl, and 2-hydroxymalonyl CoA) and transfers it to the ACP of that module to form a thioester. Once DEBS is primed with propionyl- and methylmalonyl-ACPs, the acyl group of the loading module migrates to form a thioester (trans-esterification) at the KS of the first extender module; at this stage, module one possesses an acyl-KS adjacent to a methylmalonyl ACP. The acyl group derived from the DEBS loading module is then covalently attached to the alpha-carbon of the extender group to form a carbon-carbon bond, driven by concomitant decarboxylation, and generating a new acyl-ACP that has a backbone two carbons longer than the loading unit (elongation or extension). The growing polyketide chain is transferred from the ACP to the KS of the next module of DEBS, and the process continues.

The polyketide chain, growing by two carbons for each module of DEBS, is sequentially passed as a covalently bound thioester from module to module, in an assembly line-like process. The carbon chain produced by this process alone would possess a ketone at every other carbon atom, producing a polyketone, from which the name polyketide is derived. Commonly, however, additional enzymatic activities modify the beta keto group of the polyketide chain to which the two-carbon unit has been added before the chain is transferred to the next module. Thus, in addition to the minimal module containing KS, AT, and ACP necessary to form the carbon-carbon bond, modules may contain a ketoreductase (KR) that reduces the beta-keto group to an alcohol. Modules may also contain a KR plus a dehydratase (DH) that dehydrates the alcohol to a double bond. Modules may also contain a KR, a DH, and an enoylreductase (ER) that converts the double bond to a saturated single bond using the beta carbon as a methylene function. The DEBS modules include those with only a KR domain, only an inactive KR domain, and with all three KR, DH, and ER domains.

Once a polyketide chain traverses the final module of a PKS, it encounters the releasing domain, typically a thioesterase, found at the carboxyl end of most modular PKS enzymes. Here, the polyketide is cleaved from the enzyme and, for many but not all polyketides, cyclized. The polyketide can be further modified by tailoring or modification enzymes; these enzymes add carbohydrate groups or methyl groups, or make other modifications, i.e., oxidation or reduction, on the polyketide core molecule and/or substituents thereon. For example, 6-dEB is hydroxylated and glycosylated (glycosidated), and one of the glycosyl substituents methylated to yield the well known antibiotic erythromycin A in the *Saccharopolyspora erythraea* cells in which it is naturally produced.

While the above description applies generally to modular PKS enzymes and specifically to DEBS, there are a number of variations that exist in nature. For example, many PKS enzymes comprise loading modules that, unlike the loading module of DEBS, comprise an "inactive" KS domain that functions as a decarboxylase. This inactive KS is in most instances called $KS^Q$, where the superscript is the single-letter abbreviation for the amino acid (glutamine) that is present instead of the active site cysteine required for ketosynthase activity. The epothilone PKS loading module contains a $KS^Y$ domain in which tyrosine is present instead of the active site cysteine. Moreover, the synthesis of other polyketides begins with starter units that are unlike those bound by the DEBS or epothilone loading modules. The enzymes that bind such starter units can include, for example, an AMP ligase such as that employed in the biosynthesis of FK520, FK506, and rapamycin, a non-ribosomal peptide synthase (NRPS) such as that employed in the biosynthesis of leinamycin, or a soluble CoA ligase.

Other important variations in PKS enzymes relate to the types of building blocks incorporated as extender units. As for starter units, some PKS enzymes incorporate amino acid like acylthioester building blocks using one or more NRPS modules as extender modules. The epothilone PKS, for example, contains an NRPS module. Another such variation is found in the FK506, FK520, and rapamycin PKS enzymes, which contain an NRPS that incorporates a pipecolate residue and also serves as the releasing domain of the PKS. Yet another variation relates to additional activities in an extender module. For example, one module of the epothilone PKS contains a methyltransferase (MT) domain, which incorporates a methyl group into the polyketide.

Recombinant methods for manipulating modular and iterative PKS genes are described in U.S. Pat. Nos. 5,962,290; 5,672,491; 5,712,146; 5,830,750; and 5,843,718; and in PCT patent publication Nos. 98/49315 and 97/02358, each of which is incorporated herein by reference. These and other patents describe recombinant expression vectors for the heterologous production of polyketides as well as recombinant PKS genes assembled by combining parts of two or more different PKS genes or gene clusters that produce novel polyketides. To date, such methods have been used to produce known or novel polyketides in organisms such as *Streptomyces,* which naturally produce polyketides, and *E. coli* and yeast, which do not naturally produce polyketides (see U.S. Pat. No. 6,033,883, incorporated herein by reference). In the latter hosts, polyketide production is dependent on the heterologous expression of a phosphopantetheinyl transferase, which activates the ACP domains of the PKS (see PCT publication No. 97/13845, incorporated herein by reference).

While such methods are valuable and highly useful, certain polyketides are expressed only at very low levels in, or are toxic to, the heterologous host cell employed. As an example, the anticancer agents epothilones A, B, C, and D were produced in *Streptomyces* by heterologous expression of the epothilone PKS genes (Tang et al., 28 Jan. 2000, Cloning and heterologous expression of the epothilone gene cluster, *Science,* 287: 640–642, and PCT Pub. No. 00/031247, each of which is incorporated herein by reference). Epothilones A and B were produced at less than about 50 to 100 μg/L and appeared to have a deleterious effect on the producer cells.

Epothilones A and B were first identified as an antifungal activity extracted from the myxobacterium *Sorangium cellulosum* (see Gerth et al., 1996, *J. Antibiotics* 49: 560–563 and Germany Patent No. DE 41 38 042, each of which is incorporated herein by reference) and later found to have activity in a tubulin polymerization assay (see Bollag et al., 1995, *Cancer Res.* 55:2325–2333, incorporated herein by reference). Epothilones A and B and certain naturally occurring and synthetic derivatives have since been extensively studied as potential antitumor agents for the treatment of cancer. The chemical structures of the epothilones produced by *Sorangium cellulosum* strain So ce 90 were described in Hofle et al., 1996, Epothilone A and B-novel 16-membered macrolides with cytotoxic activity: isolation, crystal structure, and conformation in solution, *Angew. Chem. Int. Ed. Engl.* 35(13/14): 1567–1569, incorporated herein by reference. Epothilones A (R=H) and B (R=$CH_3$) have the structure shown below and show broad cytotoxic activity against eukaryotic cells and noticeable activity and selectivity against breast and colon tumor cell lines.

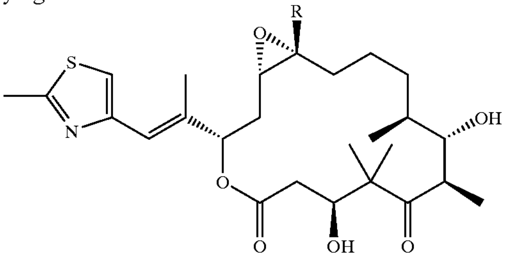

The desoxy counterparts of epothilones A and B, also known as epothilones C(R=H) and D(R=$CH_3$), have been chemically synthesized de novo but are also present as minor products in fermentations of *S. cellulosum.* Epothilones C and D are less cytotoxic than epothilones A and B; their structures are shown below.

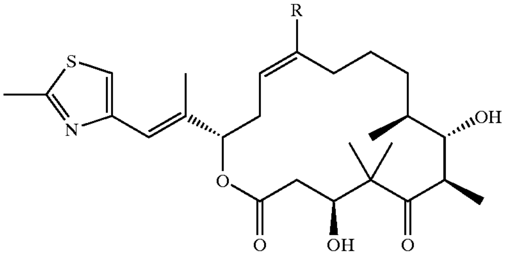

Other naturally occurring epothilones have been described. These include epothilones E and F, in which the methyl side chain of the thiazole moiety of epothilones A and B has been hydroxylated to yield epothilones E and F, respectively, as well as many other epothilone compounds (see PCT Pub. No. 99/65913, incorporated herein by reference).

Because of the potential for use of the epothilones as anticancer agents, and because of the low levels of epothilone produced by the native So ce 90 strain, a number of research teams undertook the effort to synthesize the epothilones. As noted above, this effort has been successful (see Balog et al., 1996, Total synthesis of (−)-epothilone A,

*Angew. Chem. Int. Ed. Engl.* 35(23/24): 2801–2803; Su et al., 1997, Total synthesis of (−)-epothilone B: an extension of the Suzuki coupling method and insights into structure-activity relationships of the epothilones, *Angew. Chem. Int. Ed. Engl.* 36(7): 757–759; Meng et al., 1997, Total syntheses of epothilones A and B, *JACS* 119(42): 10073–10092; and Balog et al., 1998, A novel aldol condensation with 2-methyl-4-pentenal and its application to an improved total synthesis of epothilone B, *Angew. Chem. Int. Ed. Engl.* 37(19): 2675–2678, each of which is incorporated herein by reference). Despite the success of these efforts, the chemical synthesis of the epothilones is tedious, time-consuming, and expensive. Indeed, the methods have been characterized as impractical for the full-scale pharmaceutical development of any epothilone as an anticancer agent.

A number of epothilone derivatives, as well as epothilones A–D, have been studied in vitro and in vivo (see Su et al., 1997, Structure-activity relationships of the epothilones and the first in vivo comparison with paclitaxel, *Angew. Chem. Int. Ed. Engl.* 36(19): 2093–2096; and Chou et al., August 1998, Desoxyepothilone B: an efficacious microtubule-targeted antitumor agent with a promising in vivo profile relative to epothilone B, *Proc. Natl. Acad. Sci. USA* 95: 9642–9647, each of which is incorporated herein by reference). Additional epothilone derivatives and methods for synthesizing epothilones and epothilone derivatives are described in PCT Pub. Nos. 00/23452, 00/00485, 99/67253, 99/67252, 99/65913, 99/54330, 99/54319, 99/54318, 99/43653, 99/43320, 99/42602, 99/40047, 99/27890, 99/07692, 99/02514, 99/01124, 98/25929, 98/22461, 98/08849, and 97/19086; U.S. Pat. No. 5,969,145; and Germany patent publication No. DE 41 38 042, each of which is incorporated herein by reference.

There remains a need for economical means to produce not only the naturally occurring epothilones but also the derivatives or precursors thereof, as well as new epothilone derivatives with improved properties. There remains a need for a host cell that produces epothilones or epothilone derivatives that is easier to manipulate and ferment than the natural producer *Sorangium cellulosum* and that produces more of the desired polyketide product. The present invention meets these needs by providing host cells that produce polyketides at high levels and are useful in the production of not only epothilones, including new epothilone derivatives described herein, but also other polyketides.

SUMMARY OF THE INVENTION

In one embodiment, the present invention provides recombinant host cells of the suborder Cystobacterineae containing recombinant expression vectors that encode heterologous PKS genes and produce polyketides synthesized by the PKS enzymes encoded by the genes on those vectors. In a preferred embodiment, the host cells are from the genus *Myxococcus* or the genus *Stigmatella.* In especially preferred embodiments, the host cells are selected from the group consisting of *M. stipitatus, M. fulvus, M. xanthus, M. virescens, S. erecta*, and *S. aurantiaca.*

In another embodiment, the present invention provides recombinant DNA vectors capable of chromosomal integration or extrachromosomal replication in the host cells of the invention. The vectors of the invention comprise at least a portion of a PKS coding sequence and are capable of directing expression of a functional PKS enzyme in the host cells of the invention. In a related embodiment, the present invention provides vectors and host cells that comprise the genes and gene products required to produce a substrate for polyketide biosynthesis that is either not produced or is produced in low abundance in a host cell of the invention. In one embodiment, the genes and gene products catalyze the synthesis of ethylmalonyl CoA. In another embodiment, the genes and gene products catalyze the synthesis of butyryl CoA.

In another embodiment, the present invention provides a method for producing a polyketide in a host cell of the suborder Cystobacterineae, which polyketide is not naturally produced in said host cell, said method comprising culturing the host cell transformed with a recombinant DNA vector of the invention under conditions such that a PKS gene encoded on the vector is expressed and said polyketide is produced. In a related embodiment, the present invention provides methods for fermenting the host cells of the invention that result in the production of polyketides in high yied.

In a preferred embodiment, the recombinant host cell of the invention produces epothilone or an epothilone derivative. Thus, the present invention provides recombinant host cells that produce a desired epothilone or epothilone derivative. In a preferred embodiment, the host cell produces one or more epothilones at equal to or greater than 10 mg/L. In one embodiment, the invention provides host cells that produce one or more epothilones at levels higher than the levels produced in a naturally occurring organism that produces epothilones. In another embodiment, the invention provides host cells that produce mixtures of epothilones that are less complex than the mixtures produced by a naturally occurring host cell that produces epothilones. The recombinant host cells of the invention also include host cells that produce only one desired epothilone or epothilone derivative as a major product.

In a related preferred embodiment, the invention provides recombinant DNA expression vectors that encode all or a portion of the epothilone PKS. Thus, the present invention provides recombinant DNA expression vectors that encode the proteins required to produce epothilones A, B, C, and D in the host cells of the invention. The present invention also provides recombinant DNA expression vectors that encode portions of these proteins. The present invention also provides recombinant DNA compounds that encode a hybrid protein, which hybrid protein includes all or a portion of a protein involved in epothilone biosynthesis and all or a portion of a protein involved in the biosynthesis of another polyketide or non-ribosomal-derived peptide.

In another embodiment, the present invention provides novel epothilone derivative compounds in substantially pure form useful in agriculture, veterinary practice, and medicine. These compounds include the 16-desmethyl; 14-methyl; 13-oxo; 13-oxo-11,12-dehydro; 12-ethyl; 13-hydroxy-10,11-dehydro; 11-oxo; 11-hydroxy; 10-methyl; 10,11-dehydro; 9-oxo; 9-hydroxy; 8-desmethyl; 6-desmethyl; and 2-methyl analogs of epothilones A, B, C, and D, and a variety of analogs in which the methylthiazole moiety of the naturally occurring epothilones has been replaced with another moiety. In one embodiment, the compounds are useful as fungicides. In another embodiment, the compounds are useful in cancer chemotherapy as anti-cancer agents. In a preferred embodiment, the compound is an epothilone derivative that is at least as potent against tumor cells as epothilone B or D. In another embodiment, the compounds are useful as immunosuppressants. In another embodiment, the compounds are useful in the manufacture of another compound. In a preferred embodiment, the compounds are formulated in a mixture or solution for administration to a human or animal.

In another embodiment, the present invention provides methods for purifying an epothilone. In a preferred embodiment, the epothilone is purified from fermentation broth.

In another embodiment, the present invention provides an epothilone compound in a highly purified form. In a preferred embodiment, the epothilone is more than 95% pure. In a more preferred embodiment, the epothilone is more than 99% pure. In an especially preferred embodiment, the invention provides an epothilone in crystalline form. In one especially preferred embodiment, the invention provides crystalline epothilone D.

In another embodiment, the present invention provides a method of treating cancer, which method comprises administering a therapeutically effective amount of a novel epothilone compound of the invention. The compounds and compositions of the invention are also useful in the treatment of other hyperproliferative diseases and conditions, including, but not limited to, psoriasis and inflammation.

These and other embodiments of the invention are described in more detail in the following description, the examples, and claims set forth below.

DETAILED DESCRIPTION OF THE INVENTION

Figure 1:
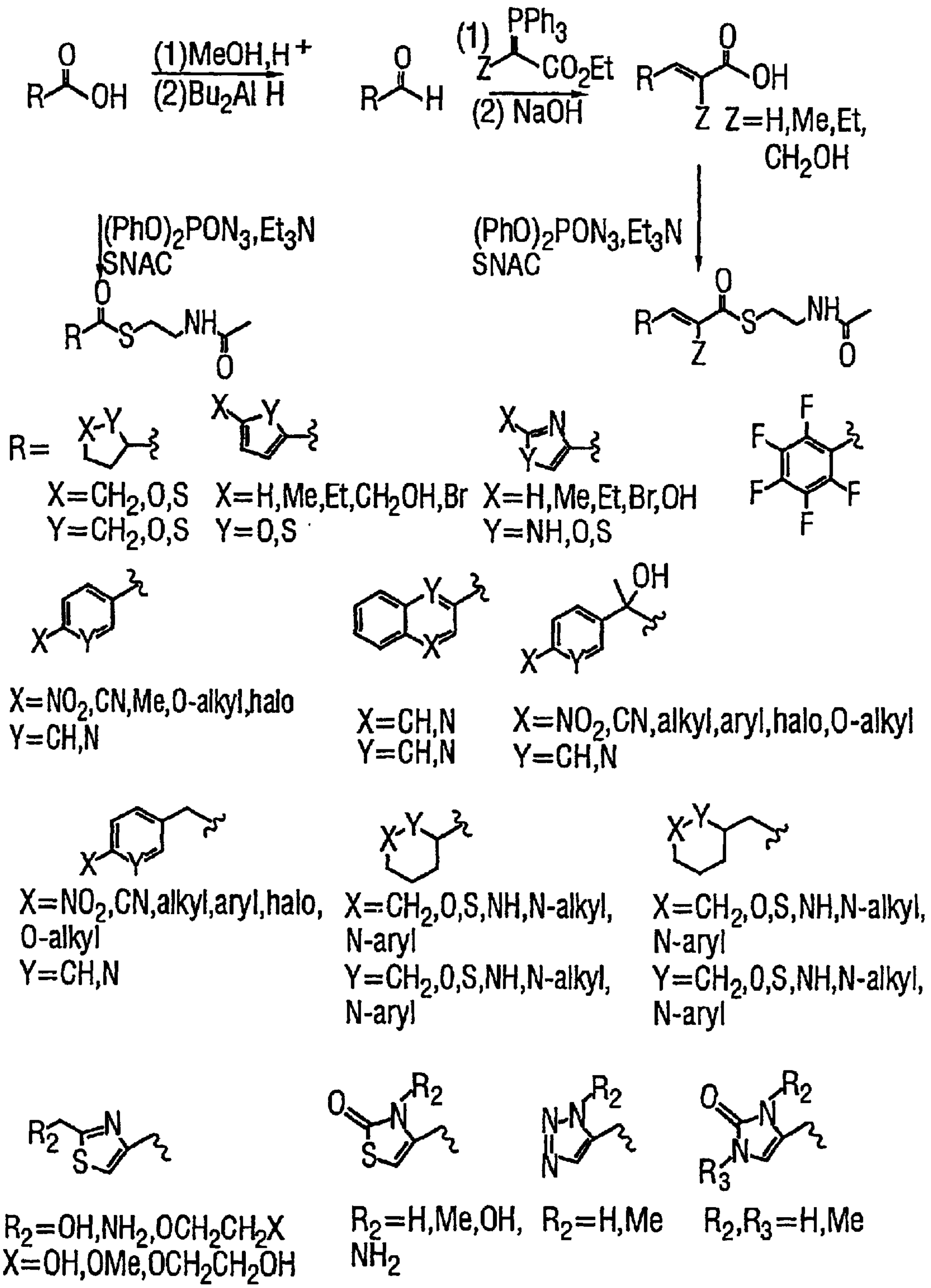
FIG. 1 shows a number of precursor compounds to N-acetyl cysteamine thioester derivatives that can be supplied to an epothilone PKS of the invention in which the NRPS-like module one or module two KS domain has been inactivated to produce a novel epothilone derivative. A general synthetic procedure for making such compounds is also shown.

Statements regarding the scope of the present invention and definitions of terms used herein are listed below. The definitions apply to the terms as they are used throughout this specification, unless otherwise limited in specific instances, either individually or as part of a larger group.

All stereoisomers of the inventive compounds are included within the scope of the invention, as pure compounds as well as mixtures thereof. Individual enantiomers, diastereomers, geometric isomers, and combinations and mixtures thereof are all encompassed by the present invention. Furthermore, some of the crystalline forms for the compounds may exist as polymorphs and as such are included in the present invention. In addition, some of the compounds may form solvates with water (i.e., hydrates) or common organic solvents, and such solvates are also encompassed within the scope of this invention.

Protected forms of the inventive compounds are included within the scope of the present invention. A variety of protecting groups are disclosed, for example, in T. H. Greene and P. G. M. Wuts, Protective Groups in Organic Synthesis, Third Edition, John Wiley & Sons, New York (1999), which is incorporated herein by reference in its entirety. For example, a hydroxy protected form of the inventive compounds are those where at least one of the hydroxyl groups is protected by a hydroxy protecting group. Illustrative hydroxyl protecting groups include but not limited to tetrahydropyranyl; benzyl; methylthiomethyl; ethylthiomethyl; pivaloyl; phenylsulfonyl; triphenylmethyl; trisubstituted silyl such as trimethyl silyl, triethylsilyl, tributylsilyl, triisopropylsilyl, t-butyldimethylsilyl, tri-t-butylsilyl, methyldiphenylsilyl, ethyldiphenylsilyl, t-butyldiphenylsilyl and the like; acyl and aroyl such as acetyl, pivaloylbenzoyl, 4-methoxybenzoyl, 4-nitrobenzoyl and aliphatic acylaryl and the like. Keto groups in the inventive compounds may similarly be protected.

The present invention includes within its scope prodrugs of the compounds of this invention. In general, such prodrugs are functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to a subject in need thereof. Conventional procedures for the selection and preparation of suitable prodrug derivatives are described, for example, in "Design of Prodrugs", H. Bundgaard ed., Elsevier, 1985.

As used herein, the term "aliphatic" refers to saturated and unsaturated straight chained, branched chain, cyclic, or polycyclic hydrocarbons that may be optionally substituted at one or more positions. Illustrative examples of aliphatic groups include alkyl, alkenyl, alkynyl, cycloalkyl, cycloalkenyl, and cycloalkynyl moieties. The term "alkyl" refers to straight or branched chain saturated hydrocarbon substituent. "Alkenyl" refers to a straight or branched chain hydrocarbon substituent with at least one carbon-carbon double bond. "Alkynyl" refers to a straight or branched chain hydrocarbon substituent with at least one carbon-carbon triple bound.

The term "aryl" refers to monocyclic or polycyclic groups having at least one aromatic ring structure that optionally include one ore more heteroatoms and preferably include three to fourteen carbon atoms. Aryl substituents may optionally be substituted at one or more positions. Illustrative examples of aryl groups include but are not limited to: furanyl, imidazolyl, indanyl, indenyl, indolyl, isooxazolyl, isoquinolinyl, naphthyl, oxazolyl, oxadiazolyl, phenyl, pyrazinyl, pyridyl, pyrimidinyl, pyrrolyl, pyrazolyl, quinolyl, quinoxalyl, tetrahydronaphththyl, tetrazoyl, thiazoyl, thienyl, thiophenyl, and the like.

The aliphatic (i.e., alkyl, alkenyl, etc.) and aryl moieties may be optionally substituted with one or more substituents, preferably from one to five substituents, more preferably from one to three substituents, and most preferably from one to two substituents. The definition of any substituent or variable at a particular location in a molecule is independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein. Examples of suitable substituents include but are not limited to: alkyl, alkenyl, alkynyl, aryl, halo; trifluoromethyl; trifluoromethoxy; hydroxy; alkoxy; cycloalkoxy; heterocyclooxy; oxo; alkanoyl (—C(═O)-alkyl which is also referred to as "acyl")); aryloxy; alkanoyloxy; amino; alkylamino; arylamino; aralkylamino; cycloalkylamino; heterocycloamino; disubstituted amines in which the two amino substituents are selected from alkyl, aryl, or aralkyl; alkanoylamino; aroylamino; aralkanoylamino; substituted alkanoylamino; substituted arylamino; substituted aralkanoylamino; thiol; alkylthio; arylthio; aralkylthio; cycloalkylthio; heterocyclothio; alkylthiono; arylthiono; aralkylthiono; alkylsulfonyl; arylsulfonyl; aralkylsulfonyl; sulfonamido (e.g., $SO_2NH_2$); substituted sulfonamido; nitro; cyano; carboxy; carbamyl (e.g., $CONH_2$); substituted carbamyl (e.g., —C(═O)NRR' where R and R' are each independently hydrogen, alkyl, aryl, aralkyl and the like); alkoxycarbonyl, aryl, substituted aryl, guanidino, and heterocyclo such as indoyl, imidazolyl, furyl, thienyl, thiazolyl, pyrrolidyl, pyridyl, pyrimidyl and the like. Where applicable, the substituent may be further substituted such as with, alkyl, alkoxy, aryl, aralkyl, halogen, hydroxy and the like.

The terms "alkylaryl" or "arylalkyl" refer to an aryl group with an aliphatic substituent that is bonded to the compound through the aliphatic group. An illustrative example of an alkylaryl or arylalkyl group is benzyl, a phenyl with a methyl group that is bonded to the compound through the methyl group ($—CH_2Ph$ where Ph is phenyl).

The term "acyl" refers to —C(═O)R where R is an aliphatic group, preferably a $C_1$–$C_6$ moiety.

The term "alkoxy" refers to —OR wherein O is oxygen and R is an aliphatic group.

The term "aminoalkyl" refers to $—RNH_2$ where R is an aliphatic moiety.

The terms "halogen," "halo", or "halide" refer to fluorine, chlorine, bromine and iodine.

The term "haloalkyl" refers to —RX where R is an aliphatic moiety and X is one or more halogens.

The term "hydroxyalkyl" refers to —ROH where R is an aliphatic moiety.

The term "oxo" refers to a carbonyl oxygen (═O).

In addition to the explicit substitutions at the above-described groups, the inventive compounds may include other substitutions where applicable. For example, the lactone or lactam backbone or backbone substituents may be additionally substituted (e.g., by replacing one of the hydrogens or by derivatizing a non-hydrogen group) with one or more substituents such as $C_1$–$C_5$ aliphatic, $C_1$–$C_5$ alkoxy, aryl, or a functional group. Illustrative examples of suitable functional groups include but are not limited to: acetal, alcohol, aldehyde, amide, amine, boronate, carbamate, carboalkoxy, carbonate, carbodiimide, carboxylic acid, cyanohydrin, disulfide, enamine, ester, ether, halogen, hydrazide, hydrazone, imide, imido, imine, isocyanate, ketal, ketone, nitro, oxime, phosphine, phosphonate, phosphonic acid, quaternary ammonium, sulfenyl, sulfide, sulfone, sulfonic acid, thiol, and the like.

The term "isolated" as used herein to refer to a compound of the present invention, means altered "by human intervention from its natural state. For example, if the compound occurs in nature, it has been changed or removed from its original environment, or both. In other words, a compound naturally present in a living organism is not "isolated," but the same compound separated from the coexisting materials of its natural state is "isolated", as the term is employed herein. The term "isolated" can also mean a compound that is in a preparation that is substantially free of contaminating or undesired materials. With respect to compounds found in nature, substantially free of the materials with which that compound or composition is associated in its natural state.

The term "purified" as it refers to a compound means that the compound is in a preparation in which the compound forms a major component of the preparation, such as constituting about 50%, about 60%, about 70%, about 80%, about 90%, about 95% or more by weight of the components in the preparation.

The term "subject" as used herein, refers to an animal, preferably a mammal, who has been the object of treatment, observation or experiment and most preferably a human who has been the object of treatment and/or observation.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "composition" is intended to encompass a product comprising the specified ingredients in the specified amounts, as well as any product that results, directly or indirectly, from combinations of the specified ingredients in the specified amounts.

The term "pharmaceutically acceptable salt" is a salt of one or more of the inventive compounds. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include but are not limited to: acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxyethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like.

The term "pharmaceutically acceptable carrier" is a medium that is used to prepare a desired dosage form of the inventive compound. A pharmaceutically acceptable carrier includes solvents, diluents, or other liquid vehicle; dispersion or suspension aids; surface active agents; isotonic agents; thickening or emulsifying agents, preservatives; solid binders; lubricants and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe, ed. (Amer. Pharmaceutical Assoc. 2000), both of which are incorporated herein by reference in their entireties, disclose various carriers used in formulating pharmaceutical compositions and known techniques for the preparation thereof.

The term "pharmaceutically acceptable ester" is an ester that hydrolzyes in vivo into a compound of the present invention or a salt thereof. Illustrative examples of suitable ester groups include, for example, those derived from pharmaceutically acceptable aliphatic carboxylic acids such as formates, acetates, propionates, butyrates, acrylates, and ethylsuccinates.

The present invention provides recombinant methods and materials for producing polyketides in recombinant host cells; recombinant host cells that produce polyketides; novel polyketides related in structure to the epothilones; methods for purifying epothilones; and crystalline forms of epothilone D.

In one embodiment, the present invention provides recombinant host cells of the suborder Cystobacterineae containing recombinant expression vectors that encode heterologous PKS genes and produce polyketides synthesized by the PKS enzymes encoded on those vectors. As used herein, the term recombinant refers to a cell, compound, or composition produced by human intervention, typically by specific and directed manipulation of a gene or portion thereof. The suborder Cystobacterineae is one of two (the other is *Sorangineae,* which includes the epothilone producer *Sorangium cellulosum*) in the order Myxococcales. The suborder Cystobacterineae includes the family Myxococcaceae and the family Cystobacteraceae. The family Myxococcacceae includes the genus *Angiococcus* (i.e., *A. disciformis*), the genus *Myxococcus,* and the genus *Corallococcus* (i.e., *C. macrosporus, C. corralloides*, and *C. exiguus*). The family Cystobacteraceae includes the genus *Cystobacter* (i.e., *C. fuscus, C. ferrugineus, C. minor, C. velatus*, and *C. violaceus*), the genus *Melittangium* (i.e., *M. boletus* and *M. lichenicola*), the genus *Stigmatella* (i.e., *S. erecta* and *S. aurantiaca*), and the genus *Archangium* (i.e., *A. gephyra*). Especially preferred host cells of the invention are those that produce a polyketide at equal to or greater than 10 to 20 mg/L, more preferably at equal to or greater than 100 to 200 mg/L, and most preferably at equal to or greater than 1 to 2 g/L.

In a preferred embodiment, the host cells of the invention are from the genus *Myxococcus* or the genus *Stigmatella*. In especially preferred embodiments, the host cells are selected from the group consisting of *M. stipitatus, M. fulvus, M. xanthus, M. virescens, S. erecta*, and *S. aurantiaca*. Especially preferred *Myxococcus* host cells of the invention are those that produce a polyketide at equal to or greater than 10 to 20 mg/L, more preferably at equal to or greater than 100 to 200 mg/L, and most preferably at equal to or greater than 1 to 2 g/L. Especially preferred are *M. xanthus* host cells that produce at these levels. *M. xanthus* host cells that can be employed for purposes of the invention include, but are not limited to, the DZ1 cell line (Campos et al., 1978, *J. Mol. Biol.* 119: 167–178, incorporated herein by reference), the TA-producing cell line ATCC 31046, the DK1219 cell line (Hodgkin and Kaiser, 1979, *Mol. Gen. Genet.* 171: 177–191, incorporated herein by reference), and the DK1622 cell line (Kaiser, 1979, *Proc. Natl. Acad. Sci. USA* 76: 5952–5956, incorporated herein by reference).

The host cells of the invention comprise a recombinant DNA expression vector, and in another embodiment, the present invention provides recombinant DNA vectors capable of chromosomal integration or extrachromosomal replication in these host cells. The vectors of the invention comprise at least a portion of a PKS coding sequence and are capable of directing expression of a functional PKS enzyme in the host cells of the invention. As used herein, the term expression vector refers to any nucleic acid that can be introduced into a host cell. An expression vector can be maintained stably or transiently in a cell, whether as part of the chromosomal or other DNA in the cell or in any cellular compartment, such as a replicating vector in the cytoplasm. An expression vector also comprises a gene that serves to direct the synthesis of RNA that is translated into a polypeptide in the cell or cell extract. Thus, the vector either includes a promoter to enhance gene expression or is integrated into a site in the chromosome such that gene expression is obtained. Furthermore, expression vectors typically contain additional functional elements, such as resistance-conferring genes to act as selectable markers and regulatory genes to enhance promoter activity.

Typically, the expression vector will comprise one or more marker genes by which host cells containing the vector can be identified and/or selected. Illustrative antibiotic resistance conferring genes for use in vectors of the invention include the ermE (confers resistance to erythromycin and lincomycin), tsr (confers resistance to thiostrepton), aadA (confers resistance to spectinomycin and streptomycin), aacC4 (confers resistance to apramycin, kanamycin, gentamicin, geneticin (G418), and neomycin), hyg (confers resistance to hygromycin), and vph (confers resistance to viomycin) resistance conferring genes. Selectable markers for use in *Myxococcus xanthus* include kanamycin, tetracycline, chloramphenicol, zeocin, spectinomycin, and streptomycin resistance conferring genes.

The various components of an expression vector can vary widely, depending on the intended use of the vector. In particular, the components depend on the host cell(s) in which the vector will be used and the manner in which it is intended to function. For example, certain preferred vectors of the invention are integrating vectors: the vectors integrate into the chromosomal DNA of the host cell. Such vectors can comprise a phage attachment site or DNA segments complementary to segments of the host cell chromosomal DNA to direct integration. Moreover, and as exemplified herein, a series of such vectors can be used to build the PKS gene cluster in the host cell, with each vector comprising only a portion of the complete PKS gene cluster. Thus, the recombinant DNA expression vectors of the invention may comprise only a portion of a PKS gene or gene cluster. Homologous recombination can also be used to delete, disrupt, or alter a gene, including a heterologous PKS gene previously introduced into the host cell.

In a preferred embodiment, the present invention provides expression vectors and recombinant *Myxococcus,* preferably *M. xanthus*, host cells containing those expression vectors that produce a polyketide. Presently, vectors that replicate extrachromosomally in *M. xanthus* have not been published, although there is an unpublished report of an artificial plasmid based on the Mx4 phage replicon. There are, however, a number of phage known to integrate into *M. xanthus* chromosomal DNA, including Mx8, Mx9, Mx81, and Mx82. The integration and attachment functions of these phages can be placed on plasmids to create phage-based expression vectors that integrate into the *M. xanthus* chromosomal DNA. Of these, phage Mx9 and Mx8 are preferred for purposes of the present invention. Plasmid pPLH343, described in Salmi et al., February 1998, Genetic determinants of immunity and integration of temperate *Myxococcus xanthus* phage Mx8, *J. Bact.* 180(3): 614–621, is a plasmid that replicates in *E. coli* and comprises the phage Mx8 genes that encode the attachment and integration functions.

A wide variety of promoters are available for use in the preferred *Myxococcus* expression vectors of the invention. See Example 8, below. For example, the promoter of the *Sorangium cellulosum* epothilone PKS gene (see PCT Pub. No. 00/031247, incorporated herein by reference) functions in *M. xanthus* host cells. The epothilone PKS gene promoter can be used to drive expression of one or more epothilone PKS genes or another PKS gene product in recombinant host cells. Another preferred promoter for use in *M. xanthus* host cells for purposes of expressing a recombinant PKS of the invention is the promoter of the pilA gene of *M. xanthus*. This promoter, as well as two *M. xanthus* strains that express high levels of gene products from genes controlled by the pilA promoter, a pilA deletion strain and a pilS deletion strain, are described in Wu and Kaiser, December 1997, Regulation of expression of the pilA gene in *Myxococcus xanthus, J. Bact.* 179(24):7748–7758, incorporated herein by reference. The present invention also provides recombinant *Myxococcus* host cells comprising both the pilA and pilS deletions. Another preferred promoter is the starvation dependent promoter of the sdeK gene.

Figure 2:
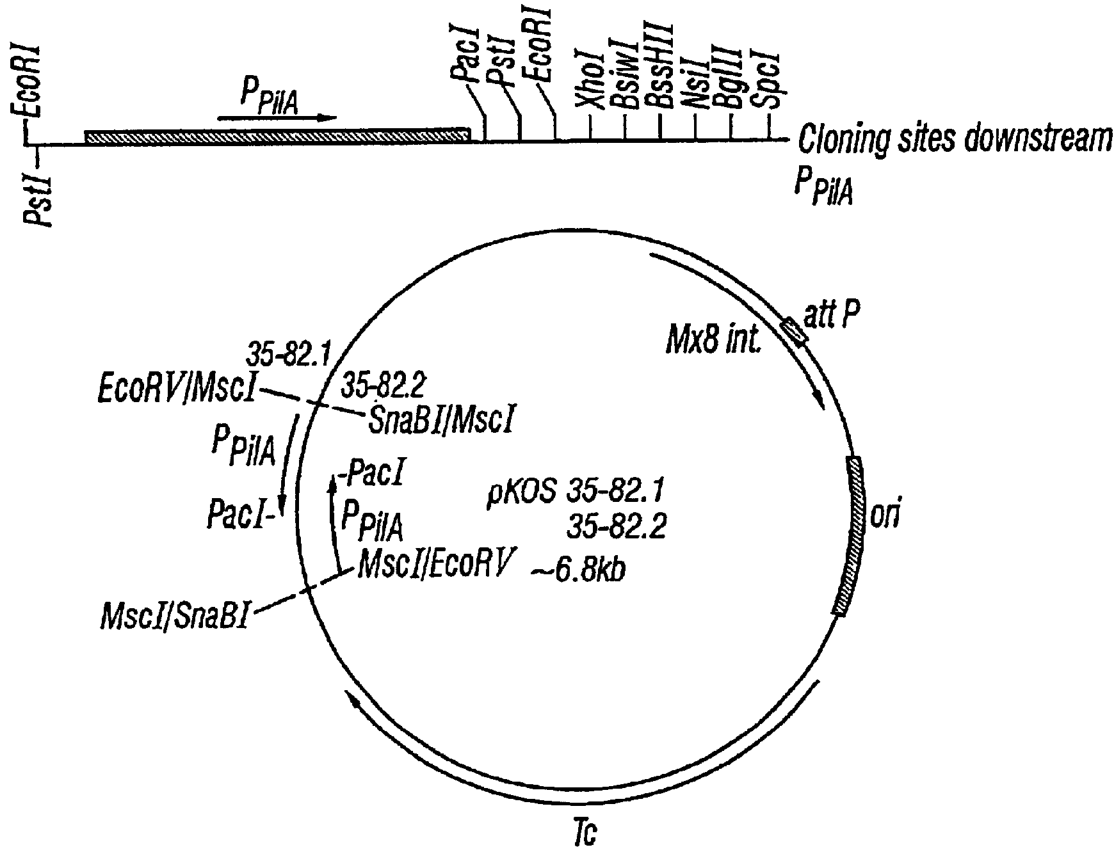
FIG. 2 shows restriction site and function maps of plasmids pKOS35-82.1 and pKOS35-82.2.

The present invention provides preferred expression vectors for use in preparing the recombinant *Myxococcus xanthus* expression vectors and host cells of the invention. These vectors, designated plasmids pKOS35-82.1 and pKOS35-82.2 (FIG. 2), are able to replicate in *E. coli* host cells as well as integrate into the chromosomal DNA of *M. xanthus*. The vectors comprise the Mx8 attachment and integration genes as well as the pilA promoter with restriction enzyme recognition sites placed conveniently downstream. The two vectors differ from one another merely in the orientation of the pilA promoter on the vector and can be readily modified to include the epothilone PKS and modification enzyme genes of the invention or other PKS and modification enzyme genes. The construction of the vectors is described in Example 1.

In another embodiment, the present invention provides a method for producing a polyketide in a host cell of the suborder Cystobacterineae, which polyketide is not naturally produced in said host cell, said method comprising culturing the host cell transformed with a recombinant DNA vector of the invention under conditions such that a PKS gene encoded on the vector is expressed and said polyketide is produced. With this method, any of the diverse members of the polyketides produced by modular or iterative PKS enzymes can be prepared. In addition, novel polyketides derived from hybrid or other recombinant PKS genes can also be prepared using this method. In a preferred embodiment, the PKS genes encode a hybrid modular PKS.

A large number of modular PKS genes have been cloned and are immediately available for use in the vectors and methods of the invention. The polyketides produced by PKS enzymes are often further modified by polyketide modification enzymes, also called tailoring enzymes, that hydroxylate, epoxidate, methylate, and/or glycosylate the polyketide product of the PKS. In accordance with the methods of the invention, these genes can also be introduced into the host cell to prepare a modified polyketide of interest. The following Table lists references describing illustrative PKS genes and corresponding PKS enzymes that can be utilized in the construction of the recombinant PKSs and the corresponding DNA compounds that encode them of the invention. Also presented are various references describing polyketide tailoring and modification enzymes and corresponding genes that can be employed to make the recombinant DNA compounds of the present invention.

PKS and Polyketide Tailoring Enzyme Genes

Avermectin

U.S. Pat. Nos. 5,252,474; 4,703,009; and EP Pub. No. 118,367 to Merck.

MacNeil et al., 1993, *Industrial Microorganisms: Basic and Applied Molecular Genetics*, Baltz, Hegeman, & Skatrud, eds. (ASM), pp. 245–256, A Comparison of the Genes Encoding the Polyketide Synthases for Avermectin, Erythromycin, and Nemadectin.

MacNeil et al., 1992, *Gene* 115: 119–125, Complex Organization of the *Streptomyces avermitilis* genes encoding the avermectin polyketide synthase.

Ikeda and Omura, 1997, *Chem. Res.* 97: 2599–2609, Avermectin biosynthesis.

Candicidin (FR008)

Hu et al., 1994, *Mol. Microbiol.* 14: 163–172.

Epothilone

PCT Pub. No. 99/66028 to Novartis.

PCT Pub. No. 00/031247 to Kosan.

Erythromycin

PCT Pub. No. 93/13663; U.S. Pat. Nos. 6,004,787; and 5,824,513 to Abbott.

Donadio et al., 1991, *Science* 252:675–9.

Cortes et al., 8 Nov. 1990, *Nature* 348:176–8, An unusually large multifunctional polypeptide in the erythromycin producing polyketide synthase of *Saccharopolyspora erythraea*.

Glycosylation Enzymes

PCT Pub. No. 97/23630 and U.S. Pat. No. 5,998,194 to Abbott.

FK-506

Motamedi et al., 1998, The biosynthetic gene cluster for the macrolactone ring of the immunosuppressant FK-506, *Eur. J. biochem.* 256: 528–534.

Motamedi et al., 1997, Structural organization of a multifunctional polyketide synthase involved in the biosynthesis of the macrolide immunosuppressant FK-506, *Eur. J. Biochem.* 244: 74–80.

Methyltransferase

U.S. Pat. Nos. 5,264,355 and 5,622,866 to Merck.

Motamedi et al., 1996, Characterization of methyltransferase and hydroxylase genes involved in the biosynthesis of the immunosuppressants FK-506 and FK-520, *J. Bacteriol.* 178: 5243–5248.

FK-520

PCT Pub. No. 00/20601 to Kosan.

Nielsen et al., 1991, *Biochem.* 30: 5789–96.

Lovastatin

U.S. Pat. No. 5,744,350 to Merck.

Nemadectin

MacNeil et al., 1993, supra.

Niddamycin

PCT Pub. No. 98/51695 to Abbott.

Kakavas et al., 1997, Identification and characterization of the niddamycin polyketide synthase genes from *Streptomyces caelestis, J. Bacteriol.* 179: 7515–7522.

Oleandomycin

Swan et al., 1994, Characterisation of a *Streptomyces antibioticus* gene encoding a type I polyketide synthase which has an unusual coding sequence, *Mol. Gen. Genet.* 242: 358–362.

PCT Pub. No. 00/026349 to Kosan.

Olano et al., 1998, Analysis of a *Streptomyces antibioticus* chromosomal region involved in oleandomycin biosynthesis, which encodes two glycosyltransferases responsible for glycosylation of the macrolactone ring, *Mol. Gen. Genet.* 259(3): 299–308.

PCT Pub. No. 99/05283 to Hoechst.

Picromycin

PCT Pub. No. 99/61599 to Kosan.

PCT Pub. No. 00/00620 to the University of Minnesota.

Xue et al., 1998, Hydroxylation of macrolactones YC-17 and narbomycin is mediated by the pikC-encoded cytochrome P450 in *Streptomyces venezuelae, Chemistry & Biology* 5(11): 661–667.

Xue et al., October 1998, A gene cluster for macrolide antibiotic biosynthesis in *Streptomyces venezuelae*: Architecture of metabolic diversity, *Proc. Natl. Acad. Sci. USA* 95: 12111 12116.

Platenolide

EP Pub. No. 791,656; and U.S. Pat. No. 5,945,320 to Lilly.

Rapamycin

Schwecke et al., August 1995, The biosynthetic gene cluster for the polyketide rapamycin, *Proc. Natl. Acad. Sci. USA* 92: 7839–7843.

Aparicio et al., 1996, Organization of the biosynthetic gene cluster for rapamycin in *Streptomyces hygroscopicus*: analysis of the enzymatic domains in the modular polyketide synthase, *Gene* 169: 9–16.

Rifamycin

PCT Pub. No. 98/07868 to Novartis.

August et al., 13 Feb. 1998, Biosynthesis of the ansamycin antibiotic rifamycin: deductions from the molecular analysis of the rif biosynthetic gene cluster of *Amycolatopsis mediterranei* S669, *Chemistry & Biology,* 5(2): 69–79.

Sorangium PKS

U.S. Pat. No. 6,090,601 to Kosan.

Soraphen

U.S. Pat. No. 5,716,849 to Novartis.

Schupp et al., 1995, *J. Bacteriology* 177: 3673–3679. A *Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes.

Spinocyn

PCT Pub. No. 99/46387 to DowElanco.

Spiramycin

U.S. Pat. No. 5,098,837 to Lilly.

Activator Gene

U.S. Pat. No. 5,514,544 to Lilly.

Tylosin

U.S. Pat. Nos. 5,876,991; 5,672,497; 5,149,638; EP Pub. No. 791,655; and EP Pub. No. 238,323 to Lilly.

Kuhstoss et al., 1996, *Gene* 183:231–6. Production of a novel polyketide through the construction of a hybrid polyketide synthase.

Tailoring Enzymes

Merson-Davies and Cundliffe, 1994, *Mol. Microbiol.* 13: 349–355. Analysis of five tylosin biosynthetic genes from the tylBA region of the *Streptomyces fradiae* genome.

Any of the above genes, with or without the genes for polyketide modification, if any, can be employed in the recombinant DNA expression vectors of the invention. Moreover, the host cells of the invention can be constructed by transformation with multiple vectors, each containing a portion of the desired PKS and modification enzyme gene cluster; see U.S. Pat. No. 6,033,883, incorporated herein by reference.

For improved production of a polyketide in a host cell of the invention, including *Myxococcus* host cells, one can also transform the cell to express a heterologous phosphopantetheinyl transferase. PKS proteins require phosphopantetheinylation of the ACP domains of the loading and extender modules as well as of the PCP domain of any NRPS. Phosphopantetheinylation is mediated by enzymes called phosphopantetheinyl transferases (PPTases). To produce functional PKS enzyme in host cells that do not naturally express a PPTase able to act on the desired PKS enzyme or to increase amounts of functional PKS enzyme in host cells in which the PPTase is limiting, one can introduce a heterologous PPTase, including but not limited to Sfp, as described in PCT Pub. Nos. 97/13845 and 98/27203, and U.S. Pat. No. 6,033,883, each of which is incorporated herein by reference. Another suitable PPTase that can be used for this purpose is MtaA from *Stigmatella aurantiaca.*

Another method provided by the present invention to improve polyketide production in any organism, including but not limited to *Myxococcus, Streptomyces,* and *Sorangium* host cells, is to select cells that are resistant to streptomycin, rifampicin, and/or gentamycin. In a preferred embodiment, the polyketide producing host cell is successively challenged with each of these compounds (or compounds similar in structure thereto), and resistant cells with increased polyketide production ability are isolated and used in the next round of selection. In this manner, one can obtain, for example and without limitation, a *Myxococcus xanthus* host cell that produces epothilone or an epothilone derivative at high levels and is resistant to streptomycin, rifampicin, and gentamycin.

The host cells of the invention can be used not only to produce a polyketide found in nature but also to produce polyketides produced by the products of recombinant PKS genes and modification enzymes. In one important embodiment, the present invention provides recombinant DNA expression vectors that comprise a hybrid PKS. For purposes of the present invention a hybrid PKS is a recombinant PKS that comprises all or part of one or more extender modules, loading module, and thioesterase/cyclase domain of a first PKS and all or part of one or more extender modules, loading module, and thioesterase/cyclase domain of a second PKS.

Those of skill in the art will recognize that all or part of either the first or second PKS in a hybrid PKS of the invention need not be isolated from a naturally occurring source. For example, only a small portion of an AT domain determines its specificity. See PCT Pub. No. 00/001838, incorporated herein by reference. The state of the art in DNA synthesis allows the artisan to construct de novo DNA compounds of size sufficient to construct a useful portion of a PKS module or domain. For purposes of the present invention, such synthetic DNA compounds are deemed to be a portion of a PKS.

As the above Table illustrates, there are a wide variety of PKS genes that serve as readily available sources of DNA and sequence information for use in constructing the hybrid PKS-encoding DNA compounds of the invention. Methods for constructing hybrid PKS-encoding DNA compounds are described in U.S. Pat. Nos. 6,022,731; 5,962,290; 5,672,491; and 5,712,146 and PCT Pub. Nos. 98/49315; 99/61599; and 00/047724, each of which is incorporated herein by reference. The hybrid PKS-encoding DNA compounds of the invention can be hybrids of more than two PKS genes. Even where only two genes are used, there are often two or more modules in the hybrid gene in which all or part of the module is derived from a second PKS gene. Those of skill in the art will appreciate that a hybrid PKS of the invention includes, but is not limited to a PKS of any of the following types: (i) a PKS that contains a module in which at least one of the domains is from a heterologous module; (ii) a PKS that contains a module from a heterologous PKS; (iii) a PKS that contains a protein from a heterologous PKS; and (iv) combinations of the foregoing.

Hybrid PKS enzymes of the invention are often constructed by replacing coding sequences for one or more domains of a module from a first PKS with coding sequences for one or more domains of a module from a second PKS to construct a recombinant coding sequence. Generally, any reference herein to inserting or replacing a KR, DH, and/or ER domain includes the replacement of the associated KR, DH, or ER domains in that module, typically with corresponding domains from the module from which the inserted or replacing domain is obtained. The KS and/or ACP of any module can also be replaced, if desired or beneficial, with another KS and/or ACP. For example, if the production of an epothilone derivative compound is low due to an alteration in a module, production may be improved by altering the KS and/or ACP domains of the succeeding module. In each of these replacements or insertions, the heterologous KS, AT, DH, KR, ER, or ACP coding sequence can originate from a coding sequence from another module of the same or different PKS or from chemical synthesis to obtain the hybrid PKS coding sequence.

While an important embodiment of the present invention relates to hybrid PKS genes, the present invention also provides recombinant PKS genes in which there is no second PKS gene sequence present but which differ from a naturally occurring PKS gene by one or more mutations and/or deletions. The deletions can encompass one or more modules or domains and/or can be limited to a deletion within one or more modules or domains. When a deletion encompasses an entire extender module (other than an NRPS module), the resulting polyketide derivative is at least two carbons shorter than the compound produced from the PKS from which the deleted version was derived. The deletion can also encompass an NRPS module and/or a loading module. When a deletion is within a module, the deletion may encompass only a single domain, typically a KR, DH, or ER domain, or more than one domain, such as both DH and ER domains, or both KR and DH domains, or all three KR, DH, and ER domains. A domain of a PKS can also be "deleted" functionally by mutation, such as by random or site-specific mutagenesis. Thus, as exemplified herein, a KR domain can be rendered non-functional or less than fully functional by mutation. Moreover, the specificity of an AT domain can also be altered by mutation, such as by random or site-specific mutagenesis.

To construct any PKS of the invention, one can employ a technique, described in PCT Pub. No. 98/27203 and U.S. Pat. No. 6,033,883, each of which is incorporated herein by reference, in which the various genes of the PKS and optionally genes for one or more polyketide modification enzymes are divided into two or more, often three, segments, and each segment is placed on a separate expression vector (see also PCT Pub. No. 00/063361, both of which are incorporated herein by reference). In this manner, the full complement of genes can be assembled and manipulated more readily for heterologous expression, and each of the segments of the gene can be altered, and various altered segments can be combined in a single host cell to provide a recombinant PKS gene of the invention. This technique makes more efficient the construction of large libraries of recombinant PKS genes, vectors for expressing those genes, and host cells comprising those vectors. In this and other contexts, the genes encoding the desired PKS not only can be present on two or more vectors, but also can be ordered or arranged differently from that which exists in the native producer organism from which the genes were derived.

In a preferred and illustrative embodiment, the recombinant host cell of the invention produces epothilone or an epothilone derivative. The naturally occurring epothilones (including epothilone A, B, C, D, E, and F) and non-naturally occurring compounds structurally related thereto (epothilone derivatives or analogs) are potent cytotoxic agents specific for eukaryotic cells. These compounds have application as anti-fungals, cancer chemotherapeutics, and immunosuppressants, and generally for the treatment of inflammation or any hyperproliferative disease, such as psoriasis, multiple sclerosis, atherosclerosis, and blockage of stents. The epothilones are produced at very low levels in the naturally occurring *Sorangium cellulosum* cells in which they have been identified. Moreover, *S. cellulosum* is very slow growing, and fermentation of *S. cellulosum* strains is difficult and time-consuming. One important benefit conferred by the present invention is the ability simply to produce an epothilone or epothilone derivative in a non-*S. cellulosum* host cell. Another advantage of the present invention is the ability to produce the epothilones at higher levels and in greater amounts in the recombinant host cells provided by the invention than possible in the naturally occurring epothilone producer cells. Yet another advantage is the ability to produce an epothilone derivative in a recombinant host cell. Thus, the present invention provides recombinant host cells that produce a desired epothilone or epothilone derivative. In a preferred embodiment, the host cell produces the epothilone or epothilone derivative at equal to or greater than 10 mg/L. In one embodiment, the invention provides host cells that produce one or more of the epothilones or epothilone derivatives at higher levels than produced in the naturally occurring organisms that produce epothilones. In another embodiment, the invention provides host cells that produce mixtures of epothilones that are less complex than the mixtures produced by naturally occurring host cells that produce epothilones.

In an especially preferred embodiment, the host cells of the invention produce less complex mixtures of epothilones than do naturally occurring cells that produce epothilones. As one example, certain host cells of the invention can produce epothilone D in a less complex mixture than is produced by a naturally occurring *Sorangium cellulosum*, because epothilone D is a major product in the former and a minor product in the latter. Naturally occurring *Sorangium cellulosum* cells that produce epothilones typically produce a mixture of epothilones A, B, C, D, E, F, and other very minor products, with only epothilones A and B present as major products. The Table 1 below summarizes the epothilones produced in different illustrative host cells of the invention.

TABLE 1

| Cell Type | Epothilones Produced | Epothilones Not Produced* |
|---|---|---|
| 1 | A, B, C, D | E, F |
| 2 | A, C | B, D, E, F |
| 3 | B, D | A, C, E, F |
| 4 | A, B | C, D |
| 5 | C, D | A, B |
| 6 | B | A, C, D, E, F |
| 7 | D | A, B, C, E, F |

*or produced only as minor products

Thus, the recombinant host cells of the invention also include host cells that produce as a major product only one desired epothilone or epothilone derivative.

Based solely on an analysis of the domains of the epothilone PKS, one could predict that the PKS enzyme catalyzes the production of epothilones arbitrarily designated "G" and "H", the structures of which are shown below:

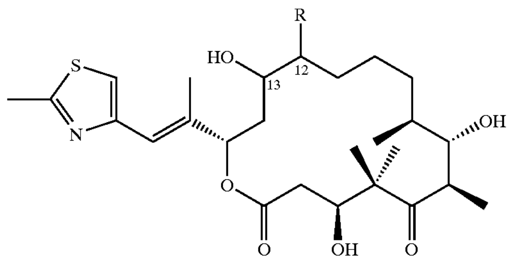

Epothilones G (R = H) and H (R = $CH_3$).

These compounds differ from one another in that epothilone G has a hydrogen at C-12 and epothilone H has a methyl group at that position. The variance at the C-12 position is predicted to arise from the ability of the corresponding AT domain (extender module 4) of the PKS to bind either malonyl CoA, leading to hydrogen, or methylmalonyl CoA, leading to methyl. However, epothilones G and H have not been observed in nature or in the recombinant host cells of the invention. Instead, the products of the PKS are believed to be epothilones C and D, which differ from epothilones G and H, respectively, by having a C-12 to C-13 double bond and lacking a C-13 hydroxyl substituent. Based on the expression of the epothilone PKS genes in heterologous host cells and the products produced by genetic alteration of those genes, as described more fully below, the dehydration reaction that forms the C12-C13 double bond in epothilones C and D is believed to be carried out by the epothilone PKS itself. Epothilones A and B are formed from epothilones C and D, respectively, by epoxidation of the C-12 to C-13 double bond by the epoK gene product. Epothilones E and F may be formed from epothilones A and B, respectively, by hydroxylation of the C-21 methyl group or by incorporation of a hydroxymalonyl CoA instead of a malonyl CoA by the loading module of the epothilone PKS, as discussed further below.

Thus expression of the epothilone PKS genes and the epoK gene in a host cell of the invention leads to the production of epothilones A, B, C, and D. If the epoK gene is not present or is rendered inactive or partially inactive by mutation, then epothilones C and D are produced as major products. If the AT domain of extender module 4 is replaced by an AT domain specific for malonyl CoA, then epothilones A and C are produced, and if there is no functional epoK gene, then epothilone C is produced as the major product. If the AT domain of extender module 4 is replaced by an AT domain specific for methylmalonyl Co A, then epothilones B and D are produced as major products, and if there is no functional epoK gene, then epothilone D is produced as the major product.

The epothilone PKS and modification enzyme genes were cloned from the epothilone producing strain, *Sorangium cellulosum* SMP44. Total DNA was prepared from this strain using the procedure described by Jaoua et al., 1992, *Plasmid* 28: 157–165, incorporated herein by reference. A cosmid library was prepared from *S. cellulosum* genomic DNA in pSupercos (Stratagene). The entire PKS and modification enzyme gene cluster was isolated in four overlapping cosmid clones (deposited on Feb. 17, 1999, under the terms of the Budapest Treaty with the American Type Culture Collection (ATCC), 10801 University Blvd., Manassas, Va., 20110-2209 USA, and assigned ATCC accession numbers as follows: pKOS35-70.1A2 (ATCC 203782), pKOS35-70.4 (ATCC 203781), pKOS35-70.8A3 (ATCC 203783), and pKOS35-79.85 (ATCC 203780)) and the DNA sequence determined, as described in PCT Pub. No. 00/031237, incorporated herein by reference. DNA sequence analysis revealed a PKS gene cluster with a loading module and nine extender modules. Downstream of the PKS sequence is an open reading frame (ORF), designated epoK, that shows strong homology to cytochrome P450 oxidase genes and encodes the epothilone epoxidase modification enzyme.

The PKS genes are organized in 6 ORFs. At the polypeptide level, the loading module and extender modules 1 (an NRPS), 2, and 9 appear on individual polypeptides; their corresponding genes are designated epoA, epoB, epoC, and epoF respectively. Modules 3, 4, 5, and 6 are contained on a single polypetide whose gene is designated epoD, and modules 7 and 8 are on another polypeptide whose gene is designated epoE. The spacing between ORFs suggests that epoC, epoD, epoE and epoF constitute an operon. The epoA, epoB, and epoK gene may be also part of this large operon, but there are spaces of approximately 100 bp between epoB and epoC and 115 bp between epoF and epoK that could contain a promoter. The epothilone PKS gene cluster is shown schematically below in Scheme 1.

epothilone at C-15–C-17. The presence of the DH domain in module 2 yields the C-16-17 dehydro moiety in the molecule. The domains in module 3 are consistent with the structure of epothilone at C-14 and C-15; the OH that comes from the action of the KR is employed in the lactonization of the molecule. Extender module 4 controls the structure at C-12 and C-13 where a double bond is found in epothilones C and D. Although the sequence of the AT domain appears to resemble those that specify malonate loading, it can also load methylmalonate, thereby accounting in part for the mixture of epothilones found in the fermentation broths of the naturally producing organisms.

A significant departure from the expected array of functions was found in extender module 4. This module was expected to contain a DH domain, thereby directing the synthesis of epothilones C and D as the products of the PKS. Analysis revealed that the space between the AT and KR domains of module 4 was not large enough to accommodate a functional DH domain. Thus, the extent of reduction at module 4 appears not to proceed beyond the ketoreduction of the beta-keto formed after the condensation directed by extender module 4. As shown herein, the epothilone PKS genes alone are sufficient to confer the ability to produce epothilones C and D to the host cells of the invention. The

SCHEME 1

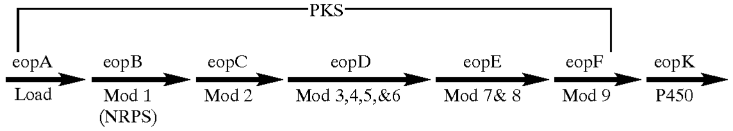

Immediately downstream of epoK, the P450 epoxidase gene, is ORF1, which encodes a polypeptide that appears to include membrane spanning domains and may be involved in epothilone transport. This ORF is followed by a number of ORFs that include genes that may encode proteins involved in transport and regulation.

A detailed examination of the modules shows an organization and composition consistent with the biosynthesis of epothilone. The description that follows is at the polypetide level. The sequence of the AT domain in the loading module and in extender modules 3, 4, 5, and 9 shows similarity to the consensus sequence for malonyl loading modules, consistent with the presence of an H side chain at C-14, C-12 (epothilones A and C), C-10, and C-2, respectively, as well as the loading module. The AT domains in modules 2, 6, 7, and 8 resemble the consensus sequence for methylmalonyl specifying AT domains, again consistent with the presence of methyl side chains at C-16, C-8, C-6, and C4 respectively.

The loading module contains a KS domain in which the cysteine residue usually present at the active site is instead a tyrosine. This domain is designated as $KS^y$ and serves as a decarboxylase, which is part of its normal function, but cannot function as a condensing enzyme. Thus, the loading module is expected to load malonyl CoA, move it to the ACP, and decarboxylate it to yield the acetyl residue required for condensation with cysteine. Extender module 1 is the non-ribosomal peptide synthetase that activates cysteine and catalyzes the condensation with acetate on the loading module. The sequence contains segments highly similar to ATP-binding and ATPase domains, required for activation of amino acids, a phosphopantetheinylation site, an oxidation domain, a cyclization domain, and an elongation domain. Extender module 2 determines the structure of heterologous production of epothilones C and D demonstrates that there must be a dehydratase function that introduces the double bond. Based on heterologous expression of the epothilone PKS genes and the products produced by altered epothilone PKS genes, the dehydration reaction that forms this double bond is believed to be mediated by the DH domain of extender module 5 of the epothilone PKS and the generation of a conjugated diene precursor prior to reduction by the ER domain of module 5.

Extender modules 5 and 6 each have the full set of reduction domains (KR, DH and ER) to yield the methylene functions at C-11 and C-9. Extender modules 7 and 9 have KR domains to yield the hydroxyls at C-7 and C-3, and extender module 8 does not have a functional KR domain, consistent with the presence of the keto group at C-5. Extender module 8 also contains a methyltransferase (MT) domain that results in the presence of the geminal dimethyl function at C4. Extender module 9 also has a thioesterase domain that terminates polyketide synthesis and catalyzes ring closure.

The genes, proteins, modules, and domains of the epothilone PKS are summarized in the following Table 2.

TABLE 2

| Gene | Protein | Modules | Domains Present |
|---|---|---|---|
| epoA | EPOA | Load | $KS^Y$ mAT ER ACP |
| epoB | EPOB | 1 | NRPS, condensation, heterocyclization, adenylation, thiolation, PCP |
| epoC | EPOC | 2 | KS mmAT DH KR ACP |

TABLE 2-continued

| Gene | Protein | Modules | Domains Present |
|---|---|---|---|
| epoD | EPOD | 3–6 | KS mAT KR ACP; KS mAT KR ACP; KS mAT DH ER KR ACP; KS mmAT DH ER KR ACP |
| epoE | EPOE | 7–8 | KS mmAT KR ACP; KS mmAT MT DH* KR* AC |
| epoF | EPOF | 9 | KS mAT KR DH* ER* ACP TE |

NRPS - non-ribosomal peptide synthetase; KS - ketosynthase; mAT - malonyl CoA specifying acyltransferase; mmAT - methylmalonyl CoA specifying acyltransferase; DH - dehydratase; ER - enoylreductase; KR - ketoreductase; MT - methyltransferase; TE thioesterase; * - inactive domain.

Inspection of the sequence has revealed translational coupling between epoA and epoB (loading module and the extender module 1 NRPS) and between epoC and epoD. Very small gaps are seen between epoD and epoE and epoE and epoF but gaps exceeding 100 bp are found between epoB and epoC and epoF and epoK. These intergenic regions may contain promoters.

Thus, the epothilone PKS is a multiprotein complex composed of the gene products of the epoA, epoB, epoC, epoD, epoE, and epoF genes. To confer the ability to produce epothilones to a host cell, one provides the host cell with the recombinant epoA, epoB, epoC, epoD, epoE, and epoF genes of the present invention, and optionally other genes, such as epoK, capable of expression in that host cell. Those of skill in the art will appreciate that, while the epothilone and other PKS enzymes may be referred to as a single entity herein, these enzymes are typically multisubunit proteins. Thus, one can make a derivative PKS (a PKS that differs from a naturally occurring PKS by deletion or mutation) or hybrid PKS (a PKS that is composed of portions of two different PKS enzymes) by altering one or more genes that encode one or more of the multiple proteins that constitute the PKS.

The post-PKS modification or tailoring of epothilone includes multiple steps mediated by multiple enzymes. These enzymes are referred to herein as tailoring or modification enzymes. Expression of the epothilone PKS genes epoA, epoB, epoC, epoD, epoE, and epoF in host cells of the invention that do not express epoK leads to the production of epothilones C and D as major products, which lack the C-12-C-13 epoxide of epothilones A and B, having instead a C-12-C-13 double bond. Thus, epothilones C and D are converted to epothilones A and B by an epoxidase encoded by the epoK gene. Epothilones A and B may be converted to epothilones E and F by a hydroxylase gene, which may be encoded by a gene associated with the epothilone PKS gene cluster or by another gene endogenous to *Sorangium cellulosum*. Alternatively, these compounds may be formed by the loading module binding a starter unit other than malonyl CoA (such as hydroxymalonyl CoA). Thus, one can produce an epothilone or epothilone derivative modified as desired in a host cell by providing that host cell with one or more recombinant modification enzyme genes provided by the invention or by utilizing a host cell that naturally expresses (or does not express) the modification enzyme and/or by providing starter units other than malonyl CoA.

Thus, the present invention provides a wide variety of recombinant DNA compounds and host cells for expressing the naturally occurring epothilones A, B, C, and D and derivatives thereof. The invention also provides recombinant host cells that produce epothilone derivatives modified in a manner similar to epothilones E and F. Moreover, any epothilone or epothilone derivative of the invention can be converted to the corresponding epothilone E or F derivative in accordance with the methods described in PCT Pat. Pub. No. 00/039276, incorporated herein by reference.

The present invention also provides a wide variety of recombinant DNA compounds and host cells that make epothilone derivatives. As used herein, the phrase epothilone derivative refers to a compound that is produced by a recombinant epothilone PKS in which at least one domain has been inserted or in which a domain has either been rendered inactive by deletion or mutation, mutated to alter its catalytic function, or replaced by a domain with a different function. In any event, the epothilone derivative PKS so produced functions to produce a compound that differs in structure from a naturally occurring epothilone selected from the group consisting of epothilones A, B, C, D, E, and F. To faciliate a better understanding of the recombinant DNA compounds and host cells provided by the invention, a detailed discussion of the loading module and each of the modules of the epothilone PKS, as well as novel recombinant derivatives thereof, is provided below.

The loading module of the epothilone PKS includes an "inactive" KS domain, designated $KS^Y$, that, due to the presence of a tyrosine (Y) residue in place of the cysteine residue found in "active" KS domains, is unable to perform the condensation reaction mediated by active KS domains. The $KS^Y$ domain does carry out the decarboxylation reaction mediated by KS domains. Such "inactive" KS domains are found in other PKS enzymes, usually with a glutamine (Q) residue in place of the active site cysteine, and are called $KS^Q$ domains. The $KS^Q$ domain in rat fatty acid synthase has been shown to be unable to perform condensation but exhibits a 2 order magnitude increase in decarboxylation. See Witkowski et al., 7 Sep. 1999, *Biochem.* 38(36): 11643–11650, incorporated herein by reference. A $KS^Q$ domain may be more efficient at decarboxylation than a $KS^Y$ domain, so the replacement of the $KS^Y$ domain in the epothilone PKS with a $KS^Q$ domain may increase the efficiency of epothilone biosynthesis in some host cells or under certain culture conditions. This can be accomplished merely by changing the codon from a tyrosine to a glutamine codon, as described in Example 6, below. This can also be accomplished by replacing the $KS^Y$ domain with a $KS^Q$ domain of another PKS, such as the oleandolide PKS or the narbonolide PKS (see the references cited in the Table above in connection with the oleandomycin, narbomycin, and picromycin PKS and modification enzymes).

The epothilone loading module also contains an AT domain specific for malonyl CoA (which is believed to be decarboxylated by the $KS^Y$ domain to yield an acetyl group), and an ACP domain. The present invention provides recombinant epothilone derivative loading modules or their encoding DNA sequences in which the malonyl specific AT domain or its encoding sequence has been changed to another specificity, such as methylmalonyl CoA, ethylmalonyl CoA, and 2-hydroxymalonyl CoA. When expressed with the other proteins of the epothilone PKS, such loading modules lead to the production of epothilones in which the methyl substituent of the thiazole ring of epothilone is replaced with, respectively, ethyl, propyl, and hydoxymethyl. The present invention provides recombinant PKS enzymes comprising such loading modules and host cells for producing such enzymes and the polyketides produced thereby. When the AT domain is changed to specify 2-hydroxymalonyl CoA, the correspoding epothilone PKS derivative will produce epothilone E and F derivatives. An AT domain specific for 2-hydroxymalonyl CoA will result in a polyketide with a hydroxyl group at the corresponding location in the polyketide produced; the hydroxyl group can be methylated to yield a methoxy group by polyketide modification enzymes. See, e.g., the references cited in connection with the FK-520 PKS in the Table above. Consequently, reference to a PKS that has a 2-hydroxymalonyl specific AT domain herein similarly refers to polyketides produced by that PKS that have either a hydroxyl or methoxyl group at the corresponding location in the polyketide.

The loading module of the epothilone PKS also comprises an ER domain. While, this ER domain may be involved in forming one of the double bonds in the thiazole moiety in epothilone (in the reverse of its normal reaction), it may be non-functional. In either event, the invention provides recombinant DNA compounds that encode the epothilone PKS loading module with and without the ER region, as well as hybrid loading modules that contain an ER domain from another PKS (either active or inactive, with or without accompanying KR and DH domains) in place of the ER domain of the epothilone loading module. The present invention also provides recombinant PKS enzymes comprising such loading modules and host cells for producing such enzymes and the polyketides produced thereby.

The loading module of the epothilone PKS can also be replaced with a loading module from a heterologous PKS to form a hybrid PKS that makes an epothilone derivative. In one embodiment, the loading module of the epothilone PKS is replaced with a NRPS, as described in the examples below.

The loading module of the epothilone PKS is followed by the first extender module of the PKS, which is an extender NRPS module specific for cysteine. This NRPS module is naturally expressed as a discrete protein, the product of the epoB gene. In one embodiment, a portion of the NRPS module coding sequence is utilized in conjunction with a heterologous coding sequence. In this embodiment, the invention provides, for example, changing the specificity of the NRPS module of the epothilone PKS from a cysteine to another amino acid. This change is accomplished by constructing a coding sequence in which all or a portion of the epothilone PKS NRPS module coding sequences have been replaced by those coding for an NRPS module of a different specificity.

In one illustrative embodiment, the specificity of the epothilone NRPS module is changed from cysteine to serine or threonine. When the thus modified NRPS module is expressed with the other proteins of the epothilone PKS, the recombinant PKS produces an epothilone derivative in which the thiazole moiety of epothilone (or an epothilone derivative) is changed to an oxazole or 5-methyloxazole moiety, respectively. Thus, in an illustrative embodiment, the present invention provides host cells, vectors, and recombinant epothilone PKS enzymes in which the NRPS domain has been altered by replacement of the adenylation domain of the epothilone NRPS with the adenylation domain of the NRPS encoded by the entF gene (for serine). In another illustrative embodiment, the present invention provides host cells, vectors, and recombinant epothilone PKS enzymes in which the NRPS domain has been altered by replacement of the adenylation domain of the epothilone NRPS with the adenylation domain of the NRPS encoded by the vibF gene (for threonine). In one embodiment, these NRPS replacements are made in an epothilone PKS that also contains an extender module 2 that binds malonyl CoA instead of methylmalonyl CoA to produce the 16-desmethyl derivatives of the oxazole and methyloxazole epothilone derivatives.

Alternatively, the present invention provides recombinant PKS enzymes composed of the products of the epoA, epoC, epoD, epoE, and epoF genes (or modified versions thereof) without an NRPS module or with an NRPS module from a heterologous PKS. The heterologous NRPS module can be expressed as a discrete protein or as a fusion protein with either the epoA or epoC genes. In replacing one module of a PKS with another, it may be important to ensure that compatible intermodular linker sequences are maintained or otherwise utilized. See PCT Pub. No. 00/047724, incorporated herein by reference.

In another embodiment, the invention provides recombinant epothilone PKS enzymes and corresponding recombinant DNA compounds and vectors in which the NRPS module has been inactivated or deleted. Inactive NRPS module proteins and the coding sequences therefore provided by the invention include those in which the PCP domain has been wholly or partially deleted or otherwise rendered inactive by changing the active site serine (the site for phosphopantetheinylation) to another amino acid, such as alanine, or the adenylation domains have been deleted or otherwise rendered inactive. In one embodiment, both the loading module and the NRPS have been deleted or rendered inactive. In any event, the resulting epothilone PKS can then function only if provided a substrate that binds to the KS domain of extender module 2 (or a subsequent module) of the epothilone PKS or a PKS for an epothilone derivative. In a method provided by the invention, the thus modified cells are then fed activated acylthioesters that are bound by preferably the second, but potentially any subsequent, extender module and processed into novel epothilone derivatives. The host cell is fed activated acylthioesters to produce novel epothilone derivatives of the invention. The host cells expressing, or cell free extracts containing, the PKS can be fed or supplied with N-acylcysteamine thioesters (NACS) of novel precursor molecules to prepare epothilone derivatives. See PCT Pub. Nos. US99/03986 and 00/044717, both of which are incorporated herein by reference, and Examples 9 and 10, below.

The second (first non-NRPS) extender module of the epothilone PKS includes a KS, an AT specific for methylmalonyl CoA, a DH, a KR, and an ACP. The second extender module of the epothilone PKS is produced as a discrete protein by the epoC gene. All or only a portion of the second extender module coding sequence can be utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting either the DH or KR or both; replacing the DH or KR or both with a DH or KR or both that specifies a different stereochemistry; and/or inserting an ER. The resulting heterologous second extender module coding sequence can be coexpressed with the other proteins that constitute a PKS that synthesizes epothilone, an epothilone derivative, or another polyketide. Alternatively, one can delete or replace the second extender module of the epothilone PKS with a module from a heterologous PKS, which can be expressed as a discrete protein or as a fusion protein fused to either the epoB or epoD gene product.

Illustrative recombinant PKS genes of the invention include those in which the AT domain encoding sequences for the second extender module of the epothilone PKS have been altered or replaced to change the AT domain encoded thereby from a methylmalonyl specific AT to a malonyl specific AT. Such malonyl specific AT domain encoding nucleic acids can be isolated, for example and without limitation, from the PKS genes encoding the narbonolide PKS, the soraphen PKS, the rapamycin PKS (i.e., extender modules 2 and 12), and the FK-520 PKS (i.e., extender modules 3, 7, and 8). When such a hybrid second extender module is coexpressed with the other proteins constituting the epothilone PKS, the resulting epothilone derivative produced is a 16-desmethyl epothilone. In one embodiment, the hybrid PKS also contains a methylmalonyl CoA specific AT domain in extender module 4 and is epressed in a host cell lacking a functional epoK gene such that the compound produced is 16-desmethyl epothilone D. In another embodiment, the hybrid PKS also contains an altered NRPS that is specific for threonine, leading to the production of the 5-methyloxazole-16-desmethylepothilones.

In addition, the invention provides DNA compounds and vectors encoding recombinant epothilone PKS enzymes and the corresponding recombinant proteins in which the KS domain of the second (or subsequent) extender module has been inactivated or deleted, as described in Example 9, below. In a preferred embodiment, this inactivation is accomplished by changing the codon for the active site cysteine to an alanine codon. As with the corresponding variants described above for the NRPS module, the resulting recombinant epothilone PKS enzymes are unable to produce an epothilone or epothilone derivative unless supplied a precursor that can be bound and extended by the remaining domains and modules of the recombinant PKS enzyme. Illustrative precursor compounds are described in Example 10, below. Alternatively, one could simply provide such precursors to a host cell that expresses only the epoD, epoE, and epoF genes.

The third extender module of the epothilone PKS includes a KS, an AT specific for malonyl CoA, a KR, and an ACP. The third extender module of the epothilone PKS is expressed as a protein, the product of the epoD gene, which also contains modules 4, 5, and 6. To make a recombinant epothilone PKS that produces an epothilone derivative due to an alteration in any of extender modules 3 through 6, one typically expresses a protein comprising all four extender modules. In one embodiment, all or a portion of the third extender module coding sequence is utilized in conjunction with other PKS coding sequences to create a hybrid module. In this embodiment, the invention provides, for example, either replacing the malonyl CoA specific AT with a methylmalonyl CoA, ethylmalonyl CoA, or 2-hydroxymalonyl CoA specific AT; deleting the KR; replacing the KR with a KR that specifies a different stereochemistry; and/or inserting a DH or a DH and an ER. The resulting heterologous third extender module coding sequence can be utilized in conjunction with a coding sequence for a PKS that synthesizes epothilone, an epothilone derivative, or another polyketide.

Illustrative recombinant PKS genes of the invention include those in which the AT domain encoding sequences for the third extender module of the epothilone PKS have been altered or replaced to change the AT domain encoded thereby from a malonyl specific AT to a methylmalonyl specific AT. Such methylmalonyl specific AT domain encoding nucleic acids can be isolated, for example and without limitation, from the PKS genes encoding DEBS, the narbonolide PKS, the rapamycin PKS, and the FK-520 PKS. When coexpressed with the remaining modules and proteins of the epothilone PKS or an epothilone PKS derivative, the recombinant PKS produces the 14-methyl epothilone derivatives of the invention.

Those of skill in the art will recognize that the KR domain of the third extender module of the PKS is responsible for forming the hydroxyl group involved in cyclization of epothilone. Consequently, abolishing the KR domain of the third extender module or adding a DH or DH and ER domains will interfere with the cyclization, leading either to a linear molecule or to a molecule cyclized at a different location than epothilones A, B, C, D, E, and F.

The fourth extender module of the epothilone PKS includes a KS, an AT that can bind either malonyl CoA or methylmalonyl CoA, a KR, and an ACP. In one embodiment, all or a portion of the fourth extender module coding sequence is utilized in conjunction with other PKS coding sequences to create a hybrid module. In this embodiment, the invention provides, for example, either replacing the malonyl CoA and methylmalonyl specific AT with a malonyl CoA, methylmalonyl CoA, ethylmalonyl CoA, or 2-hydroxymalonyl CoA specific AT; deleting the KR; and/or replacing the KR, including, optionally, to specify a different stereochemistry; and/or inserting a DH or a DH and ER. The resulting heterologous fourth extender module coding sequence is incorporated into a protein subunit of a recombinant PKS that synthesizes epothilone, an epothilone derivative, or another polyketide. Alternatively, the invention provides recombinant PKS enzymes for epothilones and epothilone derivatives in which the entire fourth extender module has been deleted or replaced by a module from a heterologous PKS.

In a preferred embodiment, the invention provides recombinant DNA compounds comprising the coding sequence for the fourth extender module of the epothilone PKS modified to encode an AT that binds methylmalonyl CoA and not malonyl CoA (or that binds malonyl CoA and not methylmalonyl CoA). In one embodiment, this change in specificity is accomplished by mutation of the coding sequence for the extender module 4 AT domain. Such mutation can be accomplished randomly using a mutagenizing agent, such as UV light, or by site-specific mutagenesis. In another embodiment, this change in specificity is accomplished by replacing all or a portion of the extender module 4 AT domain coding sequence with coding sequences for a heterologous AT domain. Thus, the invention provides recombinant DNA compounds and expression vectors and the corresponding recombinant PKS in which the hybrid fourth extender module with a methylmalonyl specific AT has been incorporated. The methylmalonyl specific AT coding sequence can originate, for example and without limitation, from coding sequences for the oleandolide PKS, DEBS, the narbonolide PKS, the rapamycin PKS, or any other PKS that comprises a methylmalonyl specific AT domain.

In accordance with the invention, the hybrid fourth extender module expressed from this coding sequence can be incorporated into the epothilone PKS (or the PKS for an epothilone derivative), typically as a derivative epoD gene product that comprises the modified fourth extender module as well as extender modules 3, 5, and 6, any one or more of which can optionally be in derivative form, of the epothilone PKS. The recombinant methylmalonyl specific epothilone fourth extender module coding sequences provided by the invention thus provide alternative methods for producing desired epothilone compounds in host cells. In particular, such compounds will be epothilones D, B, and F, with the production of epothilone B being dependent on whether a functional epoK gene is present, or derivatives thereof.

The invention also provides recombinant DNA compounds comprising the coding sequence for the fourth extender module of the epothilone PKS modified to encode an AT that binds malonyl CoA and not methylmalonyl CoA. The invention provides recombinant DNA compounds and vectors and the corresponding recombinant PKS in which this hybrid fourth extender module has been incorporated into a derivative epoD gene product. When incorporated into the epothilone PKS (or the PKS for an epothilone derivative), the resulting recombinant epothilone PKS produces epothilones C, A, and E, with production of epothilone A being dependent on whether a functional epoK gene is present.

In another embodiment, the present invention provides recombinant host cells for producing 12-desmethyl-12-ethyl-epothilone D. In this embodiment, the present invention provides a host cell that expresses a recombinant epothilone PKS derivative in which the AT domain of extender module 4 has been replaced by an ethylmalonyl CoA-specific extender module from, for example, the FK520 or niddamycin PKS enzymes. In one embodiment, the host cell is a recombinant host cell that expresses crotonyl CoA reductase encoded by a gene (a ccr gene) from a heterologous host cell or under the control of a heterologous promoter to enhance the production of ethylmalonyl CoA. In one embodiment, the host cell is a *Myxococcus* host cell that expresses a ccr gene isolated from a *Streptomyces* host cell. In another embodiment, the host cell has been modified to express or overexpress the *E. coli* atoA, D, and E genes that transport butyrate and convert it to butyryl CoA, which is converted to ethylmalonyl CoA.

In addition to the replacement of the endogenous AT coding sequence with a coding sequence for an AT specific for methylmalonyl Co A, one can also replace the KR domain coding sequences with coding sequences for another KR, a DH and KR (from, for example and without limitation, module 10 of the rapamycin PKS or modules 1 or 5 of the FK-520 PKS), or a DH, KR, and ER. If one replaces the KR for another KR or for a KR and a DH, and no changes are made in extender module 5 (or elsewhere in the PKS), then the recombinant epothilone PKS produces epothilones C and D, because the DH domain of extender module 5 mediates the formation of the C-12-C-13 double bond in epothilones C and D. If one replaces the KR with a KR, DH, and ER, and no changes are made in extender module 5 (or elsewhere in the PKS), then the recombinant epothilone PKS produces 12,13-dihydro-epothilones C and D. If one replaces the KR with an inactive KR or otherwise inactivates the KR, then the recombinant epothilone PKS produces 13-oxo-11,12-dehydro-epothilones C and D.

Thus, the present invention provides a recombinant epothilone PKS in which the KR domain of extender module 4 has been rendered inactive by mutation, deletion, or replacement with a non-functional KR domain from another PKS. This recombinant PKS produces primarily 13-oxo-11,12-dehydro epothilone B; the C-11-C-12 double bond observed in the compounds produced by this organism is believed to originate due to migration of the double bond formed in the nascent polyketide chain by the DH domain of extender module 5 prior to reduction by the ER domain of that module. The present invention also provides host cells that produce this novel polyketide. For example, *Myxococcus xanthus* strain K122-56 (this strain was deposited in compliance with the Budapest Treaty with the American Type Culture Collection, 10801 University Blvd. Manassas, Va. 20110-2209 USA on Nov. 21, 2000, and is available under accession No. PTA-2714) contains epothilone PKS genes in which the KR domain of module 4 has been rendered inactive by deletion and which produces 13-oxo epothilones A and B and dehydro derivatives thereof (primarily 13-oxo-11,12-dehydro epothilone B). The present invention also provides the novel epothilone derivatives produced by this strain.

The fifth extender module of the epothilone PKS includes a KS, an AT that binds malonyl CoA, a DH, an ER, a KR, and an ACP domain. In one embodiment, a DNA compound comprising a sequence that encodes the fifth extender module of the epothilone PKS is inserted into a DNA compound that comprises coding sequences for the epothilone PKS or a recombinant epothilone PKS that produces an epothilone derivative. In another embodiment, a portion of the fifth extender module coding sequence is utilized in conjunction with other PKS coding sequences to create a hybrid module coding sequence and the hybrid module encoded thereby. In this embodiment, the invention provides, for example, either replacing the malonyl CoA specific AT with a methylmalonyl CoA, ethylmalonyl CoA, or 2-hydroxymalonyl CoA specific AT; deleting any one, two, or all three of the ER, DH, and KR; and/or replacing any one, two, or all three of the ER, DH, and KR with either a KR, a DH and KR, or a KR, DH, and ER, including, optionally, to specify a different stereochemistry. The resulting hybrid fifth extender module coding sequence can be utilized in conjunction with a coding sequence for a PKS that synthesizes epothilone, an epothilone derivative, or another polyketide. Alternatively, the fifth extender module of the epothilone PKS can be deleted or replaced in its entirety by a module of a heterologous PKS to produce a protein that in combination with the other proteins of the epothilone PKS or derivatives thereof constitutes a PKS that produces an epothilone derivative.

Illustrative recombinant PKS genes of the invention include recombinant epoD gene derivatives in which the AT domain encoding sequences for the fifth extender module of the epothilone PKS have been altered or replaced to change the AT domain encoded thereby from a malonyl specific AT to a methylmalonyl specific AT. Such methylmalonyl specific AT domain encoding nucleic acids can be isolated, for example and without limitation, from the PKS genes encoding DEBS, the narbonolide PKS, the rapamycin PKS, and the FK-520 PKS. When such recombinant epoD gene derivatives are coexpressed with the epoA, epoB, epoC, epoE, epoF, and/or epoK genes (or derivatives thereof), the PKS composed thereof produces the 10-methyl epothilones or derivatives thereof. Another recombinant epoD gene derivative provided by the invention includes not only this altered module 5 coding sequence but also module 4 coding sequences that encode an AT domain that binds only methylmalonyl CoA. When incorporated into a PKS with the epoA, epoB, epoC, epoE, epoF, and/or epoK genes, the recombinant epoD gene derivative product leads to the production of 10-methyl epothilone B and/or D derivatives.

Other illustrative recombinant epoD gene derivatives of the invention include those in which one or more of the ER, DH, and KR domain encoding sequences for the fifth extender module of the epothilone PKS have been either replaced or mutated to provide: (i) no functional ER, DH, or KR domains; (ii) only a functional KR domain; (iii) only functional KR and DH domains; or (iv) functional ER, DH, or KR domains from another PKS. The discovery that the DH domain of extender module 5 is responsible for the formation of the C-12-C-13 double bond in epothilones C and D provides a novel method of the invention for making epothilones and epothilone derivatives in any organism, including *Sorangium cellulosum* and recombinant host cells, that contain the epothilone PKS genes. Moreover, it has now been discovered that the DH domain of extender module 6 can also act on the beta-carbonyl of the nascent polyketide bound to the preceding module, which can be exploited in accordance with the methods of the present invention to make novel epothilone derivatives.

Thus, when all three extender module 5 KR, DH, and ER domains are deleted or otherwise inactivated, the recombinant epothilone PKS produces the 13-hydroxy-11-oxo analogs of epothilones A and B. When the DH and ER domains are deleted or otherwise inactivated, the recombinant epothilone PKS produces the 13-hydroxy-10,11-dehydro-epothilones, primarily 13-hydroxy-10,11-dehydro-epothilone D. The present invention also provides host cells that produce this novel polyketide. For example, *Myxococcus xanthus* strain K122-148 (this strain was deposited in accordance with the terms of the Budapest Treaty with the American Type Culture Collection, 10801 University Blvd. Manassas, Va. 20110-2209 USA on Nov. 21, 2000, and is available under accession No. PTA-2711) contains epothilone PKS genes in which the DH, KR, and ER domains of extender module 5 have been replaced with only a KR domain and which produces 13-hydroxy-10,11-dehydro-epothilone D. The present invention also provides the novel epothilone derivatives produced by this strain. When only the ER domain is deleted or otherwise inactivated, the recombinant epothilone PKS produces the 10,11-dehydro analogs of epothilones C and D, primarily 10,11-dehydro epothilone. Thus, in one aspect, the present invention provides a recombinant epothilone PKS in which the ER domain of extender module 5 has been deleted or rendered inactive by mutation and which produces 10,11-dehydro-epothilone D. In another embodiment, the present invention provides a *Sorangium cellulosum* host cell that produces 10,11-dehydro-epothilone D due to a mutation in the coding sequence for the ER domain of extender module 5 of the epothilone PKS.

These recombinant epoD gene derivatives of the invention are coexpressed with the epoA, epoB, epoC, epoE, and epoF genes or with recombinant epo genes containing other alterations (and can themselves contain additional alterations) to produce a PKS that makes the corresponding epothilone derivatives. For example, one recombinant epoD gene derivative provided by the invention also includes module 4 coding sequences that encode an AT domain that binds only methylmalonyl CoA. As noted above, functionally similar epoD genes for producing the epothilone C-11 derivatives can also be made by inactivation of one, two, or all three of the ER, DH, and KR domains of the epothilone fifth extender module. Another mode for altering such domains in any module is by replacement with the complete set of desired domains taken from another module of the same or a heterologous PKS coding sequence. In this manner, the natural architecture of the PKS is conserved. Also, when present, KR and DH or KR, DH, and ER domains that function together in a native PKS are preferably used in the recombinant PKS. Illustrative replacement domains for the substitutions described above include, for example and without limitation, the inactive KR domain from the rapamycin PKS extender module 3, the KR domain from the rapamycin PKS extender module 5, and the KR and DH domains from the rapamycin PKS extender module 4. Other such inactive KR, active KR, and active KR and DH domain encoding nucleic acids can be isolated from, for example and without limitation, the PKS genes encoding DEBS, the narbonolide PKS, and the FK-520 PKS. Each of the resulting PKS enzymes produces a polyketide compound that can be further derivatized in vitro by standard chemical methodology to yield semi-synthetic epothilone derivatives of the invention.

The sixth extender module of the epothilone PKS includes a KS, an AT that binds methylmalonyl CoA, a DH, an ER, a KR, and an ACP. In one embodiment, a portion of the sixth extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting any one, two, or all three of the ER, DH, and KR; and/or replacing any one, two, or all three of the ER, DH, and KR with either a KR, a DH and KR, or a KR, DH, and ER, including, optionally, to specify a different stereochemistry. The resulting heterologous sixth extender module coding sequence can be utilized in conjunction with a coding sequence for a protein subunit of a PKS that makes epothilone, an epothilone derivative, or another polyketide. Alternatively, the sixth extender module of the epothilone PKS can be deleted or replaced in its entirety by a module from a heterologous PKS to produce a PKS for an epothilone derivative.

Illustrative recombinant PKS genes of the invention include those in which the AT domain encoding sequences for the sixth extender module of the epothilone PKS have been altered or replaced to change the AT domain encoded thereby from a methylmalonyl specific AT to a malonyl specific AT. Such malonyl specific AT domain encoding nucleic acids can be isolated from, for example and without limitation, the PKS genes encoding the narbonolide PKS, the rapamycin PKS, and the FK-520 PKS. When a recombinant epoD gene of the invention encoding such a hybrid module 6 is coexpressed with the other epothilone PKS genes, the recombinant PKS makes the 8-desmethyl epothilone derivatives. This recombinant epoD gene derivative can also be coexpressed with recombinant epo gene derivatives containing other alterations or can itself be further altered to produce a PKS that makes the corresponding 8-desmethyl epothilone derivatives. For example, one recombinant epoD gene provided by the invention also includes module 4 coding sequences that encode an AT domain that binds only methylmalonyl CoA. When incorporated into a PKS with the epoA, epoB, epoC, epoE, and epoF genes, the recombinant epoD gene product leads to the production of the 8-desmethyl derivatives of epothilones B (if a functional epoK gene is present) and D.

Other illustrative recombinant epoD gene derivatives of the invention include those in which the ER, DH, and KR domain encoding sequences for the sixth extender module of the epothilone PKS have been replaced with those that encode (i) a KR and DH domain; (ii) a KR domain; and (iii) an inactive KR domain. These recombinant epoD gene derivatives of the invention, when coexpressed with the other epothilone PKS genes make the corresponding (i) C-9 alkene, (ii) C-9 hydroxy (both epimers, only one of which may be processed by downstream modules, unless additional KS and/or ACP replacements are made in the next module), and (iii) C-9 keto (C-9-oxo) epothilone derivatives. Functionally equivalent sixth extender modules can also be made by inactivation of one, two, or all three of the ER, DH, and KR domains of the epothilone sixth extender module. For example, the present invention provides *Myxococcus xanthus* strain K39-164 (this strain was deposited in accordance with the terms of the Budapest Treaty with the American Type Culture Collection, 10801 University Blvd. Manassas, Va. 20110-2209 USA on Nov. 21, 2000, and is available under accession No. PTA-2711), which contains epothilone PKS genes in which the KR domain of extender module 6 has been rendered inactive by mutation and which produces 9-keto-epothilone D. The present invention also provides the novel epothilone derivative produced by this strain.

Thus, the recombinant epoD gene derivatives can also be coexpressed with other recombinant epo gene derivatives containing other alterations or can themselves be further altered to produce a PKS that makes the corresponding C-9 epothilone derivatives. For example, one recombinant epoD gene derivative provided by the invention also includes module 4 coding sequences that encode an AT domain that binds only methylmalonyl CoA. When incorporated into a PKS with the epoA, epoB, epoC, epoE, and epoF genes, the recombinant epoD gene product leads to the production of the C-9 derivatives of epothilones B and D, depending on whether a functional epoK gene is present.

Illustrative replacement domains for the substitutions described above include but are not limited to the inactive KR domain from the rapamycin PKS module 3 to form the ketone, the KR domain from the rapamycin PKS module 5 to form the alcohol, and the KR and DH domains from the rapamycin PKS module 4 to form the alkene. Other such inactive KR, active KR, and active KR and DH domain encoding nucleic acids can be isolated from for example and without limitation the PKS genes encoding DEBS, the narbonolide PKS, and the FK-520 PKS. Each of the resulting PKSs produces a polyketide compound that comprises a functional group at the C-9 position that can be further derivatized in vitro by standard chemical methodology to yield semi-synthetic epothilone derivatives of the invention.

The seventh extender module of the epothilone PKS includes a KS, an AT specific for methylmalonyl CoA, a KR, and an ACP. The seventh extender module of the epothilone PKS is contained in the gene product of the epoE gene, which also contains the eighth extender module. In one embodiment, a DNA compound comprising a sequence that encodes the seventh extender module of the epothilone PKS is expressed to form a protein that, together with other proteins, constitutes the epothilone PKS or a PKS that produces an epothilone derivative. In these and related embodiments, the seventh and eighth extender modules of the epothilone PKS or a derivative thereof are typically expressed as a single protein and coexpressed with the epoA, epoB, epoC, epoD, and epoF genes or derivatives thereof to constitute the PKS. In another embodiment, a portion or all of the seventh extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting the KR; replacing the KR with a KR that specifies a different stereochemistry; and/or inserting a DH or a DH and an ER. The resulting heterologous seventh extender module coding sequence is utilized, optionally in conjunction with other coding sequences, to express a protein that together with other proteins constitutes a PKS that synthesizes epothilone, an epothilone derivative, or another polyketide. Alternatively, the coding sequences for the seventh extender module in the epoE gene can be deleted or replaced by those for a heterologous module to prepare a recombinant epoE gene derivative that, together with the epoA, epoB, epoC, epoD, and epoF genes, can be expressed to make a PKS for an epothilone derivative.

Illustrative recombinant epoE gene derivatives of the invention include those in which the AT domain encoding sequences for the seventh extender module of the epothilone PKS have been altered or replaced to change the AT domain encoded thereby from a methylmalonyl specific AT to a malonyl specific AT. Such malonyl specific AT domain encoding nucleic acids can be isolated from for example and without limitation the PKS genes encoding the narbonolide PKS, the rapamycin PKS, and the FK-520 PKS. When coexpressed with the other epothilone PKS genes, epoA, epoB, epoC, epoD, and epoF, or derivatives thereof, a PKS for an epothilone derivative with a C-6 hydrogen, instead of a C-6 methyl, is produced. Thus, if the genes contain no other alterations, the compounds produced are the 6-desmethyl epothilones.

The eighth extender module of the epothilone PKS includes a KS, an AT specific for methylmalonyl CoA, inactive KR and DH domains, a methyltransferase (MT) domain, and an ACP. In one embodiment, a DNA compound comprising a sequence that encodes the eighth extender module of the epothilone PKS is coexpressed with the other proteins constituting the epothilone PKS or a PKS that produces an epothilone derivative. In another embodiment, a portion or all of the eighth extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting the inactive KR and/or the inactive DH; replacing the inactive KR and/or DH with an active KR and/or DH; and/or inserting an ER. The resulting heterologous eighth extender module coding sequence is expressed as a protein that is utilized in conjunction with the other proteins that constitute a PKS that synthesizes epothilone, an epothilone derivative, or another polyketide. Alternatively, the coding sequences for the eighth extender module in the epoE gene can be deleted or replaced by those for a heterologous module to prepare a recombinant epoE gene that, together with the epoA, epoB, epoC, epoD, and epoF genes, can be expressed to make a PKS for an epothilone derivative.

The eighth extender module of the epothilone PKS also comprises a methylation or methyltransferase (MT) domain with an activity that methylates the epothilone precursor. This function can be deleted to produce a recombinant epoD gene derivative of the invention, which can be expressed with the other epothilone PKS genes or derivatives thereof that makes an epothilone derivative that lacks one or both methyl groups, depending on whether the AT domain of the eighth extender module has been changed to a malonyl specific AT domain, at the corresponding C-4 position of the epothilone molecule.

The ninth extender module of the epothilone PKS includes a KS, an AT specific for malonyl CoA, a KR, an inactive DH, and an ACP. The ninth extender module of the epothilone PKS is expressed as a protein, the product of the epoF gene, which also contains the TE domain of the epothilone PKS. In one embodiment, a DNA compound comprising a sequence that encodes the ninth extender module of the epothilone PKS is expressed as a protein together with other proteins to constitute an epothilone PKS or a PKS that produces an epothilone derivative. In these embodiments, the ninth extender module is typically expressed as a protein that also contains the TE domain of either the epothilone PKS or a heterologous PKS. In another embodiment, a portion or all of the ninth extender module coding sequence is utilized in conjunction with other PKS coding sequences to create a hybrid module. In this embodiment, the invention provides, for example, either replacing the malonyl CoA specific AT with a methylmalonyl CoA, ethylmalonyl CoA, or 2-hydroxy malonyl CoA specific AT; deleting the KR; replacing the KR with a KR that specifies a different stereochemistry; and/or inserting a DH or a DH and an ER. For example, replacement of the AT domain of extender module 9 with an AT domain specific for methylmalonyl CoA results in a recombinant epothilone PKS that produces 2-methyl-epothilones A, B, C, and D in the recombinant *Myxococcus* host cells of the invention. The resulting heterologous ninth extender module coding sequence is coexpressed with the other proteins constituting a PKS that synthesizes epothilone, an epothilone derivative, or another polyketide. Alternatively, the present invention provides a PKS for an epothilone or epothilone derivative in which the ninth extender module has been replaced by a module from a heterologous PKS or has been deleted in its entirety. In the latter embodiment, the TE domain is expressed as a discrete protein or fused to the eighth extender module.

In another embodiment, the present invention provides a host cell of the invention that comprises a heterologous PKS gene cluster (a PKS gene cluster that is not present in an unmodified, naturally occurring host cell of the same type) as well as a gene that encodes a thioesterase type II protein ("TE II"). In a preferred embodiment, the TE II gene is heterologous to the PKS gene cluster—the TE II gene is not derived from the same gene cluster as the PKS. As one example, the recombinant host cells of the invention in one embodiment comprise the genes that code for the expression of the epothilone PKS or an epothilone PKS derivative. In accordance with this aspect of the invention, the host cells are modified to contain a TE II gene isolated from a PKS gene cluster other than the epothilone PKS gene cluster. Illustrative embodiments include, for example, the TE II gene from the picromycin PKS gene cluster of *Streptomyces venezuelae* and the TE II gene from the tmbA PKS gene cluster of *Sorangium cellulosum* (this PKS gene cluster is described in U.S. Pat. No. 6,090,601; U.S. patent application Ser. No. 144,085, filed 31 Aug. 1998; and provisional U.S. patent application Ser. No. 60/271,245, filed 15 Feb. 2001, each of which is incorporated herein by reference).

Illustrative examples of recombinant epothilone derivative PKS genes of the invention, which are identified by listing the altered specificities of the hybrid modules (the other modules having the same specificity as the epothilone PKS), include:

(a) module 4 with methylmalonyl specific AT (mmAT) and a KR and module 2 with a malonyl specific AT (mAT) and a KR;
(b) module 4 with mmAT and module 3 with mmAT;
(c) module 4 with mmAT and module 5 with mmAT;
(d) module 4 with mmAT and module 5 with mmAT and only a DH and KR;
(e) module 4 with mmAT and module 5 with mmAT and only a KR;
(f) module 4 with mmAT and module 5 with mmAT and only an inactive KR;
(g) module 4 with mmAT and module 6 with mAT;
(h) module 4 with mmAT and module 6 with mAT and only a DH and KR;
(i) module 4 with mmAT and module 6 with mAT and only a KR;
(j) module 4 with mmAT and module 6 with mAT and only an inactive KR;
(k) module 4 with mmAT and module 7 with mAT;
(l) hybrids (d) through (f), except that module 5 has an mAT;
(m) hybrids (h) through (j) except that module 6 has an mmAT; and
(n) hybrids (a) through (m) except that module 4 has an mAT.

The above list is illustrative only and should not be construed as limiting the invention, which includes other recombinant epothilone PKS genes and enzymes with not only two hybrid modules other than those shown but also with three or more hybrid modules.

The host cells of the invention can be grown and fermented under conditions known in the art for other purposes to produce the compounds of the invention. The present invention also provides novel methods for fermenting the host cells of the invention. The compounds of the invention can be isolated from the fermentation broths of these cultured cells and purified by methods such as those in Example 3, below.

The present invention provides a number of methods relating to the fermentation of *Myxococcus* strains for production of polyketides and other products. Prior to the present invention, fermentation of *Myxococcus* has not been conducted for production purposes for any polyketides other than TA and saframycin, which are produced naturally by certain *Myxococcus* strains. Thus, in one aspect, the present invention enables the use of *Myxococcus* as a production host for the production by fermentation of useful bioactive compounds, including, but not limited to, polyketides, non-ribosomal peptides, epothilones, lipases, proteases, other proteins, lipids, glycolipids, rhamnolipids, and polyhydroxyalkanoates.

Among the methods provided by the invention are methods for preparing and storing cell banks and methods for adapting a *Myxococcus* strain to a fermentation medium. These methods are important, because prior to the present invention, frozen cell banks of *Myxococcus* strains adapted for production in oil-based fermentation medium have not been made, and in the absence of adaptation, *Myxococcus* strains frequently die, especially in oil-based fermentation medium.

The present invention also provides a fermentation method for growing *Myxococcus* and a fermentation medium useful in the method. Surprisingly, *Myxococcus xanthus* and other *Myxococcus* strains cannot utilize carbohydrates, glycerol, alcohol, or TCA cycle intermediates as a carbon source. Prior to the present invention, *M. xanthus* fermentations were carried out in protein based media. However, $NH_4$ builds up to levels toxic to growth in protein based media and so limits fermentation. In accordance with the present invention, *Myxococcus* strains are fermented in a medium that contains oil and/or fatty acids as a carbon source.

Illustrative oils and fatty acids useful in the method include, but are not limited to, methyl oleate; oils derived from coconut, lard, rapeseed, sesame, soy, and sunflower; salad oil; self emulsifying oils such as Agrimul CoS2, R5O5, and R5O3; glycerol oleate, including glycerol mono oleate and glycerol tri oleate; odd chain esters such as methyl heptadecanoate, methyl nonadecanoate, and methyl pelargonate; ester chains such as propyl oleate and ethyl oleate; vegetable methyl oleate; methyl stearate; methyl linoleate; oleic acid; and phosphatidyl choline, whether pure or derived from soy or egg yolk. Thus, any plant or grain derived oil, such as sunflower or soy oil, any animal derived oil, such as lard oil, free and esterified fatty acids of any chain length both saturated or unsaturated, natural and synthetic fatty acid mixtures such as phosphatidyl choline or methyl pelargonate, respectively, and industrial fermentation oils, such as Cognis Corporation's Agrimul series, can be employed in the method. In a preferred embodiment, the fermentation medium utilizes methyl oleate as the carbon source. Generally, oils that are liquid at room temperature are more preferred than solid oils, primarily primarily due to the ease of dispersion. Other important components of the fermentation medium include trace metals such as Fe and Cu, which improve growth and production in complex and defined media and in batch and fed batch processes. A medium containing methyl oleate and trace metals is preferred for the production of epothilones.

In one embodiment, the present invention provides a fermentation medium for host cells of the invention that contains reduced or no amounts of animal-derived materials. Due to the potential for contamination by infectious agents, such as viruses and prions, the use of animal by-products in fermentation processes for the production of compounds to be administered to humans or animals, one may prefer to use a fermentation medium that contains reduced or no amounts of animal-derived materials. Such media is provided for use in the methods of the invention. The oils or fatty acids contained in the fermentation medium can be derived from a non-animal source, such as a plant. For example, vegetable-derived methyl oleate can be obtained commercially. Moreover, one can replace an animal-derived material with an equivalent but non-identical material derived from a non-animal source. For example, casitone, which is a pancreatic digest of casein, a milk protein, can be replaced with a hydrolysate of a protein from a non-animal source, including but not limited to a plant, such as a vegetable-derived protein hydrolysate.

Generally, fed-batch processes are preferred for fermentation. Feeds force the cells to use nutrients efficiently (for example, the cells metabolize carbon down to $CO_2$ and $H_2O$ instead of generating toxic organic acids). High nutrient levels can repress secondary metabolism, and if the fermentation feeds nutrients at rate below the threshold of inhibition, production can be higher.

The fermentation methods of the invention also include methods related specifically to the production of epothilones and fermentation media useful in those methods. As one example, propionate and acetate can be used to influence the epothilone D:C (or B:A) ratio and the titers of epothilones obtained. While this effect is minimal in the preferred methyl oleate/trace metals fermentation medium, the effect can be quite significant effect in other media, such as CTS medium. Increasing amounts of acetate in the fermentation media can increase *Myxococcus* growth and epothilone production. Acetate alone increases epothilone C (or epothilone A) titers dramatically, and reduces epothilone D (or epothilone A) titers. Propionate alone does not increase epothilone titers and at high concentrations can reduce titers. However, propionate and acetate together can shifts the production from epothilone C (or epothilone A) to epothilone D (or epothilone B). One preferred medium for the production of epothilone D contains casitone, 10 mM acetate, and 30 mM propionate. Media containing odd chain fatty acids can reduce production of epothilone C in fermentations of *Myxococcus xanthus* cells that produce epothilones C and D. Trace metals can also enhance epothilone D production and increase epothilone D:C ratios in the presence of acetate and without any oil in the fermentation media.

The present invention also provides methods for purifying epothilones from fermentation media and for preparing crystalline forms of epothilone. In general, the purification method involves capture of the epothilone onto XAD resin during fermentation, elution from the resin, solid phase extraction, chromatography, and crystallization. The method is described in detail in Example 3, and while the method is preferred and exemplified for epothilone D, the method can be used to prepare crystalline epothilones generally, including but not limited to other naturally occurring epothilones, and the epothilone analogs produced by the host cells of the invention.

Thus, in another embodiment, the present invention provides novel epothilone derivative compounds in isolated and purified forms useful in agriculture, veterinary practice, and medicine. In one embodiment, the compounds are useful as fungicides. In another embodiment, the compounds are useful in cancer chemotherapy. In another embodiment, the compounds are useful for the prevention of undesired cell growth, including but not limited to the treatement of hyperproliferative diseases such as inflammation, autoimmune disease, and psoriasis, and to the prevention of cell growth in stents. In a preferred embodiment, the compound is an epothilone derivative that is at least as potent against tumor cells as epothilone B or D. In another embodiment, the compounds are useful as immunosuppressants. In another embodiment, the compounds are useful in the manufacture of another compound. In a preferred embodiment, the compounds are formulated in a mixture or solution for administration to a human or animal.

The novel epothilone analogs of the present invention, as well as the epothilones produced by the host cells of the invention, can be derivatized and formulated as described in PCT patent publication Nos. 93/10121, 97/19086, 98/08849, 98/22461, 98/25929, 99/01124, 99/02514, 99/07692, 99/27890, 99/39694, 99/40047, 99/42602, 99/43320, 99/43653, 99/54318, 99/54319, 99/54330, 99/65913, 99/67252, 99/67253, and 00/00485, and U.S. Pat. No. 5,969, 145, each of which is incorporated herein by reference.

Compounds of the invention include the 14-methyl epothilone derivatives (made by utilization of the hybrid module 3 of the invention that has an AT that binds methylmalonyl CoA instead of malonyl CoA); the 8,9-dehydro epothilone derivatives (made by utilization of the hybrid module 6 of the invention that has a DH and KR instead of an ER, DH, and KR); the 10-methyl epothilone derivatives (made by utilization of the hybrid module 5 of the invention that has an AT that binds methylmalonyl CoA instead of malonyl CoA); the 9-hydroxy epothilone derivatives (made by utilization of the hybrid module 6 of the invention that has a KR instead of an ER, DH, and KR); the 8-desmethyl-14-methyl epothilone derivatives (made by utilization of the hybrid module 3 of the invention that has an AT that binds methylmalonyl CoA instead of malonyl CoA and a hybrid module 6 that binds malonyl CoA instead of methylmalonyl CoA); the 8-desmethyl-8,9-dehydro epothilone derivatives (made by utilization of the hybrid module 6 of the invention that has a DH and KR instead of an ER, DH, and KR and an AT that specifies malonyl CoA instead of methylmalonyl CoA); and 9-oxo-epothilone D. Other preferred novel epothilones of the invention include those described in Example 11 and below.

In one aspect of the present invention, compounds of the following formula

I

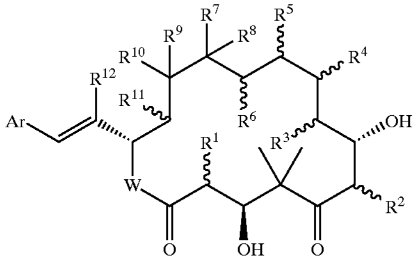

are provided wherein:

$R^1$, $R^2$, $R^3$, $R^5$, $R^{11}$, and $R^{12}$ are each independently hydrogen, methyl or ethyl;

$R^4$, $R^6$ and $R^9$ are each independently hydrogen, hydroxyl, or oxo; alternatively $R^5$ and $R^6$ together form a carbon carbon double bond;

$R^7$ is hydrogen, methyl, or ethyl;

$R^8$ and $R^{10}$ are both hydrogen or together form a carbon carbon double bond or an epoxide;

Ar is aryl; and,

W is O or $NR^{13}$ where $R^{13}$ is hydrogen, $C_1$–$C_{10}$ aliphatic, aryl or alkylaryl. In another embodiment, compounds of formula I are provided wherein $R^1$, $R^2$, $R^3$, $R^4$, $R^5$, $R^6$, $R^7$, $R^8$, $R^9$, $R^{10}$, $R^{11}$, $R^{12}$, $R^{13}$, Ar and W are as described previously provided that at least one of $R^1$, $R^4$, $R^5$, $R^6$, $R^9$ and $R^{11}$ is not hydrogen.

In another embodiment, compounds of formula I are provided wherein $R^1$, $R^2$, $R^3$, and $R^{11}$ are each independently hydrogen or methyl;

$R^4$ and $R^9$ are each independently hydrogen, hydroxyl, or oxo;

$R^5$ and $R^6$ are both hydrogen or together form a carbon carbon double bond;

$R^7$ and $R^{12}$ are both methyl;

$R^8$ and $R^{10}$ are both hydrogen or together form a carbon carbon double bond;

Ar is heteroaryl; and,

W is O or $NR^{13}$ where $R^{13}$ is hydrogen or $C_1$–$C_5$ alkyl, provided that at least one of $R^1$, $R^4$, $R^5$, $R^6$, $R^9$ and $R^{11}$ is not hydrogen.

In another aspect of the present invention, compounds of the formula

II

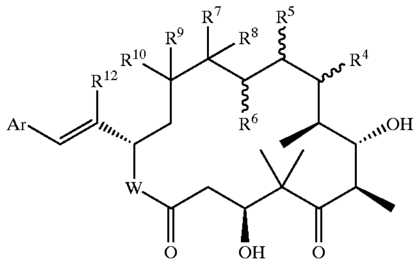

$R^4$, $R^6$ and $R^9$ are each independently hydrogen, hydroxyl, or oxo;

$R^5$, $R^{11}$, $R^{12}$ are each independently hydrogen, methyl or ethyl; alternatively, $R^5$ and $R^6$ together form a carbon carbon double bond;

$R^7$ is hydrogen, methyl, or ethyl;

$R^8$ and $R^{10}$ are both hydrogen or together form a carbon carbon double bond or an epoxide;

Ar is aryl; and,

W is O or $NR^{13}$ where $R^{13}$ is hydrogen or $C_1$–$C_5$ alkyl. In another embodiment, compounds of formula II are provided wherein $R^4$, $R^5$, $R^6$, $R^7$, $R^8$, $R^9$, $R^{10}$, $R^{12}$, $R^{13}$, Ar and W are as described previously provided that at least one of $R^4$, $R^5$, $R^6$ and $R^9$ is not hydrogen.

In another embodiment, compounds of formula II are provided wherein $R^4$ and $R^9$ are each independently hydrogen, hydroxyl, or oxo;

$R^5$ and $R^6$ are each hydrogen or together form a carbon carbon double bond;

$R^7$ and $R^{12}$ are both methyl;

$R^8$ and $R^{10}$ are both hydrogen or together form a carbon carbon double bond;

Ar is 2-methyl-1,3-thiazolinyl, 2-methyl-1,3-oxazolinyl, 2-hydroxymethyl-1,3-thiazolinyl, or 2-hydroxymethyl-1,3-oxazolinyl; and, W is O or NH provided that at least one of $R^4$, $R^5$, $R^6$, and $R^9$ is not hydrogen.

In another aspect of the present invention, compounds of the formula

III

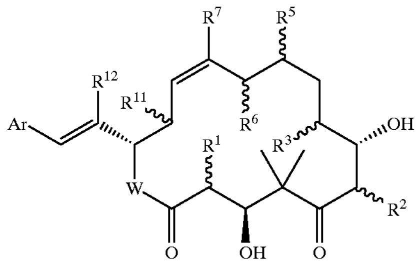

are provided wherein $R^1$, $R^2$, $R^3$, $R^5$, $R^{11}$, $R^{12}$ are each independently hydrogen, methyl or ethyl;

$R^6$ is hydrogen; alternatively $R^5$ and $R^6$ together form a carbon carbon double bond;

$R^7$ is hydrogen, methyl, or ethyl;

Ar is aryl; and,

W is O or $NR^{13}$ where $R^{13}$ is hydrogen or $C_1$–$C_5$ alkyl. In another embodiment, compounds of formula III are provided wherein $R^1$, $R^2$, $R^3$, $R^5$, $R^6$, $R^7$, $R^{11}$, $R^{12}$, $R^{13}$, Ar and W are as described previously provided that at least one of $R^1$, $R^5$, $R^6$, and $R^{11}$ is not hydrogen.

In another embodiment, compounds of formula III are provided wherein $R^1$, $R^2$, $R^3$, $R^{11}$ are each independently hydrogen, methyl or ethyl;

$R^5$ and $R^6$ are both hydrogen or together form a carbon carbon double bond;

$R^7$ and $R^{12}$ are both methyl;

Ar is 2-methyl-1,3-thiazolinyl, 2-methyl-1,3-oxazolinyl, 2-hydroxymethyl-1,3-thiazolinyl, or 2-hydroxymethyl-1,3-oxazolinyl; and, W is O or NH provided that at least one of $R^1$, $R^5$, $R^6$, and $R^{11}$ is not hydrogen.

In another aspect of the present invention, compounds of the formula

IV

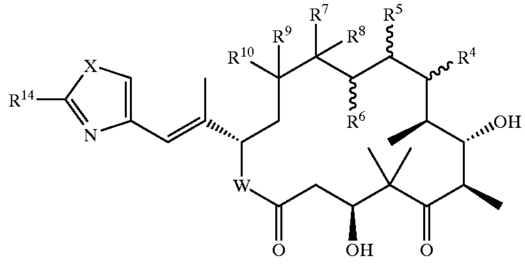

are provided wherein $R^4$ is hydrogen or oxo;

$R^5$ and $R^6$ are both hydrogen or together form a carbon carbon double bond;

$R^7$ is hydrogen or methyl;

$R^9$ is hydrogen or hydroxyl;

$R^8$ and $R^{10}$ are both hydrogen or together form a carbon carbon double bond or an epoxide;

W is O or NH;

X is O or S; and $R^{14}$ is methyl or hydroxymethyl.

In another aspect of the present invention, compounds are of the formula

IV

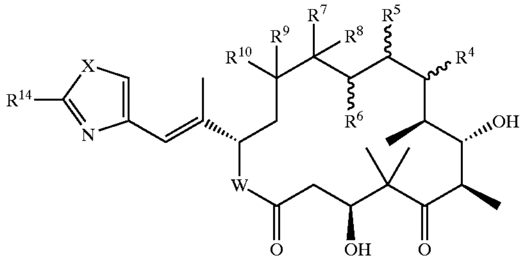

$R^4$ is hydrogen or oxo;

$R^5$ and $R^7$ are each independently hydrogen or methyl;

$R^6$ is hydrogen;

$R^8$ and $R^{10}$ are both hydrogen or together form a carbon carbon double bond or an epoxide; alternatively, $R^6$ and $R^8$ together form a double bond;

$R^9$ is hydrogen, hydroxyl or oxo;

W is O or NH;

X is O or S; and $R^{14}$ is methyl or hydroxymethyl.

In another aspect of the present invention, the following compounds are provided:

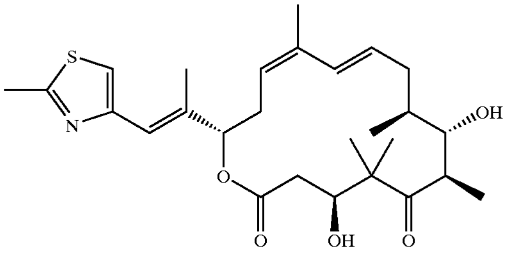

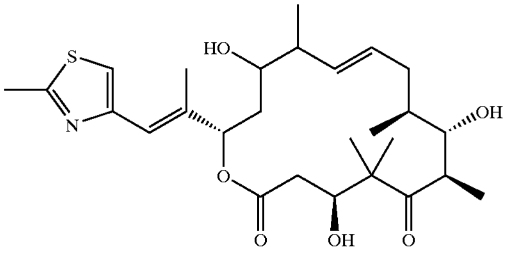

-continued

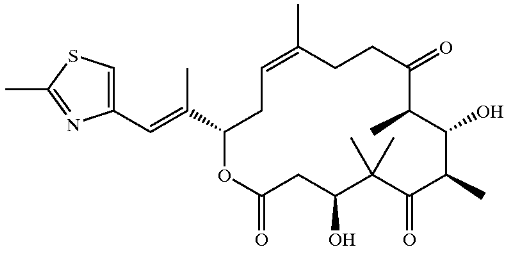

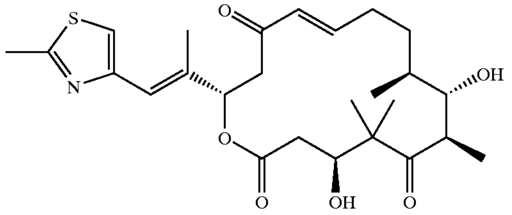

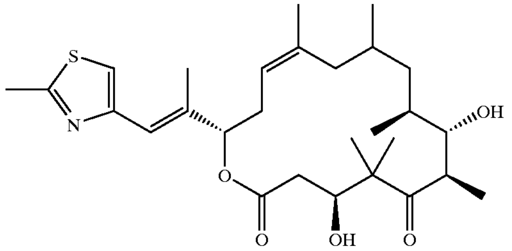

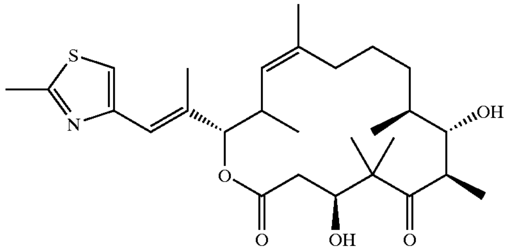

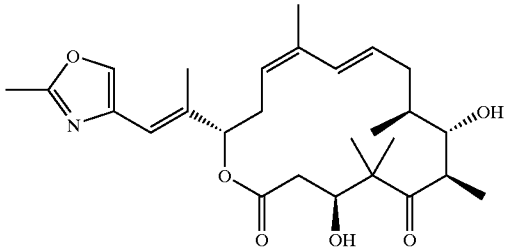

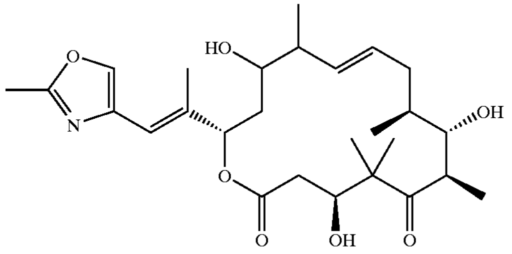

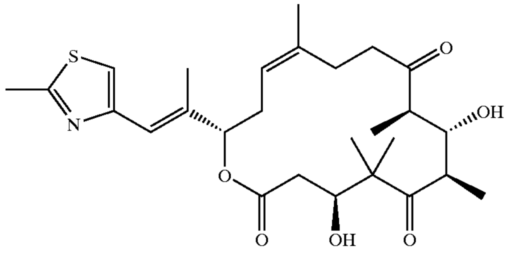

-continued

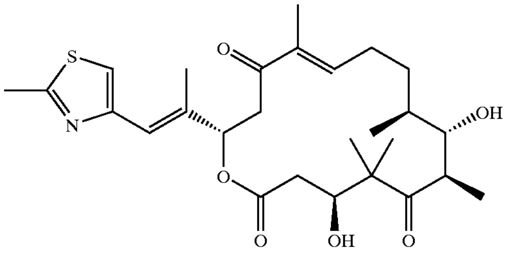

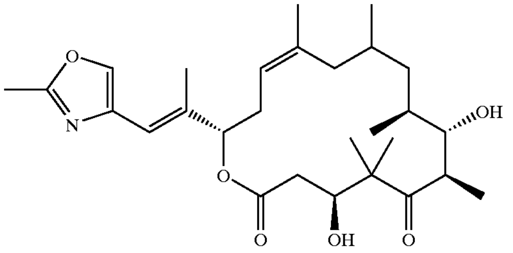

and

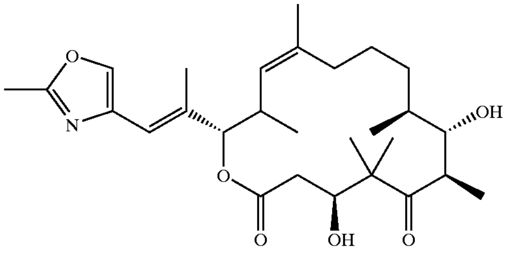

The compounds of the present invention are cytotoxic agents and may be used in any suitable manner including but not limited to as anti-cancer agents. An illustrative assay for assessing the degree of cytotoxicy and tubulin polyermization is described in Example 12.

The compounds of the present invention can be made using a number of methods. In one aspect of the present invention, the compounds are produced by recombinant host cells that express an epothilone PKS. In one embodiment, compounds of the formula

V

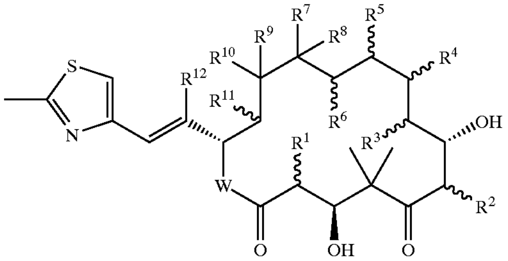

(where $R^1$ through $R^{12}$ are as previously described for formula I) are made by altering the AT specificity at one or more modules and/or altering the enzymatic domains at one or more modules. Example 11 describes the types of modifications and specific compounds that may be made using this method.

In another embodiment of the present invention, oxazole counterparts of formula V can be made by modulating the fermentation conditions of the host cells that would normally make compounds of formula V. The thiazole moiety of compounds of formula V is derived from the binding of cysteine at the NRPS. Epothilones $H_1$ and $H_2$, which are the oxazole counterparts to epothilones C and D, is made by host cells in trace quantities and is believed to occur from the occasional binding of serine instead of cysteine at the epothilone NRPS.

The present method takes advantage of the apparent competition of serine with cysteine at the NRPS binding site of the epothilone PKS and uses fermentation conditions to favor the binding of serine instead of cysteine at the epothilone NRPS. It has been found that by growing host cells in medium that is supplemented with serine (e.g. 50 fold increase above basal levels) results in the production of mostly oxazole-containing compounds instead of the thiazole-containing compounds that are normally produced. Consequently, recombinant host cells that are engineered to make a particular epothilone compound or compounds of formula V can be grown in medium that is supplemented with serine so that these same cells now favor the production of oxazole counterparts, the compounds of formula VI:

VI

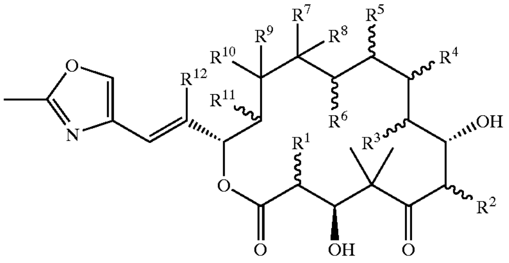

In other words, the present method is a simple and elegant way of obtaining two compounds, one corresponding to formula V and its counterpart corresponding to formula VI for the price of one. The serine supplementation method for making oxazole-containing compounds is described in greater detail in Example 13. This example describes the conditions that were used to decrease the levels of epothilones D and C that is normally produced by strain K111-40-1 to favor the production of epothilones $H_2$ and $H_1$, the oxazole counterparts to epothilones D and C respectively. Other recombinant constructs that make other compounds of formula V of the invention can be grown using similar conditions to make compounds of formula VI.

In another aspect of the present invention, compounds are produced using a method referred to as chemobiosynthesis. This method uses an epothilone PKS that has been altered in such a way so that the PKS accepts and binds a synthetic precursor at a designated site. The synthetic precursor is then processed by the PKS in the normal manner from that point forward.

An illustrative example of the types of alteration required for chemobiosynthesis is described in Example 9 which describes the construction of a KS2 knockout version of a *M. xanthus* strain that normally produces epothilones A, B, C, and D as major products. A KS2 knockout refers to an inactivation of the KS domain of extender module 2 so that the resulting PKS is unable to load and process the product of the previous modules, the loading domain and the NRPS (which is considered extender module 1). Consequently, the PKS-directed synthesis stalls at the ACP of extender module 2 and no epothilone product is made by such a strain in the absence of a synthetic precursor. However, when the strain is provided with a synthetic precursor, it mimics the product of the loading domain and extender module 1 so that the ACP of extender module 2 binds the precursor and the PKS processes the precursor from that point forward. For example, providing the knockout strain of Example 9 with the synthetic precursor

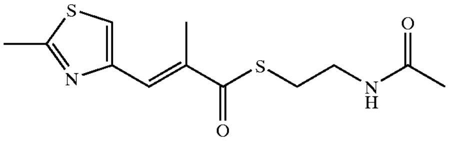

results in the production of epothilones B and D (epothilones A and B are also produced but in trace quantities) as described in greater detail in Example 10. See also FIG. 1. In another example providing the knockout strain of Example 9 with the synthetic precursors, for example,

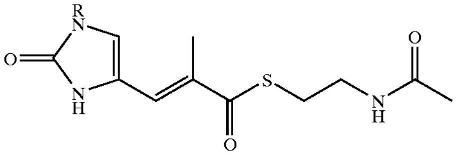

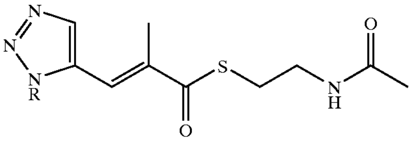

where R is hydrogen, hydroxy, halogen, amino, $C_1$–$C_5$ alkyl, $C_1$–$C_5$ hydroxyalkyl, $C_1$–$C_5$ alkoxy, and $C_1$–$C_5$ aminoalkyl, more preferably hydrogen or methyl, results in the following epothilone compounds

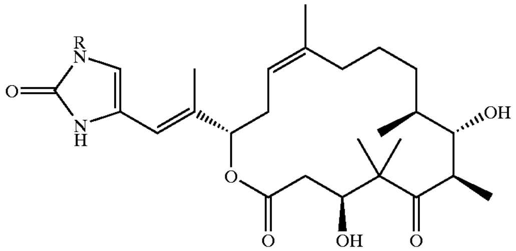

and

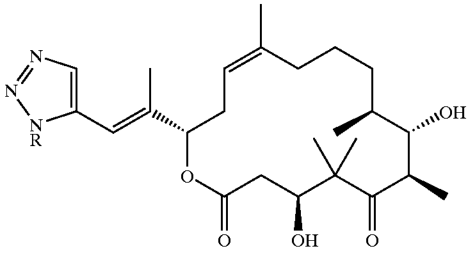

and their 12, 13-epoxide counterparts respectively.

Thus, by varying the synthetic precursor, a single KS2 knockout strain can be used to make a wide variety of compounds. In fact, the strain described in Example 9 can be used to make compounds of the formulas

VII

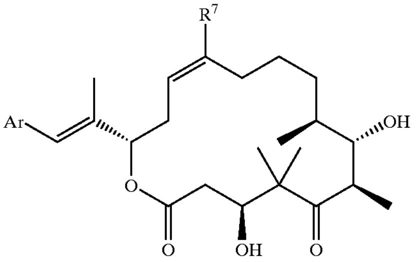

and

VIII

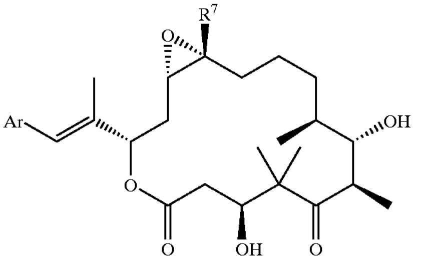

where Ar is aryl and $R^7$ is hydrogen or methyl by providing it with synthetic precursors of the formula

IX

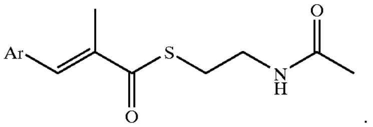

Illustrative examples of suitable Ar groups include but are not limited to

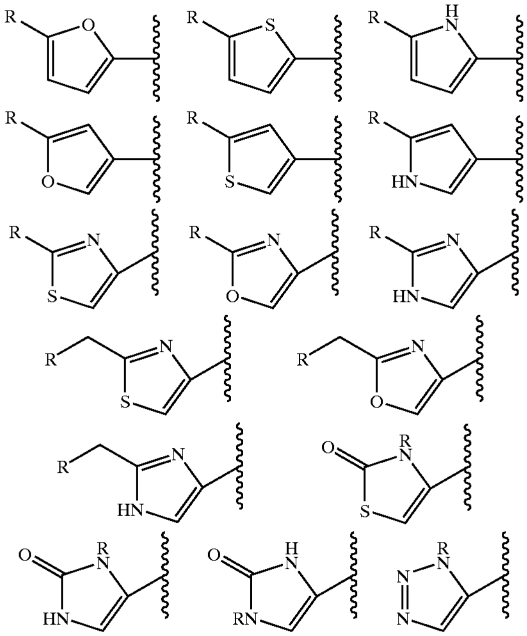

-continued

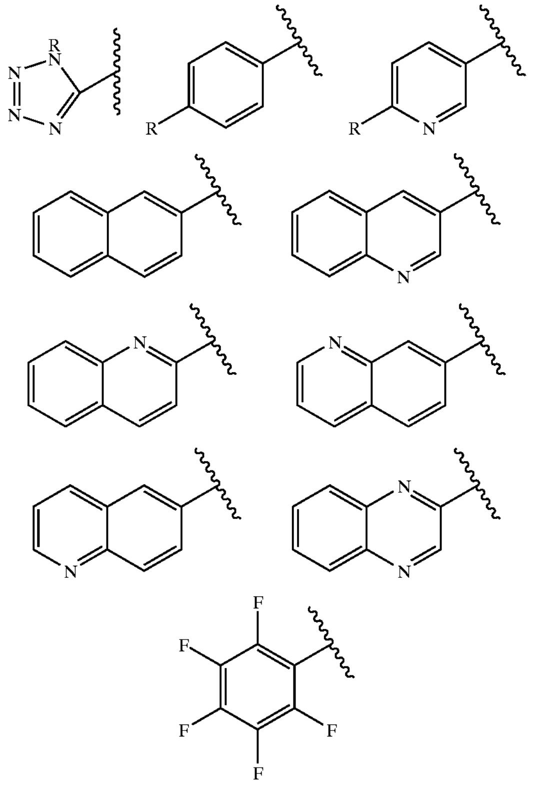

where R is hydrogen, hydroxy, halogen, amino, $C_1$–$C_5$ alkyl, $C_1$–$C_5$ hydroxyalkyl, $C_1$–$C_5$ alkoxy, and $C_1$–$C_5$ aminoalkyl. In more preferable embodiments, R is hydrogen or methyl. Example 10 describes the synthesis of various precursors and their use in chemobiosynthesis and their 12, 13-epoxide counterparts respectively.

In another embodiment, a loading domain knockout is used to make certain compounds of the present invention. For example, a loading domain knockout of the starting material used in Example 9 can also be used to make compounds of formulas VII and VIII by providing synthetic precursors of the formula

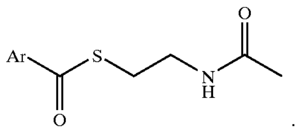

In other embodiments, KS2 or loading domain knockouts of other strains of the invention are made including but not limited to those strains described in Example 11 and used to make compounds having aryl moieties other than 2-methyl thiazole. For example, feeding synthetic precursors of formula IX to a KS2 knockout of a construct that makes predominantly 9-oxo-epothilone D will result in compounds of the formula

X

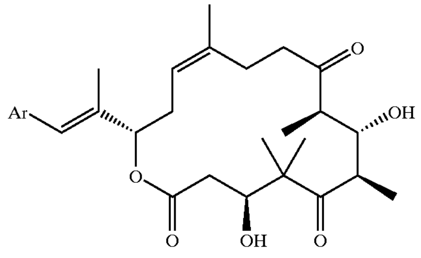

where Ar is aryl.

In another aspect of the present invention, compounds made from host cells expressing an epothilone PKS can be further modified using biological and/or synthetic methods. In one embodiment, compounds of formula I where Ar is

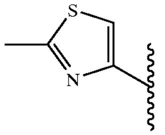
or
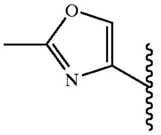

can be hydroxylated at the C-21 carbon using a microbially-derived hydroxylase. Protocols for effectuating such a transformation are described for example by PCT Publication No. WO 00/39276 which is incorporated herein in its entirety by reference, and by Example 14 herein.

In another embodiment, compounds of the invention having a carbon-carbon double bond at the positions corresponding to C-12 and C-13 of epothilones A–D can be epoxidated using EpoK or another P450 epoxidase. A general method for using EpoK for epoxidation is described by Example 5 of PCT publication WO 00/31247 which is incorporated herein by reference, and by Example 15 herein. Alternatively, the epoxidation reaction can occur by contacting an epothilone compound containing a double bond at a position that corresponds to the bond between carbon-12 and carbon 13 to a culture of cells that expresses a functional Epo K. Such cells include the myxobacterium *Sorangium cellulosum*. In particularly preferred embodiments, the *Sorangium cellulosum* expresses Epo K but does not contain a functional epothilone polyketide synthase ("PKS") gene. Such strains may be made by mutagenesis where one or more mutations in the epothilone PKS gene render it inoperative. Such mutants can occur naturally (which may be found by screening) or can be directed using either mutagens such as chemicals or irradation or by genetic manipulation. A particularly effective strategy for making strains with an inoperative epothilone PKS is homologous recombination as described by PCT publication WO 00/31247.

In another embodiment, the epoxidation reaction can occur using synthetic methods. For example, as shown by Scheme 2, desoxy compounds of the invention can be transformed to the epoxy counterparts by reacting the desoxy compounds with dimethyldioxirane.

SCHEME 2

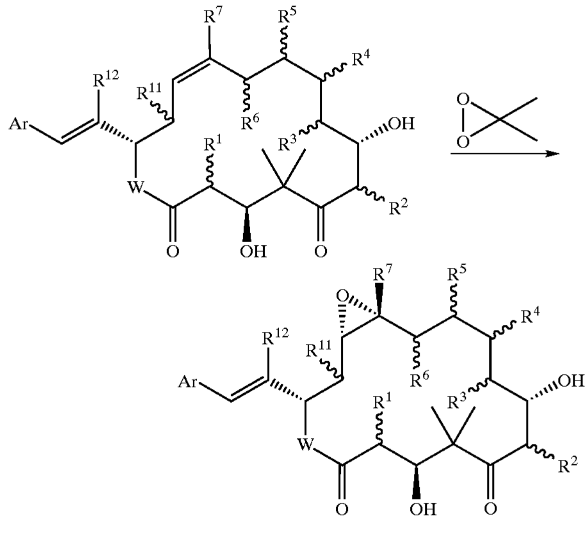

Example 16 describes this synthetic method in greater detail.

In another embodiment, the macrolactones of the invention can be converted into macrolactams of the invention. As illustrated by Scheme3, a desoxy macrolactone of the invention is epoxidated using dimethyldioxirane as previously described by Scheme 2 to provide the oxycounterpart.

SCHEME 3

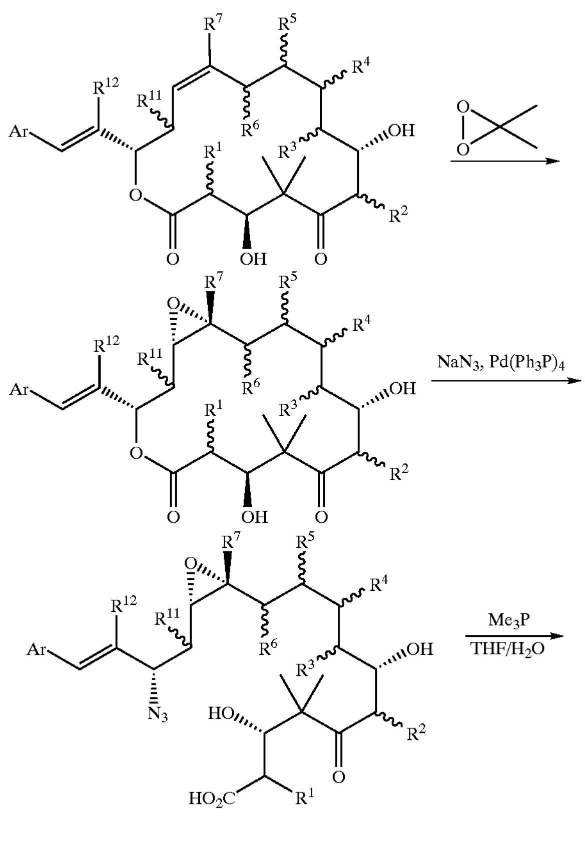

-continued

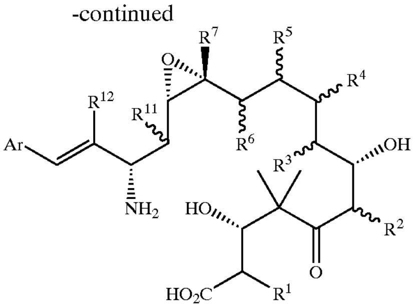

The oxy-macrolactone is treated with sodium azide and tetrakis(triphenylphosline) palladium to open the ring and form the azido acid. The azide is then reduced with trimethylphosphine to form the amino carboxyacid.

Epoxy-compounds of the invention where W is NH can be made from the macrolactamization of the amino carboxy-acid.

SCHEME 4

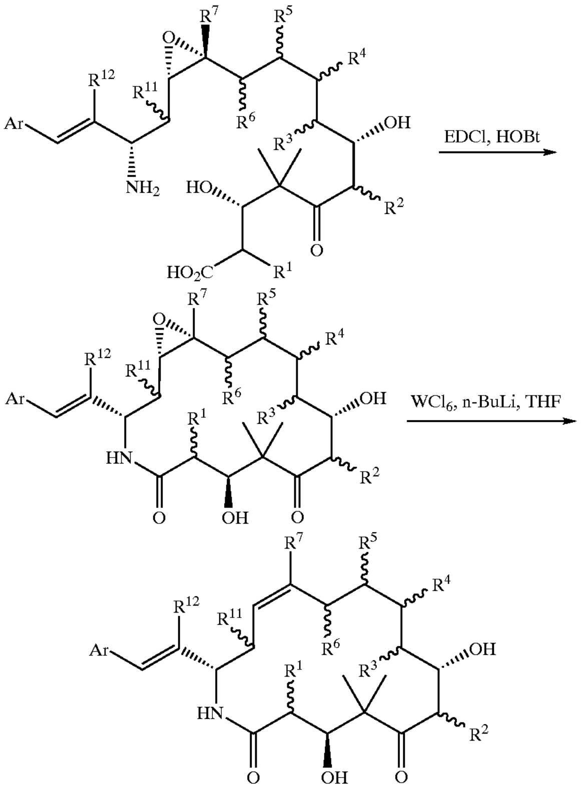

As shown by Scheme 4, the amino carboxyacid is treated with 1-(3-dimethylaminopropyl)-3-ethyl-carbodiimide and 1-hydroxybenzotriazole to form the epoxy-macrolactam. The desoxy-macrolactam can be made by treating the epoxy-macrolactam with tungsten hexachloride and butyllithium.

Epoxy-compounds of the invention where W is $NR^{13}$ and $R^{13}$ is not hydrogen can be made by treating the amino carboxyacid with an aldehyde and sodium cyanoborohydride prior to macrolactamization.

SCHEME 5

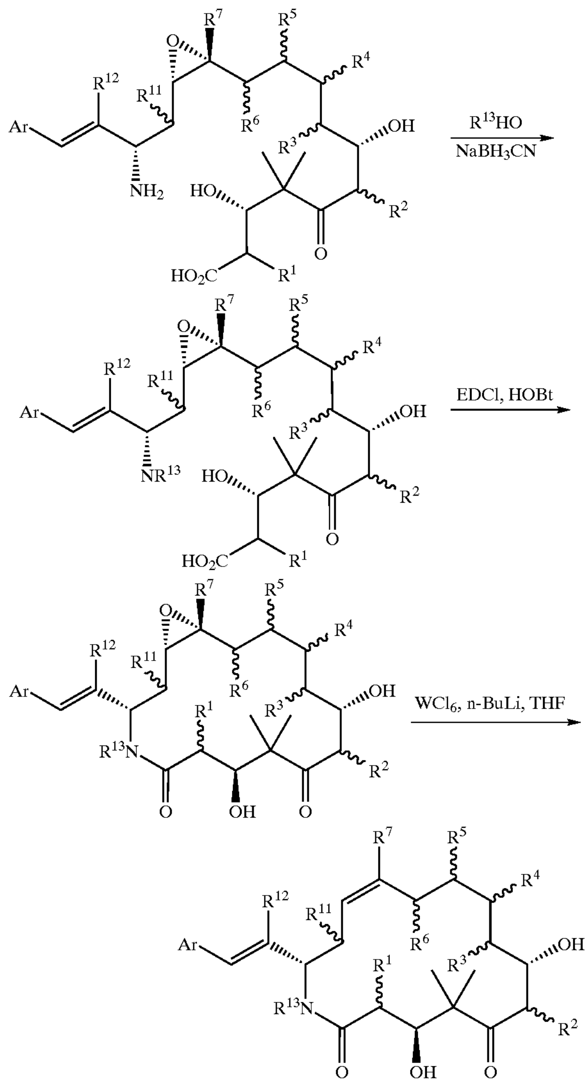

As shown by Scheme 5, the amino carboxyacid is treated with aldehyde, $R^{13}HO$, and sodium cyanoborohydride to form a substituted amino acid which is then macrolactamized and optionally deoxygenated as described previously in Scheme 4 to provide the epoxy and desoxy macrolactams where $R^{13}$ is not hydrogen.

The synthetic methods for making the macrolactams of the invention are also described in greater detail by the Examples 17–19. Example 17 describes the formation of the amino acid using 9-oxo-epothilone D as an illustrative starting material. Examples 18 and 19 describe the formation of the epoxy and desoxy macrolactam versions of 9-oxo-epothilone D respectively. Examples 20 and 21 describe the formation of the epoxy and desoxy substituted macrolactam versions of 9-oxo-epothilone D respectively.

A composition of the present invention generally comprises an inventive compound and a pharmaceutically acceptable carrier. The inventive compound may be free form or where appropriate as pharmaceutically acceptable derivatives such as prodrugs, and salts and esters of the inventive compound.

The composition may be in any suitable form such as solid, semisolid, or liquid form. See Pharmaceutical Dosage Forms and Drug Delivery Systems, $5^{th}$ editions Lippicott Williams & Wilkins (1991) which is incorporated herein by reference. In general, the pharmaceutical preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used.

In one embodiment, the compositions containing an inventive compound are Cremophor®-free. Cremophor® (BASF Aktiengesellschaft) is a polyethoxylated castor oil which is typically used as a surfactant in formulating low soluble drugs. However, because Cremophor® can case allergic reactions in a subject, compositions that minimize or eliminate Cremophor® are preferred. Formulations of epothilone A or B that eliminate Cremophor® are described for example by PCT Publication WO 99/39694 which is incorporated herein by reference and may be adapted for use with the inventive compounds.

Where applicable, the inventive compounds may be formulated as microcapsules and nanoparticles. General protocols are described for example, by Microcapsules and Nanoparticles in Medicine and Pharmacy by Max Donbrow, ed., CRC Press (1992) and by U.S. Pat. Nos. 5,510,118; 5,534,270; and 5,662,883 which are all incorporated herein by reference. By increasing the ratio of surface area to volume, these formulations allow for the oral delivery of compounds that would not otherwise be amenable to oral delivery.

The inventive compounds may also be formulated using other methods that have been previously used for low solubility drugs. For example, the compounds may form emulsions with vitamin E or a PEGylated derivative thereof as described by WO 98/30205 and 00/71163 which are incorporated herein by reference. Typically, the inventive compound is dissolved in an aqueous solution containing ethanol (preferably less than 1% w/v). Vitamin E or a PEGylated-vitamin E is added. The ethanol is then removed to form a pre-emulsion that can be formulated for intravenous or oral routes of administration. Another strategy involves encapsulating the inventive compounds in liposomes. Methods for forming liposomes as drug delivery vehicles are well known in the art. Suitable protocols include those described by U.S. Pat. Nos. 5,683,715; 5,415,869, and 5,424,073 which are incorporated herein by reference relating to another relatively low solubility cancer drug taxol and by PCT Publication WO 01/10412 which is incorporated herein by reference relating to epothilone B. Of the various lipids that may be used, particularly preferred lipids for making epothilone-encapsulated liposomes include phosphatidylcholine and polyethyleneglycol-derivitized distearyl phosphatidylethanolamine. Example 22 provides an illustrative protocol for making liposomes containing 9-oxo-epothilone D, the general method which can be readily adapted to make liposomes containing other compounds of the present invention.

Yet another method involves formulating the inventive compounds using polymers such as polymers such as biopolymers or biocompatible (synthetic or naturally occurring) polymers. Biocompatible polymers can be categorized as biodegradable and non-biodegradable. Biodegradable polymers degrade in vivo as a function of chemical composition, method of manufacture, and implant structure. Illustrative examples of synthetic polymers include polyanhydrides, polyhydroxyacids such as polylactic acid, polyglycolic acids and copolymers thereof, polyesters polyamides polyorthoesters and some polyphosphazenes. Illustrative examples of naturally occurring polymers include proteins and polysaccharides such as collagen, hyaluronic acid, albumin, and gelatin.

Another method involves conjugating the compounds of the present invention to a polymer that enhances aqueous solubility. Examples of suitable polymers include polyethylene glycol, poly-(d-glutamic acid), poly-(l-glutamic acid), poly-(l-glutamic acid), poly-(d-aspartic acid), poly-(l-aspartic acid), poly-(l-aspartic acid) and copolymers thereof. Polyglutamic acids having molecular weights between about 5,000 to about 100,000 are preferred, with molecular weights between about 20,000 and 80,000 being more preferred and with molecular weights between about 30,000 and 60,000 being most preferred. The polymer is conjugated via an ester linkage to one or more hydroxyls of an inventive epothilone using a protocol as essentially described by U.S. Pat. No. 5,977,163 which is incorporated herein by reference, and by Example 23. Preferred conjugation sites include the hydroxyl off carbon-21 in the case of 21-hydroxy-derivatives of the present invention. Other conjugation sites include the hydroxyl off carbon 3 and the hydroxyl off carbon 7.

In another method, the inventive compounds are conjugated to a monoclonal antibody. This strategy allows the targeting of the inventive compounds to specific targets. General protocols for the design and use of conjugated antibodies are described in Monoclonal Antibody-Based Therapy of Cancer by Michael L. Grossbard, ed. (1998) which is incorporated herein by reference.

The amount of active ingredient that may be combined with the carrier materials to produce a single dosage form will vary depending upon the subject treated and the particular mode of administration. For example, a formulation for intravenous use comprises an amount of the inventive compound ranging from about 1 mg/mL to about 25 mg/mL, preferably from about 5 mg/mL to 15 mg/mL, and more preferably about 10 mg/mL. Intravenous formulations are typically diluted between about 2 fold and about 30 fold with normal saline or 5% dextrose solution prior to use.

In one aspect of the present invention, the inventive compounds are used to treat cancer. In one embodiment, the compounds of the present invention are used to treat cancers of the head and neck which include tumors of the head, neck, nasal cavity, paranasal sinuses, nasopharynx, oral cavity, oropharynx, larynx, hypopharynx, salivary glands, and paragangliomas. In another embodiment, the compounds of the present invention are used to treat cancers of the liver and biliary tree, particularly hepatocellular carcinoma. In another embodiment, the compounds of the present invention are used to treat intestinal cancers, particularly colorectal cancer. In another embodiment, the compounds of the present invention are used to treat ovarian cancer. In another embodiment, the compounds of the present invention are used to treat small cell and non-small cell lung cancer. In another embodiment, the compounds of the present invention are used to treat breast cancer. In another embodiment, the compounds of the present invention are used to treat sarcomas which includes fibrosarcoma, malignant fibrous histiocytoma, embryonal rhabdomysocarcoma, leiomysosarcoma, neurofibrosarcoma, osteosarcoma, synovial sarcoma, liposarcoma, and alveolar soft part sarcoma. In another embodiment, the compounds of the present invention are used to treat neoplasms of the central nervous systems, particularly brain cancer. In another embodiment, the compounds of the present invention are used to treat lymphomas which include Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma.

The method comprises administering a therapeutically effective amount of an inventive compound to a subject suffering from cancer. The method may be repeated as necessary either to contain (i.e. prevent further growth) or to eliminate the cancer. Clinically, practice of the method will result in a reduction in the size or number of the cancerous growth and/or a reduction in associated symptoms (where applicable). Pathologically, practice of the method will produce at least one of the following: inhibition of cancer cell proliferation, reduction in the size of the cancer or tumor, prevention of further metastasis, and inhibition of tumor angiogenesis.

The compounds and compositions of the present invention can be used in combination therapies. In other words, the inventive compounds and compositions can be administered concurrently with, prior to, or subsequent to one or more other desired therapeutic or medical procedures. The particular combination of therapies and procedures in the combination regimen will take into account compatibility of the therapies and/or procedures and the desired therapeutic effect to be achieved.

In one embodiment, the compounds and compositions of the present invention are used in combination with another anti-cancer agent or procedure. Illustrative examples of other anti-cancer agents include but are not limited to: (i) alkylating drugs such as mechlorethamine, chlorambucil, Cyclophosphamide, Melphalan, Ifosfamide; (ii) antimetabolites such as methotrexate; (iii) microtubule stabilizing agents such as vinblastin, paclitaxel, docetaxel, and discodermolide; (iv) angiogenesis inhibitors; (v) and cytotoxic antibiotics such as doxorubicon (adriamycin), bleomycin, and mitomycin. Illustrative examples of other anti-cancer procedures include: (i) surgery; (ii) radiotherapy; and (iii) photodynamic therapy.

In another embodiment, the compounds and compositions of the present invention are used in combination with an agent or procedure to mitigate potential side effects from the inventive compound or composition such as diarrhea, nausea and vomiting. Diarrhea may be treated with antidiarrheal agents such as opioids (e.g. codeine, diphenoxylate, difenoxin, and loeramide), bismuth subsalicylate, and octreotide. Nausea and vomiting may be treated with antiemetic agents such as dexamethasone, metoclopramide, diphenyhydramine, lorazepam, ondansetron, prochlorperazine, thiethylperazine, and dronabinol. For those compositions that includes polyethoxylated castor oil such as Cremophor®, pretreatment with corticosteroids such as dexamethasone and methylprednisolone and/or $H_1$ antagonists such as diphenylhydramine HCl and/or $H_2$ antagonists may be used to mitigate anaphylaxis. Illustrative formulations for intravenous use and pretreatment regiments are described by Examples 24 and 25 respectively.

In another aspect of the present invention, the inventive compounds are used to treat non-cancer disorders that are characterized by cellular hyperproliferation. In one embodiment, the compounds of the present invention are used to treat psoriasis, a condition characterized by the cellular hyperproliferation of keratinocytes which builds up on the skin to form elevated, scaly lesions. The method comprises administering a therapeutically effective amount of an inventive compound to a subject suffering from psoriasis. The method may be repeated as necessary either to decrease the number or severity of lesions or to eliminate the lesions. Clinically, practice of the method will result in a reduction in the size or number of skin lesions, diminution of cutaneous symptoms (pain, burning and bleeding of the affected skin) and/or a reduction in associated symptoms (e.g., joint redness, heat, swelling, diarrhea, abdominal pain). Pathologically, practice of the method will result in at least one of the following: inhibition of keratinocyte proliferation, reduction of skin inflammation (for example, by impacting on: attraction and growth factors, antigen presentation, production of reactive oxygen species and matrix metalloproteinases), and inhibition of dermal angiogenesis.

In another embodiment, the compounds of the present invention are used to treat multiple sclerosis, a condition characterized by progressive demyelination in the brain. Although the exact mechanisms involved in the loss of myelin are not understood, there is an increase in astrocyte proliferation and accumulation in the areas of myelin destruction. At these sites, there is macrophage-like activity and increased protease activity which is at least partially responsible for degradation of the myelin sheath. The method comprises administering a therapeutically effective amount of an inventive compound to a subject suffering from multiple sclerosis. The method may be repeated as necessary to inhibit astrocyte proliferation and/or lessen the severity of the loss of motor function and/or prevent or attenuate chronic progression of the disease. Clinically, practice of the method will result in in improvement in visual symptoms (visual loss, diplopia), gait disorders (weakness, axial instability, sensory loss, spasticity, hyperreflexia, loss of dexterity), upper extremity dysfunction (weakness, spasticity, sensory loss), bladder dysfunction (urgency, incontinence, hesitancy, incomplete emptying), depression, emotional lability, and cognitive impairment. Pathologically, practice of the method will result in the reduction of one or more of the following, such as myelin loss, breakdown of the blood-brain barrier, perivascular infiltration of mononuclear cells, immunologic abnormalities, gliotic scar formation and astrocyte proliferation, metalloproteinase production, and impaired conduction velocity.

In another embodiment, the compounds of the present invention are used to treat rheumatoid arthritis, a multisystem chronic, relapsing, inflammatory disease that sometimes leads to destruction and ankyiosis of affected joints. Rheumatoid arthritis is characterized by a marked thickening of the synovial membrane which forms villous projections that extend into the joint space, multilayering of the synoviocyte lining (synoviocyte proliferation), infiltration of the synovial membrane with white blood cells (macrophages, lymphocytes, plasma cells, and lymphoid follicles; called an "inflammatory synovitis"), and deposition of fibrin with cellular necrosis within the synovium. The tissue formed as a result of this process is called pannus and, eventually the pannus grows to fill the joint space. The pannus develops an extensive network of new blood vessels through the process of angiogenesis that is essential to the evolution of the synovitis. Release of digestive enzymes (matrix metalloproteinases (e.g., collagenase, stromelysin)) and other mediators of the inflammatory process (e.g., hydrogen peroxide, superoxides, lysosomal enzymes, and products of arachadonic acid metabolism) from the cells of the pannus tissue leads to the progressive destruction of the cartilage tissue. The pannus invades the articular cartilage leading to erosions and fragmentation of the cartilage tissue. Eventually there is erosion of the subchondral bone with fibrous ankylosis and ultimately bony ankylosis, of the involved joint.

The method comprises administering a therapeutically effective amount of an inventive compound to a subject suffering from rheumatoid arthritis. The method may be repeated as necessary to accomplish to inhibit synoviocyte proliferation and/or lessen the severity of the loss of movement of the affected joints and/or prevent or attenuate chronic progression of the disease. Clinically, practice of the present invention will result in one or more of the following: (i) decrease in the severity of symptoms (pain, swelling and tenderness of affected joints; morning stiffness, weakness, fatigue, anorexia, weight loss); (ii) decrease in the severity of clinical signs of the disease (thickening of the joint capsule, synovial hypertrophy, joint effusion, soft tissue contractures, decreased range of motion, ankylosis and fixed joint deformity); (iii) decrease in the extra-articular manifestations of the disease (rheumatic nodules, vasculitis, pulmonary nodules, interstitial fibrosis, pericarditis, episcleritis, iritis, Felty's syndrome, osteoporosis); (iv) increase in the frequency and duration of disease remission/symptom-free periods; (v) prevention of fixed impairment and disability; and/or (vi) prevention/attenuation of chronic progression of the disease. Pathologically, practice of the present invention will produce at least one of the following: (i) decrease in the inflammatory response; (ii) disruption of the activity of inflammatory cytokines (such as IL-I, TNFa, FGF, VEGF); (iii) inhibition of synoviocyte proliferation; (iv) inhibition of matrix metalloproteinase activity, and/or (v) inhibition of angiogenesis.

In another embodiment, the compounds of the present invention are used to threat atherosclerosis and/or restenosis, particularly in patients whose blockages may be treated with an endovascular stent. Atheroschlerosis is a chronic vascular injury in which some of the normal vascular smooth muscle cells ("VSMC") in the artery wall, which ordinarily control vascular tone regulating blood flow, change their nature and develop "cancer-like" behavior. These VSMC become abnormally proliferative, secreting substances (growth factors, tissue-degradation enzymes and other proteins) which enable them to invade and spread into the inner vessel lining, blocking blood flow and making that vessel abnormally susceptible to being completely blocked by local blood clotting. Restenosis, the recurrence of stenosis or artery stricture after corrective procedures, is an accelerated form of atherosclerosis.

The method comprises coating a therapeutically effective amount of an inventive compound on a stent and delivering the stent to the diseased artery in a subject suffering from atherosclerosis. Methods for coating a stent with a compound are described for example by U.S. Pat. Nos. 6,156,373 and 6,120,847. Clinically, practice of the present invention will result in one or more of the following: (i) increased arterial blood flow; (ii) decrease in the severity of clinical signs of the disease; (iii) decrease in the rate of restenosis; or (iv) prevention/attenuation of the chronic progression of atherosclerosis. Pathologically, practice of the present invention will produce at least one of the following at the site of stent implanataion: (i) decrease in the inflammatory response, (ii) inhibition of VSMC secretion of matrix metalloproteinases; (iii) inhibition of smooth muscle cell accumulation; and (iv) inhibition of VSMC phenotypic dedifferentiation.

In one embodiment, dosage levels that are administered to a subject suffering from cancer or a non-cancer disorder characterized by cellular proliferation are of the order from about 1 $mg/m^2$ to about 200 $mg/m^2$ which may be administered as a bolus (in any suitable route of administration) or a continuous infusion (e.g. 1 hour, 3 hours, 6 hours, 24 hours, 48 hours or 72 hours) every week, every two weeks, or every three weeks as needed. It will be understood, however, that the specific dose level for any particular patient depends on a variety of factors. These factors include the activity of the specific compound employed; the age, body weight, general health, sex, and diet of the subject; the time and route of administration and the rate of excretion of the drug; whether a drug combination is employed in the treatment; and the severity of the condition being treated.

In another embodiment, the dosage levels are from about 10 $mg/m^2$ to about 150 $mg/m^2$, preferably from about 10 to about 75 $mg/m^2$ and more preferably from about 15 $mg/m^2$ to about 50 $mg/m^2$ once every three weeks as needed and as tolerated. In another embodiment, the dosage levels are from about 1 mg to about 150 $mg/m^2$, preferably from about 10 $mg/m^2$ to about 75 $mg/m^2$ and more preferably from about 25 $mg/m^2$ to about 50 $mg/m^2$ once every two weeks as needed and as tolerated. In another embodiment, the dosage levels are from about 1 $mg/m^2$ to about 100 $mg/m^2$, preferably from about 5 $mg/m^2$ to about 50 $mg/m^2$ and more preferably from about 10 $mg/m^2$ to about 25 $mg/m^2$ once every week as needed and as tolerated. In another embodiment, the dosage levels are from about 0.1 to about 25 $mg/m^2$, preferably from about 0.5 to about 15 $mg/m^2$ and more preferably from about 1 $mg/m^2$ to about 10 $mg/m^2$ once daily as needed and tolerated.

A detailed description of the invention having been provided above, the following examples are given for the purpose of illustrating the present invention and shall not be construed as being a limitation on the scope of the invention or claims.

EXAMPLE 1

Construction of a *Myxococcus xanthus* Expression Vector

The DNA providing the integration and attachment function of phage Mx8 was inserted into commercially available pACYC184 (New England Biolabs). An ~2360 bp MfeI-SmaI from plasmid pPLH343, described in Salmi et al., February 1998, *J. Bact.* 180(3): 614–621, was isolated and ligated to the large EcoRI-XmnI restriction fragment of plasmid pACYC184. The circular DNA thus formed was ~6 kb in size and called plasmid pKOS35-77.

Plasmid pKOS35-77 serves as a convenient plasmid for expressing recombinant PKS genes of the invention under the control of the epothilone PKS gene promoter. In one illustrative embodiment, the entire epothilone PKS gene with its homologous promoter is inserted in one or more fragments into the plasmid to yield an expression vector of the invention.

The present invention also provides expression vectors in which the recombinant PKS genes of the invention are under the control of a *Myxococcus xanthus* promoter. To construct an illustrative vector, the promoter of the pilA gene of *M. xanthus* was isolated as a PCR amplification product. Plasmid pSWU357, which comprises the pilA gene promoter and is described in Wu and Kaiser, December 1997, *J. Bact.* 179(24):7748–7758, was mixed with PCR primers Seq1 and Mxpil1 primers:

```
                                         (SEQ ID NO:1)
Seq1:   5'-AGCGGATAACAATTTCACACAGGAAACAGC-3'; and

                                          SEQ ID NO:2)
Mxpil1: 5'-TTAATTAAGAGAAGGTTGCAACGGGGGGC-3',
```

and amplified using standard PCR conditions to yield an ~800 bp fragment. This fragment was cleaved with restriction enzyme KpnI and ligated to the large KpnI-EcoRV restriction fragment of commercially available plasmid pLitmus 28 (New England Biolabs). The resulting circular DNA was designated plasmid pKOS35-71B.

The promoter of the pilA gene from plasmid pKOS35-71B was isolated as an ~800 bp EcoRV-SnaBI restriction fragment and ligated with the large MscI restriction fragment of plasmid pKOS35-77 to yield a circular DNA ~6.8 kb in size. Because the ~800 bp fragment could be inserted in either one of two orientations, the ligation produced two plasmids of the same size, which were designated as plasmids pKOS35-82.1 and pKOS35-82.2. Restriction site and function maps of these plasmids are presented in FIG. 2.

Plasmids pKOS35-82.1 and pKOS35-82.2 serve as convenient starting materials for the vectors of the invention in which a recombinant PKS gene is placed under the control of the *Myxococcus xanthus* pilA gene promoter. These plasmids comprise a single PacI restriction enzyme recognition sequence placed immediately downstream of the transcription start site of the promoter. In one illustrative embodiment, the entire epothilone PKS gene without its homologous promoter is inserted in one or more fragments into the plasmids at the PacI site to yield expression vectors of the invention.

The sequence of the pilA promoter in these plasmids is shown below (SEQ ID NO:3),

```
CGACGCAGGTGAAGCTGCTTCGTGTGCTCCAGGAGCGGAAGGTGAAGCCG

GTCGGCAGCGCCGCGGAGATTCCCTTCCAGGCGCGTGTCATCGCGGCAAC

GAACCGGCGGCTCGAAGCCGAAGTAAAGGCCGGACGCTTTCGTGAGGACC

TCTTCTACCGGCTCAACGTCATCACGTTGGAGCTGCCTCCACTGCGCGAG

CGTTCCGGCGACGTGTCGTTGCTGGCGAACTACTTCCTGTCCAGACTGTC

GGAGGAGTTGGGGCGACCCGGTCTGCGTTTCTCCCCCGAGACACTGGGGC

TATTGGAGCGCTATCCCTTCCCAGGCAACGTGCGGCAGCTGCAGAACATG

GTGGAGCGGGCCGCGACCCTGTCGGATTCAGACCTCCTGGGGCCCTCCAC

GCTTCCACCCGCAGTGCGGGGCGATACAGACCCCGCCGTGCGTCCCGTGG

AGGGCAGTGAGCCAGGGCTGGTGGCGGGCTTCAACCTGGAGCGGCATCTC

GACGACAGCGAGCGGCGCTATCTCGTCGCGGCGATGAAGCAGGCCGGGGG

CGTGAAGACCCGTGCTGCGGAGTTGCTGGGCCTTTCGTTCCGTTCATTCC

GCTACCGGTTGGCCAAGCATGGGCTGACGGATGACTTGGAGCCCGGGAGC

GCTTCGGATGCGTAGGCTGATCGACAGTTATCGTCAGCGTCACTGCCGAA

TTTTGTCAGCCCTGGACCCATCCTCGCCGAGGGGATTGTTCCAAGCCTTG

AGAATTGGGGGGCTTGGAGTGCGCACCTGGGTTGGCATGCGTAGTGCTAA

TCCCATCCGCGGGCGCAGTGCCCCCCGTTGCAACCTTCTCTTAATTAA
```

To make the recombinant *Myxococcus xanthus* host cells of the invention, *M. xanthus* cells are grown in CYE media (Campos and Zusman, 1975, Regulation of development in *Myxococcus xanthus*: effect of 3':5'-cyclic AMP, ADP, and nutrition, *Proc. Natl. Acad. Sci. USA* 72: 518–522) to a Klett of 100 at 30° C. at 300 rpm. The remainder of the protocol is conducted at 25° C. unless otherwise indicated. The cells are then pelleted by centrifugation (8000 rpm for 10 min. in an SS34 or SA600 rotor) and resuspended in deionized water. The cells are again pelleted and resuspended in 1/100 th of the original volume.

DNA (one to two $\mu$L) is electroporated into the cells in a 0.1 cm cuvette at room temperature at 400 ohm, 25 $\mu$FD, 0.65 V with a time constant in the range of 8.8–9.4. The DNA is free of salts and is resuspended in distilled and deionized water or dialyzed on a 0.025 $\mu$m Type VS membrane (Millipore). For low efficiency electroporations, the DNA is spot dialyzed, and outgrowth is in CYE. Immediately after electroporation, 1 mL of CYE is added, and the cells in the cuvette pooled with an additional 1.5 mL of CYE previously added to a 50 mL Erlenmeyer flask (total volume 2.5 ml). The cells are grown for four to eight hours (or overnight) at 30 to 32° C. at 300 rpm to allow for expression of the selectable marker. Then, the cells are plated in CYE soft agar on plates with selection. With kanamycin as the selectable marker, typical yields are $10^3$ to $10^5$ per $\mu$g of DNA. With streptomycin as the selectable marker, it is included in the top agar, because it binds agar.

With this procedure, the recombinant DNA expression vectors of the invention are electroporated into *Myxococcus* host cells that express recombinant PKSs of the invention and produce the epothilone, epothilone derivatives, and other novel polyketides encoded thereby.

EXAMPLE 2

Chromosomal Integration and a Bacterial Artificial Chromosome (BAC) for Expression of Epothilone in *Myxococcus xanthus*

To express the epothilone PKS and modification enzyme genes in a heterologous host to produce epothilones by fermentation, *Myxococcus xanthus*, which is closely related to *Sorangium cellulosum* and for which a number of cloning vectors are available, is employed in accordance with the methods of the invention. *M. xanthus* and *S. cellulosum* are myxobacteria and so may share common elements of gene expression, translational control, and post translational modification. *M. xanthus* has been developed for gene cloning and expression: DNA can be introduced by electroporation, and a number of vectors and genetic markers are available for the introduction of foreign DNA, including those that permit its stable insertion into the chromosome. *M. xanthus* can be grown with relative ease in complex media in fermentors and can be subjected to manipulations to increase gene expression, if required.

To introduce the epothilone gene cluster into *Myxococcus xanthus*, one can build the epothilone cluster into the chromosome by using homologous recombination to assemble the complete gene cluster. Alternatively, the complete epothilone gene cluster can be cloned on a bacterial artificial chromosome (BAC) and then moved into *M. xanthus* for integration into the chromosome.

Figure 3:
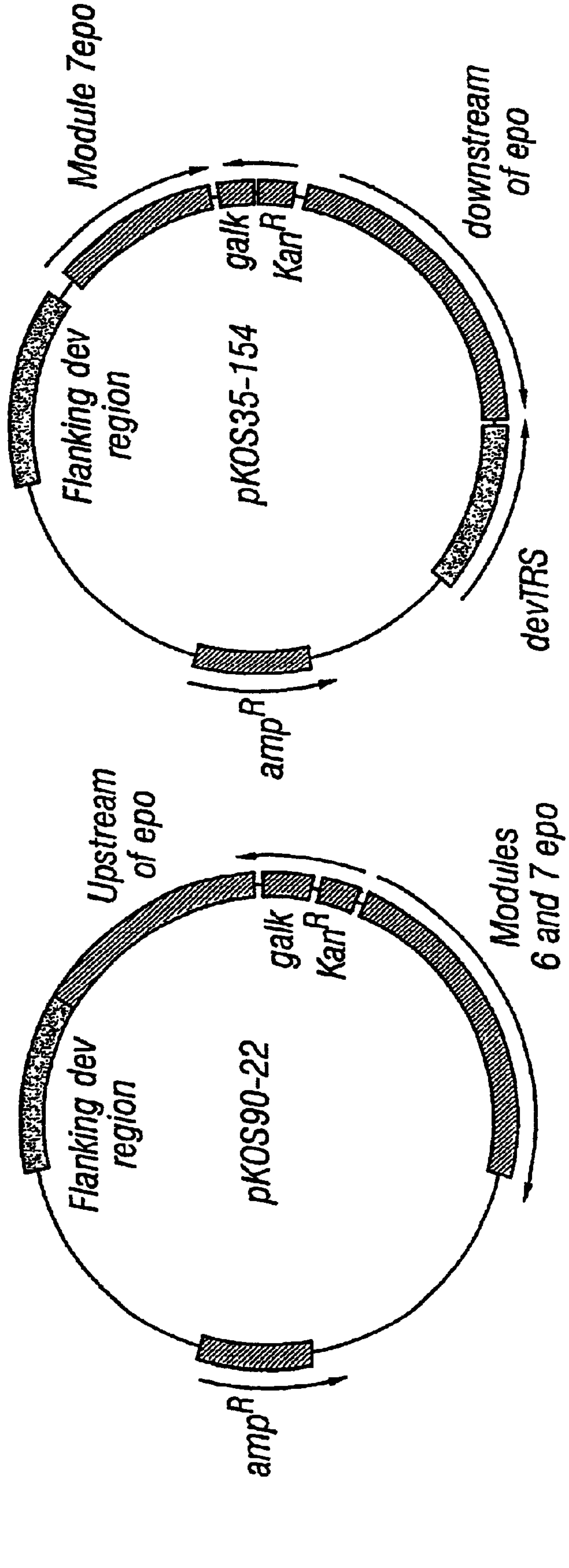
FIG. 3 shows restriction site and function maps of plasmids pKOS35-154 and pKOS90-22.
Figure 4:
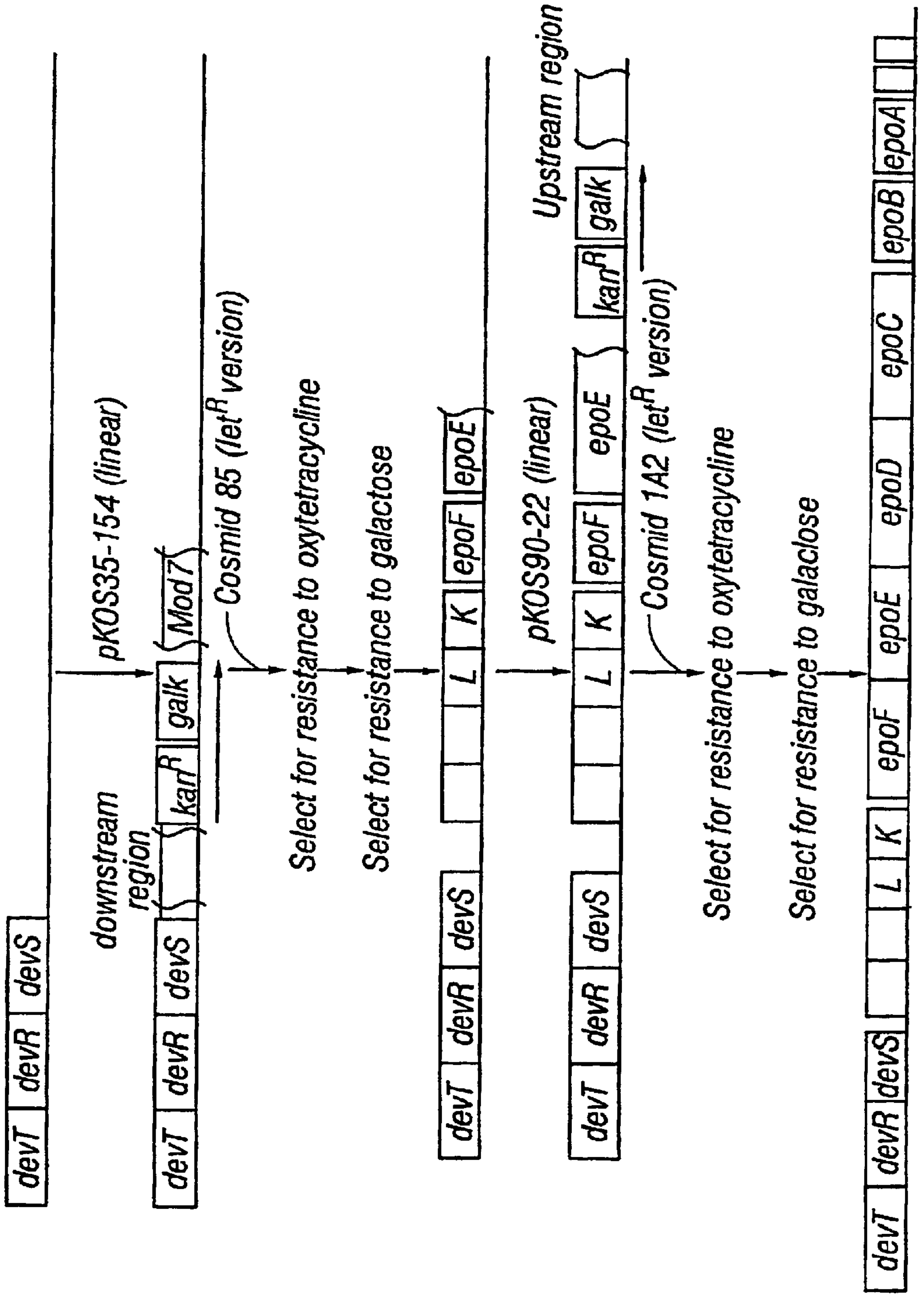
FIG. 4 shows a schematic of a protocol for introducing the epothilone PKS and modification enzyme genes into the chromosome of a *Myxococcus xanthus* host cell as described in Example 2.

To assemble the gene cluster from cosmids pKOS35–70.1A2, and pKOS35-79.85, small regions (~2 kb or larger) of homology from these cosmids are introduced into *Myxococcus xanthus* to provide recombination sites for larger pieces of the gene cluster. As shown in FIG. 3, plasmids pKOS35-154 and pKOS90-22 are created to introduce these recombination sites. The strategy for assembling the epothilone gene cluster in the *M. xanthus* chromosome is shown in FIG. 4. Initially, a neutral site in the bacterial chromosome is chosen that does not disrupt any genes or transcriptional units. One such region is downstream of the devS gene, which has been shown not to affect the growth or development of *M. xanthus*. The first plasmid, pKOS35-154, is linearized with DraI and electroporated into *M. xanthus*. This plasmid contains two regions of the dev locus flanking two fragments of the epothilone gene cluster. Inserted in between the epo gene regions is a cassette composed of a kanamycin resistance marker and the *E. coli* galK gene. See Ueki et al., 1996, *Gene* 183: 153–157, incorporated herein by reference. Kanamycin resistance arises in colonies if the DNA recombines into the dev region by a double recombination using the dev sequence as regions of homology.

This strain, K35-159, contains small (~2.5 kb) regions of the epothilone gene cluster that will allow for recombination of pKOS35-79.85. Because the resistance markers on pKOS35-79.85 are the same as that in K35-159, a tetracycline transposon was transposed into the cosmid, and cosmids that contain the transposon inserted into the kanamycin marker were selected. This cosmid, pKOS90-23, was electroporated into K35-159, and oxytetracycline resistant colonies were selected to create strain K35-174. To remove the unwanted regions from the cosmid and leave only the epothilone genes, cells were plated on CYE plates containing 1% galactose. The presence of the galK gene makes the cells sensitive to 1% galactose. Galactose resistant colonies of K35-174 represent cells that have lost the galK marker by recombination or by a mutation in the galK gene. If the recombination event occurs, then the galactose resistant strain is sensitive to kanamycin and oxytetracycline. Strains sensitive to both antibiotics are verified by Southern blot analysis. The correct strain is identified and designated K35-175 and contains the epothilone gene cluster from module 7 to 4680 bp downstream of the stop codon of epoK.

To introduce modules 1 through module 7, the above process is repeated once more. The plasmid pKOS90-22 is linearized with DraI and electroporated into K35-175 to create K111-13.2. This strain is electroporated with the tetracycline resistant version of pKOS35-70.1A2, pKOS90-38, and colonies resistant to oxytetracycline are selected. This creates strain K111-13.23. Recombinants that now have the whole epothilone gene cluster are selected by resistance to 1% galactose. This results in clones K111-32.25, K111-32.26, and K111-32.35. Strain K111-32.25 was deposited Apr. 14, 2000, with the American Type Culture Collection, Manassas, Va. 20110-2209, USA, in compliance with the Budapest Treaty and is available under accession No. PTA-1700. This strain contains all the epothilone genes and their promoter(s).

Fermentation was performed by inoculating strains into 5 mL of CYE (10 g casitone, 5 g yeast extract, and 1 g $MgSO_4.7H_2O$ per liter) in a 50 mL flask and growing overnight until the culture was in mid log growth phase. A 100 $\mu$L aliquot was spread onto a CTS plate, and the plate incubated at 32° C. for 4 to 5 days. To extract epothilones, the agar and cells from the plate was macerated, put in a 50 mL conical tube, and acetone added to fill the tube. The solution was incubated with rocking for 4 to 5 hours, the acetone evaporated, and the remaining liquid extracted twice with an equal volume of ethyl acetate. The water was removed from the ethyl acetate extract by adding magnesium sulfate. The magnesium sulfate was filtered out, and the liquid was evaporated to dryness. The epothilones were resuspended in 200 $\mu$L of acetonitrile and analyzed by LC/MS. The analysis showed that the strain produced epothilones A and B, with epothilone B present at about 0.1 mg/L in the culture, and epothilone A at 5 to 10-fold lower levels.

This strain can also be used to produce epothilones in liquid culture. A flask containing CYE is inoculated with an epothilone producing strain. The next day, while the cells are in mid-log growth phase, a 5% inoculum is added to a flask containing 0.5% CMM (0.5% casitone, 0.2% $MgSO_4 \cdot 7H_2O$, 10 mM MOPS pH 7.6) along with 1 mg/mL serine, alanine, and glycine and 0.1% sodium puyruvate. The sodium pyruvate can be added to 0.5% to increase epothilone B production but causes a decrease in the ratio of epothilone B to epothilone A. The culture is grown at 30° C. for 60–72 hours. Longer incubations result in a decrease in titers of epothilones. To recover epothilones, the cultures are centrifuged at 10,000 rpm for 10 minutes in an SS34 rotor. The supernatants are extracted twice with ethyl acetate and rotary evaporated ("rotavaped") to dryness. Liquid cultures produced 2 to 3 mg/L of epothilones A and B, with ratios similar to that observed with plate cultures. If XAD (0.5–2%) was added to the culture, epothilones C and D were observed, with epothilone D present at 0.1 mg/L and epothilone C present at 5 to 10-fold lower levels.

Figure 5:
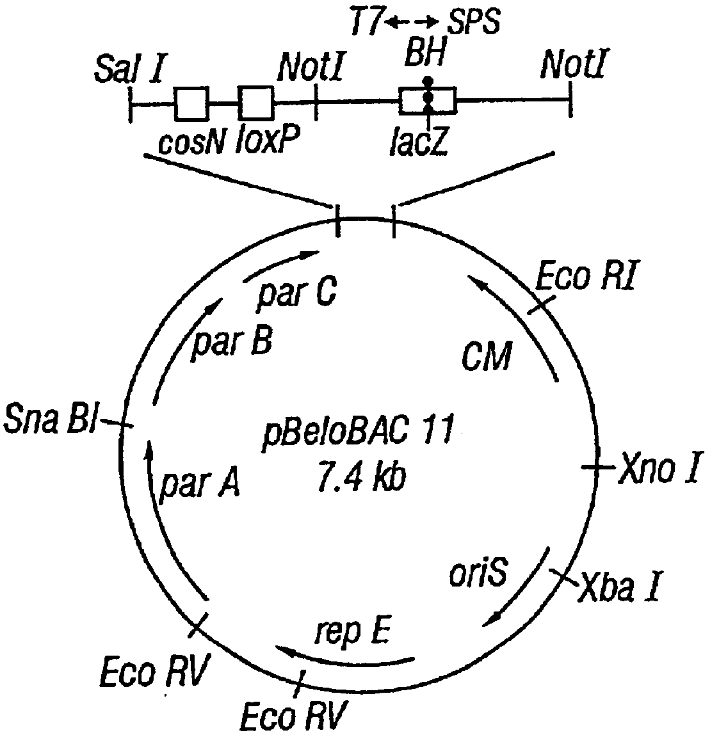
FIG. 5 shows a map of pBeloBACII as described in Example 2.

To clone the whole gene cluster as one fragment, a bacterial artifical chromosome (BAC) library is constructed. First, SMP44 cells are embedded in agarose and lysed according to the BIO-RAD genomic DNA plug kit. DNA plugs are partially digested with restriction enzyme, such as Sau3AI or HindIII, and electrophoresed on a FIGE or CHEF gel. DNA fragments are isolated by electroeluting the DNA from the agarose or using gelase to degrade the agarose. The method of choice to isolate the fragments is electroelution, as described in Strong et al., 1997, *Nucleic Acids Res.* 19: 3959–3961, incorporated herein by reference. The DNA is ligated into the BAC (pBeloBACII) cleaved with the appropriate enzyme. A map of pBeloBACII is shown in FIG. 5.

The DNA is electroporated into DH10B cells by the method of Sheng et al., 1995, *Nucleic Acids Res.* 23: 1990–1996, incorporated herein by reference, to create a *Sorangium cellulosum* genomic library. Colonies are screened using a probe from the NRPS region of the epothilone cluster. Positive clones are picked and DNA is isolated for restriction analysis to confirm the presence of the complete gene cluster. This positive clone is designated pKOS35-178.

To create a strain that can be used to introduce pKOS35-178, a plasmid, pKOS35-164, is constructed that contains regions of homology that are upstream and downstream of the epothilone gene cluster flanked by the dev locus and containing the kanamycin resistance galK cassette, analogous to plasmids pKOS90-22 and pKOS35-154. This plasmid is linearized with DraI and electroporated into *Myxococcus xanthus*, in accordance with the method of Kafeshi et al., 1995, *Mol. Microbiol.* 15: 483–494, to create K35-183. The plasmid pKOS35-178 can be introduced into K35-183 by electroporation or by transduction with bacteriophage P1, and chloramphenicol resistant colonies are selected. Alternatively, a version of pKOS35-178 that contains the origin of conjugative transfer from pRP4 can be constructed for transfer of DNA from *E. coli* to K35-183. This plasmid is made by first constructing a transposon containing the oriT region from RP4 and the tetracycline resistance maker from pACYC184 and then transposing the transposon in vitro or in vivo onto pKOS35-178. This plasmid is transformed into S17-1 and conjugated into *M. xanthus*. This strain, K35-190, is grown in the presence of 1% galactose to select for the second recombination event. This strain contains all the epothilone genes as well as all potential promoters. This strain is fermented and tested for the production of epothilones A and B.

Alternatively, the transposon can be recombined into the BAC using either the temperature sensitive plasmid pMAK705 or pKO3 by transposing the transposon onto either pMAK705 or pKO3, selecting for tetR and camS plasmids; the recombination is accomplished as described in Hamilton et al., September 1989, *J. Bact.* 171(9): 4617–4622 and Link et al., October 1997, *J. Bact.* 179(20): 6228–6237, each of which is incorporated herein by reference.

Besides integrating pKOS35-178 into the dev locus, it can also be integrated into a phage attachment site using integration functions from myxophages Mx8 or Mx9. A transposon is constructed that contains the integration genes and att site from either Mx8 or Mx9 along with the tetracycline gene from pACYC184. Alternative versions of this transposon may have only the attachment site. In this version, the integration genes are then supplied in trans by coelectroporation of a plasmid containing the integrase gene or having the integrase protein expressed in the electroporated strain from any constitutive promoter, such as the mgl promoter (see Magrini et al., July 1999, *J. Bact.* 181(13): 4062–4070, incorporated herein by reference). Once the transposon is constructed, it is transposed onto pKOS35-178 to create pKOS35-191. This plasmid is introduced into *Myxococcus xanthus* as described above. This strain contains all the epothilone genes as well as all potential promoters. This strain is fermented and tested for the production of epothilones A and B. Alternatively, a strain that contains the att site and the oriT region can be transposed onto the BAC and the resulting BAC conjugated into *M. xanthus*.

Once the epothilone genes have been established in a strain of *Myxococcus xanthus*, manipulation of any part of the gene cluster, such as changing promoters or swapping modules, can be performed using the kanamycin resistance and galK cassette, as described below. Cultures of *Myxococcus xanthus* containing the epo genes are grown in a number of media and examined for production of epothilones. If the levels of production of epothilones (in particular B or D) are low, then the *M. xanthus*-producing clones are subjected to media development and mutation based strain improvement, as described in the following example.

EXAMPLE 3

Processes for the Production and Purification of Epothilones

A. Optimizing the Heterologous Production of Epothilone D in *Myxococcus xanthus*

The heterologous production of epothilone D in *Myxococcus xanthus* was improved by 140-fold from an initial titer of 0.16 mg/L with the incorporation of an adsorber resin, the identification of a suitable carbon source, and the implementation of a fed-batch process.

To reduce the degradation of epothilone D in the basal medium, XAD-16 (20 g/L) was added to stabilize the extracellular product. This greatly facilitated its recovery and enhanced the yield by three-fold. The use of oils as a carbon source for cell growth and product formation was also evaluated. From a screen of various oils, methyl oleate was shown to have the greatest impact. At the optimal concentration of 7 mL/L in a batch process, the maximum cell density was increased from 0.4 g dry cell weight (DCW)/L to 2 g DCW/L. Product yield depended on the presence of trace elements in the production medium. With an exogenous supplement of trace metals to the basal medium, the peak epothilone D titer was enhanced eight-fold, demonstrating the significant role of metal ions in cell metabolism and in epothilone biosynthesis. To increase the product yield further, a continuous fed-batch process was employed to promote a higher cell density and to maintain an extended production period. The optimized fed-batch cultures consistently yielded a cell density of 7 g DCW/L and an average production titer of 23 mg/L.

Epothilones are secondary metabolites that are naturally produced by various strains of the myxobacterium *Sorangium cellulosum* (Gerth et al., 1996; Gerth et al., 2001; references cited in this example are listed at the end of this section and are incorporated herein by reference). They are potent inhibitors of microtubule depolymerization, with a mechanism of action similar to that of the anti-cancer drug Taxol (Bollag et al., 1995). Their cytotoxic effect against multiple-drug resistant tumor cell lines expressing the P-glycoprotein renders them potential therapeutic compounds with great commercial value (Su et al., 1997; Kowalski et al., 1997). Their comparatively high solubility in water also facilitates their formulation for clinical evaluation.

Epothilones A and B are the major fermentation products of the natural host (Gerth et al., 1996). The macrocyclic core of these polyketide molecules is formed by the successive decarboxylative condensations of acetate and propionate units (Gerth et al., 2000). Epothilones A and B differ by a single methyl group at the C-12 position of their carbon skeleton. This structural variance results from the incorporation of an acetate in the assembly of epothilone A and a propionate in that of epothilone B. Epothilones C and D are intermediates in the biosynthetic pathway of epothilones A and B, respectively (Tang et al., 2000; Molnár et al., 2000). They are excreted as minor products during the fermentation process, with a combined yield of about 0.4 mg/L. Because preliminary in vivo studies revealed epothilone D to be the most promising of the four compounds as an anti-tumor drug (Chou et al., 1998), it is of considerable interest to produce this molecule on a large scale.

The gene cluster responsible for the biosynthesis of the epothilones has been sequenced (Tang et al., 2000; Molnár et al., 2000) and used to produce these compounds in *Myxococcus xanthus*, a microbial host closely-related to *S. cellulosum* but more amenable to genetic manipulation. To foster the production of epothilone D, a deletion mutant of this recombinant strain (described in Example 4, below) was constructed to inactivate the P450 epoxidase that catalyzes the conversion of epothilones C and D to epothilones A and B, respectively (Tang et al., 2000). This genetic alteration effectively promoted the secretion of epothilones C and D as sole products of the *M. xanthus* fermentation, with an epothilone D to C ratio of 4 to 1. The resulting mutant offers a distinct advantage over the natural host in the recovery and purification of the desired product. In this example, improvements in media composition and fermentation strategy are described that result in a 140-fold increase in the production of epothilone D in *M. xanthus.*

Adsorber resins have been used in the fermentations of myxobacteria for the continuous capture of biologically active molecules produced at low quantities (Reichenbach and Höfle, 1993). To facilitate the isolation of epothilone D, the hydrophobic resin XAD-16 was added to the culture medium. Because the bound product can readily be eluted from the resin with an appropriate solvent, its recovery was greatly simplified. Moreover, the use of XAD-16 minimized epothilone degradation through product stabilization.

*Myxococcus xanthus* has been traditionally cultivated in media consisting primarily of enzymatic hydrolysates of casein, such as peptone and casitone, relying on amino acids as the sole carbon and nitrogen source (Reichenbach and Dworkin, 1991). Consequently, ammonia is accumulated in the fermentation broth as a result of amino acid degradation. It was demonstrated by Gerth et al. (1986) that an extracellular ammonia concentration of 35–42 mM in a *Myxococcus virescens* culture corresponded to a surprisingly high ammonia concentration of 80–140 mM within the cells. More importantly, it was shown that by continuously removing the excess ammonia to below 8 mM with an in situ membrane process, both cell mass and secondary metabolite production dramatically increased (Hecht et al., 1990). Because the generation of high levels of ammonia is speculated to be inhibitory to the growth of *M. xanthus* and epothilone D production, an alternative carbon source to reduce the consumption of amino acids is desirable.

Although an adaptation process was required, methyl oleate was identified from an extensive screen of different oils as a substrate that can be metabolized by *M. xanthus*. With the addition of an exogenous trace element solution to the growth medium, epothilone D production was enhanced 8-fold, with a yield of 3.3 mg/L in a simple batch fermentation. To optimize the process further, a fed-batch approach using intermittent or continuous feeds of casitone and methyl oleate was adopted to prolong the production phase of the cells. A comparison of the results obtained with the two different feed strategies is reported in this example.

Materials and Methods

Inoculum Preparation

For the production of epothilone D in culture media without methyl oleate, 1 mL of frozen cells of the *Myxococcus xanthus* strain K111-40.1 in 20% (v/v) glycerol was inoculated into 3 mL of CYE medium consisting of 10 g/L casitone (Difco), 5 g/L yeast extract (Difco), 1 g/L $MgSO_4.7H_2O$, and 50 mM HEPES, pH 7.6, in a 50-mL glass culture tube. The HEPES buffer solution was titrated to pH 7.6 with potassium hydroxide. The cells were incubated at 30° C. and 175 rpm on a rotary shaker for 3 days. They were then transferred to a 250-mL Erlenmeyer flask containing 50 mL of CYE medium and grown for 2 days under the same conditions. The resulting seed culture was used to inoculate 50-mL production flasks at an inoculum size of 5% (v/v).

For the cultivation of *M. xanthus* in media containing methyl oleate, the cells had to be adapted to growth in the presence of the oil. One seed vial of frozen cells was inoculated into 3 mL of CYE medium that was supplemented with 3 μL of methyl oleate (Emerest 2301) (Cognis Corp.). The cells were grown in a glass culture tube for 2–6 days at 30° C. and 175 rpm until the culture was sufficiently dense under a microscope. They were then transferred into a 250 mL Erlenmeyer flask containing 50 mL of CYE-MOM medium consisting of 10 g/L casitone (Difco), 5 g/L yeast extract (Difco), 1 g/L $MgSO_4.7H_2O$, 2 mL/L methyl oleate, and 50 mM HEPES, pH 7.6. After 2 days of growth, the cells were frozen and stored at −80° C. as 1 mL aliquots in 20% (v/v) glycerol.

For the production of epothilone D in media containing methyl oleate, 1 mL of the frozen oil-adapted cells was inoculated into 3 mL of CYE-MOM medium in a glass culture tube. The cells were incubated at 30° C. and 175 rpm for 2 days and transferred to a 250 mL Erlenmeyer flask containing 50 mL of CYE-MOM medium. The resulting seed culture was grown for 2 days under the same conditions and was used to inoculate 50 mL production flasks at an inoculum size of 5% (v/v).

In preparing the inoculum for 5-L fermentations, 25 mL of the oil-adapted seed culture were transferred into a 2.8 L Fernbach flask containing 475 mL of CYE-MOM medium. The cells were grown at 30° C. and 175 rpm for 2 days. Subsequently, 250 mL of this secondary seed culture was inoculated into 5-L fermentors containing 4.75 L of production medium to yield a final inoculum concentration of 5% (v/v).

Shake Flask Production

Batch cultivations of *M. xanthus* K111-40-1 in the absence of methyl oleate were prepared as follows. One gram of XAD-16 resin (Rohm and Haas) was autoclaved at 121° C. for 30 min in a 250-mL Erlenmeyer flask with 5 mL of deionized water. The excess water was then removed from the flask, and 50 mL of CTS medium consisting of 5 g/L casitone, 2 g/L $MgSO_4.7H_2O$, and 50 mM HEPES, pH 7.6, were added. Because autoclaving of the adsorber resin in the presence of the production medium led to the binding of essential nutrients required by the cells, the resin and medium components were sterilized separately. The production flasks were inoculated with 2.5 mL of seed culture and incubated at 30° C. and 175 rpm for 6 days.

Batch cultivations in the presence of methyl oleate were prepared as described above. In addition, the production medium was supplemented with 7 mL/L of methyl oleate and 4 mL/L of a filter-sterilized trace element solution that was composed of 10 mL/L concentrated $H_2SO_4$, 14.6 g/L $FeCl_3.6H_2O$, 2.0 g/L $ZnCl_3$, 1.0 g/L $MnCl_2.4H_2O$, 0.43 g/L $CuCl_2.2H_2O$, 0.31 g/L $H_3BO_3$, 0.24 g/L $CaCl_2.6H_2O$, and 0.24 g/L $Na_2MO_4.2H_2O$. The production flasks were then inoculated with 2.5 mL of the oil-adapted seed culture and grown at 30° C. and 175 rpm for 5 days.

Fed-batch cultures with intermittent feeds of casitone and methyl oleate were prepared as follows. One gram of XAD-16 resin was autoclaved at 121° C. for 30 min. in a 250 mL Erlenmeyer flask with 5 mL of deionized water. After sterilization, the excess water was removed from the flask, and 50 mL of CTS medium supplemented with 2 mL/L methyl oleate, 4 mL/L trace element solution, and 50 mM HEPES, pH 7.6, were added. The production flasks were inoculated with 2.5 mL of the oil-adapted seed culture and incubated at 30° C. and 175 rpm. Two days after inoculation, 2 g/L of casitone and 3 mL/L of methyl oleate were added to the culture medium at 24 h intervals. The casitone feed was prepared as a concentrated 100 g/L solution. The cultures were grown for 10–12 days until substantial cell lysis was observed.

All the production cultures can be grown on a 500-mL scale in 2.8-L Fernbach flasks under the same growth conditions.

Fementor Production

Fed-batch fermentations on a 5-L scale with intermittent or continuous feeds of casitone and methyl oleate were prepared as follows. Twenty grams per liter of XAD-16 and 2 g/L of $MgSO_4.7H_2O$ was autoclaved at 121° C. for 30 min in a 5-L fermentor (B. Braun) with 4.75 L of deionized water. After sterilization, a concentrated casitone solution (150 g/L), methyl oleate, and trace elements were added to the bioreactor aseptically to attain a final casitone, methyl oleate, and trace element concentration of 5 g/L, 2 mL/L, and 4 mL/L, respectively. The medium was then inoculated with 250 mL of the oil-adapted seed culture. The fermentation was performed at 30° C. with an aeration rate of 0.4–0.5 v/v/m and an initial agitation rate of 400 rpm. The dissolved oxygen was controlled at 50% of saturation by a stirring cascade between 400–700 rpm. Cultivation pH was maintained at 7.4 by the automated addition of 2.5 N KOH and 2.5 M $H_2SO_4$. Twenty-four hours after inoculation, casitone (150 g/L) and methyl oleate were added to the production medium at a feed rate of 2 g/L/day casitone and 3 mL/L/day methyl oleate. The feeds were delivered either as a single bolus every 24 h or continuously with peristaltic pumps (W. Marlow). The cells were allowed to grow for 10–12 days until considerable cell lysis was noted.

Epothilone Quantitation

Prior to the use of the XAD-16 resin in the fermentations, 1 mL of culture broth was sampled from the production flasks or bioreactors and centrifuged at 13,000 g for 10 min. Quantitation of the epothilone products in the supernatant was carried out using a Hewlett Packard 1090 HPLC with UV detection at 250 nm. Five hundred microliters of the supernatant were injected across a 4.6×10 mm guard column (Inertsil, ODS-3, 5 μm). An online extraction was then performed at a flow rate of 1 mL/min. with a 100% water wash for 0.5 min., followed by a gradient to 50% acetonitrile over 1.5 min. The eluant was diverted to waste for the first two minutes and was passed onto a longer separation column (4.6×150 mm, Inertsil, ODS-3, 5 μm) thereafter. Separation of epothilones C and D was performed with a gradient from 50% to 100% acetonitrile over 8 min, followed by a 100% acetonitrile wash for 3 min. Under these conditions, epothilone C eluted at 9.4 minutes and epothilone D eluted at 9.8 minutes.

With the use of the XAD-16 resin, 5–50 mL of well-mixed culture broth and resin were sampled from the production flasks or bioreactors. After the resin was settled by gravity, the culture broth was decanted. The resin was washed with 5–50 mL of water and allowed to settle by gravity again. The aqueous mixture was completely removed, and the epothilone products were extracted from the resin with 100% methanol. The amount of solvent used was equivalent to 50% of the sample volume. Quantitation of epothilones C and D was carried out by HPLC analysis with UV detection at 250 nm. Fifty microliters of the methanol extract were injected across two 4.6×10 mm guard columns (Inertsil, ODS-3, 5 μm) and a longer 4.6×150 mm column (Inertsil, ODS-3, 5 μm). The assay method was isocratic, eluting with 60% acetonitrile and 40% water for 18 min at a flow rate of 1 mL/min. Under these conditions, epothilone C was detected at 10.3 minutes and epothilone D was detected at 13.0 minutes. Standards were prepared using purified epothilone D.

Cell Growth Determination

Cell growth in the absence of methyl oleate was monitored by measuring the optical density (OD) at 600 nm. Samples were diluted with water until the final OD values were less than 0.4. Because the addition of methyl oleate to culture medium results in the formation of an emulsion that has a strong absorbance at 600 nm, cell growth in the presence of methyl oleate was determined by dry cell weight (DCW). Forty milliliters of culture broth were centrifuged at 4200 g for 20 min in preweighed test tubes. The pellets were then washed with 40 mL of water and dried for 2 days at 80° C. before weighing.

Ammonia Determination

One milliliter of fermentation broth was clarified by centrifugation at 13,000 g for 5 min. The supernatant was then used for ammonia analysis with an ammonia assay kit (Sigma). Samples were diluted 20–100 fold with water until the final concentrations were less than 880 μM.

Methyl Oleate Determination

The residual methyl oleate in 1-mL of fermentation broth was extracted with 5 mL of acetonitrile. The mixture was vortexed and clarified by centrifugation at 4200 g for 20 min. Quantitation of methyl oleate was carried out by HPLC analysis with UV detection at 210 nm. Fifty microliters of the supernatant were injected across two 4.6×10 mm guard columns (Inertsil, ODS3, 5 μm) and a longer 4.6×150 mm column (Inertsil, ODS-3, 5 μm). The column was washed with acetonitrile-water (1:1) for 2 min. at a flow rate of 1 mL/min. It was then eluted with a gradient of 50% to 100% acetonitrile over 24 min., followed by a 100% acetonitrile wash for 5 min. Because of the heterogeneity of the carbon chain lengths of commercial methyl oleate, this compound was eluted as two main peaks that were detected at 25.3 minutes and 27.1 minutes. Methyl oleate bound to the XAD-16 resin was quantitated from the methanol extract using the same HPLC method. Standards of methyl oleate were prepared in 83.3% acetonitrile. Consumption of methyl oleate by the cells was calculated as: (total methyl oleate added)−(residual methyl oleate in medium)−(methyl oleate bound to resin).

Results

Figure 6:
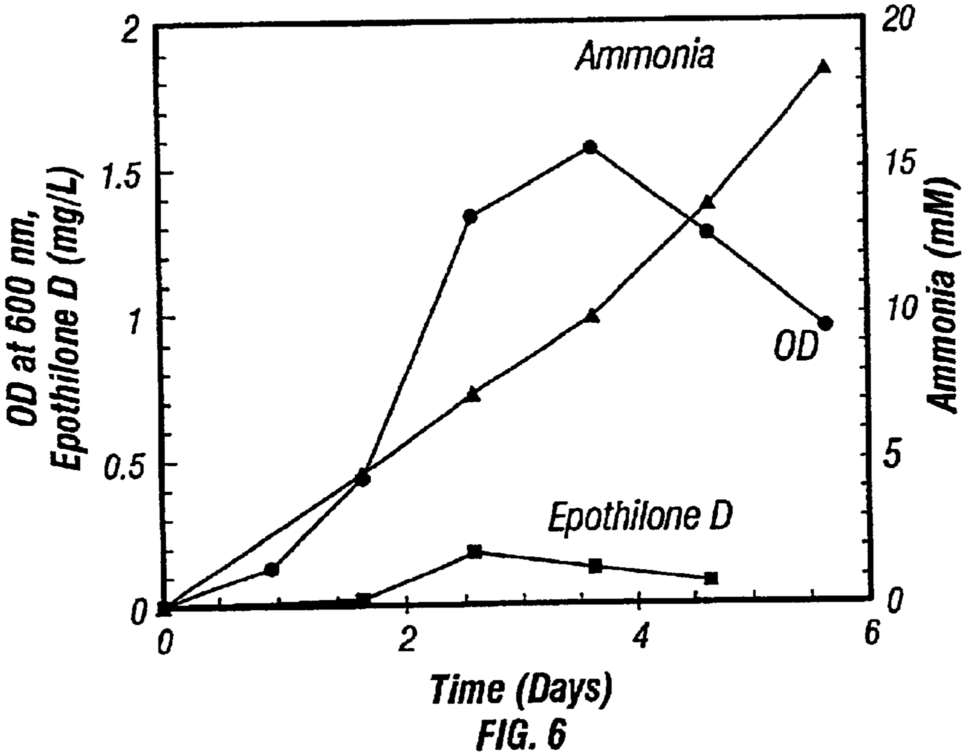
FIG. 6 shows the baseline performance of *Myxococcus xanthus* strain K111-40-1 in a simple production medium consisting only of 5 g/L casitone (a pancreatic casein digest) and 2 g/L magnesium sulfate. Legend: Growth (•), production (■), and ammonia generation (▲) profiles for the basal CTS medium in a batch process; culture conditions were as described in Materials and Methods in Example 3.

The *Myxococcus xanthus* strain K111-40-1 was initially cultivated in a batch fermentation process with a simple production medium consisting only of 5 g/L casitone (a pancreatic casein digest) and 2 g/L magnesium sulfate. The baseline performance of the cells is shown in FIG. 6.

Maximum cell density and epothilone D production were attained three days after inoculation at an $OD_{600}$ of 1.6 and a corresponding titer of 0.16 mg/L. Both cell density and product yield decreased substantially thereafter. With the consumption of casitone by the cells, a gradual accumulation of ammonium was also detected in the production medium. The final ammonia concentration approached 20 mM at the end of the 5-day fermentation.

Effect of XAD-16 on Product Stability

Figure 7:
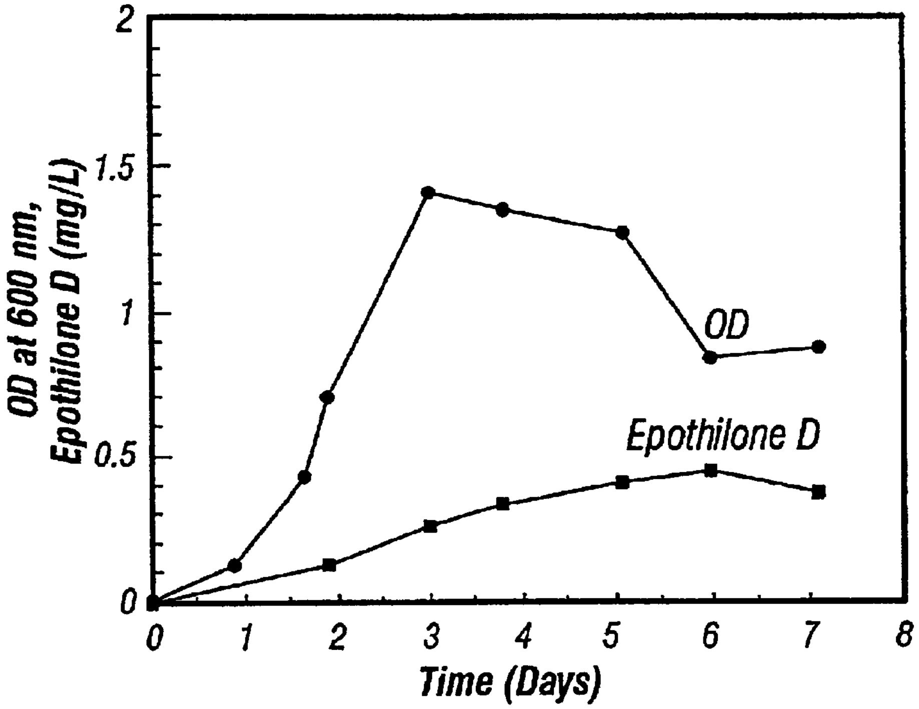
FIG. 7 shows the effect of XAD-16 resin on the fermentation performance of *Myxococcus xanthus* strain K111-40-1 in CTS production medium. Legend: Growth (•) and production (■) profiles with the incorporation of 20 g/L XAD-16 resin to the CTS production medium in a batch process.

To prevent the rapid degradation of epothilone D, the hydrophobic adsorber resin, XAD-16, was added to the production medium to bind and stabilize the excreted product. XAD-16 is a polyaromatic resin that had previously been used by Gerth et al. (1996) for the isolation of epothilones A and B from fermentations of the microbial producer, *Sorangium cellulosum* So ce90. As shown in FIG. 7, the presence of the adsorber resin did not affect the growth of the cells. However, it effectively reduced the loss of epothilone D in the fermentation broth, which led to a three-fold enhancement in the recovery of this product.

Media Development

Figure 8:
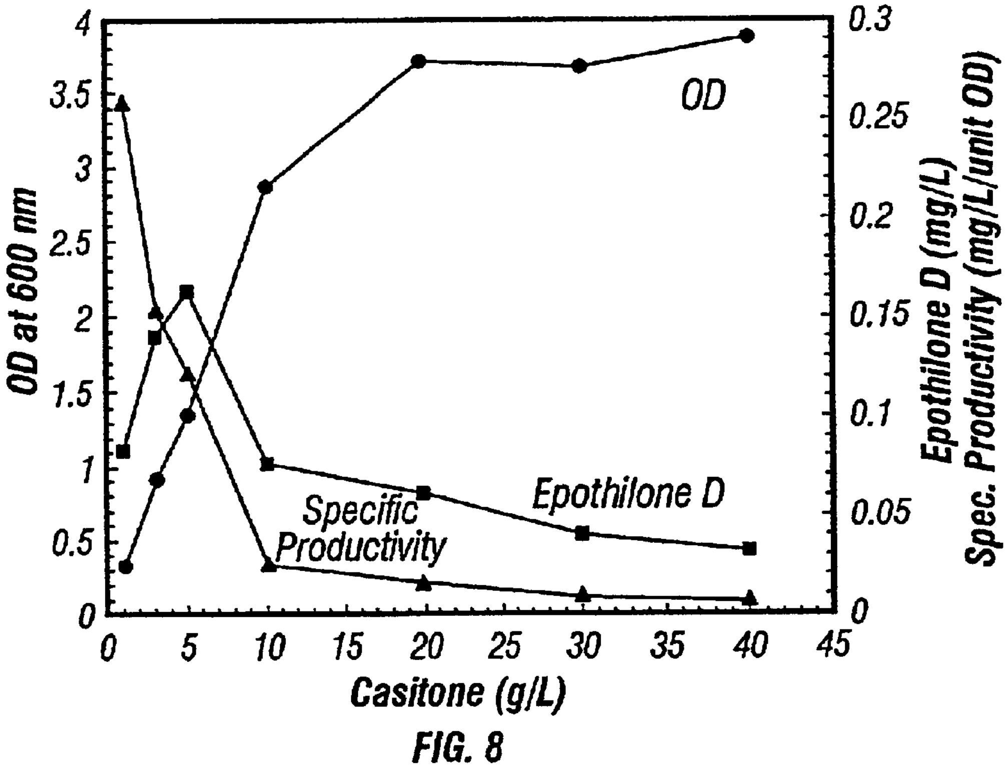
FIG. 8 shows the influence of casitone on growth and product yield. Legend: Effect of casitone concentration on growth (•), production (■), and specific productivity (▲).

In an effort to develop a medium that can support higher cell density and epothilone production, the influence of casitone on growth and product yield was evaluated by varying its concentration from 1 g/L to 40 g/L in the production medium. Although cell growth was stimulated with increasing casitone concentrations, the specific productivity of the cells declined significantly, as shown in FIG. 8. The optimal casitone concentration for epothilone D production was reached at 5 g/L, with higher concentrations resulting in decreased titers.

Because media improvements were limited with the use of casitone, alternative substrates were evaluated as supplements to the basal production medium. From a detailed screen of different oils, methyl oleate was identified as a carbon source that promoted the greatest increase in epothilone D production, as summarized in Table 3.

TABLE 3

| Oil (7 mL/L) | Epothilone D production relative to control with no oil supplements (%) |
|---|---|
| Methyl Oleate | 780 |
| Ethyl Oleate | 740 |
| Coconut Oil | 610 |
| Lard | 470 |
| Propyl Oleate | 420 |
| Sesame Oil | 380 |
| Glycerol Tri-oleate | 370 |
| Salad Oil | 360 |
| Sunflower Oil | 330 |
| Soy Oil | 290 |
| Methyl Heptadecanoate | 190 |
| No Oil (Control) | 100 |
| Methyl Nonadecanoate | 96 |
| Methyl Pelargoante | 40 |
| Rapeseed Oil | 40 |

However, the direct addition of methyl oleate to the production medium resulted in premature cell lysis. Therefore, the seed cultures were grown in the presence of methyl oleate prior to the production fermentations. Interestingly, this adaptation process rendered the cells less susceptible to lysis. As shown in Table 4 (Improvements in Growth and Production Compared to Baseline Performance in CTS Medium in Batch Fermentation), a peak biomass concentration of 2.1 g/L and an epothilone D titer of 3.3 mg/L were achieved with a methyl oleate concentration of 7 mL/L and a trace elements concentration of 4 mL/L.

TABLE 4

| Fermentation Conditions | Maximum Cell Density (g DCW/L) | Maximum Epothilone D Production (mg/L) |
|---|---|---|
| CTS medium with no XAD-16 in batch process | 0.44 ± 0.04 | 0.16 ± 0.03 |
| CTS medium with XAD-16 in batch process | 0.44 ± 0.04 | 0.45 ± 0.09 |
| CTS medium with 7 mL/L methyl oleate in batch process | 1.2 ± 0.1 | 0.12 ± 0.02 |
| CTS medium with 7 mL/L methyl oleate and 4 mL/L trace elements in batch process | 2.1 ± 0.2 | 3.3 ± 0.7 |
| Intermittent fed-batch process | 6.3 ± 0.6 | 9.8 ± 2.0 |
| Continuous fed-batch process | 7.3 ± 0.7 | 23 ± 4.6 |

Figure 9:
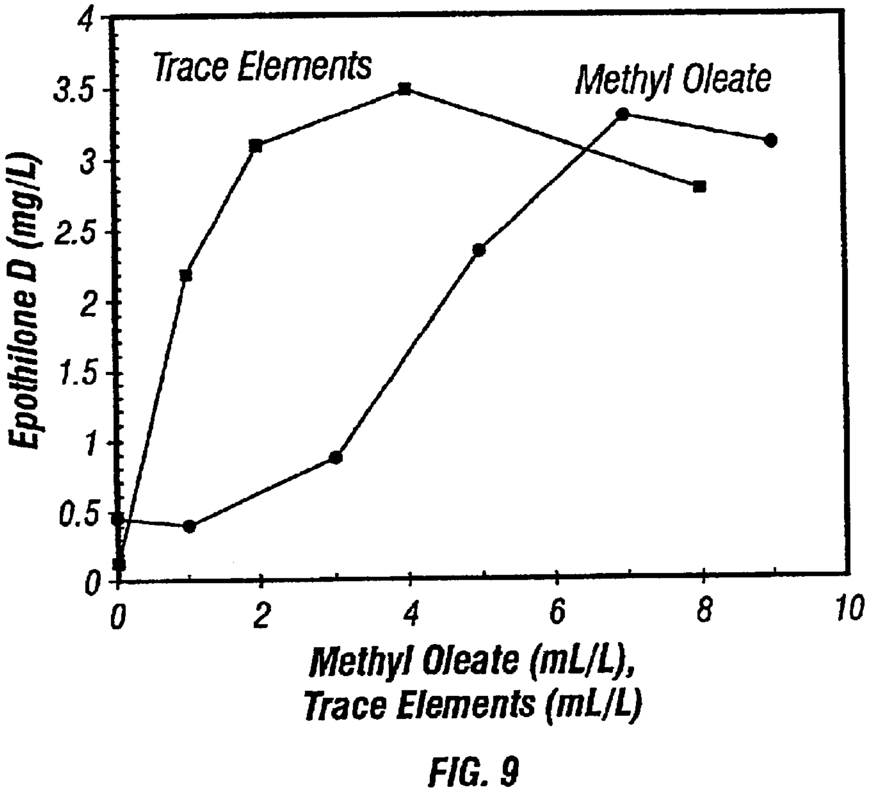
FIG. 9 shows the influence of trace elements and higher methyl oleate concentrations on growth and product yield. Legend: Effect of methyl oleate (•) and trace elements (■) on production.

Further titer improvements were not observed at higher methyl oleate concentrations, as shown in FIG. 9.

In addition to demonstrating the significance of methyl oleate on cell growth and production, the above graph also emphasizes the importance of trace elements in the production medium. In anticipation that the nutrients supplied by casitone may not be sufficient for vigorous cell growth, an exogenous addition of trace metals was added in conjunction with the methyl oleate. Surprisingly, this supplement was found to be essential for both growth and production enhancement. In its absence, the maximum biomass concentration and epothilone D titer were only 1.2 g/L and 0.12 mg/L, respectively. This low titer was comparable to that obtained with the basal medium.

Fed-Batch Development

Figure 10A:
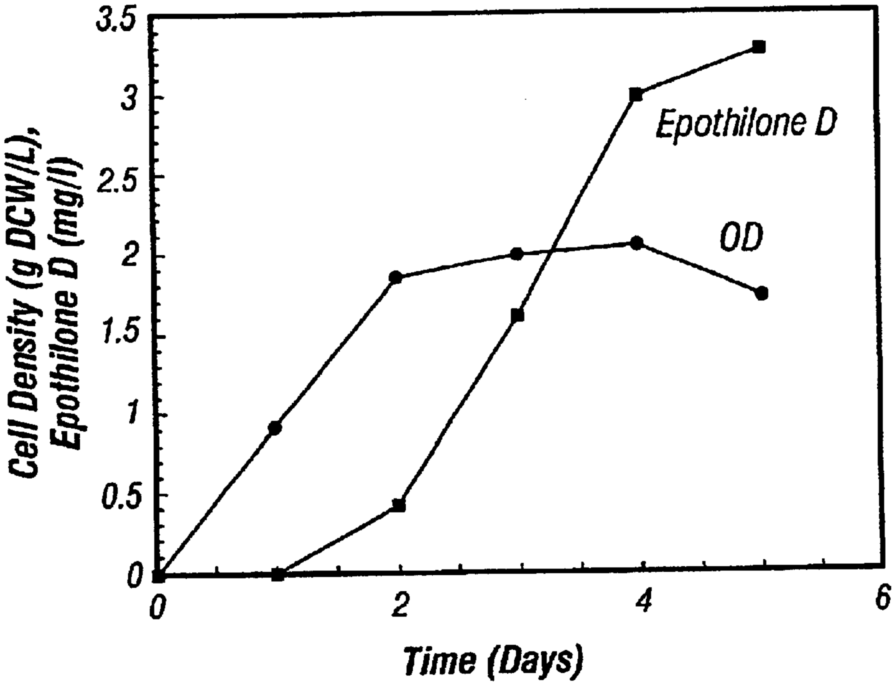
FIG. 10A shows the growth and production of the *M. xanthus* strain in the presence of optimal concentrations of methyl oleate and trace elements in a batch fermentation process. Exponential growth of the occurred during the first two days after inoculation. Production of epothilone D began at the onset of the stationary phase and ceased when cell lysis occurred with the depletion of methyl oleate on day 5.
Figure 10B:
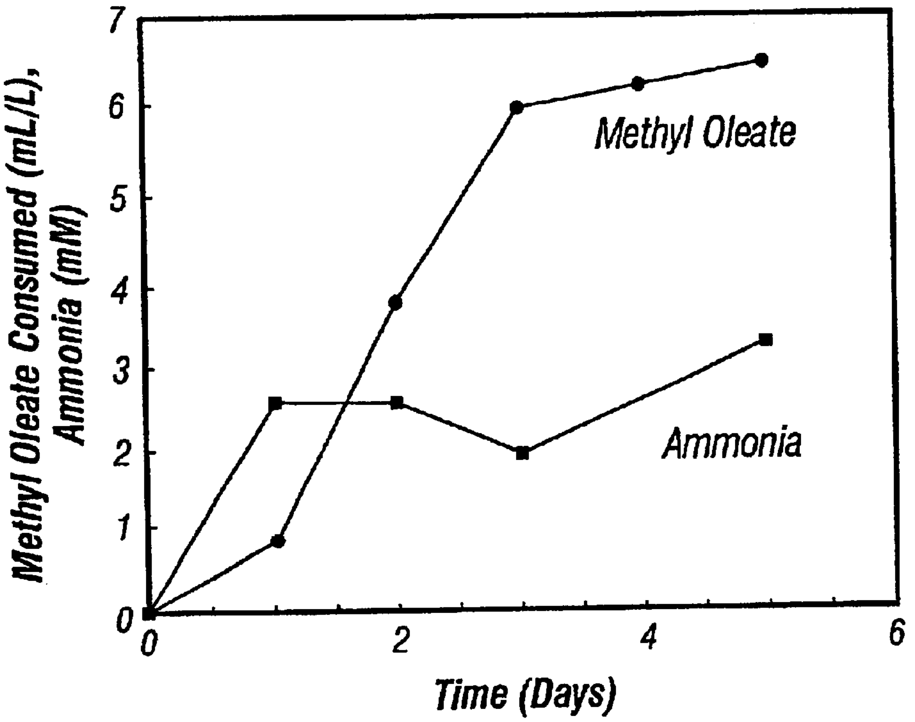
FIG. 10B shows the time courses corresponding to the consumption of methyl oleate and generation of ammonia during the growth and proudction of the *M. xanthus* strain in the presence of optimal concentrations of methyl oleate and trace elements in a batch fermentation process. Legend: A.) Growth (•) and production (■) profiles with the addition of optimal concentrations of methyl oleate (7 mL/L) and trace elements (4 mL/L) to the CTS production medium in a batch process. B.) Time courses corresponding to the consumption of methyl oleate (•) and the generation of ammonia (■).

In the presence of optimal concentrations of methyl oleate and trace elements in a batch fermentation process, exponential growth of the *M. xanthus* strain occurred during the first two days after inoculation. Production of epothilone D began at the onset of the stationary phase and ceased when cell lysis occurred with the depletion of methyl oleate on day 5, as shown in FIGS. 10A and 10B. The time courses for methyl oleate consumption and ammonia generation are also shown. The concentration of ammonia in the production medium was <4 mM throughout the course of the fermentation.

Figure 11A:
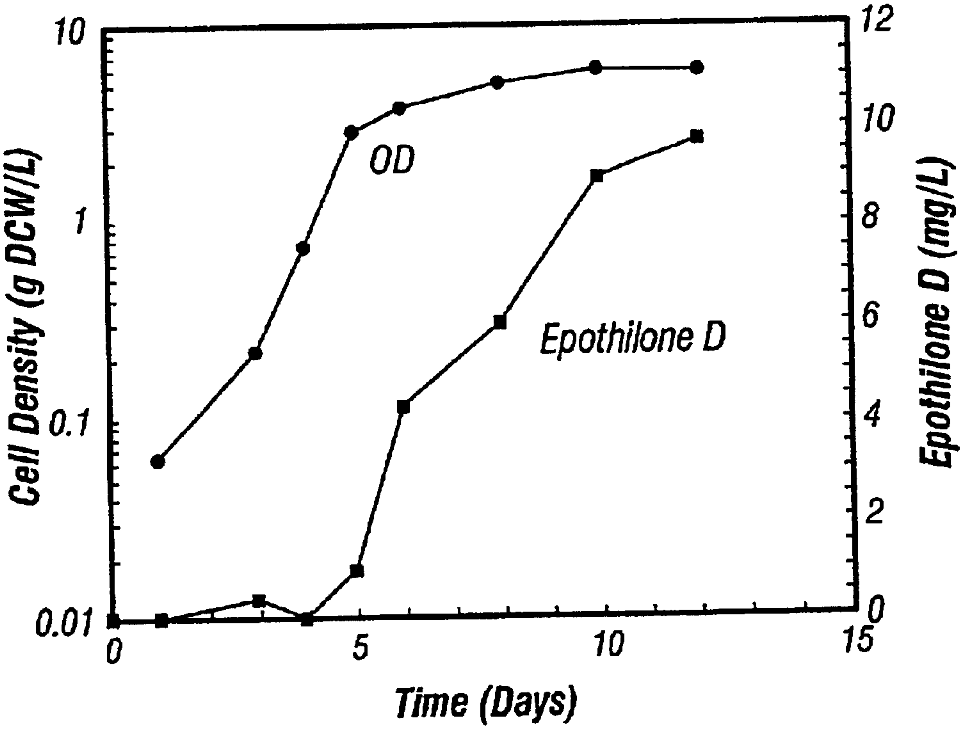
FIG. 11A shows the influence of intermittent fed-batch process on the growth and production of the *M. xanthus* strain. Legend: Growth (•) and production (■) profiles for the intermittent fed-batch process in shake-flasks. The casitone and methyl oleate feed rates were 2 g/L/day and 3 mL/L/day, respectively.
Figure 11B:
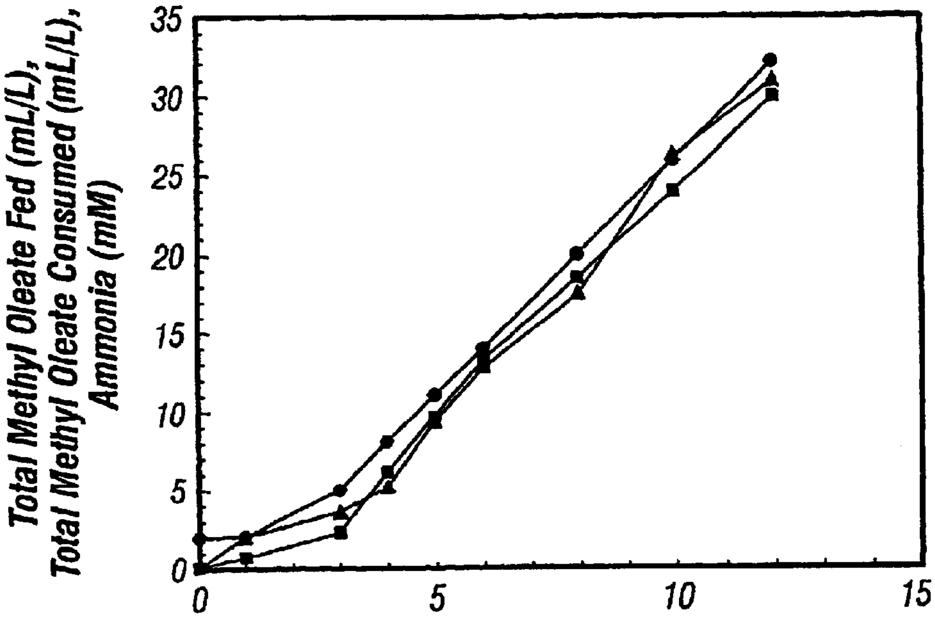
FIG. 11B shows the constant rates of consumption of methyl oleate and generation of ammonia during the course of the fermentation. Legend: Time courses corresponding to the total addition of methyl oleate to the cultures (•), the total consumption of methyl oleate (■), and the generation of ammonia (▲).

To extend the production period of the cells in the flask cultures, casitone and methyl oleate were added to the medium once a day at a rate of 2 g/L/day and 3 mL/L/day, respectively. The substrate feeds were initiated 48 h after inoculation, and the cells grew exponentially for three days thereafter. As shown in FIG. 11A, the biomass concentration began to plateau on day 5 and reached a maximum at 6.3 g/L on day 10. Again, epothilone D production coincided with the stationary growth phase, and a final yield of 9.8 mg/L was attained at the end of day 12. As shown in the FIG. 11B, both the consumption of methyl oleate and the generation of ammonia increased at constant rates over the course of the fermentation.

Methyl oleate was depleted at the same rate it was fed to the bioreactor, and ammonia accumulated at a rate of 3.2 mM/day. Lower feed rates of casitone or methyl oleate greatly reduced the epothilone D titer, while higher feed rates led to the premature lysis of the cells before significant production was achieved.

Figure 12:
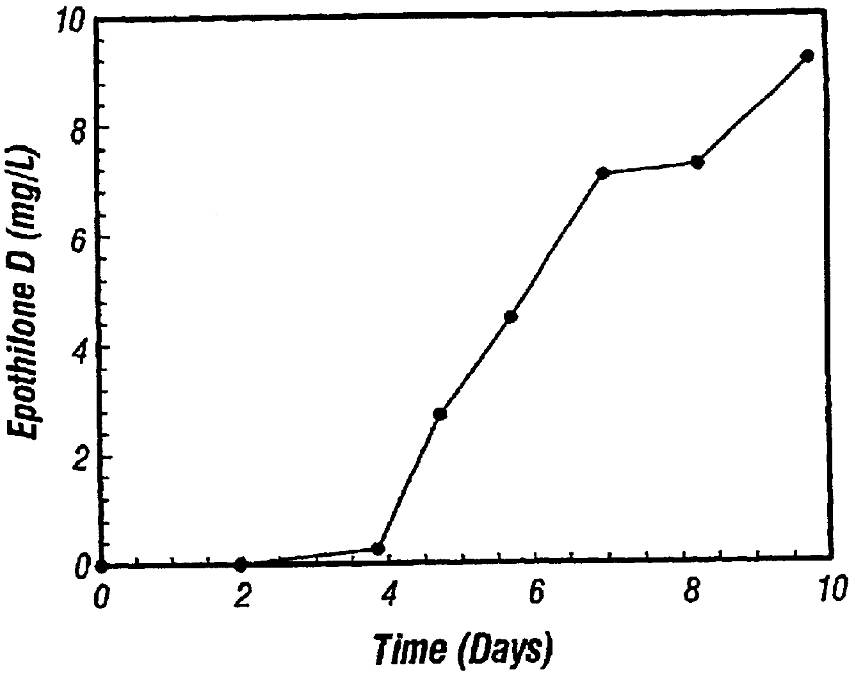
FIG. 12 shows the production profile for the intermittent fed-batch process in a 5-L bioreactor. The casitone and methyl oleate feed rates were 2 g/L/day and 3 mL/L/day, respectively.

To test the effectiveness of the fed-batch process on a larger scale, casitone and methyl oleate were added intermittently at 24-h intervals to a 5-L fermentation in a bioreactor. As shown in FIG. 12, the resulting production curve closely resembled that for the flask cultures. The substrate feeds were initiated 24 h after inoculation, and the production of epothilone began on day 4. A peak epothilone D titer of 9.2 mg/L was obtained ten days after inoculation.

Figure 13A:
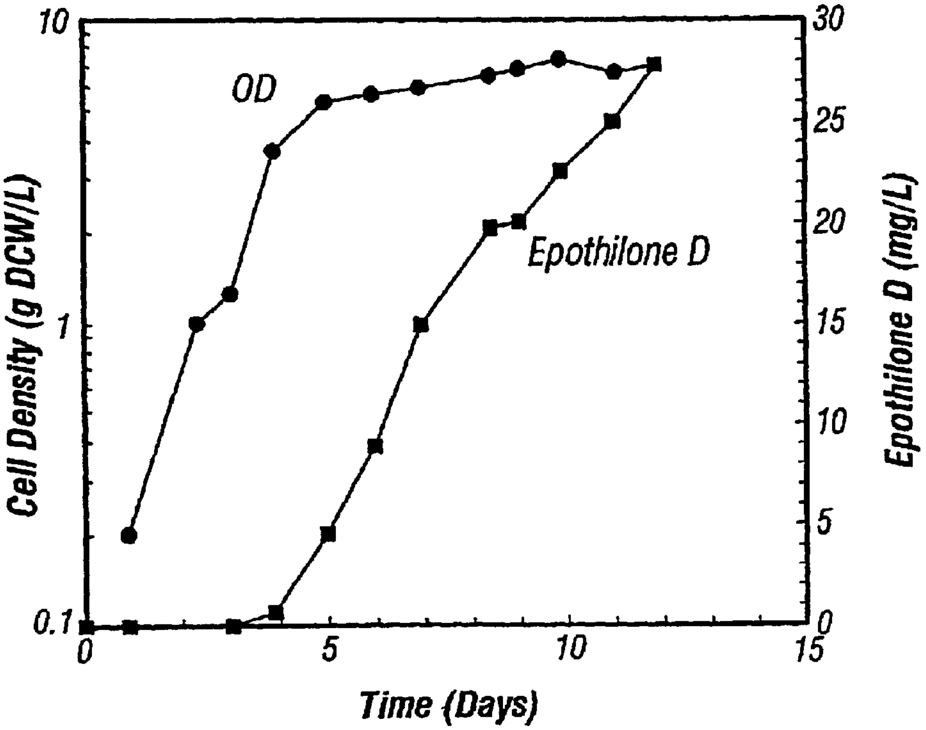
FIG. 13A shows the impact of continous feeds on growth and production. Legend: Growth (•) and production (■) profiles for the continuous fed-batch process in a 5-L bioreactor. The casitone and methyl oleate feed rates were 2 g/L/day and 3 mL/L/day, respectively.
Figure 13B:
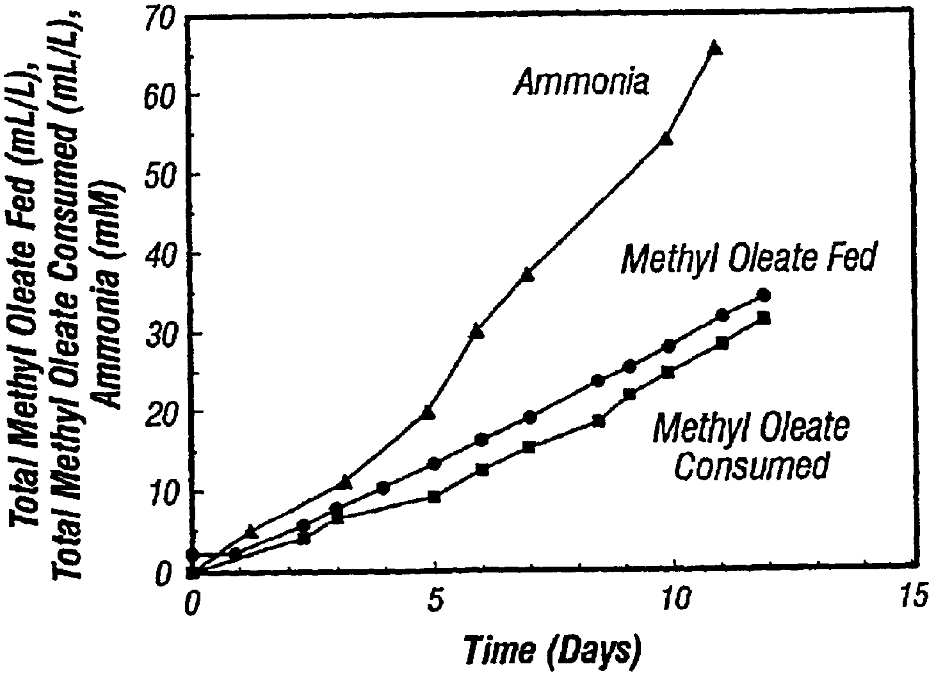
FIG. 13B shows the time course of methyl oleate addition and consumption as well as the generation of ammonia during the continuous fed-batch process. Legend: Time courses corresponding to the total addition of methyl oleate to the cultures (•), the total consumption of methyl oleate (■), and the generation of ammonia (▲); culture conditions were as described in Materials and Methods

To assess the impact of a more refined feeding strategy on growth and production, the dual feeds were delivered continuously to the bioreactor. As illustrated in FIG. 13A, the implementation of the continuous feeds did not affect the growth of the cells, but it increased their productivity by nearly three-fold. A final epothilone D titer of 27 mg/L was achieved 10 days after inoculation. As shown in FIG. 13B, methyl oleate was consumed at the same rate it was added to the production medium, and ammonia was released at a steady rate of 6.4 mM/day over the course of the fermentation.

Discussion

Although the chemical synthesis of epothilone D has recently been achieved (Harris et al., 1999; Meng et al., 1998; Sinha et al., 1998), the complex 20-step process is not an economically viable method for the large-scale production of the compound. While the initial production yield for epothilone D in *Myxococcus xanthus* strain was 0.16 mg/L, the improved fermentation processes of the invention substantially increased the production level to 23 mg/L.

One of the major barriers to attaining a higher epothilone D titer was rapid degradation of the product in the fermentation broth. This problem was alleviated with the incorporation of an adsorber resin to the culture medium. The addition of XAD-16 did not affect the growth of the cells but minimized the loss of the excreted product and increased its recovery by three-fold.

Another obstacle to enhancing the production yield is the limited improvement in titer with the use of casitone as the primary carbon and nitrogen source. Although growth of the *M. xanthus* strain was stimulated with increasing casitone concentrations, a concentration that exceeded 5 g/L resulted in a dramatic decrease in titer. This inhibitory effect in secondary metabolite production at high concentrations of peptone or casitone has previously been demonstrated in several other myxobacterial fermentations and has been attributed to the accumulation of ammonia in the culture medium.

Because *M. xanthus* is incapable of metabolizing polysaccharides and sugars (Reichenbach and Dworkin, 1991), its ability to utilize oils as a carbon source was examined. Oils are attractive carbon substrates, because the oxidation of fatty acids not only can serve as a source of energy for the cells, but the formation of acetyl-CoA as a degradation product can also provide precursors for epothilone biosynthesis. The addition of oils to the fermentation of *Saccharopolyspora erythraea, Streptomyces fradiae*, and *Streptomyces hygroscopicus* has been shown to enhance the production of polyketide molecules, such as erythromycin, tylosin, and the immunoregulant L-683590, respectively (Mirjalili et al., 1999; Choi et al., 1998; Junker et al., 1998).

From a screen of different oils, methyl oleate was identified as the leading candidate in promoting cell growth and epothilone D production. These improvements, however, were observed only with the simultaneous addition of trace metals to the production medium. The sole addition of methyl oleate at 7 mL/L increased the maximum cell density from 0.4 g DCW/L to 1.2 g DCW/L, but the production remained at the baseline level. With the exogenous supplement of 4 mL/L of trace elements, the peak biomass concentration increased to 2.1 g DCW/L, and the epothilone D titer was boosted from 0.45 mg/L to 3.3 mg/L. These findings indicate that nutritional components deficient in casitone may be important for the growth of *M. xanthus* and the formation of epothilones.

With the establishment of optimal concentrations of methyl oleate and trace elements for a batch process, efforts were made to develop a feeding strategy to maintain vigorous cell growth and to prolong the production period. Intermittent and continuous feeds of casitone and methyl oleate at constant rates were evaluated, and both methods resulted in similar improvements in the growth profiles. With optimal feeds of the two substrates, maximum cell densities of about 6.8 g DCW/L were obtained. In both cases, methyl oleate was depleted as it was added to the fermentation medium.

In contrast to cell growth and methyl oleate consumption, epothilone production and ammonia generation were greatly influenced by the choice of the feeding strategy. In the continuous fed-batch culture, a peak epothilone D titer of 23 mg/L was obtained. This was nearly 2.5 times the titer obtained for the intermittent fed-batch culture. With the continuous feeds, the rate at which ammonia was released by the cells was also twice as high, suggesting a higher rate of casitone consumption. Together, these results indicate that the lower titers associated with the intermittent fed-batch process may have been caused by catabolite repression and not ammonia accumulation. Moreover, they suggest that the productivity of the *M. xanthus* strain is sensitive to the amount of substrates present in the culture medium and may be maximal under substrate-limiting conditions. This is also consistent with the observation that increasing casitone concentration in the production medium results in higher cell densities but lower titers.

Compared to the batch cultures with the basal medium, the continuous fed-batch cultures yielded a 17-fold increase in cell density and a 140-fold increase in titer. This process has been scaled from 5-L to 1000-L and shown to perform equivalently. The results shown for producing epothilone D on a manufacturing scale demonstrate that *M. xanthus* can be used as a host for the production of other biologically active molecules from myxobacteria.

References

Bollag et al. 1995. Epothilones, a new class of microtubule-stabilizing agents with a taxol-like mechanism of action. Cancer Res 55:2325–2333.

Choi et al. 1998. Effects of rapeseed oil on activity of methylmalonyl-CoA carboxyltransferase in culture of *Streptomyces fradiae*. Biosci Biotechnol Biochem 62:902–906.

Chou et al. 1998. Desoxyepothilone B: An efficacious microtubule-targeted antitumor agent with a promising in vivo profile relative to epothilone B. Proc Natl Acad Sci USA 95:9642–9647.

Gerth et al. 1996. Epothilons A and B: Antifungal and cytotoxic compounds from *Sorangium cellulosum* (myxobacteria)—production, physico-chemical, and biological properties. J Antibiot (Tokyo) 49:560–563.

Gerth et al. 2000. Studies on the biosynthesis of epothilones: the biosynthetic origin of the carbon skeleton. J Antibiot (Tokyo) 53:1373–1377.

Gerth et al. 2001. Studies on the biosynthesis of epothilones: The PKS and epothilone C/D monooxygenase. J Antibiot (Tokyo) 54:144–148.

Harris et al. 1999. New chemical synthesis of the promising cancer chemotherapeutic agent 12,13-desoxyepothilone B: Discovery of a surprising long-range effect on the diastereoselectivity of an aldol condensation. J Am Chem Soc 12:7050–7062.

Hecht et al. 1990. Hollow fiber supported gas membrane for in situ removal of ammonium during an antibiotic fermentation. Biotechnol Bioeng 35:1042–1050.

Junker et al. 1998. Use of soybean oil and ammonium sulfate additions to optimize secondary metabolite production. Biotechnol Bioeng 60:580–588.

Kowalski et al. 1997. Activities of the microtubule-stabilizing agents epothilones A and B with purified tubulin and in cells resistant to paclitaxel. J Biol Chem 272:2534–41.

Meng et al. 1997. Remote effects in macrolide formation through ring-forming olefin metathesis: An application to the synthesis of fully active epothilone congeners. J Am Chem Soc 119:2733–2734.

Mirjalili et al. 1999. The effect of rapeseed oil uptake on the production of erythromycin and triketide lactone by *Saccharopolyspora erythraea*. Biotechnol Prog 15:911–918.

Molnár et al. 2000. The biosynthetic gene cluster for the microtubule-stabilizing agents epothilones A and B from *Sorangium cellulosum* So ce90. Chem Biol 7:97–109.

Reichenbach et al. The Prokaryotes II Eds. New York: Springer-Verlag. p 3417–3487.

Reichenbach et al. 1993. Production of Bioactive Secondary Metabolites. In: Dworkin M, Kaiser D, editor. Myxobacteria II. Washington, D.C.: American Society for Microbiology. p 347–397.

Sinha et al. 1998. The antibody catalysis route to the total synthesis of epothilones. Proc Natl Acad Sci USA 95:14603–14608.

Su et al. 1997. Structure-activity relationships of the epothilones and the first in vivo comparison with paclitaxel. Angew Chem Int Ed Engl 36:2093–2096.

Tang et al. 2000. Cloning and heterologous expression of the epothilone gene cluster. Science 287:640–642.

B. Production of Epothilone B

Flasks

A 1 mL vial of the K111-32-25 strain is thawed and the contents transferred into 3 mL of CYE seed media in a glass tube. This culture is incubated for 72±12 hours at 30° C., followed by the subculturing of 3 mL of this tube culture into 50 mL of CYE media within a 250 mL baffled Erlenmeyer flask. This CYE flask is incubated for 24±8 hours at 30° C., and 2.5 mL of this seed (5% v/v) used to inoculate the epothilone production flasks (50 mL of CTS-TA media in a 250 mL baffled Erlenmeyer flask). These flasks are then incubated at 30° C. for 48±12 hours, with a media pH at the beginning of 7.4.

Fermentors

A similar inoculum expansion of K111-32-25 as described above is used, with the additional step that 25 mL of the 50 mL CYE seed is subcultured into 500 mL of CYE. This secondary seed is used to inoculate a 10 L fermentor containing 9.5 L of CTS-TA, and 1 g/L of sodium pyruvate. The process parameter setpoints for this fermentation are: pH—7.4; agitation—400 rpm; sparge rate—0.15 vvm. These parameters were sufficient to maintain the DO at greater than 80% of saturation. The pH control is provided by addition of 2.5 N sulfuric acid and sodium hydroxide to the cultures. Peak epothilone titers are achieved at 48±8 hours.

C. Production of Epothilone D

Flasks

A 1 mL vial of the K111-40-1 strain (described in Example 4) is thawed and the contents transferred into 3 mL of CYE seed media in a glass tube. This culture is incubated for 72±12 hours at 30° C., followed by the subculturing of 3 mL of this tube culture into 50 mL of CYE media within a 250 mL baffled Erlenmeyer flask. This CYE flask is incubated for 24±8 hours at 30° C., and 2.5 mL of this seed (5% v/v) used to inoculate the epothilone production flasks (50 mL of 1× wheat gluten media in a 250 mL baffled Erlenmeyer flask). These flasks are then incubated at 30° C. for 48±12 hours, with a media pH at the beginning of 7.4.

Fermentors

A similar inoculum expansion of K111-40-1 as described above is used, with the additional step that 25 mL of the 50 mL CYE seed is subcultured into 500 mL of CYE. 250 mL of this secondary seed is used to inoculate a 5 L fermentor containing 4.5 L of CTS-TA, with a 1 g/L daily feed of sodium pyruvate. The process parameter setpoints for this fermentation are: pH—7.4; agitation—400 rpm; sparge rate—0.15 vvm. These parameters were sufficient to maintain the DO at greater than 80% of saturation. The pH control is provided by addition of 2.5 N sulfuric acid and sodium hydroxide to the cultures. Peak epothilone titers are achieved at 36±8 hours. The peak epothilone C titer is 0.5 mg/L, and the peak epothilone D titer is 1.6 mg/L.

Table 5 is a summary of the media that were used and their respective components.

TABLE 5

| Component | Concentration |
|---|---|
| CYE Seed Media | |
| Casitone (Difco) | 10 g/L |
| Yeast Extract (Difco) | 5 g/L |
| $MgSO_4.7H_2O$ (EM Science) | 1 g/L |
| HEPES buffer | 50 mM |
| CTS-TA Production Media | |
| Casitone (Difco) | 5 g/L |
| $MgSO_4.7H_2O$ (EM Science) | 2 g/L |
| L-alanine, L-serine, glycine | 1 mg/L |
| HEPES buffer | 50 mM |
| 1x Wheat Gluten Production Media | |
| Wheat Gluten (Sigma) | 5 g/L |
| $MgSO_4.7H_2O$ (EM Science) | 2 g/L |
| HEPES buffer | 50 mM |

The CYE seed media and the CTS-TA production media are sterizlied by autoSterilized autoclaving for 30 minutes at 121° C. The wheat gluten production media is sterilized by autoclaving for 45 minutes at at 121° C.

D. Production of Epothilone C and D from *Myxococcus xanthus*

In one aspect, the present invention provides an improved fermentation process for Myxococcus strains, including but not limited to *M. xanthus* K111-40-1, in which the fermentation media provides carbon sources that can be utilized without generation of ammonia. In one preferred embodiment, the carbon source is an oil, such as methyl oleate or a similar oil. In shake flask tests with a variety of feed ratios, these methods resulted in the production of epothilones C and D, predominantly epothilone D, at levels ranging from 15 to 25 mg/L, as described below.

Seed Culture

A frozen 1 mL vial of *M. xanthus* K111-40-1 cells that had been grown in 50 mL of CYE medium with 2 mL/L methyl oleate was used to inoculate 3 mL of fresh CYE medium with 1 mL/L methyl oleate in a sterile glass tube. The tube was incubated at 30° C. in a 250 RPM shaker for 24 hrs. The inoculum in the glass tube was then transferred into a 256 mL unbaffled flask that contained 50 mL of fresh CYE medium with 2 mL/L methyl oleate. The flask was incubated at 30° C. in a 250 RPM shaker for 48 hrs.

Production Flask 1 g of Amberlite XAD-16 was sterilized in a 250-mL unbaffled flask by autoclaving at 121° C. for 30 min. 50 mL of sterile production media were then added to the flask. The flask was inoculated with 5% (v/v) of the seed culture and was placed in an incubator shaker operating at 250 RPM and 30° C. A 3 mL/L/day feed of sterile methyl oleate was initiated two days after the time of inoculation, and a 2 g/L/day feed of casitone was initiated one day after the time of inoculation.

Product Extraction

After 14 days, the XAD resin in the production flask was transferred into a 50 mL centrifuge tube. Excess medium in the tube was decanted without removing any of the resin. The XAD resin was then washed with 25 mL of water and allowed to settle. The water in the tube was decanted without removing any of the resin, and 20 mL of methanol were added to the tube. The centrifuge tube was placed on a shaker at 175 RPM for 20–30 min. to extract the epothilone products from the resin. The methanol extract was transferred to a new centrifuge tube for storage and LC/MS analysis.

Table 6 is a summary of the media that were used and their respective components.

TABLE 6

| Component | Concentration |
|---|---|
| CYE Media | |
| Casitone (Difco) | 10 g/L |
| Yeast Extract (Difco) | 5 g/L |
| $MgSO_4.7H_2O$ (EM Science) | 1 g/L |
| Production Media | |
| Casitone (Difco) | 5 g/L |
| $MgSO_4.7H_2O$ (EM Science) | 2 g/L |
| Added to Production Media after autoclaving | |
| 1000x Trace Element Solution | 4 mL/L |
| Methyl Oleate | 2 mL/L |

The CYE media and the production media are sterizlied by autoSterilized autoclaving for 30 minutes at 121° C. The trace element solution is filter-sterilized; the methyl oleate is autoclaved separately.

Trace element solution is made by combining all of the components in Table 7, adding 10 mL/L concentrated $H_2SO_4$ to the solution and brining the final volume to 1 L.

TABLE 7

| Component | Concentration |
|---|---|
| 1000x Trace Element Solution | |
| $FeCl_3$ | 8.6 g/L |
| $ZnCl_2$ | 2.0 g/L |
| $MnCl_2.4H_2O$ | 1.0 g/L |
| $CuCl_2.2H_2O$ | 0.43 g/L |
| $H_3BO_3$ | 0.31 g/L |
| $CaCl_2.6H_2O$ | 0.24 g/L |
| $Na_2MoO_4.2H_2O$ | 0.24 g/L |

The resulting solution is filtered sterilized.

E. Fermentation, Production, and Purification of Epothilones from *Myxococcus xanthus*

Description of *M. xanthus* strains

Strain K111-25-1 is the epothilone B producing strain, which also produces epothilone A. Strain K111-40-1 is the epothilone D producing strain, which also produces epothilone C.

Maintainance of *M. xanthus* on plates

The *M. xanthus* strains are maintained on CYE agar plates (see Table 8 for plate composition). Colonies appear approximately 3 days after streaking out on the plates. Plates are incubated at 32° C. for the desired level of growth and then stored at room temperature for up to 3 weeks (storage at 4° C. on plates can kill the cells).

TABLE 8

| Component | Concentration |
|---|---|
| CYE Agar Plates* | |
| Hydrolyzed casein (pancreatic digest) | 10 g/L |
| Yeast extract | 5 g/L |
| Agar | 15 g/L |
| $MgSO_4$ | 1 g/L |
| 1 M MOPS buffer solution (pH 7.6) | 10 mL/L |

*1 L agar media batches are autoclaved for 45 minutes, then poured out into petri dishes.

Oil Adaptation of *M. xanthus* for Cell Banking

Transfer a non-oil adapted colony from a CYE plate or a frozen vial of cells into a 50 mL glass culture tube containing 3 mL of CYE seed media and 1 drop of methyl oleate from a 100 $\mu$L pipet. Allow cells to grow for 2–6 days (30° C., 175 rpm) until the culture appears dense under a microscope. Start several (5–7) tubes in parallel, as these cells do not always adapt well to the oil.

Cell Banking Procedure (Master Cell Bank)

Start an oil-adapted tube culture as described above. When the tube culture is sufficiently dense (OD=5+/−1), transfer the entire contents of the tube into a sterile 250 mL shake flask containing 50 mL of CYE-MOM seed media (see table below for media composition). After 48±12 hours of growth in a shaker incubator (30° C., 175 rpm), transfer 5 mL of this seed culture into 100 mL of CYE-MOM in a 500 mL shake flask. Allow this culture to grow for 1 day in a shaker incubator (30° C., 175 rpm). Check culture microscopically for appropriate growth and lack of contamination.

Combine 80 mL of this seed culture and 24 mL of sterile 90% glycerol in a sterile 250 mL shake flask. Swirl to thoroughly mix, and aliquot 1 mL of this mixture into 100 sterile, prelabeled cryovials. Slow freeze vials by placing them in a −80° C. freezer.

Cell Banking Procedure (Working Cell Bank)

Start a tube culture by thawing one of the master cell bank vials produced as described above at room temperature, then depositing its entire contents into a glass tube containing 3 mL of CYE-MOM seed media. When this tube culture is sufficiently dense (OD=5+/−1), transfer the entire contents of the tube into a sterile 250 mL shake flask containing 50 mL of CYE-MOM seed media. After 48±12 hours of growth (at 30° C., 175 rpm), transfer 5 mL of this seed culture into 100 mL of CYE-MOM in a 500 mL shake flask. Allow this to grow for 1 day (30° C., 175 rpm). Check microscopically for growth and contamination.

Combine 80 mL of this seed culture and 24 mL of sterile 90% glycerol in a sterile 250 mL shake flask. Swirl to thoroughly mix, and aliquot 1 mL of this mixture into 100 sterile, prelabeled cryovials. Slow freeze vials by placing them in a −80° C. freezer.

Composition of Seed Media

The same seed media as described by Table 9 is used for cell banking and the expansion of the cell bank vials up to any required volume.

TABLE 9

| Component | Concentration |
|---|---|
| CYE-MOM Seed Medium* | |
| Hydrolyzed casein (pancreatic digest) - Difco | 10 g/L |
| Yeast extract - Difco | 5 g/L |
| $MgSO_4.7H_2O$ - EM Science | 1 g/L |
| Methyl Oleate - Cognis | 2 mL/L |

*Note: the methyl oleate is added after the other ingredients, as it forms an emulsion in the casitone and does not completely mix with the other components.

Inocula Scaleup for Shake Flask, 5 L, and 1000 L Fermentations

Thaw a frozen working cell bank vial of the methyl oleate adapted cells. Transfer the entire contents of the vial into a 50 mL glass culture tube, containing 3 mL of the CYE-MOM seed media. Place tube in a shaker (30° C., 175 rpm), and grow for 48±24 hours. Transfer the entire contents of the culture tube into a 250 mL shake flask containing 50 mL of CYE-MOM seed media. Place flask in a shaker (30° C., 175 rpm) and grow for 48±24 hours. For use in shake flask experiments, expand this seed by subculturing 10 mL of this culture into 40 mL of fresh CYE-MOM in 5 new seed flasks. Incubate seed flasks in shaker (30° C., 175 rpm) for 24±12 hours for use as an inoculum for flask volume (30–100 mL) production cultures. Inoculate production flasks at 4.5% of the combined (seed and production media) initial volume.

To prepare seeds for small scale (5–10 L) fermentations, subculture the entire contents of one of these 50 mL seed flasks into a sterile 2.8 L fernbach flask containing 500 mL of CYE-MOM. Incubate this fernbach flask in a shaker (30° C., 175 rpm) for 48±24 hours for use as the fermentor inoculum. Inoculate the production fermentation at about 5% of the combined initial volume.

Further seed expansion is required for large scale (1000 L) fermentations. Here, 1 L of the fernbach flask seed is used to inoculate (5% by volume) a 10 L seed fermentor containing 9 L of CYE-MOM. The fermentor pH is controlled at 7.4 by addition of 2.5 N potassium hydroxide and 2.5 N sulfuric acid. The temperature is set at 30° C. The dissolved oxygen is maintained at or above 50% of saturation by cascading of the stir rate between 400–700 rpm. The initial agitation rate is set at 400 rpm, and the sparging rate was maintained at 0.1 v/v/m. After 24±12 hours of growth in the 10 L fermentor, the entire culture is transferred into a 150 L fermentor containing 90 L CYE-MOM. The pH is once again controlled at 7.4 with 2.5 N potassium hydroxide and 2.5 N sulfuric acid. The temperature is set at 30° C. The dissolved oxygen is maintained at or above 50% of saturation by cascading of the stir rate between 400–700 rpm. The initial agitation rate is set at 400 rpm, and the sparging rate is maintained at 0.1 v/v/m.

XAD-16 Resin Preparation for Fermentations

Transfer the required amount of XAD-16 resin (Rohm & Haas) into a methanol safe container with a minimum volume of 3 times the weight of XAD-16 resin (i.e., 1.2 kg of resin requires a container of at least 3.6 L). Wash the resin thoroughly with 100% methanol to remove any monomers present on the virgin resin. Add two times the amount of methanol in liters as the weight of the resin in kilograms (i.e. 6 liters of methanol for 3 kilograms of XAD-16). Mix the methanol and XAD slurry for 5 minutes to remove any monomers present on the XAD-16. Stir the slurry gently while mixing to minimize resin fragmentation. Stop mixing, and allow the resin to gravity settle for not less than 15 minutes. Drain the methanol from the container, leaving a 0.5 to 1 inch layer of methanol above the XAD bed. Transfer the XAD and methanol from the mixing container to an Amicon VA250 column. Attach the top bed support to the column and seal the bed support by turning the seal adjust knob clockwise. Wash the XAD in the column with not less than 5 column volumes of methanol at 300±50 cm/hr. Collect methanol flow through in the solvent waste receptacle. Wash the XAD in the column with not less than 10 column volumes of deionized water at 300±50 cm/hr.

The composition of the epothilone production media is described in Table 10.

TABLE 10

| Component | Concentration |
|---|---|
| CTS-MOM Production Media | |
| Casitone (Difco) | 5 g/L |
| $MgSO_4.7H_2O$ (EM Science) | 2 g/L |
| XAD-16 | 20 g/L |
| Added after autoclaving | |
| 1000x Trace Element Solution | 4 mL/L |
| Methyl Oleate | 2 mL/L |

*Note: the methyl oleate is added after the other ingredients, as it forms an emulsion in the casitone and does not completely mix with the other components. Trace Element Solution is as described in Table 7.

Preparation and Flask-Scale (50 mL) Epothilone Production Fermentation

Autoclave 1 g of XAD-16 in a 250 mL shake flask with sufficient deionized water (~3 mL) to cover the resin. Flasks are sterilized by autoclaving for 30 minutes at 121° C. Add the following media components to the flask aseptically: 50 mL of CTS-MOM production medium, and 2.5 mL of 1 M HEPES buffer (titrated to a pH of 7.6 with potassium hydroxide). Inoculate the cultures with 2.5 mL of the CYE seed flask (4.5% volume/volume inoculum). Incubate the production flasks on a shaker at 30° C. and 175 rpm.

Start the casitone and methyl oleate feeds 24±6 hours after inoculation. At this point, and every 24±6 hours thereafter, feed 1 mL of a 100 g/L casitone solution and 150 $\mu$L of methyl oleate. Continue this feeding regimen for up to 13 days following the initial feed, or until cells are observed to begin lysis (day 11–14). To determine epothilone production kinetics, a representative 5 mL sample of well-mixed fermentation broth and XAD can be sampled. Additionally, a small (0.25–0.5 mL) sample of broth without the XAD can be taken daily to check on the status of the culture growth visually. When massive cell lysis is observed, the remainder of the culture volume should be harvested.

Preparation and 5 L-Scale Epothilone Production Fermentation 100 g XAD and 8 g $MgSO_4.7H_2O$ are combined with 3.9 L of deionized water, and sterilized (90 minutes, 121° C.) in a 5 L B-Braun bioreactor. A sufficient volume (133 mL) of a presterilized casitone/deionized water solution (150 g/L) is pumped in aseptically to attain a final casitone concentration of 5 g/L in the fermentor. An initial methyl oleate concentration of 2 mL/L is achieved by addition of 10 mL of this oil. Finally, 16 mL of a presterilized trace elements solution are added aseptically prior to inoculation. The fermentor is then inoculated with 200 mL of the CYE seed culture (4.8% volume/volume) and permitted to grow for 24±6 hours. At this point, the casitone (2 g/L/day, continuous feed) and methyl oleate (3 mL/L/day total, fed semi-continuously every 90 minutes) feeds are initiated. Airflow is held constant in the bioreactor at 0.4–0.5 vvm (the increasing fermentation volume as the feeds progress causes this variation). The dissolved oxygen concentration is controlled at 50% of saturation by a stirring cascade (400–700 rpm). The 100% of saturation dissolved oxygen calibration point is established by setting the initial agitation at 400 rpm, and the initial airflow at 0.5 vvm. The pH setpoint of 7.4 is maintained by automated addition of 2.5N $H_2SO_4$ and 2.5N KOH. Epothilone production continues for 11–14 days following inoculation, with the bioreactor is harvested when cell lysis is apparent in the broth samples and the demand for oxygen (as indicated by the agitation rate) abruptly decreases. Epothilone D titers generally reach 18–25 mg/L in this fermentation process.

Preparation and 1000 L-Scale Epothilone Production Fermentation

The 1000 L fermentor was prepared for epothilone production as follows. 600 L of water and 18 L (11.574 kg) of XAD-16 was sterilized (45 minutes, 121° C.) in the fermentor. Trace metals and $MgSO_4$ were filter sterilized (through a presterilized 0.2 micron polyethersulfone membrane capsule filter) directly into the fermentation vessel. 2.9 L of the trace elements solution as well as a sufficient quantity of a concentrated $MgSO_4$ solution (to 2 g/L final concentration in the fermentor) were added through the same capsule filter. About 200 L of a mixture of 117 g/L casitone and 175 mL/L methyl oleate was sterilized in a 260 L feed tank. About 32 L of this sterile mixture was added to the 1000 L fermentor. Water was filtered into the vessel (through the same capsule filter) to bring final volume to 710 L. Agitation was 100 rpm. Backpressure was maintained at 100–300 mbar. When the dissolved oxygen (DO) reached 50% after inoculation, agitation was increased to 150 rpm. When the DO again reached 50%, agitation was increased to 200 rpm. DO was controlled at 50% of saturation by cascading the airflow (0 Lpm–240 Lpm). The pH setpoint was maintained at 7.4 by automated addition of 2.5 M KOH and 2.5 N $H_2SO_4$. The fermentor was inoculated with 38 L seed from the 150 L fermentor (5% volume/volume).

Addition of 0.570 L/hour of the casitone-methyl oleate feed solution began after the DO reached 50% (for the second time, about 10±5 hours after inoculation) and continued until the fermentor was harvested. The bioreactor was harvested 10 days following inoculation. Final epothilone D titers were determined to be about 20±5 mg/L.

Fermentation Sampling Procedure

For kinetic experiments in flasks, 5–50 mL of thoroughly mixed broth and XAD resin were sampled with a 25 mL pipet and deposited in a 10 or 50 mL conical tube. For bioreactor samples, a 50 mL sample of the mixed broth and resin was deposited in a 50 mL conical tube. The conical tube was then permitted to sit for 10 minutes to permit the XAD to settle to the bottom of the tube. The broth at this point can be decanted from the XAD resin. If the XAD does not settle, then one can remove the broth using a 10–25 mL pipette.

Methanol Extraction of XAD Resin for Epothilone Titer Quantitation

After the XAD resin has gravity settled to the bottom of the sample tube (as per the sampling procedure), all of the supernatant is transferred to a new 50 mL conical tube. Wash the XAD resin once by adding water back to the 50 mL mark, mix thoroughly by inversion, and let the XAD resin gravity settle again. Decant the aqueous mixture from the tube, without pouring out the XAD. The last few mL of water can be removed by using a 1 mL pipetman with the tip pushed down into the base of the tube. Add methanol to the tube up to the 25 mL point, and cap the tube. Place the conical tube horizontally on a shaker for 30 minutes (at 20–30° C.) to thoroughly extract all of the epothilone from the XAD resin.

HPLC Procedure for Epothilone Quantitation

Analysis of epothilones C and D is carried out using a Hewlett Packard 1090 HPLC with UV detection at 250 nm. The methanol-extracted solution from the XAD resin (50 $\mu$L) was injected across two 4.6×10 mm guard columns (Inertsil, C18 OD 53, 5 $\mu$m), and a longer column of the same material for chromatographic separation (4.6×150 mm). The method was isocratic with 60% acetonitrile and 40% water over an 18 minute run. With this method, epothilone D eluted at 13 minutes and epothilone C eluted at 10.3 minutes. Standards were prepared using epothilone D purified from fermentation broth.

Dry Cell Weight Procedure for Growth Curve

Set the temperature on a Sorvall RC5B centrifuge (with the SH-3000 bucket rotor) to 20° C. Weigh a 50 mL conical tube that has been in the 80° C. oven for at least a day. Record the tare weight and fermentation sample identification on the side of the tube. Pour or pipet 40 mL of broth (containing no XAD) into the tared tube. Spin the conical tube at 4700 RPM (4200 g) for 30 minutes. After sedimentation, pour off the supernatant, and resuspend the cell pellet in 40 mL of deionized water to wash the pellet. Spin the tube again (4200 g, 30 minutes). Decant the supernatant, and place tube in an 80° C. drying oven for at least 2 days. Weigh tube, and record the final weight on the tube. The dried cell weight (DCW) can then be calculated by the following equation:

$$DCW(\text{g/L})=(\text{Final tube weight(g)}-\text{Tare tube weight(g)})/0.04\ \text{L}$$

Determination of Ammonium Ion Concentration

The ammonia concentration of the fermentation broth is routinely assayed in the epothilone fermentations. One mL of fermentation broth is clarified by centrifugation in a microcentrifuge (5 minutes, 12000 rpm). An ammonia assay kit from Sigma (Catalog #171-UV) is used for quantitation, with the clarified fermentation broth substituted in place of the blood plasma described in the kit protocol. As the linear response range of this colorimetric assay is only 0.01176–0.882 mmoles/L, the clarified fermentation samples are typically diluted 20–100 fold in deionized water to assay ammonium concentrations within this range.

Determination of Residual Methyl Oleate Concentration

The amount of residual methyl oleate present in the fermentation broth can be estimated by extracting fermentation broth samples with methanol, and running these extracted broth samples on an HPLC. Quantitation of the methyl oleate concentration was carried out using a Hewlett Packard 1090 HPLC with UV detection at 210 nm. Whole broth samples (1–4 mL) were extracted with an equivalent volume of methanol and centrifuged at 12,000 g to sediment any insoluble components. The clarified supernatant (50 $\mu$L) was injected onto a 4.6×10 mm extraction column (Inertsil, C18 OD 53, 5 $\mu$m), washed with 50% acetonitrile for 2 minutes, then eluted onto the main column (4.6×150 mm, same stationary phase and flow rate) with a 24 minute gradient starting at 50% acetonitrile and ending at 100% acetonitrile. The 100% acetonitrile column flow was maintained for 5 minutes. Due to its heterogeneous nature, the methyl oleate elutes as a number of disparate peaks, instead of as single pure compound. However, approximately 64–67% of the total methyl oleate extractables appear in two primary peaks that elute at 25.3±0.2 and 27.1±0.2 minutes, respectively. Methyl oleate in methanol extracted fermentation samples can be estimated by quantitating the summed area of these two peaks, then calibrating them against the summed area of these two peaks in methyl oleate standards prepared in a 50% water/methanol solution.

Purification and Crystallization of Epothilone D

The present invention provides a purification process for epothilones and epothilone D and highly purified preparations of epothlone D, including epothilone D in crystalline form. The advantages of the present process include initial purification steps that require only alcohol (such as methanol) and water, which allows for efficient use of product pools and minimizes the necessity for time-consuming and labor-intensive evaporation steps. The present method requires only a single evaporation step, which requires the evaporation of 1 L of ethanol for every 10–15 g of epothilone. In the process, a column packed with synthetic polystyrene-divinylbenzene resin such as HP20SS is used to remove both polar and lipophilic impurities. This column generates an intermediate product that contains 10% epothilones and eliminates the need for liquid/liquid extractions that use either highly flammable or toxic solvents.

Another improvement relates to the use of a C18 resin with a 40–60 micron particle distribution, such as Bakerbond C18, that allows the use of low pressure columns and pumps (less than 50 psi), which reduces cost significantly. The starting material for the C18 chromatography step is solution loaded in a dilute loading solvent. The solvent is weak enough so that epothilones stick at the top of the column in a highly concentrated, tight band, which allows the column to perform well under heavy loading (2–5 g epothilone/L resin). Because typical column loading is 1 g/l or less, and chromatography is usually the most expensive step in purification, this improvement-results in significant cost savings. Moreover, the present method allows for the use of an alcohol, such as methanol, instead of acetonitrile in the chromatography step. The pool containing the epothilone is crystallized from a binary solvent system in which water is the forcing solvent to provide the epothilone in crystalline form.

The purification process, in one embodiment, consists of the following steps and materials. The XAD resin in the fermentation broth is (1) collected in a filter basket, and (2) eluted to provide an XAD extract, which is (3) diluted with water, and (4) passed through an HP20SS column to provide the HP20SS pool. The HP20SS pool is (5) diluted with water, and (6) subjected to C18 chromatography to provide an epothilone pool, which is (7) diluted with water, and (8) subjected to solvent exchange to provide a concentrated epothilone pool. The concentrated epothilone pool is (9) subjected to charcoal filtration, (10) evaporated, and (11) crystallized to provide highly purified material.

A total of 11 g of epothilone D was isolated and purified to a white crystalline powder from two 1000-L *Myxococcus xanthus* fermentation runs (1031001K and 1117001K). The purity of the final product was >95%, and the recovery of epothilone D was 71%.

Table 11 summarizes the HPLC Methods used during purification.

TABLE 11

| | |
|---|---|
| Epo1 Method | |
| Column | Inertsil ODS3, 5 $\mu$m, 4.6 × 150 mm |
| Flow rate | 1 ml/min |
| Column Oven | 50° C. |
| Run Time | 15 minutes |
| Detection | UV at 250 nm |
| Gradient | 0 min; 60:40 ACN/$H_2O$<br>12 min; 100:0 ACN/$H_2O$<br>12.1 min; 60:40 ACN/$H_2O$ |
| Epo78 Method | |
| Column | Intersil ODS3, 5 $\mu$m, 4.6 × 150 mm |
| Flow rate | 1 ml/min |
| Column Oven | 50° C. |
| Run Time | 5 minutes |
| Detection | UV at 250 nm |
| Gradient | 0 min; 78:22 ACN/$H_2O$ |

The Materials used in this section are as follows. HP20SS resin was purchased from Mitsubishi. The C18 resin was purchased from Bakerbond C18 40 g and the methanol was puchased from Fisher Bulk (55 gal). Deionized water was used.

Fermentation Run 1031001K

Step 1 XAD Elution (K125-173)

Seventeen liters (17 L) of XAD-16 resin were filtered from the fermentation culture using a Mainstream filtration unit with a thirteen-liter 150 $\mu$m capture basket. The captured XAD resin was packed into an Amicon VA250 column and was washed with 65 L (3.8 column volumes) of water at 1.0 L/min. The epothilone D product was then eluted from the resin using 230 L of 80% methanol in water.

Step 2 Solid Phase Extraction (K125-175)

Seventy-seven liters (77 L) of water were added to the step 1 product pool (230 L) to dilute the loading solvent to 60% methanol in water. The resulting suspension (307 L) was mixed and loaded onto an Amicon VA180 column packed with 5 L of HP20SS resin that had previously been equilibrated with 5 column volumes of 60% methanol. The loading flow rate was 1 L/min. After loading, the column was washed with 13 L of 60% methanol and eluted with 77 L of 75% methanol at a flow rate of 325 mL/min. Thirty-one 2.5-L fractions were collected. Fractions 10–26 (42.5 L) were found to contain epothilone D, and these fractions were pooled together.

Step 3 Chromatography (K125-179)

The step 2 product pool was evaporated to an oil using two 20-L rotovaps. During evaporation it was necessary to add ethanol in order to minimize foaming. The dried material was re-suspended in 1.0 L of methanol and diluted with 0.67 L of water to make 1.67 L of a 60% methanol solution. The resulting solution was loaded onto a 1-L C18 chromatography column (55×4.8 cm) that had previously been equilibrated with 3 column volumes of 60% methanol. The loading flow rate averaged at 64 mL/min. The loaded column was washed with one liter of 60% methanol, and elution of the epothilone D product was carried out isocratically using 70% methanol at a flow rate of 33 mL/min. A total of 27 fractions were collected, with the first fraction containing 3.8 L by volume. This was followed by three 500-mL fractions and twenty-three 250-mL fractions. Fractions 5–20 were taken as the best pool (K125-179-D), containing 4.8 g of epothilone D. Fractions 3–4 (K125-179-C) contained 1.4 g of epothilone D. Because this pool also contained high concentrations of epothilone C, it was set aside for re-work.

Step 4 Chromatography (K119-153)

Epothilone D fractions that also contained high concentrations of the C analog were re-chromatographed on C18 resin as follows. A 2.5×50 cm column was packed with C18 resin, washed with 1 L of 100% methanol, and equilibrated with 1 L of 55% methanol in water at a flow rate of 20 mL/min. The pressure drop was 125 psi. The starting material (K125-179-C, 1040 mL) was diluted with 260 mL of water so that the loading solution contained 55% methanol in water. The resulting solution (1300 mL) was loaded onto the resin, and an additional 250 mL of 55% methanol was passed through the column. The column was first eluted with 5 L of 65% methanol, followed by 3 L of 70% methanol in water. During the 65% methanol elution, a total of forty-eight 100-mL fractions were collected. After switching to 70% methanol, a total of ten 250-mL fractions were collected. The best epothilone D pool (K119-153-D), consisting of Fractions 50–58, contained 1.0 g of the desired product.

Step 5a Crystallization (K119-158)

The starting material for this step was a combination of chromatography products from step 3 and 4. Initially, 120 mL of ethanol was added to 7.9 g of solids containing 5.5 g of epothilone D. With gentle mixing, the solids were completely dissolved, and the solution was transferred to a 400-mL beaker that was placed on a stir plate in a fume hood. A 1" stir bar was added, and the solution was rapidly stirred. Meanwhile, 100 mL of water were slowly added over a period of about 5 minutes. When the formation of small white crystals were observed, the solution was stirred for 15 more minutes until the solution became thick with white solids. The beaker was then removed from the stir plate, covered with aluminum foil, and placed in a refrigerator (2° C.) for 12 hours. The white solids were filtered using Whatman #50 filter paper, and no additional wash was performed on this first crop. The solids were placed to a crystallization dish and dried in a vacuum oven (40° C. at 15 mbar) for 1 hour. Subsequently, the material was removed from the oven, made into finer particles, and dried in the vacuum oven for another four hours. This crystallization process yielded 3.41 g of off white solids. The Epo1 HPLC method was used to determine the chromatographic purity of the final product. The HPLC results, along with the corresponding $^1H$ and $^{13}C$ NMR data, all confirmed that the dried material contained >95% epothilone D. The recovery for this first crop was 58%.

Step 5b Crystallization (K119-167)

The starting material for this step was the evaporated mother liquor from step 5a. Initially, 70 mL of ethanol and 30 mL of water were added to 3.4 g of solids containing 2.1 g of epothilone D. This clear solution was transferred to a beaker; and 1 g of decolorizing charcoal was added to it. The mixture was stirred on a medium setting for 10 min. and was then filtered using a Whatman #50 filter paper. The charcoal was washed with two 10-mL aliquots of ethanol and was filtered again. The combined filtrate was brought to dryness using a rotovap, and the solids were re-suspended in 50 mL of ethanol. The resulting solution was placed in a 250-mL beaker, and with good stirring, 50 mL of water was slowly added. To promote crystal formation, a small amount of seed crystal (1 mg) was added to the mixture. After several minutes of stirring, the formation of additional white solids was observed. A stream of nitrogen was set to gently blow over the mixture while the stirring continued. After 15 minutes, the beaker was placed in the refrigerator at 2° C. for 36 hours. The mixture was filtered using a Whatman #50 filter paper to capture the crystals, and an additional 7 mL of 50:50 ethanol:water was used to wash the solids. The crystals were subsequently dried in the vacuum oven for 4 hours. This crystallization step yielded 1.46 g of white crystals, which contain >95% epothilone D.

Fermentation Run 1117001K

Step 1 XAD Elution (K125-182)

Seventeen liters (17 L) of XAD-16 resin were filtered from the fermentation culture using a Mainstream filtration unit with a thirteen-liter 150 μm capture basket. The captured XAD resin was packed into an Amicon VA250 column and was washed with 58 L (3.4 column volumes) of water at 1.0 L/min. The epothilone D product was then eluted from the resin using 170 L of 80% methanol in water. During the water wash and the first column volume of elution, the column backpressure increased steadily to above 3 bars with a final flow rate of under 300 mL/min. Therefore, the XAD resin was removed from the column and repacked into an alternate Amicon VA250 column. After the exchange, the backpressure decreased below 1 bar and the flow rate was maintained at 1.0 L/min. A single 170-L fraction was collected in a 600-L stainless steel tank. Based on HPLC analysis, the step 1 product pool was found to contain 8.4 g of epothilone D.

Step 2 Solid Phase Extraction (K145-150)

Fifty-seven liters (57 L) of water were added to the step 1 product pool (170 L) to dilute the loading solvent to 60% methanol in water. The resulting suspension (227 L) was stirred with an overhead lightning mixer and loaded onto an Amicon VA180 column packed with 6.5-L of HP20SS resin that had previously been equilibrated with 5 column volumes of 60% methanol. The loading flow rate was 1 L/min. After loading, the column was washed with 16 L of 60% methanol and eluted with 84 L of 75% methanol at a flow rate of 300 mL/min. Seven fractions were collected with volumes of 18 L, 6 L, 6 L, 6 L, 36 L, 6 L, and 6 L, respectively. Fractions 4 and 5, which contained a total of 8.8 g of epothilone D, were pooled together.

Step 3 Chromatography (K145-160)

The step 2 product pool was evaporated to an oil using two 20-L rotovaps. To minimize foaming during the evaporation process, 10 L of ethanol were added to the mixture. The dried material was resuspended in 2.8 L of methanol and diluted with 3.4 L of water to make 6.2 L of a 45% methanol solution. The resulting solution was pumped onto a 1-L C18 chromatography column (55×4.8 cm) that had previously been equilibrated with 5 column volumes of 45% methanol. The loading flow rate averaged at 100 mL/min. The loaded column was washed with one liter of 60% methanol, and the epothilone D product was eluted from the resin using a step gradient at a flow rate of 100 mL/min. The column was eluted with 5 L of 55% methanol, 11.5 L of 60% methanol, and 13.5 L of 65% methanol. During the 55% methanol elution, a total of ten 500-mL fractions were collected. After switching to 60% methanol, a total of twenty-three 500-mL fractions were collected. During the final 65% methanol elution, eleven 500-mL fractions were collected, followed by eight 1-L fractions. The best epothilone D pool (K145-160-D), consisting of Fractions 28–50, contained 8.3 g of the desired product. Fractions 26–27 (K145-160-C), which were contaminated with 0.4 g of the epothilone C, contained 0.2 g of epothilone D. All of these 25 fractions were combined.

To dilute product pool to 40% methanol in water, 9.5 L of water was added to 15.8 L of the loading solution. The resulting solution (25.3 L) was then pumped onto a 700-mL C18 chromatography column (9×10 cm) that had previously been equilibrated with 4 column volumes of 40% methanol. The loading flow rate averaged at 360 mL/min. The loaded column was washed with one liter of 40% methanol, and the epothilone D product was eluted from the resin with 3.75 L of 100% ethanol. The eluant was evaporated to dryness using a rotovap. The solids were resuspended in 100 mL of acetone, and the undissolved material was filtered from the solution using a Whatman #2 filter paper. The filtered particles were washed with an additional 115 mL of acetone and filtered once more. Following the acetone extraction, 2 g of decolorizing charcoal were added to the combined filtrate. The mixture was stirred on a medium setting for 1 hour and was filtered using a Whatman #50 filter paper. The charcoal was washed with 180 mL of ethanol and was filtered again. The filtrates were pooled together and rotovaped to dryness.

Step 4 Chromatography (K119-174)

The dried material from step 3 was resuspended in 5.0 L of 50% methanol in water and was loaded onto a 1-L C18 chromatography column (55×4.8 cm) that had previously been equilibrated with 3 column volumes of 50% methanol. The loading flow rate averaged at 80 mL/min. The column was subsequently washed with one liter of 50% methanol, and the epothilone D product was eluted isocratically from the resin using 70% methanol at the same flow rate. A total of 48 fractions were collected, with the first 47 fractions containing 240 mL and the last fraction containing 1 L. Fractions 25–48 were taken as the best pool (K119-174-D), containing 7.4 g of epothilone D. Fractions 21–24 (K119-174-C) contained 1.1 g of epothilone D. Because this pool also contained high concentrations of epothilone C, it was set aside for re-work.

Step 5 Crystallization (K119-177)

To perform a solvent exchange prior to the crystallization step, 3.9 L of water was added to 6.4 L of the best epothilone D pool (K119-174-D) from step 5 to dilute the loading solution to 40% methanol in water. The resulting solution was then loaded onto a 200-mL C18 chromatography column (2.5×10 cm) that had previously been equilibrated with 3 column volumes of 40% methanol. The loaded column was washed with 200 mL of 40% methanol, and the epothilone D product was eluted from the resin with 1 L of 100% ethanol. The eluant was evaporated to dryness using a rotovap, and the solids were re-suspended with 150 mL of 100% ethanol. The clear solution was transferred to a beaker and with good stirring, 175 mL of water was slowly added. A small (1 mg) seed crystal was also added to the solution to promote crystal formation. When the formation of small white crystals were observed, the solution was stirred for 15 more minutes until the solution became thick with white solids. The beaker was then removed from the stir plate, covered with aluminum foil, and placed in a refrigerator (2° C.) for 12 hours. The white solids were filtered using Whatman #50 filter paper, and no additional wash was performed on this first crop. The solids were placed to a crystallization dish and dried in a vacuum oven (40° C. at 15 mbar) for 6 hours. This crystallization process yielded 6.2 g of white solids, which contained >95% epothilone D. The recovery for this first crop was 74%.

Results

The epothilone D recovery for run 1031001K was 4.8 g of crystalline material at a purity of about 97.5–98.8%. The epothilone D recovery for run 1117001K was 6.2 g of crystalline material at a purity of about 97.7%. The impurity profiles for these runs are shown in Table 12.

TABLE 12

| | Step | Product | Epo C | Epo490 | Epo D |
|---|---|---|---|---|---|
| 1031001K run | 2 | SPE | 23 | 4 | 74 |
| | 3–4 | Total Chrom | 0.7 | 0.7 | 90.6 |
| | 5a | Crystallization | 1.0 | 1.0 | 97.5 |
| | 5b | Crystallization | 0.7 | 0.5 | 98.8 |
| 1117001K run | 2 | SPE | 18 | 2 | 60 |
| | 3 | C18 Chrom | 5.2 | 1.6 | 81.4 |
| | 4 | C18 Chrom | 1.6 | 1.8 | 96.6 |
| | 5 | Crystallization | 0.8 | 1.4 | 97.7 |

"Epo490" is a novel epothilone compound of the invention, 10,11-dehydro-epothilone D, that is produced by the Myxococcus host cells.

This purification methodology arose out of efforts to scale-up modifications made to the epothilone D purification process to accommodate the use of methyl oleate in the fermentation medium. The elution of the epothilone D product from the XAD resin was carried out in a straight-forward manner. Instead of using 100% methanol, 10 column volumes of 80% methanol were used to elute the product from the beads in a column. During the XAD elution step, it was noted that the presence of lysed cells in the fermentation broth may contribute to the clogging of the purification columns. The harvest of the 103100-1K fermentation run had occurred before significant cell lysis had taken place, while the 111700-1K fermentation run was harvested only after considerable cell lysis had occurred. However, a high backpressure and a low flow rate were observed only for the latter run during the elution process. Therefore, it is likely that the lysed cells in this run may have aggregated and subsequently fouled the column filter.

These purification runs show that epothilone D is stable at room temperature in 80% methanol for at least one day. Based on HPLC analysis, degradation of the product under these conditions is not detectable. This finding allowed storage of the 170-L product pool from the XAD elution step in a 600-L stainless steel tank overnight without refrigeration. To further improve the process, a solvent-exchange column was employed, which is much less time-consuming and labor-intensive than the use of a rotovap in concentrating the volume of the product pools. Therefore, one can replace large-scale rotovaping with a solvent-exchange step.

Although a significant amount oil remained bound to the resin during the XAD elution step, a sizable amount was still present in the eluant. Even after the HP20SS solid phase extraction, oil droplets were clearly visible in the product pool and proved to problematic during the C18 chromatography. For optimal chromatography performance, the concentration of epothilone D in the loading solution should be kept below 2 g/L. At higher concentrations, the starting material has a tendency to oil out on the column.

Crystallization was not possible when feed material contained more than 3% of either epothilone C or epo490. This was the case during the purification of 1117001K. The first chromatography step gave a product that contained 5% epothilone C. After numerous attempts, crystallization of this material was not achieved. However, taking this material through a second chromatography step reduced epothilone C to 1% and generated a feed material that was easily crystallized.

EXAMPLE 4

Construction of a *Myxococcus* Strain with a Non-Functional epoK Gene

Strain K111-40-1 was constructed from strain K111-32.25 by insertional inactivation of the epoK gene. To construct this epoK mutant, a kanamycin resistance cassette was inserted into the epoK gene. This was done by isolating the 4879 bp fragment from pKOS35-79.85, which contains epoK, and ligating it into the NotI site of pBluescriptSKII+. This plasmid, pKOS35-83.5, was partially cleaved with ScaI, and the 7.4 kb fragment was ligated with the 1.5 kb EcoRI-BamHI fragment containing the kanamycin resistance gene from pBJ180-2, which had the DNA ends made blunt with the Klenow frangment of DNA polymerase I, to yield plasmid pKOS90-55. Finally, the ~400 bp RP4 oriT fragment from pBJ183 was ligated into the XbaI and EcoRI sites to create pKOS90-63. This plasmid was linearized with DraI and electroporated into the *Myxococcus xanthus* strain K111-32.25, and transformants selected to provide *M. xanthus* strain K111-40.1. Strain K111-40.1 was deposited in compliance with the Budapest Treaty with the American Type Culture Collection, Manassas, Va. 20110-2209, USA on Nov. 21, 2000, and is available under accession No. PTA-2712.

To create a markerless epoK mutation, pKOS35-83.5 was cleaved with ScaI and the 2.9 kb and 4.3 kb fragments were ligated together. This plasmid, pKOS90-101, has an in-frame deletion in epoK. Next, the 3 kb BamHI and NdeI fragment from KG2, which had the DNA ends made blunt with the Klenow fragment of polymerase I and contains the kanamycin resistance and galK genes, was ligated into the DraI site of pKOS90-101 to create pKOS90-105. This plasmid was electroporated into K111-32.25 and kanamycin resistant electroporants were selected. To replace the wild type copy of epoK with the deletion, the second recombination event was selected by growth on galactose plates. These galactose resistant colonies are tested for production of epothilone C and D, and a producing strain was designated K111-72.4.4 and deposited in compliance with the Budapest Treaty with the American Type Culture Collection, Manassas, Va. 20110-2209, USA on Nov. 21, 2000, and is available under accession No. PTA-2713.

EXAMPLE 5

Addition of matBC

The matBC genes encode a malonyl-CoA synthetase and a dicarboxylate carrier protein, respectively. See An and Kim, 1998, *Eur. J. Biochem.* 257: 395-402, incorporated herein by reference. These two proteins are responsible for the conversion of exogenous malonate to malonyl-CoA inside the cell. The products of the two genes can transport dicarboxylic acids and convert them to CoA derivatives (see PCT patent application No. US00/28573, incorporated herein by reference). These two genes can be inserted into the chromosome of *Myxococcus xanthus* to increase the cellular concentrations of malonyl-CoA and methymalonyl-CoA to increase polyketide production. This is accomplished by cleaving pMATOP-2 with BglII and SpeI and ligating it into the BglII and SpeI sites of pKOS35-82.1, which contains the tetracycline resistance conferring gene, the Mx8 att site and the *M. xanthus* pilA promoter to drive expression of matBC. This plasmid can be electroporated into *M. xanthus*. Because the pilA promoter is highly transcribed, it may be necessary to insert a weaker promoter in the event that too much MatB and MatC affect cell growth. Alternative promoters include the promoter of the kanamycin resistance conferring gene.

EXAMPLE 6

Mutation of the $KS^Y$ in the Loading Module

The proposed mechanism of initiation of epothilone biosynthesis is the binding of malonate to the ACP of the loading domain and the subsequent decarboxylation by the loading KS domain. The loading KS domain contains a tyrosine at the active site cysteine ($KS^Y$) which renders it unable to perform the condensation reaction. However, it is believed to still perform the decarboxylation reaction. Experiments with rat fatty acid synthase has shown that a KS domain that contains a glutamine in the active site cysteine ($KS^Q$) increases the decarboxylation by two orders of magnatude whereas changing this amino acid to serine, alanine, asparagine, glycine or threonine resulted in no increase relative to wild type. Therefore, changing the $KS^Y$ to $KS^Q$ may increase the priming of epothilone resulting in an increase in epothilone production. To make the change in strain K111-32.25, the plasmid pKOS39-148 was constructed that has ~850 bp of the epothilone KS loading module coding sequence. The $KS^Q$ mutation was created in this plasmid by site directed mutagenesis. To perform a gene replacement in K111-32.25, the kanamycin resistance and galK genes from KG2 were inserted into the DraI sites of pKOS39-148 to create plasmids pKOS111-56.2A and pKOS111-56.2B. The plasmids differ in their orientation of the kanamycin-galK cassette. These plasmids were electroporated into K111-32.25 and kanamycin resistant colonies were selected to create strain K111-63. To replace the wild type loading module KS, K111-63 was plated on CYE galactose plates, and colonies were screened for the presence of the $KS^Q$ mutation by PCR and sequencing.

EXAMPLE 7

Addition of mtaA

To increase the levels of phosphopantetheinyl transferase (PPTase) protein, the PPTase from *Stigmatella aurantiaca* strain DW4 can be added to K111-32.25. This is done by PCR amplification of mtaA from DW4 chromosomal DNA using the primers 111-44.1 (AAAAGCTTCGGGGCACCT-CCTGGCTGTCGGC) (SEQ ID NO4) and 111-44.4 (GGTTAATTAATCACCCTCCTCCCACCCCGGGCAT) (SEQ ID NO:5). See Silakowski et al., 1999, *J. Biol. Chem.* 274(52):37391–37399, incorporated herein by reference. The ~800 bp fragment was cleaved with NcoI and ligated into the pUHE24-2B that had been cleaved with PstI, the DNA ends made blunt with the Klenow fragment of DNA polymerase I, and cleaved with NcoI. This plasmid is designated pKOS111-54. The mtaA gene is transfered to plasmid pKOS35-82.1, which contains the tetracycline resistance conferring gene, the Mx8 att site and the *Myxococcus xanthus* pilA promoter to drive expression of mtaA. This plasmid is introduced into *M. xanthus* and integrated into the Mx8 phage attachment site.

EXAMPLE 8

Construction of Promoter Replacement Plasmids

To improve epothilone production levels and to illustrate the wide variety of promoters that can be used to express PKS genes in host cells of the invention, a series of vectors and host cells can be constructed to replace the *Sorangium cellulosum* epothilone PKS gene promoter with other suitable promoters, as described in this example.

A. Construction of Plasmid with Downstream Flanking Region

Cosmid pKOS35-70.8A3 was cut with NsiI and AvrII. The 9.5 kb fragment was ligated with pSL1190 cut with PstI and AvrII to yield pKOS90-13. Plasmid pKOS90-13 is ~12.9 kb. Plasmid pKOS90-13 was cut with EcoRI/AvrII. The 5.1 kb fragment was ligated with pBluescript digested with EcoRI/SpeI to create pKOS90-64 (~8.1 kb). This plasmid contains the downstream flanking region for the promoter (epoA and some sequence upstream of the start codon). The EcoRI site is ~220 bp upstream from the start codon for the epoA gene. The AvrII site is 5100 bp downstream from the EcoRI site.

B. Cloning of Upstream Flanking Region

Primers 90-66.1 and 90-67 (shown below) were used to clone the upstream flanking region. Primer 90-67 is at the 5' end of the PCR fragment and 90-66.1 is at the 3' end of the PCR fragment. The fragment ends 2481 bp before the start codon for the epoA gene. The ~2.2 kb fragment was cut with HindIII. Klenow polymerase was added to blunt the HindIII site. This fragment was ligated into the HincII site of pNEB193. Clones with the proper orientation, those with the EcoRI site at the downstream end of the insert and HindIII at the upstream end of the insert, were selected and named pKOS90-90.

(SEQ ID NO: 6)

90-66.1: 5′ GCGGGAAGCTT TCACGGCGCAGGCCCTCGTGGG 3′
linker HindIII primer (SEQ ID NO: 7)

90-67: 5′ GCGGTACC TTCAACAGGCAGGCCGTCTCATG 3′
linker KpnI primer

C. Construction of Final Plasmid

Plasmid pKOS90-90 was cut with EcoRI and HindIII. The 2.2 kb fragment was ligated with pKOS90-64 digested with EcoRI/HindIII to create pKOS 90-91 (10.3 kb). Plasmid pKOS90-91 contains the upstream flanking region of the promoter followed by the downstream flanking region in pBluescript. There is a PacI site between the two flanking regions to clone promoters of interest. The galK/kan$^r$ cassette was then inserted to enable recombination into *Myxococcus xanthus*. Plasmid pKOS90-91 was cut with DraI. DraI cuts once in the amp gene and twice in the vector (near the amp gene). Plasmid KG-2 was cut with BamHI/NdeI and Klenow polymerase added to blunt the fragment. The 3 kb fragment (containing galK/kan$^r$ genes) was ligated with the ~9.8 kb DraI fragment of pKOS90-91 to create pKOS90-102 (12.8 kb).

D. Construction of Plasmid with Alternative Leader

The native leader region of the epothilone PKS genes can be replaced a leader with a different ribosome binding site. Plasmid pKOS39-136 (described in U.S. patent application Ser. No. 09/443,501, filed Nov. 19, 1999) was cut with PacI/AscI. The 3 kb fragment containing the leader sequence and part of epoA was isolated and ligated with the 9.6 kb PacI/AscI fragment of pKOS90-102 to create pKOS90-106 (~12.7 kb).

E. Construction of Promoter Replacement Plasmids

I. MTA (Myxothiazol) Promoter

The myxothiazol promoter was PCR amplified from *Stigmatella aurantiaca* chromosomal DNA (strain DW4) using primers 111-44.3 and 111-44.5 (shown below). The ~554 bp band was cloned into the HincII site of pNEB193 to create pKOS90-107. Plasmid pKOS90-107 was cut with PstI and XbaI and Klenow filled-in. The 560 bp band was cloned into pKOS90-102 and pKOS90-106 cut with PacI and Klenow filled-in (PacI cuts only once in pKOS90-102 and pKOS90-106). Plasmids were screened for the correct orientation. The MTA promoter/pKOS90-102 plasmid was named pKOS90-114 (13.36 kb) and MTA promoter/pKOS90-106 plasmid was named pKOS90-113 (13.26 kb).

(SEQ ID NO:8)

111-44.3 5′ AA AAGCTT AGGCGGTATTGCTTTCGTTGCACT 3′
linker HindIII primer (SEQ ID NO:9)

111-44.5 5′ GG TTAATTAA GGTCAGCACACGGTCCGTGTGCAT 3′
linker PacI primer

These plasmids are electroporated into Myxococcus host cells containing the epothilone PKS genes, and kanamycin resistant transformants selected to identify the single crossover recombinants. These transformants are selected for galactose resistance to identify the double crossover recombinants, which are screened by Southern analysis and PCR to identify those containing the desired recombination event. The desired recombinants are grown and tested for epothilone production.

II. TA Promoter

The putative promoter for TA along with taA, which encodes a putative transcriptional anti-terminator, was PCR amplified from strain TA using primers 111-44.8 (AAAGATCTCTCCCGATGCGGGAAGGC) (SEQ ID NO:10) and 111-44.9 (GGGGATCCAATGGAAGGGGATGTCCGCGGAA) (SEQ ID NO:11). The ca. 1.1 kb fragment was cleaved with BamHI and BglII and ligated into pNEB193 cleaved with BamHI. This plasmid is designated pKOS111-56.1. The plasmid pKOS111-56.1 was cut with EcoRI and HindIII and Klenow filled-in. The ~1.1 kb band was cloned into pKOS90-102 and pKOS90-106 cut with PacI and Klenow filled-in (PacI cuts only once in pKOS90-102 and pKOS90-106). Plasmids were screened for the correct orientation. The TA promoter/90-102 plasmid was named pKOS90-115 (13.9 kb), and the TA promoter/pKOS90-106 plasmid was named pKOS90-111 (13.8 kb).

These plasmids are electroporated into *Myxococcus* host cells containing the epothilone PKS genes, and kanamycin resistant transformants selected to identify the single crossover recombinants. These transformants are selected for galactose resistance to identify the double crossover recombinants, which are screened by Southern analysis and PCR to identify those containing the desired recombination event. The desired recombinants are grown and tested for epothilone production.

III. pilA Promoter

Plasmid pKOS35-71B was cut with EcoRI and Klenow filled-in. The 800 bp fragment was cloned into pKOS90-102 and pKOS90-106 cut with PacI and Klenow filled-in. Plasmids were screened for the correct orientation. The pilA promoter/pKOS90-102 plasmid was named pKOS90-120 (13.6 kb), and the pilA promoter/pKOS90-106 plasmid was named pKOS90-121 (13.5 kb).

These plasmids are electroporated into *Myxococcus* host cells containing the epothilone PKS genes, and kanamycin resistant transformants selected to identify the single crossover recombinants. These transformants are selected for galactose resistance to identify the double crossover recombinants, which are screened by Southern analysis and PCR to identify those containing the desired recombination event. The desired recombinants are grown and tested for epothilone production.

IV. kan Promoter

Plasmid pBJ180-2 was cut with BamHI/BglII and Klenow filled-in. The 350 bp fragment was cloned into pKOS90-102 and pKOS90-106 cut with PacI and Klenow filled-in. Plasmids were screened for the correct orientation. The kan promoter/pKOS90-102 plasmid was named pKOS90-126 (13.15 kb), and the kan promoter pKOS/90-106 plasmid was named pKOS90-122 (13.05 kb).

These plasmids are electroporated into *Myxococcus* host cells containing the epothilone PKS genes, and kanamycin resistant transformants selected to identify the single crossover recombinants. These transformants are selected for galactose resistance to identify the double crossover recombinants, which are screened by Southern analysis and PCR to identify those containing the desired recombination event. The desired recombinants are grown and tested for epothilone production.

V. So ce90 Promoter

The So ce90 promoter was amplified from So ce90 chromosomal DNA using primers 111-44.6 and 111-44.7 (shown below). The ~900 bp band was cut with PacI and cloned into pNEB193 cut with PacI to create pKOS90-125. Plasmid pKOS90-125 was cut with PacI. The 924 bp band was cloned into pKOS90-102 and pKOS90-106 cut with PacI. Plasmids were screened for the correct orientation. The Soce90 promoter/pKOS90-102 plasmid was named pKOS90-127 (13.6 kb), and the Soce90 promoter/pKOS90-106 plasmid was named pKOS90-128 (13.7 kb).

These plasmids are electroporated into *Myxococcus* host cells containing the epothilone PKS genes, and kanamycin resistant transformants selected to identify the single crossover recombinants. These transformants are selected for galactose resistance to identify the double crossover recombinants, which are screened by Southern analysis and PCR to identify those containing the desired recombination event. The desired recombinants are grown and tested for epothilone production.

(SEQ ID NO:12)

111-44.6 5′ GG TTAATTAA CATCGCGCTATCAGCAGCGCTAG 3′ linker PacI primer (SEQ ID NO:13)

111-44.7 5′ GG TTAATTAA TCCTCAGCGGCTGACCCGCTCGCG 3′ linker PacI primer

EXAMPLE 9

Construction of a KS2 Knockout Strain

This example describes the construction of an epothilone PKS derivative in which the KS domain of extender module 2 is rendered inactive by a mutation changing the active site cysteine codon to an alanine codon. The resulting derivative PKS can be provided with synthetic precursors (as described in the following Example) to make epothilone derivatives of the invention.

The downstream flanking region of the epothilone PKS gene was PCR amplified using primers 90-103 (5'-AAAAAATGCATCTACCTCGCTCGTGGCGGTT-3') (SEQ ID NO:14) and 90-107.1 (5'-CCCCC TCTAGA ATAGGTCGGCAGCGGTACCCG-3') (SEQ ID NO:15) from plasmid pKOS35-78.2. The ~2 kb PCR product was cut with NsiI/XbaI and ligated with pSL1190 digested with NsiI and SpeI to create pKOS90-123 (~5.4 kb). A ~2 kb PCR fragment amplified with primers 90-105 (5'-TTTTTATGCATGCGGCAGTTTGAACGG-AGATGCT-3') (SEQ ID NO:16) and 90-106 (5'-CCCCCGAATTCTCCCGGAAGGCACACGGAGAC-3') (SEQ ID NO:17) from pKOS35-78.2 DNA was cut with NsiI and ligated with pKOS90-123 digested with NsiI/EcoRV to create pKOS90-130 (~7.5 kb). When this plasmid is cut with NsiI, and the DNA ends made blunt with the Klenow fragment of DNA polymerase I and religated, plasmid pKOS90-131 is created. To clone the galK/kan$^r$ cassette into this plasmid, plasmid KG-2 is cut with BamHI/NdeI and made blunt with the Klenow fragment of DNA polymerase I. The 3 kb fragment is cloned into the DraI site of pKOS90-131 (DraI cuts three times in the vector) to create plasmid pKOS90-132 (10.5 kb). The NsiI site is used for the purpose of creating the desired change from cysteine to alanine to effect the KS2 knockout. When pKOS90-130 is cut with NsiI, made blunt with the Klenow fragment from DNA polymerase I and religated, the codon for cysteine is replaced with a codon for alanine. The resulting plasmid can be introduced into *Myxococcus xanthus* strains of the invention in accordance with the protocols described above to create the desired strains.

*Myxococcus xanthus* strain K90-132.1.1.2 was constructed by this procedure (using the epothilone A, B, C, and D producer K111-32.25) and deposited under the terms of the Budapest Treaty with the American Type Culture Collection, Manassas, Va. 20110-2209, USA, on Nov. 21, 2000, from which it can be obtained under accession No. PTA-2715. To demonstrate that the resulting PKS produced by the strain could synthesize epothilones when provided the appropriate "diketide" starter unit, strain K90-132.1.1.2 was grown in 50 mL of CTS plus 20% XAD for three days at 30° C. and then provided 200 mg/mL of the thiazole diketide shown below:

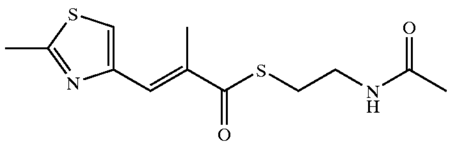

The strain was cultured for an additional five days, and the XAD was collected and the epothilones extracted with 10% methanol. The extract was dried and resuspended in 0.2 mL of acetonitrile, and an 0.05 mL sample analyzed by LC/MS, which showed the presence of epothilones B and D, as expected. As discussed in the following example, this system can be used to produce a variety of epothilone analogs.

EXAMPLE 10

Modified Epothilones from Chemobiosynthesis

This Example describes a series of thioesters for production of epothilone derivatives via chemobiosynthesis. The DNA sequence of the biosynthetic gene cluster for epothilone from *Sorangium cellulosum* indicates that priming of the PKS involves a mixture of polyketide and amino acid components. Priming involves loading of the PKS-like portion of the loading module with malonyl CoA followed by decarboxylation and loading of the extender module one NRPS with cysteine, then condensation to form enzyme-bound N-acetylcysteine. Cyclization to form a thiazoline is followed by oxidation to form enzyme bound 2-methylthiazole-4-carboxylate, the product of the loading module and NRPS. Subsequent condensation with methylmalonyl CoA by the ketosynthase of module two provides the equivalent of a diketide, as shown in Scheme 6.

-continued

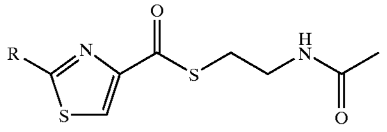

SCHEME 6

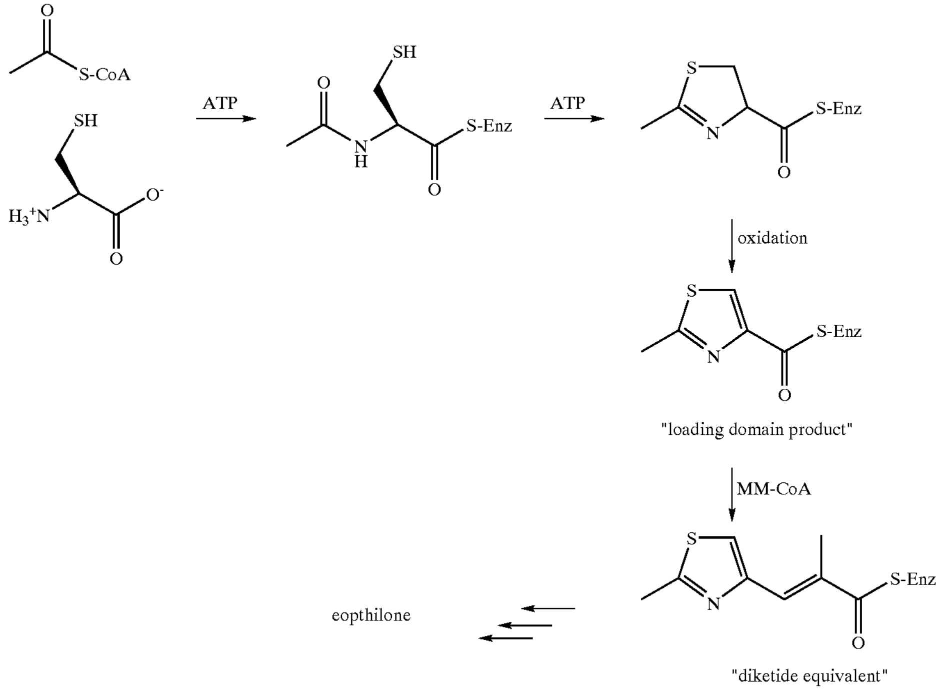

The present invention provides methods and reagents for chemobiosynthesis to produce epothilone derivatives in a manner similar to that described to make 6-dEB and erythromycin analogs in PCT Pub. Nos. 99/03986 and 97/02358. Two types of feeding substrates are provided: analogs of the NRPS product, and analogs of the diketide equivalent. The NRPS product analogs are used with PKS enzymes with a mutated NRPS-like domain, and the diketide equivalents are used with PKS enzymes with a mutated KS domain in module two (as described in Example 9). In the structures in Schemes 7 and 8 below, R, $R_1$ and $R_2$ can be independently selected from the group consisting of methyl, ethyl, lower alkyl ($C_1$–$C_6$), and substituted lower alkyl.

Scheme 7 shows illustrative loading module analogs.

SCHEME 7

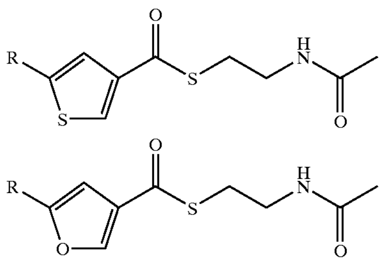

-continued

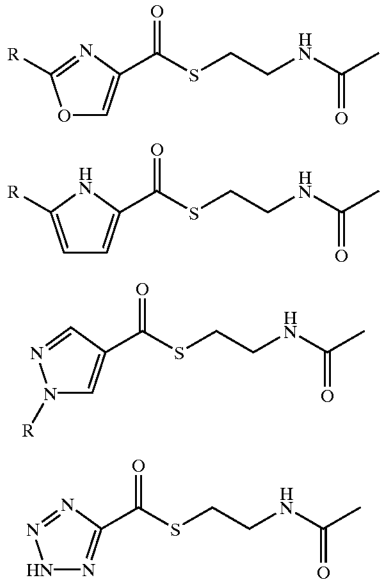

-continued

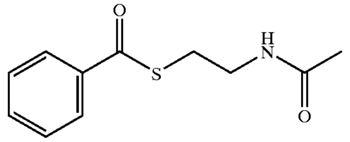

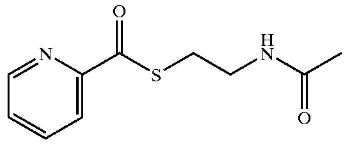

The loading module analogs are prepared by activation of the corresponding carboxylic acid and treatment with N-acetylcysteamine. Activation methods include formation of the acid chloride, formation of a mixed anhydride, or reaction with a condensing reagent such as a carbodiimide.

Scheme 8 shows illustrative diketide equivalents.

SCHEME 8

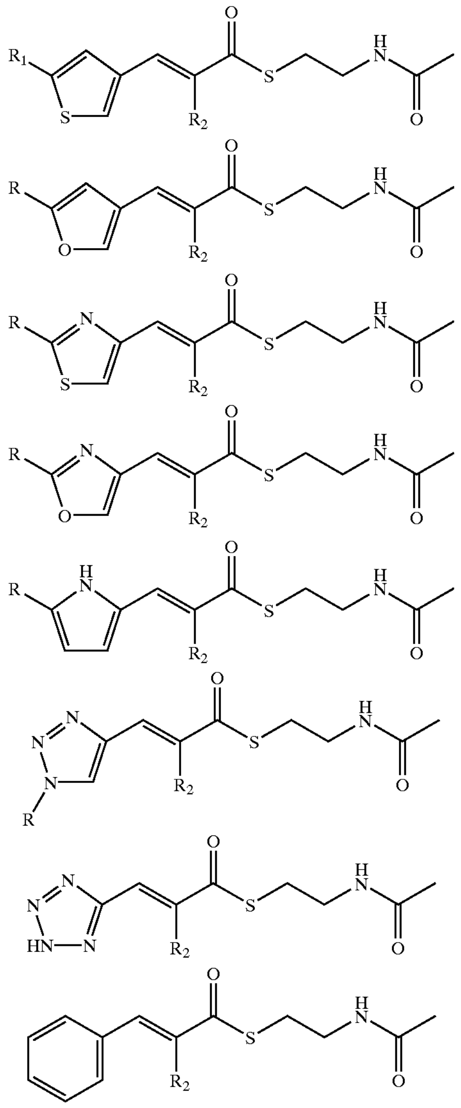

-continued

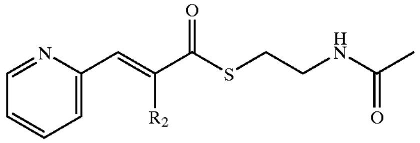

The diketide equivalents are prepared in a three-step process. First, the corresponding aldehyde is treated with a Wittig reagent or equivalent to form the substituted acrylic ester. The ester is saponified to the acid, which is then activated and treated with N-acetylcysteamine.

Illustrative reaction schemes for making loading module product analogs and diketide equivalents follow. Additional compound suitable for making diketide equivalents are shown in FIG. 1 as carboxylic acids (or aldehydes that can be converted to carboxylic acids) that are converted to the N-acylcysteamides for supplying to the host cells of the invention.

A. Thiophene-3-carboxylate N-acetylcysteamine thioester

A solution of thiophene-3-carboxylic acid (128 mg) in 2 mL of dry tetrahydrofuran under inert atmosphere was treated with triethylamine (0.25 mL) and diphenylphosphoryl azide (0.50 mL). After 1 hour, N-acetylcysteamine (0.25 mL) was added, and the reaction was allowed to proceed for 12 hours. The mixture was poured into water and extracted three times with equal volumes of ethyl acetate. The organic extracts were combined, washed sequentially with water, 1 N HCl, sat. $CuSO_4$, and brine, then dried over $MgSO_4$, filtered, and concentrated under vacuum. Chromatography on $SiO_2$ using ether followed by ethyl acetate provided pure product, which crystallized upon standing.

B. Furan-3-carboxylate N-acetylcysteamine thioester

A solution of furan-3-carboxylic acid (112 mg) in 2 mL of dry tetrahydrofuran under inert atmosphere was treated with triethylamine (0.25 mL) and diphenylphosphoryl azide (0.50 mL). After 1 hour, N-acetylcysteamine (0.25 mL) was added and the reaction was allowed to proceed for 12 hours. The mixture was poured into water and extracted three times with equal volumes of ethyl acetate. The organic extracts were combined, washed sequentially with water, 1 N HCl, sat. $CuSO_4$, and brine, then dried over $MgSO_4$, filtered, and concentrated under vacuum. Chromatography on $SiO_2$ using ether followed by ethyl acetate provided pure product, which crystallized upon standing.

C. Pyrrole-2-carboxylate N-acetylcysteamine thioester

A solution of pyrrole-2-carboxylic acid (112 mg) in 2 mL of dry tetrahydrofuran under inert atmosphere was treated with triethylamine (0.25 mL) and diphenylphosphoryl azide (0.50 mL). After 1 hour, N-acetylcysteamine (0.25 mL) was added and the reaction was allowed to proceed for 12 hours. The mixture was poured into water and extracted three times with equal volumes of ethyl acetate. The organic extracts were combined, washed sequentially with water, 1 N HCl, sat. $CuSO_4$, and brine, then dried over $MgSO_4$, filtered, and concentrated under vacuum. Chromatography on $SiO_2$ using ether followed by ethyl acetate provided pure product, which crystallized upon standing.

D. 2-Methyl-3-(3-thienyl)acrylate N-acetylcysteamine thioester (1) Ethyl 2-methyl-3-(3-thienyl)acrylate: A mixture of thiophene-3-carboxaldehyde (1.12 g) and (carbethoxyethylidene)triphenylphosphorane (4.3 g) in dry tetrahydrofuran (20 mL) was heated at reflux for 16 hours. The mixture was cooled to ambient temperature and concentrated to dryness under vacuum. The solid residue was suspended in 1:1 ether/hexane and filtered to remove triphenylphosphine oxide. The filtrate was filtered through a pad of $SiO_2$ using 1:1 ether/hexane to provide the product (1.78 g, 91%) as a pale yellow oil.

(2) 2-Methyl-3-(3-thienyl)acrylic acid: The ester from (1) was dissolved in a mixture of methanol (5 mL) and 8 N KOH (5 mL) and heated at reflux for 30 minutes. The mixture was cooled to ambient temperature, diluted with water, and washed twice with ether. The aqueous phase was acidified using 1N HCl then extracted 3 times with equal volumes of ether. The organic extracts were combined, dried with $MgSO_4$, filtered, and concentrated to dryness under vacuum. Crystallization from 2:1 hexane/ether provided the product as colorless needles.

(3) 2-Methyl-3-(3-thienyl)acrylate N-acetylcysteamine thioester: A solution of 2-Methyl-3-(3-thienyl)acrylic acid (168 mg) in 2 mL of dry tetrahydrofuran under inert atmosphere was treated with triethylamine (0.56 mL) and diphenylphosphoryl azide (0.45 mL). After 15 minutes, N-acetylcysteamine (0.15 mL) is added and the reaction is allowed to proceed for 4 hours. The mixture is poured into water and extracted three times with equal volumes of ethyl acetate. The organic extracts are combined, washed sequentially with water, 1 N HCl, sat. $CuSO_4$, and brine, then dried over $MgSO_4$, filtered, and concentrated under vacuum. Chromatography on $SiO_2$ using ethyl acetate provided pure product, which crystallized upon standing.

The above compounds are supplied to cultures of host cells containing a recombinant epothilone PKS of the invention in which either the NRPS or the KS domain of extender module 2 has been inactivated by mutation to prepare the corresponding epothilone derivative of the invention.

EXAMPLE 11

Production of Epothilone Analogs

A. Production of 13-keto-epothilone Analogs

Inactivation of the KR domain in extender moduler 4 of the epothilone PKS results in a hybrid PKS of the invention useful in the production of 13-keto epothilones. The extender module 4 KR domain was modified by replacing the wild-type gene with various deleted versions as described below. First, fragments were amplified using plasmid pKOS39-118B (a subclone of the epoD gene from cosmid pKOS35-70.4) as a template. The oligonucleotide primers for forming the left side of the deletion were TL3 and TL4, shown below:

(SEQ ID NO:18)
TL3: 5'-ATG*AATTC*ATGATGGCCCGAGCAGCG; and (SEQ ID NO:19)
TL4: 5'-AT*CTGCAG*CCAGTACCGCTGCCGCTGCCA.

The oligonucleotide primers for forming the right side of the deletion were TL5 and TL6, shown below:

(SEQ ID NO:20)
TL5: 5'-*GCTCTAGA*ACCCGGAACTGGCGTGGCCTGT; and (SEQ ID NO:21)
TL6: 5-GC*AGATCT*ACCGCGTGAGGACACGGCCTT.

The PCR fragments were cloned into vector Litmus 39 and sequenced to verify that the desired fragments were obtained. Then, the clone containing the TL3/TL4 fragment was digested with restriction enzymes PstI and BamHI, and the ~4.6 kb fragment was isolated. The 2.0 kb PCR fragment obtained using primers TL5/TL6 was treated with restriction enzymes BglII and XbaI and then ligated to either (i) the "short" KR linkers TL23 and TL24 (that are annealed together to form a double-stranded linker with single-stranded overhangs) to yield pKOS122-29; or (ii) the "long" (epoDH3*) linker, obtained by PCR using primers TL33TL34 and then treatment with restriction enzymes NsiI and SpeI, to yield plasmid pKOS122-30. The sequences of these oligonucleotide linkers and primers are shown below:

(SEQ ID NO:22)
TL23: 5'-GGCGCCGGCCAAGAGCGCCGCGCCGGTCGGCGGGCCAGCCGGGGACGGGT;

(SEQ ID NO:23)
TL24: 5'-CTAGACCCGTCCCCGGCTGGCCCGCCGACCGGCGCGGCGCTCTTGGCCG-GCGCCTGCA;

(SEQ ID NO:24)
TL33: 5'-GG*ATGCAT*GCGCCGGCCGAAGGGCTCGGA; and (SEQ ID NO:25)
TL34: 5'-TC*ACTAGT*CAGCGACACCGGCGCTGCGTTT.

The plasmids containing the desired substitution were confirmed by sequencing and then digested with restriction enzyme DraI. Then, the large fragment of each clone was ligated with the kanamycin resistance and galK gene (KG or kan-gal) cassette to provide the delivery plasmids. The delivery plasmids were transformed into epothilone B producer *Myxococcus xanthus* K111-32.25 by electroporation. The transformants were screened and kanamycin-sensitive, galactose-resistant survivors were selected to identify clones that had eliminated the KG genes. Confirmation of the KG elimination and the desired gene replacement for the recombinant strains was performed by PCR. The recombinant strains were fermented in flasks with 50 mL of CTS medium and 2% XAD-16 for 5 days, and epothilone analogs were eluted from XAD with 10 mL of methanol. Structure determination was based on the LC/MS spectrum and NMR. One such strain, designated K122-56, was deposited with the American Type Culture Collection, Manassa, Va. 20110-2209, USA, on Nov. 21, 2000, under the terms of the Budapest Treaty and is available under accession No. PTA-2714. The K122-56 strain (derived from plasmid pKOS122-29) produces 13-keto-11,12-dehydro-epothilone D as a major product whose structure is shown below

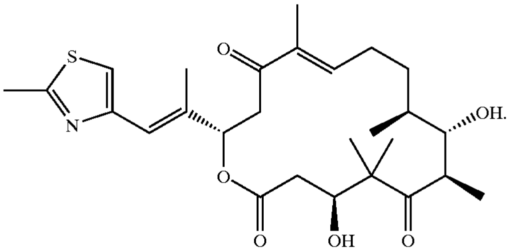

The K122-56 strain also produces 13-keto-epothilones C and D as minor products whose respective structures are shown below

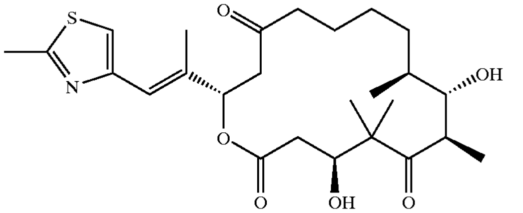

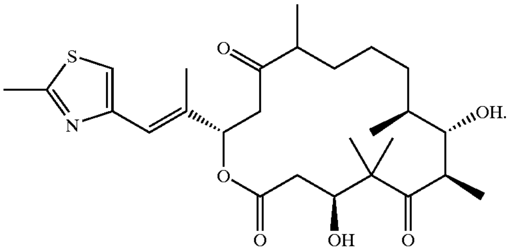

Similar results were obtained from strain K122-30, derived from plasmid pKOS122-30. These compounds and the strains and PKS enzymes that produce them are novel compounds, strains, and PKS enzymes of the invention.

Other strains of the invention that produce the 13-keto-11,12-dehydroepothilones include those in which the KR domain is rendered inactive by one or more point mutations. For example, mutating the constitutive tyrosine residue in the KR domain to a phenylalanine results in about a 10% decrease in KR activity and results in some production of 13-keto-epothilones. Additional mutations in the KR domain can eliminate more or all of the KR activity but can also lead to decreased epothilone production.

B. Production of 13-hydroxy-epothilone Analogs

Replacement of the extender module 5 KR, DH, and ER domains of the epothilone PKS with a heterologous KR domain, such as the KR domain from extender module 2 of the rapainycin PKS or extender module 3 of the FK520 PKS, results in a hybrid PKS of the invention useful in the production of 13-hydroxy epothilones. This construction is carried out in a manner similar to that described in part A of this example. The oligonucleotide primers for amplifying the desired portions of the epoD gene, using plasmid pKOS39-118B as a template, were:

(SEQ ID NO:26)
TL7: 5'-GCG*CTCGAGAG*CGCGGGTATCGCT;

(SEQ ID NO:27)
TL8: 5'-GAG*ATGCAT*CCAATGGCGCTCACGCT;

-continued (SEQ ID NO:28)
TL9: 5'-GC*TCTAGA*GCCGCGCGCCTTGGGGCGCT; and (SEQ ID NO:29)
TL10: 5-GC*AGATCT*TGGGGCGCTGCCTGTGGAA.

The PCR fragment generated from primers TL7/TL8 was cloned into vector LITMUS 28, and the resulting clone was digested with restriction enzymes NsiI and BglII, and the 5.1 kb fragment was isolated and ligated with the 2.2 kb PCR fragment generated from TL9/TL10treated with restriction enzymes BglII and XbaI and ligated to the KR cassettes. The KR cassette from the FK520 PKS was generated by PCR using primers TL31 and TL32 and then digestion with restriction enzymes XbaI and PstI. These primers are shown below:

(SEQ ID NO:30)
TL31: 5'-GG*CTGCAG*ACCCAGACCGCGGGCGACGC; and (SEQ ID NO:31)
TL32: 5'-GC*TCTAGA*GGTGGCGCCGGCCGCCCGGCG.

The remainder of the strain construction proceeded analogously to that described in part A of this Example, except that *Myxococcus xanthus* K111-72.4.4 was used as the recipient. The strain in which the KR domain of extender module 3 of the FK520 PKS replaced the KR, DH, and ER domains of extender module 5 of the epothilone PKS was designated K122-148 and deposited with the American Type Culture Collection, Manassas, Va. 20110-2209, USA, on Nov. 21, 2000, under the terms of the Budapest Treaty and is available under accession No. PTA-2711. Strain K122-148 produces 13-hydroxy-10,11-dehydro epothilone D as a major product and the C derivative as a minor product whose structures are shown below

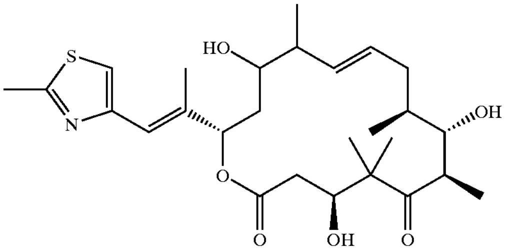

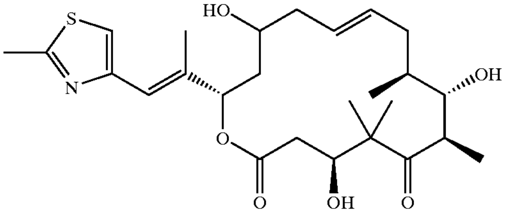

A similar strain, designated K122-52, in which the KR domain of extender module 2 of the rapamycin PKS was used for the replacement, produced the same compounds. These compounds and the strains and PKS enzymes that produce them are novel compounds, strains, and PKS enzymes of the invention.

C. Production of 9-keto-epothilone Analogs

Inactivation of the KR domain of extender module 6 of the epothilone PKS results in a novel PKS of the invention capable of producing the 9-keto-epothilones. The KR domain can be inactivated by site-specific mutagenesis by altering one or more conserved residues. The DNA and amino acid sequence of the KR domain of extender module 6 of the epothilone PKS is shown below:

```
                                            (SEQ ID NO:32)
 36710      36720      36730      36740      36750
GACGGCACCTACCTCGTGACCGGCGGTCTGGGTGGGCTCGGTCTGA
 D  G  T  Y  L  V  T  G  G  L  G  G  L  G  L>

    36760      36770      36780      36790      36800
GCGTGGCTGGATGGCTGGCCGAGCAGGGGGCTGGGCATCTGGTGCTGGTG
S  V  A  G  W  L  A  E  Q  G  A  G  H  L  V  L  V>

    36810      36820      36830      36840      36850
GGCCGCTCCGGTGCGGTGAGCGCGGAGCAGCAGACGGCTGTCGCCGCGCT
 G  R  S  G  A  V  S  A  E  Q  Q  T  A  V  A  A  L>

    36860      36870      36880      36890      36900
CGAGGCGCACGGCGCGCGTGTCACGGTAGCGAGGGCAGACGTCGCCGATC
  E  A  H  G  A  R  V  T  V  A  R  A  D  V  A  D>

    36910      36920      36930      36940      36950
GGGCGCAGATCGAGCGGATCCTCCGCGAGGTTACCGCGTCGGGGATGCCG
R  A  Q  I  E  R  I  L  R  E  V  T  A  S  G  M  P>

    36960      36970      36980      36990      37000
CTCCGCGGCGTCGTTCATGCGGCCGGTATCCTGGACGACGGGCTGCTGAT
L  R  G  V  V  H  A  A  G  I  L  D  D  G  L  L  M>
```

-continued

```
    37010      37020      37030      37040      37050
GCAGCAAACCCCCGCGCGGTTCCGCGCGGTCATGGCGCCCAAGGTCCGAG
  Q  Q  T  P  A  R  F  R  A  V  M  A  P  K  V  R>

    37060      37070      37080      37090      37100
GGGCCTTGCACCTGCATGCGTTGACACGCGAAGCGCCGCTCTCCTTCTTC
G  A  L  H  L  H  A  L  T  R  E  A  P  L  S  F  F>

    37110      37120      37130      37140      37150
GTGCTGTACGCTTCGGGAGCAGGGCTCTTGGGCTCGCCGGGCCAGGGCAA
 V  L  Y  A  S  G  A  G  L  L  G  S  P  G  Q  G  N>

    37160      37170      37180      37190      37200
CTACGCCGCGGCCAACACGTTCCTCGACGCTCTGGCACACCACCGGAGGG
  Y  A  A  A  N  T  F  L  D  A  L  A  H  H  R  R>

    37210      37220      37230      37240      37250
CGCAGGGGCTGCCAGCATTGAGCATCGACTGGGGCCTGTTCGCGGACGTG
A  Q  G  L  P  A  L  S  I  D  W  G  L  F  A  D  V>

GGTTTG
                                            (SEQ ID NO:33)
 G  L>
```

The DNA and amino acid sequence of the mutated and inactive KR domain of extender module 6 of the novel 9-keto-epothilone PKS provided by the present invention is shown below:

```
                                            (SEQ ID NO:34)
 36710      36720      36730      36740      36750
GACGGCACCTACCTCGTGACCGGCGCTCTGGGTGGGCTCGGTCTGA
 D  G  T  Y  L  V  T  G  A  L  G  G  L  G  L>

    36760      36770      36780      36790      36800
GCGTGGCTGGATGGCTGGCCGAGCAGGGGGCTGGGCATCTGGTGCTGGTG
S  V  A  G  W  L  A  E  Q  G  A  G  H  L  V  L  V>

    36810      36820      36830      36840      36850
GGCCGCTCCGGTGCGGTGAGCGCGGAGCAGCAGACGGCTGTCGCCGCGCT
 G  R  S  G  A  V  S  A  E  Q  Q  T  A  V  A  A  L>

    36860      36870      36880      36890      36900
CGAGGCGCACGGCGCGCGTGTCACGGTAGCGAGGGCAGACGTCGCCGATC
  E  A  H  G  A  R  V  T  V  A  R  A  D  V  A  D>

    36910      36920      36930      36940      36950
GGGCGCAGATCGAGCGGATCCTCCGCGAGGTTACCGCGTCGGGGATGCCG
R  A  Q  I  E  R  I  L  R  E  V  T  A  S  G  M  P>

    36960      36970      36980      36990      37000
CTCCGCGGCGTCGTTCATGCGGCCGGTATCCTGGACGACGGGCTGCTGAT
 L  R  G  V  V  H  A  A  G  I  L  D  D  G  L  L  M>

    37010      37020      37030      37040      37050
GCAGCAAACCCCCGCGCGGTTCCGCGCGGTCATGGCGCCCAAGGTCCGAG
  Q  Q  T  P  A  R  F  R  A  V  M  A  P  K  V  R>

    37060      37070      37080      37090      37100
GGGCCTTGCACCTGCATGCGTTGACACGCGAAGCGCCGCTCTCCTTCTTC
G  A  L  H  L  H  A  L  T  R  E  A  P  L  S  F  F>

    37110      37120      37130      37140      37150
GTGCTGTACGCTTCGGGAGCAGGGCTCTTGGGCTCGCCGGGCCAGGGCAA
 V  L  Y  A  S  G  A  G  L  L  G  S  P  G  Q  G  N>

    37160      37170      37180      37190      37200
CTTCGCCACGGCCAACACGTTCCTCGACGCTCTGGCACACCACCGGAGGG
  F  A  T  A  N  T  F  L  D  A  L  A  H  H  R  R>

    37210      37220      37230      37240      37250
CGCAGGGGCTGCCAGCATTGAGCATCGACTGGGGCCTGTTCGCGGACGTG
A  Q  G  L  P  A  L  S  I  D  W  G  L  F  A  D  V>
```

-continued

```
GGTTTG
                                               (SEQ ID NO:35)
 G  L>
```

The strain comprising this mutated KR domain coding sequence was constructed generally as described in part A of this Example, except that *Myxococcus xanthus* K111-72.4.4 was used as the recipient. The strain in which the KR domain of extender module 6 was inactivated was designated K39-164 and deposited with the American Type Culture Collection, Manassas, Va. 20110-2209, USA, on Nov. 21, 2000, under the terms of the Budapest Treaty and is available under accession No PTA-2716. Strain K39-164 produces 9-keto-epothilone D as a major product and the C derivative as a minor product whose structures are shown below

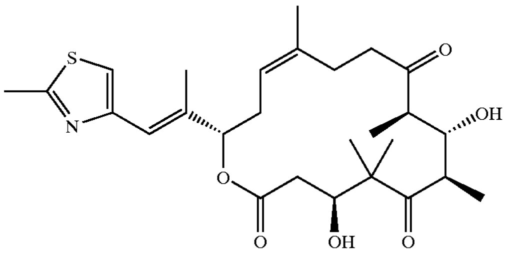

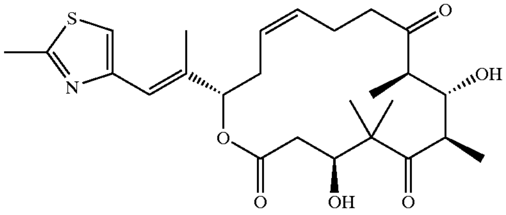

These compounds and the strain and PKS enzymes that produce them are novel compounds, strain, and PKS enzymes of the invention.

D. Production of 2-methyl-epothilone Analogs

The 2-methyl-epothilone analogs of epothilones A, B, C, and D can be constructed by replacing the coding sequence for the extender module 9 AT domain ("epoAT9") with coding sequences for an AT domain specific for methylmalonyl CoA. Suitable replacement AT domain coding sequences can thus be obtained from, for example, the genes that encode extender module 2 of the FK520 PKS ("FKAT2"; see PCT Pub. No. 00/020601, incorporated herein by reference); extender module 2 of the epothilone PKS ("epoAT2"); and extender module 3 of the PKS encoded by the tmbA genes ("tmbAT3"; see U.S. Pat. No. 6,090,601 and U.S. patent application Ser. No. 60/271,245, filed Feb. 15, 2001, each of which is incorporated herein by reference). The replacements are performed generally as described above, and the particular epothilones produced depend merely upon what epothilones are produced by the *Myxococcus* host in which the replacement is conducted.

Thus, the epoAT9 coding sequence (from nucleotide 50979 to nucleotide 52026) is replaced by either epoAT2 (nucleotide 12251 to nucleotide 13287) or FKAT2, or tmbAT3 coding sequences with engineered BglII (AGATCT) and NsiI (ATGCAT) restriction enzyme recognition sequences at junctions.

A first PCR is used to generate an ~1.6kb fragment from pKOS39-125 DNA used as template. The PCR fragment is subcloned into vector LITMUS28at the HindIII and BglII sites and sequenced; a plasmid with the desired sequence is designated P1. The oligonucleotides used in this PCR are:

```
                                     (SEQ ID NO:36)
TLII-1: 5'-ACAAGCTTGCGAAAAAGAACGCGTCT; and
                                     (SEQ ID NO:37)
TLII-2: 5'-CGAGATCTGCCGGGCGAGGAAGCGGCCCTG
```

A second PCR is used to generate an ~1.9 kb fragment using pKOS39-125 DNA as template. The PCR fragment is subcloned into vector LITMUS28 at the NsiI and SpeI sites and sequenced; a plasmid with the desired sequence is designated P2. The oligonucleotides used in this PCR are:

```
                                     (SEQ ID NO:38)
TLII-3b:  5'-GCATGCATGCGCCGGTCGATGGTGAG; and
                                     (SEQ ID NO:39)
TLII-4: 5'-AGACTAGTCACCGGCTGGCCCACCACAAGG.
```

Plasmid P1 is then digested with restriction enzymes BglII and SpeI, and the 4.5 kb fragment is isolated and ligated with the ~1.9 kb NsiI-SpeI restriction fragment from plasmid P2 and with one of the three replacement AT fragments (FKAT2, epoAT2, tmbAT3) isolated as NsiI-BglII restriction fragments to obtain plasmids P3.1, P3.2, and P3.3. The replacement AT fragments are generated by PCR using the following oligonucleotide primers:

```
for FKAT2:
                                            (SEQ ID NO:40)
TLII-20: 5'-GCATGCATCCAGTAGCGGTCACGGCGGA; and
                                            (SEQ ID NO:41)
TLII-21: 5'-CGAGATCTGTGTTCGCGTTCCCCGGGCAG;
for tmbAT3:
                                            (SEQ ID NO:42)
TLII-13: 5'-GCATGCATCCAGTAGCGCTGCCGCTGGAAT; and
                                            (SEQ ID NO:43)
TLII-14: 5'-GCAGATCTGTGTTCGTGTTCCCCGGCCA; and
for epoAT2:
                                            (SEQ ID NO:44)
TLII-17: 5'-GCATGCATCCAGTACCGCTCGCGCTG; and
                                            (SEQ ID NO:45)
TLII-18: 5'-CGAGATCTGTCTTCGTCTTTCCCGGCCAG.
```

Plasmids P3.1, P3.2, and P3.3 are then modified by insertion at the DraI site of the kan-gal cassete. The resulting plasmids are transformed into an epothilone-producing *Myxococcus xanthus* host cell of the invention (i.e., K111-72.4.4), and the cells are cultured and selected for the double-crossover recombination event as described above. Selected colonies are screened by PCR. Colonies exhibiting the desired recombination event are cultured in 50 mL cultures and screened by LC/MS for production of the desired compound. The expected products are 2-methyl-epothilone D and 2-methyl-epothilone C whose structures are shown below.

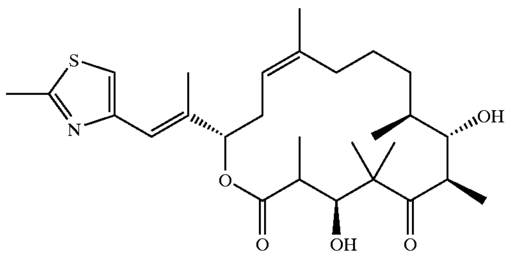

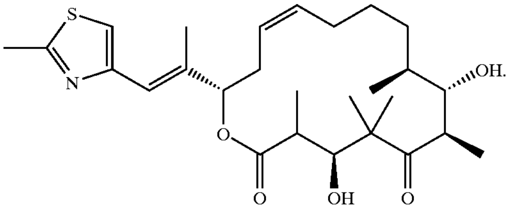

E. Production of 6-desmethyl-epothilone Analogs

The 6-desmethyl-epothilone analogs of epothilones A, B, C, and D can be constructed by replacing the coding sequence for the extender module 7 AT domain ("epoAT7") with coding sequences for an AT domain specific for malonyl CoA. Suitable replacement AT domain coding sequences can thus be obtained from, for example, the genes that encode extender module 3 of the FK520 PKS; extender module 5 of the epothilone PKS ("epoAT5"); and extender module 4 of the PKS encoded by the tmbA genes, each of which is incorporated herein by reference). The replacements are performed generally as described above, and the particular epothilones produced depend merely upon what epothilones are produced by the *Myxococcus* host in which the replacement is conducted.

Thus, the epoAT7 coding sequence (from nucleotide 39585 to nucleotide 40626) is replaced by either epoAT5 (nucleotide 26793 to nucleotide 27833) or FKAT3, or tmbAT4 coding sequences with engineered BglII (AGATCT) and NsiI (ATGCAT) restriction enzyme recognition sequences at junctions.

A first PCR is used to generate an ~1.8 kb fragment from pKOS39-125 DNA used as template. The PCR fragment is subcloned into vector LITMUS28 at the NsiI and SpeI sites and sequenced; a plasmid with the desired sequence is designated P4. The oligonucleotides used in this PCR are:

```
                                      (SEQ ID NO:46)
TLII-5: 5'-GGATGCATGTCGAGCCTGACGCCCGCCG; and

                                      (SEQ ID NO:47)
TLII-6: 5'-GCACTAGTGATGGCGATCTCGTCATCCGCCGCCAC.
```

A second PCR is used to generate an ~2.1 kb fragment using pKOS039-118B DNA as template. The oligonucleotides used in this PCR are:

```
                                      (SEQ ID NO:48)
TL16: ACAGATCTCGGCGCGCTGCCGCCGGAG; and

                                      (SEQ ID NO:49)
TL15: GGTCTAGACTCGAACGGCTCGCCACCGC.
```

The PCR fragment is subcloned into LITMUS 28 at the EcoRV restriction site, and a plasmid with the desired sequence is identified by sequencing and designated as plasmid pKQS 122-4. Plasmid pKOS122-4 is then digested with restriction enzymes BglH and SpeI, and the 4.8 kb fragment is isolated and ligated with the ~1.8 kb NsiI-SpeI restriction fragment from plasmid P4 and with one of the three replacement AT fragments (FKAT3, epoAT5, tmbAT4) isolated as NsiI-BglII restriction fragments to obtain plasmids P5.1, P5.2, and P5.3. The replacement AT fragments are generated by PCR using the following oligonucleotide primers:

```
for FKAT3:
                                      (SEQ ID NO:50)
TLII-11: 5'-GTATGCATCCAGTAGCGGACCCGCTCGA; and
                                      (SEQ ID NO:51)
TLII-12: 5'-GCAGATCTGTGTGGCTCTTCTCCGGACA;

for tmbAT4:
                                      (SEQ ID NO:52)
TLII-15; 5'-GCATGCATCCAGTAGCGCTGCCGCTGGAAC; and
                                      (SEQ ID NO:53)
TLII-16; 5'-GCATGCATCCAGTAGCGCTGCCGCTGGAAC; and

for PCR epoAT5:
                                      (SEQ ID NO:54)
TLII-19; 5'-GTAGATCTGCTTTCCTGTTCACCGGACA; and
TL8 (see part B of this Example).
```

Plasmids P5.1, P5.2, and P5.3 are then modified by insertion at the DraI site of the kan-gal cassete. The resulting plasmids are transformed into an epothilone-producing *Myxococcus xanthus* host cell of the invention (i.e., K111-72.4.4), and the cells are cultured and selected for the double-crossover recombination event as described above. Selected colonies are screened by PCR. Colonies exhibiting the desired recombination event are cultured in 50 mL cultures and screened by LC/MS for production of the desired compound. The expected compounds are 6-desmethyl-epothilone D and 6-desmethyl-epothilone C whose structures are shown below.

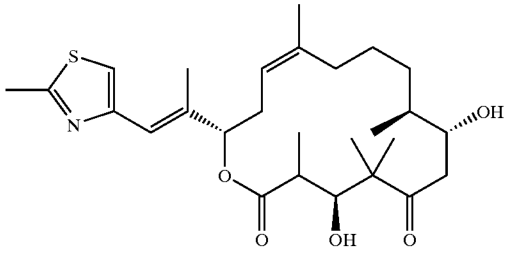

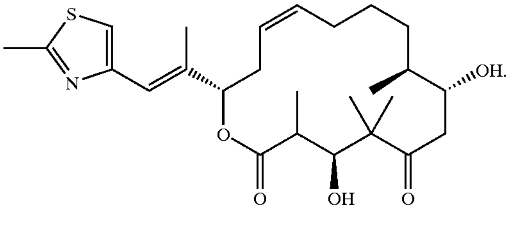

F. Production of 10-methyl-epothilone Analogs

The 10-methyl-epothilone analogs of epothilones A, B, C, and D can be constructed by replacing the coding sequence for the extender module 5 AT domain ("epoAT5") with coding sequences for an AT domain specific for methylmalonyl CoA. Suitable replacement AT domain coding sequences can thus be obtained from, for example, the genes that encode extender module 2 of the FK520 PKS, incorporated herein by reference); extender module 2 of the epothilone PKS ("epoAT2"); and extender module 3 of the PKS encoded by the tmbA genes. The replacements are performed generally as described above, and the particular epothilones produced depend merely upon what epothilones are produced by the *Myxococcus* host in which the replacement is conducted.

Thus, the epoAT5 coding sequence (from nucleotide 26793 to nucleotide 27833) is replaced by either epoAT2 (nucleotide 12251 to nucleotide 13287) or FKAT2, or tmbAT3 coding sequences with engineered BglII (AGATCT) and NsiI (ATGCAT) restriction enzyme recognition sequences at junctions.

The PCR fragment generated from primers TL11 and TL12 using plasmid pKOS39-118B as a template is cloned into vector LITMUS 28. The PCR primers used are:

```
                              (SEQ ID NO:55)
TL11: 5'-GGATGCATCTCACCCCGCGAAGCG; and

                              (SEQ ID NO:56)
TL12: 5'-GTACTAGTCAAGGGCGCTGCGGAGG.
```

A plasmid containing the desired insert is identified by DNA sequencing. This plasmid is then digested with restriction enzymes NsiI and XbaI, and the 4.6 kb fragment isolated. This fragment is ligated with the 2.0 kb PCR fragment obtained from primers TL5 and TL6 (described in Section A of this Example) that has been digested with restriction enzymes BglII and XbaI and with one of the three replacement AT fragments (FKAT2, epoAT2, tmbAT3) isolated as NsiI-BglII restriction fragments to obtain plasmids P6.1, P6.2, and P6.3. These latter three plasmids are then modified by insertion at the DraI site of the kan-gal cassete. The resulting plasmids are transformed into an epothilone-producing *Myxococcus xanthus* host cell of the invention (i.e., K111-72.4.4), and the cells are cultured and selected for the double-crossover recombination event as described above. Selected colonies are screened by PCR. Colonies exhibiting the desired recombination event are cultured in 50 mL cultures and screened by LC/MS for production of the desired compound. The expected compounds are 10-methyl-epothiklone D and 10-methyl-epothilone C whose structures are shown below

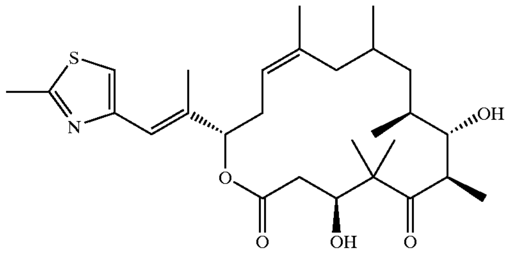

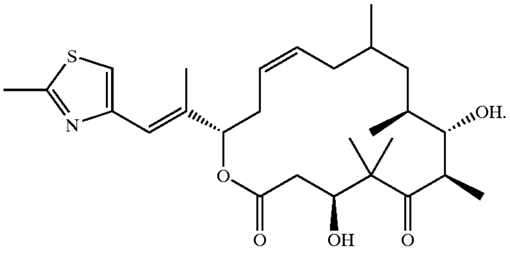

G. Production of 14-methyl-epothilone Analogs

The 14-methyl-epothilone analogs of epothilones A, B, C, and D can be constructed by replacing the coding sequence for the extender module 3 AT domain ("epoAT3") with coding sequences for an AT domain specific for methylmalonyl CoA. Suitable replacement AT domain coding sequences can thus be obtained from, for example, the genes that encode extender module 2 of the FK520 PKS; extender module 2 of the epothilone PKS ("epoAT2"); and extender module 3 of the PKS encoded by the tmbA genes. The replacements are performed generally as described above, and the particular epothilones produced depend merely upon what epothilones are produced by the *Myxococcus* host in which the replacement is conducted.

Thus, the epoAT3 coding sequence (from nucleotide 17817 to nucleotide 18858) is replaced by either epoAT2 (nucleotide 12251 to nucleotide 13287) or FKAT2, or tmbAT3 coding sequences with engineered BglII (AGATCT) and NsiI (ATGCAT) restriction enzyme recognition sequences at junctions.

A first PCR is used to generate an ~1.8 kb fragment from pKOS39-124 DNA used as template. The PCR fragment is subcloned into vector LITMUS28 at the XbaI and BglII sites and sequenced; a plasmid with the desired sequence is designated P9. The oligonucleotides used in this PCR are:

```
                                    (SEQ ID NO:57)
TLII-7: 5'-GCAGATCTGCCGCGCGAGGAGCTCGCGAT; and

                                    (SEQ ID NO:88)
TLII-8: 5'-CATCTAGAGCCGCTCCTGTGGAGTCAC.
```

A second PCR is used to generate an ~1.9 kb fragment using pKOS39-124 DNA used as template. The PCR fragment is subcloned into vector LITMUS28 at the NsiI and SpeI sites and sequenced; a plasmid with the desired sequence is designated P10. The oligonucleotides used in this PCR are:

```
                                    (SEQ ID NO:59)
TLII-9B: 5'-GGATGCATGCGCCGGCCGAAGGGCTCGGAG; and

                                    (SEQ ID NO:60)
TLII-10: 5'-GCACTAGTGATGGCGATCGGGTCCTCTGTCGC.
```

Plasmid P9 is then digested with restriction enzymes BglII and SpeI, and the 4.5 kb fragment is isolated and ligated with the ~1.9 kb NsiI-SpeI restriction fragment from plasmid P10 and with one of the three replacement AT fragments (FKAT2, epoAT2, tmbAT3) isolated as NsiI-BglII restriction fragments to obtain plasmids P11.1, P11.2, and P11.3. These latter three plasmids are then modified by insertion at the DraI site of the kan-gal cassete. The resulting plasmids are transformed into an epothilone-producing *Myxococcus xanthus* host cell of the invention (i.e., K111-72.4.4), and the cells are cultured and selected for the double-crossover recombination event as described above. Selected colonies are screened by PCR. Colonies exhibiting the desired recombination event are cultured in 50 mL cultures and screened by LC/MS for production of the desired compound. The expected compounds are 14-methyl-epothilone D and 14-methyl-epothilone C whose structures are shown below

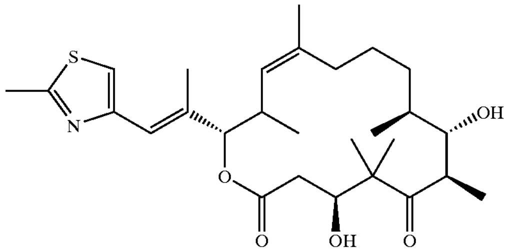

-continued

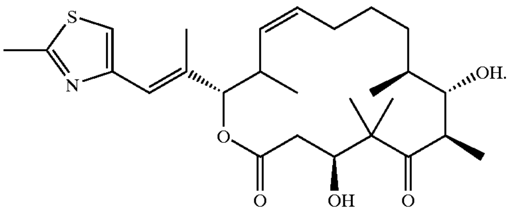

H. Production of 10,11-dehydro-epothilone Analogs

In one embodiment, the present invention provides a novel epothilone, 10,11-dehydro-epothilone D, and a recombinant host cells that produces this compound. The structure of 10,11-dehydro-epothilone D is shown below.

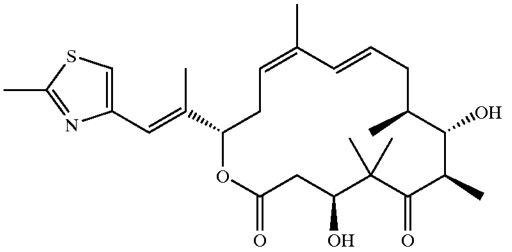

In another embodiment, the present invention provides a method for making any 10,11-dehydro-epothilone analogs by inactivation of the ER domain of extender module 5 of the epothilone PKS that produces the corresponding epothilone.

In one embodiment, a strain that produces 10, 11-dehydroepothilone D is constructed by inactivating the enoyl reductase (ER) domain of extender module 5. In one embodiment, the ER inactivation is accomplished by changing the two glycines (-Gly-Gly-) in the NADPH binding region to an alanine and serine (-Ala-Ser-). The 2.5 kb BbvCI-HindIII fragment from plasmid pKOS39-118B (a subclone of the epoD gene from cosmid pKOS35-70.4) has been cloned into pLitmus28 as pTL7 which is used as a template for site directed mutagenesis. The oligonucleotide primers for introducing the -Gly-Gly- to -Ala-Ser- mutations into the NADPH binding domain are:

(SEQ ID NO:61)
TLII-22, 5'-TGATCCATGCTGCGGCCGCTAGCGTGGGCATGGCCGC.

(SEQ ID NO:62)
TLII-23, 5'-GCGGCCATGCCCACGCTAGCGGCCGCAGCATGGATCA.

The PCR clones containing the substitutions are confirmed by sequencing and are digested with the restriction enzyme DraI and treated with shrimp alkaline phosphatase. Then, the large fragment of each clone is ligated with the kanamycin resistance and galK gene (KG or kan-gal) cassette to provide the delivery plasmids. The delivery plasmids are transformed into the epothilone D producer *M. xanthus* K111-72-4.4 or K111-40-1 by electroporation. The transformants are screened and kanamycin-sensitive, galactose-resistant survivors are selected to identify clones from which the KG genes have been eliminated. Confirmation of the KG elimination and the desired gene replacement for the recombinant strains is performed by PCR. The recombinant strains are fermented in flasks with 50 mL of CTS medium (casitone, 5 g/L; MgSO4, 2 g/L; L-alanine, 1 mg/L; L-serine, 1 mg/L; glycine, 1 mg/L; and HEPES buffer, 50 mM) and 2% XAD-16 for 7 days, and 10,11-dehydro-epothilone D is eluted from the XAD resin with 10 mL of methanol.

I. Production of Oxazole-Containing Epothilones by Fermentation

In one embodiment, the present invention provides a method for obtaining the oxazole containing epothilones (in which the thiazole moiety of the corresponding epothilone is replaced by an oxazole) by fermenting an epothilone producing strain, such as a *Sorangium cellulosum* strain or a *Myxococcus* strain provided by the present invention, in media supplemented with L-serine.

To illustrate this aspect of the invention, a cultures of *Myxococcus xanthus* strain K111-40.1 or K111-72.4.4 is fermented in accordance with the methods of Example 3, except that L-serine is present at 11×, 51×, 101×, and 201× the basal serine concentration in the batch media (2.3 mM). The batch media-containing 50 mL cultures thus contain: 20 g/L XAD-16; 5 g/L casitone; 2 g/L MgSO4; 7 mL/L methyl oleate; and 4 mL/L trace metals solution, and an appropriate concentration of a filter-sterilized 1.25 M solution of L-serine is added. The batch titers observed in basal media were: Epo C: 0.4 mg/L, Epo D: 2 mg/L, Epo H1 (the C analog of the oxazole): Not detectable, and Epo H2 (the D analog of the oxazole): 0.02 mg/L. Increasing the serine concentration decreased the epoC and epoD concentrations (almost to undetectable levels at 51× supplementation). Thus, the batch titers in 51× supplementation of L-serine in basal media were: Epo C: 0.03 mg/L, Epo D: 0.05 mg/L, Epo H1: 0.12 mg/L, and Epo H2: 0.13 mg/L. A fed-batch protocol could increase the observed titers by about 10 fold.

J. Construction of Epothilone Analogs

In one embodiment, the present invention provides epothilones and epothilone derivatives produced by recombinant epothilone PKS enzymes of the invention in which (i) the specificity of the extender module 1 NRPS has been changed from cysteine to another amino acid; (ii) the loading domain has been changed to an NRPS or CoA ligase; or (iii) both (i) and (ii). This example describes how such recombinant epothilone PKS enzymes of the invention are constructed; references cited in this example are listed at the end of this example and are referred to in the text by a citation number and are incorporated herein by reference.

Epothilones contain the amino acid cysteine that has been cyclized and oxidized to form the thiazole. Two other amino acids, serine and threonine, can undergo similar cyclization and oxidation to yield an oxazole and methyloxazole, respectively. For example, the oxazole and methyloxazole derivatives of epothilone D are shown below

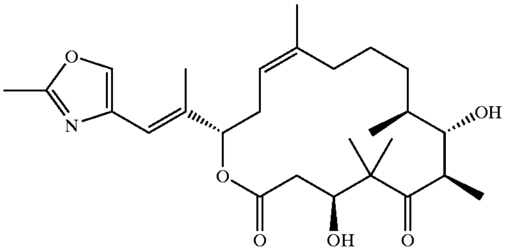

-continued

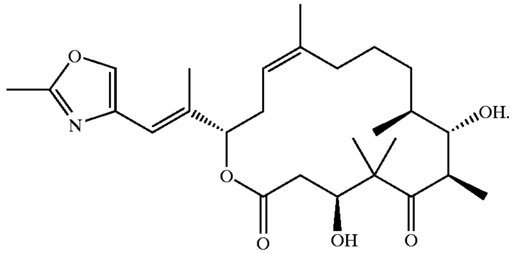

To construct analogs of epothilone with either the oxazole or methyloxazole, engineering of extender module 1, the NRPS module, can be performed. NRPS modules that extend a growing molecule are minimally composed of a domain that activates an amino acid, the adenylation domain, a PCP or peptidyl carrier protein domain, which tethers the amino acid to the NRPS, and a condensation domain, which condenses the amino acid to a carboxyl group of the growing molecule to form a peptide bond (5, 7). The recognition sequence for determining the specificity of the amino acid is found within the adenylation domain, specifically between the A4 and A5 consensus sequence (4). Analysis of the region has shown that key amino acids in this protein region can predict which amino acid will be used by the NRPS (2, 8). Experiments have been performed that exchange the complete NRPS adenylation region for that of another, which results in a hybrid NRPS that has the amino acid specificity of the new adenylation domain (6, 9). Experiments using smaller regions of the adenylation region, such as the one between the A4 and A5 consensus sequence have not been reported. In one embodiment, a hybrid PKS of the invention is constructed by replacing the region between the A4 and A5 consensus region of the adenylation domain from epoB with those from vibF and blmVII, which utilize threonine, and with the NRPS-4 region from blmVI of the bleomycin gene cluster, which utilizes serine (3).

Recent experiments suggest that the condensation domain may be able to detect if an incorrect amino acid has been attached to the PCP (1). Once an incorrect amino acid is detected the efficiency of the condensation reaction is reduced. To avoid this, in addition to swapping the adenylation domain, one can also bring along the cognate condensation domain in order to change the specificity of the adenylation domain and engineer a fully active NRPS.

The present invention also provides recombinant epothilone PKS enzymes that produce the 16 desmethyl derivatives of the oxazole and methyloxazole forms of epothilone. Such enzymes are constructed by changing the AT domain of extender module 2, epoC, from methymalonyl specific to malonyl specific. AT domains that can be used to make the constructs include those from extender module 5 and 9 of the epothilone cluster and extender modules 2 and 4 from the soraphen gene cluster.

The present invention also provides recombinant PKS enzymes in which the EpoA protein has been replaced by an NRPS. The present invention also provides the novel epothilones produced by such enzymes. Epothilone biosynthesis begins by the loading of malonate onto the ACP of the loading module, EpoA. This malonate is subsequently decarboxylated by the KS domain and then transferred as an acetyl moiety to EpoB, the NRPS module. After the molecule has been acted on by EpoB, the resulting compound is 2-methylthiazole.

To make analogs that have an amino acid attached at the 2 position on the thiazole, deletion of epoA and the insertion of a NRPS module are needed. Any NRPS module can be used; however, to make the most conservative change, one can employ an NRPS module to replace epoA that naturally communicates with a downstream NRPS module. Moreover, because the NRPS replacing epoA is the loading module, it does not need a condensation domain. This can be done by taking an extender NRPS module and removing the condensation domain or using an NRPS that is naturally a loading module and thus lacks the condensation domain. An illustrative NRPS loading module is the one from safB, which utilizes alanine and is from a *M. xanthus.*

In constructing *M. xanthus* strains that contain the safB loading module in the place of epoA, one can determine the optimum boundaries for the new loading module and epoB. The linker region between PKS proteins is often critical for "communication" between those proteins. One can construct three different strains to examine the optimum linker. In the first, the ACP domain of EpoA is fused to the adenylation domain of loading domain of safB. This construct requires that the ACP of EpoA function as a PCP. Although PCP and ACP domains are functionally similar, they do not show high sequence identity and thus may be restricted on what they can recognize and bind. The second construct fuses the last several amino acids of EpoA downstream of the PCP domain of the SafB loading module, thus providing the necessary linker region for the hybrid loading module to "communicate" with EpoB. Finally, a fusion of the SafB loading module with EpoB will be constructed. Because SafB is composed of two modules, it is possible to take all of the loading module of SafB and fuse it directly to EpoB to give a fusion protein, which should optimal for communication between the SafB loading module and EpoB.

Once SafB or any another loading NRPS domain has been used to replace the 2-methyl on the thiazole of epothilone with an amino acid, then changes can be made in the new loading NRPS module so that any amino acid could be used to start the synthesis of the epothilone analogs. A comprehensive list of potential amino acids and their corresponding NRPS modules that could be used for these swaps are provide by Challis et al. (2).

All of the replacements can be made in K111-32.25, the *M. xanthus* strain that contains the epothilone genes, or K111-40-1, the *M. xanthus* strain that contains the epothilones genes and in which the epoK gene does not produce a functional product, or any other epothilone producing strain of the invention or in *Sorangium cellulosum.* In *Myxococcus,* the appropriate constructs can be made on plasmids and, using the galK and kanamycin selection, used to replace the wild type genes with the engineered ones. For example, a replacement of the NRPS in K111-40-1 with an NRPS specific for serine is expected to make the 2-methyl-oxazole derivative of epothilone D and 2-methyl-oxazole derivative of epothilone C as the major and minor products respectively. The structure of these compounds are shown below

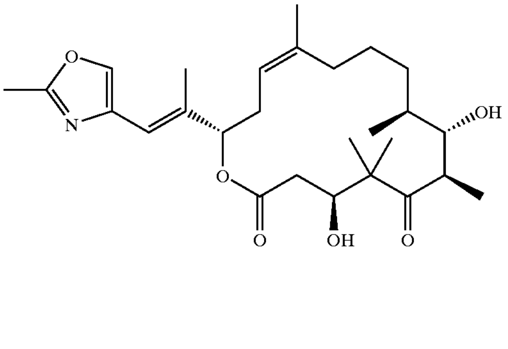

-continued

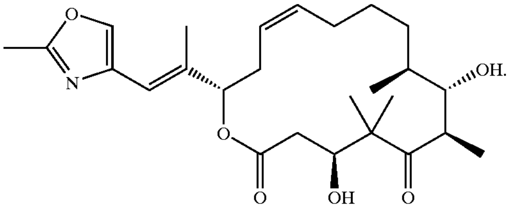

Replacement of the NRPS in K111-40-1 with an NRPS specific for threonine is expected to the the following compounds and the major and minor products respectively

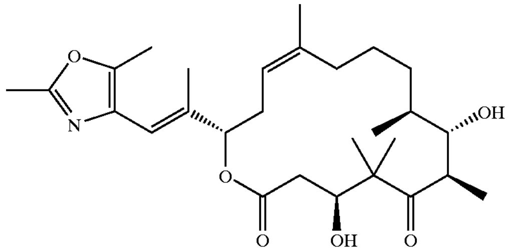

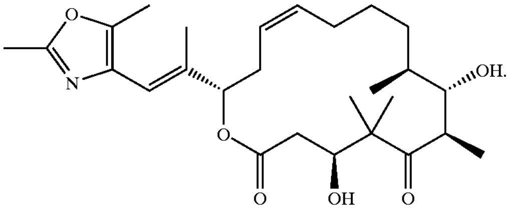

Replacement of the NRPS in K111-40-1 with an NRPS specific for glycine, alanine, glutamic acid, aspartic acid, phenylalanine, histidine, isoleucine, leucine, methionine, asparagine, glutamine, arginine, valine, and tyrosine are each expected to make the following compounds as the major and minor products respectively

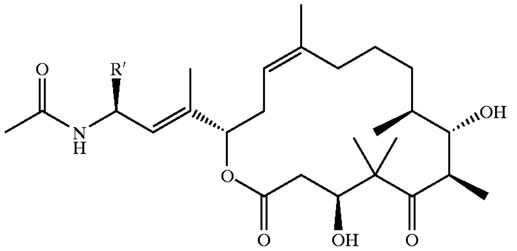

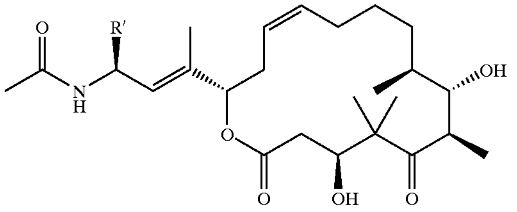

where R' corresponds to the specific side chain in the amino acid (for example, R' is H in the general amino acid formula $NH_2$—CHR'COOH for glycine and is methyl for alanine and so on).

Replacement of the NRPS in K111-40-1 with an NRPS specific for proline is expected to make the following compounds as the major and minor products respectively

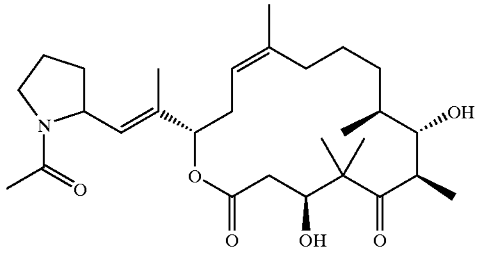

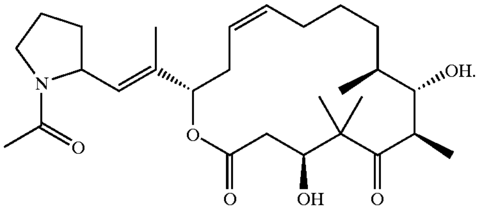

The references cited in this subsection are as follows.

1 Belshaw et al. 1999. Aminoacyl-CoAs as probes of condensation domain selectivity in nonribosomal peptide synthesis Science. 284:486–9.

2. Challis et al. 2000. Predictive, structure-based model of amino acid recognition by nonribosomal peptide synthetase adenylation domains Chem Biol. 7:211–24.

3. Du et al. 2000. The biosynthetic gene cluster for the antitumor drug bleomycin from Streptomyces verticillus ATCC15003 supporting functional interactions between nonribosomal peptide synthetases and a polyketide synthase Chem Biol. 7:623–42.

4. Konz et al. 1999. How do peptide synthetases generate structural diversity? Chem Biol. 6:R39–48.

5. Marahiel et al. 1997. Modular peptide synthetases involved in non-ribosomal peptide synthesis Chem. Rev. 97:2651–2673.

6. Schneider et al. 1998. Targeted alteration of the substrate specificity of peptide synthetases by rational module swapping Mol Gen Genet. 257:308–18.

7. Stachelhaus et al. 1995. Modular structure of peptide synthetases revealed by dissection of the multifunctional enzyme GrsA J Biol Chem. 270:6163-9.

8. Stachelhaus et al. 1999. The specificity-conferring code of adenylation domains in nonribosomal peptide synthetases Chem Biol. 6:493–505.

9. Stachelhaus et al. 1995. Rational design of peptide antibiotics by targeted replacement of bacterial and fungal domains Science. 269:69–72.

EXAMPLE 12

Biological Activity 10,11-dehydroepothilone D was screened for anticancer activity in four different human tumor cell lines using sulforhodamine B (SRB) assay. 10,11-dehydroepothilone D shows growth inhibitory effect on all four cell lines with $IC_{50}$s ranging from 28 nM to 40 nM. The mechanism of action was determined by a cell-based tubulin polymerization assay which revealed that the compound promotes tubulin polymerization. Human cancer cell lines MCF-7 (breast), NCI/ADR-Res (breast, MDR), SF-268 (glioma), NCI-H460 (lung) were obtained from National Cancer Institute. The cells were maintained in a 5% CO2-humidified atmosphere at 37 degree in RPMI 1640 medium (Life Technology) supplemented with 10% fetal bovine serum (Hyclone) and 2 mM L-glutamine.

Cytotoxicity of 10,11-dehydroepothilone D was determined by SRB assay (Skehan et al., *J. Natl. Cancer Inst.* 82: 1107–1112 (1990) which is incorporated herein by reference). Cultured cells were trypsinized, counted and diluted to the following concentrations per 100 μl with growth medium: MCF-7, 5000; NCI/ADR-Res, 7500; NCI-H460, 5000; and, SF-268, 7500. The cells were seeded at 100 μl/well in 96-well microtiter plates. Twenty hours later, 100 μl of 10,11-dehydroepothilone D (ranging from 1000 nM to 0.001 nM diluted in growth medium) were added to each well. After incubation with the compound for 3 days, the cells were fixed with 100 μl of 10% trichloric acid ("TCA") at 4 degree for 1 hour, and stained with 0.2% SRB/1% acetic acid at room temperature for 20 minutes. The unbound dye was rinsed away with 1% acetic acid, and the bound SRB was then extracted by 200 μl of 10 mM Tris base. The amount of bound dye was determined by OD 515 nm, which correlates with the total cellular protein contents. The data were then analyzed using Kaleida Graph program and the $IC_{50}$'s calculated. Epothione D that was chemically synthesized was tested in parallel for comparison.

For tubulin polymerization assay, MCF-7 cells were grown to confluency in 35 mm-culture dishes and treated with 1 μM of either 10,11-dehydroepothilone D or epothilone D for 0, 1 or 2 hours at 37 degree (Giannakakou et al., *J. Biol. Chem.* 271:17118–17125 (1997); *Int. J. Cancer* 75: 57–63 (1998) which are incorporated herein by reference). After washing the cells twice with 2 ml of PBS without calcium or magnesium, the cells were lysed at room temperature for 5–10 minutes with 300 μl of lysis buffer (20 mM Tris, PH 6.8, 1 mM $MgCl_2$, 2 mM EGTA, 1% Triton X-100, plus protease inhibitors). The cells were scraped and the lysates transferred to 1.5-ml Eppendof tubes. The lysates were then centrifuged at 18000 g for 12 minutes at room temperature. The supernatant containing soluble or unpolymerized (cytosolic) tubulin were separated from pellets containing insoluble or polymerized (cytoskeletal) tubulin and transferred to new tubes. The pellets were then resuspended in 300 μl of lysis buffer. Changes in tubulin polymerization in the cell were determined by analyzing same volume of aliquots of each sample with SDS-PAGE, followed by immunoblotting using an anti-tubulin antibody (Sigma).

The results of several experiments showed that 10,11-dehydroepothilone D (designated as "Epo490") has an $IC_{50}$ in the range of 28 nM to 40 nM against four different human tumor cells lines.

TABLE 13

| Cell lines | EpoD (nM) N = 3 | Epo49O (nM) N = 2 |
|---|---|---|
| MCF-7 | 21 ± 10 | 28 ± 8 |
| NCI/ADR | 40 ± 12 | 35 ± 9 |
| SF-268 | 34 ± 8 | 40 ± 5 |
| NCI-H460 | 30 ± 2 | 34 ± 1 |

Tubulin polymerization assays reveal that 10,11-dehydroepothilone D has the same mechanism of action as epothilone D. In MCF-7 cells, 10,11-dehydroepothilone D strongly promoted tubulin polymerization at the conditions tested, with similar kinetics and effect as epothilone D. Other compounds of the invention may be tested in a similar manner by replacing the compound of interest for 10,11-dehydroepothilone D.

EXAMPLE 13

Oxazole Derivatives

This example describes modulating the types of epothilone compounds produced by host cells using fermentation conditions. By supplementing host cells with excess serine, the compounds normally produced by host cells are modulated in such a way to favor the production of the oxazole counterparts. For example, cells that predominantly produce a compound or compounds of formula V can be made to favor the production of oxazole counterparts corresponding to compounds of formula VI.

In one embodiment, *M. xanthus* strain K111-40-1, a strain that predominantly makes epothilones C and D is made to significantly increase the production of epothilones $H_1$ and $H_2$, the oxazole counterparts to epothilones C and D. Strain K111-40-1 (PTA-2712) was deposited in the American Type Culture Collection ("ATCC"), 10801 University Blvd., Manassas, Va., 20110-2209 USA on Nov. 21, 2000. Strain K111-40-1 was grown in medium that was either supplemented or not supplemented with additional serine. The final concentrations of the components in unsupplemented medium were: hydrolyzed casein (pancreatic digest, purchased from Difco under the brand name Casitone), 5 g/L; MgSO4.7$H_2O$, 2 g/L; XAD-16, 20 g/L; trace elements solution 4 mL/L; methyl oleate 7 ml/L; and Hepes buffer, 40 mM (titrated to a pH of 7.6 with KOH). Trace elements solution comprises: concentrated $H_2SO_4$, 10 mL/L; $FeCl_3.6H_2O$, 14.6 g/L; $ZnCl_2$, 2.0 g/L; $MnCl_2.4H_2O$, 1.0 g/L; $CuCl_2.2H_2O$, 0.42 g/L; $H_3BO_3$, 0.31 g/L; $CaCl_2.6H_2O$, 0.24 g/L; and $Na_2MoO_4.2H_2O$, 0.24 g/L. The basal level of serine was taken as 4.82% w/w, the value determined by Difco' amino acid analysis of the particular lot of Casitone. Consequently, the basal serine concentration was 2.3 mM, a value calculated from the final concentration of 5 g/L of Casitone in the medium. Serine supplemented medium contained a fifty fold higher concentration of serine, 117 mM.

Cells were grown in flasks at 30° C. for 120 hours on a coffin shaker at 250 rpm. Compounds produced by the strains during fermentation were extracted by capturing the resin, washing the resin once in water, and the extracting the compounds in the resin for 30 minutes in 20 mL of methanol. The samples were analyzed on HPLC and by mass spectroscopy.

Analysis of the compounds produced by cells showed that a fifty fold increase in serine levels resulted in a 30 fold increase in the production of epothilone $H_1$ (0.12 mg/L) and a 5 fold increase in the production of epothilone $H_2$ (0.12 mg/L) over that produced by cells grown in medium that was not supplemented with serine. Notably, the cells produced almost undetectable quantities of epothilones C and D (<50 μg/L).

The concomitant increase in oxazole-containing compounds and the decrease in thiazole-containing compounds from serine feeding provides a way to obtain the oxazole compounds from host cells that normally would make the thiazole-containing counterparts. For example, the recombinant construct to make 9-oxo epothilone D (as decribed in subpart C of Example 11) can be grown in conditions similar to that described above to make 17-des(2-methyl-4-thiazolyl)-17-(2-methyl-4-oxazolyl)-9-oxo-epothilone D, the oxazole-counterpart to 9-oxo-epothilone D. Similarly, other recombinant constructs of the invention including those described by Example 11 can be grown with excess serine to provide the corresponding oxazole compounds.

EXAMPLE 14

Microbial Transformation of C-21 Methyl to C-21 Hydroxymethyl

This example describes the microbial transformation of C-21 methyl to C-21 hydroxymethyl of compounds of formula I where Ar is

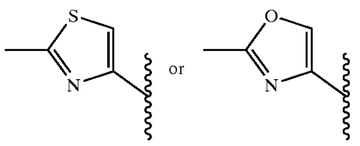

A frozen vial (approximately 2 ml) of *Amycolata autotrophica* ATCC 35203 or *Actinomyces* sp. strain PTA-XXX as described by PCT Publication No. WO 00/39276 is used to inoculate 1 500 ml flask containing 100 mL of medium. The vegetative medium consists of 10 g of dextrose, 10 g of malt extract, 10 g of yeast extract, and 1 g of peptone in liter of deionized water. The vegetative culture is incubated for three days at 28° C. on a rotary shaker operating at 250 rpm. One mL of the resulting culture is added to each of sixty-two 500 mL flasks containing the transformation medium which as the same composition as the vegetative medium. The cultures are incubated at 28° C. and 250 rpm for 24 hours. A suitable compound of the invention is dissolved in 155 ml of ethanol and the solution is distributed to the sixty-two flasks. The flasks are then returned to the shaker and incubated for an additional 43 hours at 28° C. and 250 rpm. The reaction culture is then processed to recover 21-hydroxy counterpart of the starting compound.

EXAMPLE 15

Epoxidation Using EpoK

This example describes the enzymatic epoxidation of compounds of formula I where $R^8$ and $R^{10}$ together form a carbon carbon double bond (desoxy compounds of the invention). The epoK gene product was expressed in *E. coli* as a fusion protein with a polyhistidine tag (his tag) and purified as described by PCT publication, WO 00/31247 which is incorporated herein by reference. The reaction consists of 50 mM Tris (pH 7.5), 21 $\mu$M spinach ferredoxin, 0.132 units of spinach ferredoxin: $NADP^+$ oxidoreductase, 0.8 units of glucose-6-phosphate dehydrogenase, 1.4 mM NADP, and 7.1 mM glucose-6-phosphate, 100 $\mu$M or 200 $\mu$M desoxy compound of the present invention, and 1.7 $\mu$M amino terminal histidine tagged EpoK or 1.6 $\mu$M carboxy terminal histidine tagged EpoK in a 100 $\mu$L volume. The reactions are incubated at 30° C. for 67 minutes and stopped by heating at 90° C. for 2 minutes. The insoluble material is removed by centrifugation, and 50 $\mu$L of the supernatant containing the desired product is analyzed by LC/MS.

EXAMPLE 16

Chemical Epoxidation

This example describes the chemical epoxidation of a compound of formula I where $R^8$ and $R^{10}$ together form a carbon carbon double bond (desoxy compound of the invention). A solution of dimethyldioxirane (0.1 M in acetone, 17 mL) is added dropwise to a solution of a desoxy compound of the invention (505 mg) in 10 mL of $CH_2Cl_2$ at −78° C. The mixture is warmed to −50° C., kept for 1 hour, and then another portion of dimethyldioxirane solution (5 mL) is added and the reaction is continued for an additional 1.5 hour at −50° C. The reaction is then dried under a stream of $N_2$ at −50° C. The product is purified by flash chromatography on $SiO_2$.

EXAMPLE 17

(3S,6R,7S,8R,12R,13S,15S,16E)-15-amino-3,7-dihydroxy-5,9-dioxo-12,13-epoxy-4,4,6,8,12,16-hexamethyl-17-(2-methylthiazol-4-yl)-16-heptadecenoic acid

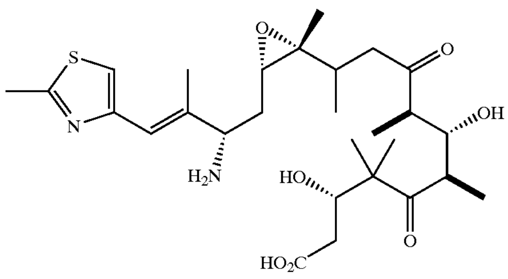

Step 1. 9-oxoepothilone B. A solution of dimethyldioxirane (0.1 M in acetone, 17 mL) is added dropwise to a solution of 9-oxoepothilone D (505 mg) in 10 mL of $CH_2Cl_2$ at −78° C. The mixture is warmed to −50° C., kept for 1 hour, and then another portion of dimethyldioxirane solution (5 mL) is added and the reaction is continued for an additional 1.5 hour at −50° C. The reaction is then dried under a stream of $N_2$ at −50° C. The product is purified by flash chromatography on $SiO_2$.

Step 2. (3S,6R,7S,8R,12R,13S,15S,16E)-15-azido-3,7-dihydroxy-5,9-dioxo-12,13-epoxy-4,4,6,8,12,16-hexamethyl-17-(2-methylthiazol-4-yl)-16-heptadecenoic acid.

A solution of 9-oxoepothilone B (2.62 g) and sodium azide (0.49 g) in 55 mL of degassed tetrahydrofuran/water (10:1 v/v) is treated with tetrakis(triphenylphosphine)palladium (0.58 g) under an argon atmosphere. The mixture is kept at 45° C. for 1 hour, then diluted with 50 mL of water and extracted with ethyl acetate. The extract is washed with brine, dried over $Na_2SO_4$, filtered, and evaporated. The product is purified by flash chromatography on $SiO_2$.

Step 3. (3S,6R,7S,8R,12R,13S,15S,16E)-15-amino-3,7-dihydroxy-5,9-dioxo-12,13-epoxy-4,4,6,8,12,16-hexamethyl-17-(2-methylthiazol-4-yl)-16-heptadecenoic acid. A solution of (3S,6R,7S,8R,12R,13S,15S,16E)-15-azido-3,7-dihydroxy-5,9-dioxo-12,13-epoxy-4,4,6,8,12,16-hexamethyl-17-(2-methylthiazol-4-yl)-16-heptadecenoic acid acid (565 mg) in 15 mL of THF/water (10:1 v/v) is treated with a 1.0 M solution of trimethylphosphine in toluene (3 mL) under argon for 2 hours at ambient temperature. The mixture is concentrated, and the product is purified by flash chromatography on $SiO_2$.

EXAMPLE 18

(4S,7R,8S,9R,13R,14S,16S)-13,14-epoxy-4,8-dihydroxy-2,6,10-trioxo-5,5,7,9,13-pentamethyl-16-(1-(2-methylthiazol-4-yl)propen-2-yl)-1-aza-11-cyclohexadecene.

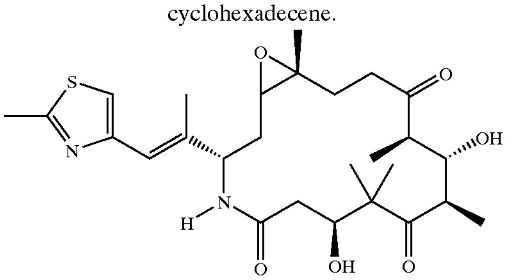

A solution of (3S,6R,7S,8R,12R,13S,15S,16E)-15-amino-3,7-dihydroxy-5,9-dioxo-12,13-epoxy-4,4,6,8,12,16-hexamethyl-17-(2-methylthiazol-4-yl)-16-heptadecenoic acid (540 mg) in acetonitrile/dimethylformamide (20:1 v/v, 150 mL) is cooled to 0° C. and treated sequentially with 1-hydroxybenzotriazole (0.135 g) and 1-(3-dimethylaminopropyl)-3-ethylcarbodiimide hydrochloride (0.5 g). The mixture is warmed to ambient temperature and kept for 12 hours, then diluted with water and extracted with ethyl acetate. The extract is washed sequentially with water, sat. $NaHCO_3$, and brine, then dried over $Na_2SO_4$, filtered, and evaporated. The product is purified by flash chromatography on $SiO_2$.

EXAMPLE 19

(4S,7R,8S,9R,13Z,16S)-4,8-dihydroxy-2,6,10-trioxo-5,5,7,9,13-pentamethyl-16-(1-(2-methylthiazol-4-yl)propen-2-yl)-1-aza-11-cyclohexadecene

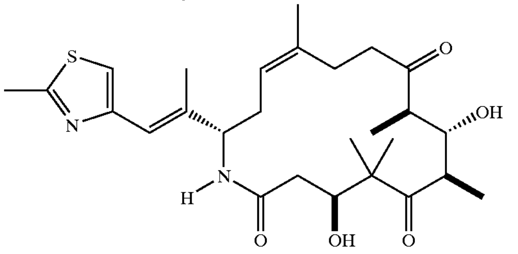

A solution of tungsten hexachloride (0.76 g) in tetrahydrofuran (20 mL) at −78° C. is treated with a 1.6 M solution of n-butyllithium in hexane (2.5 mL). The mixture is allowed to warm to ambient temperature over 20 minutes. A 13.8 mL portion of the resulting green solution is added to a solution of (4S,7R,8S,9R,13R,14S,16S)-4,8-dihydroxy-13,14-epoxy-2,6,10-trioxo-5,5,7,9,13-pentamethyl-16-(1-(2-methylthiazol-4-yl)propen-2-yl)-1-aza-11-cyclohexadecene (360 mg) in 2 mL of tetrahydrofuran at ambient temperature. After 30 min, the reaction is cooled to 0° C. and treated with sat. $NaHCO_3$ (10 mL). The mixture is diluted with water and extracted with $CH_2Cl_2$. The extract is dried over $Na_2SO_4$, filtered, and evaporated. The product is purified by flash chromatography on $SiO_2$.

EXAMPLE 20

(4S,7R,8S,9R,13R,14S,16S)-13,14-epoxy-4,8-dihydroxy-2,6,10-trioxo-1,5,5,7,9, 13-hexamethyl-16-(1-(2-methylthiazol-4-yl)propen-2-yl)-1-aza-11-cyclohexadecene.

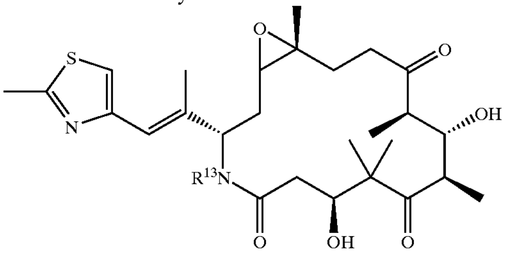

Step 1. (3S,6R,7S,8R,12R,13S,15S,16E)-3,7-dihydroxy-5,9-dioxo-12,13-epoxy-4,4, 6,8,12,16-hexamethyl-15-(methylamino)-17-(2-methylthiazol-4-yl)-16-heptadecenoic acid. A solution of (3S,6R,7S,8R,12R,13S,15S,16E)-15-amino-3,7-dihydroxy-5,9-dioxo-12,13-epoxy-4,4,6,8,12,16-hexamethyl-17-(2-methylthiazol-4-yl)-16-heptadecenoic acid (540 mg) in 10 mL of methanol is treated with 37% aqueous formaldehyde (1 mL), acetic acid (25 uL), and sodium cyanoborohydride (100 mg). After 1 hour, then mixture is treated with 1N HCl then diluted with ethyl acetate and water. The aqueous phase is extracted with ethyl acetate, and the organic phases are combined, dried over $Na_2SO_4$, filtered, and evaporated. The product is purified by flash chromatography on $SiO_2$.

Step 2. (4S,7R,8S,9R,13R,14S,16S)-13,14-epoxy-4,8-dihydroxy-2,6,10-trioxo-1,5,5,7,9, 13-hexamethyl-16-(1-(2-methylthiazol-4-yl)propen-2-yl)-1-aza-11-cyclohexadecene. A solution of (3S,6R,7S,8R,12R,13S,15S, 16E)-3,7-dihydroxy-5,9-dioxo-12,13-epoxy-4,4,6,8,12,16-hexamethyl-15-(methylamino)-17-(2-methylthiazol-4-yl)-16-heptadecenoic acid (554 mg) in acetonitrile/dimethylformamide (20:1 v/v, 150 mL) is cooled to 0° C. and treated sequentially with 1-hydroxybenzotriazole (0.135 g) and 1-(3-dimethylaminopropyl)-3-ethylcarbodiimide hydrochloride (0.5). The mixture is warmed to ambient temperature and kept for 12 hours, then diluted with water and extracted with ethyl acetate. The extract is washed sequentially with water, sat. $NaHCO_3$, and brine, then dried over $Na_2SO_4$, filtered, and evaporated. The product is purified by flash chromatography on $SiO_2$.

EXAMPLE 21

(4S,7R,8S,9R,13Z,16S)-4,8-dihydroxy-2,6,10-trioxo-1,5,5,7,9,13-hexamethyl-16-(1-(2-methylthiazol-4-yl)propen-2-yl)-1-aza-11-cyclohexadecene

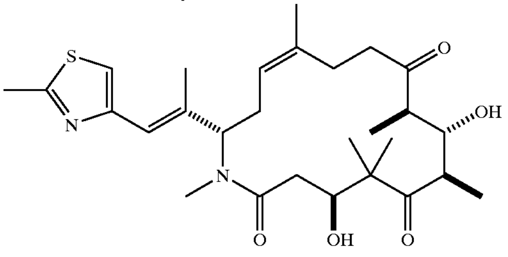

A solution of tungsten hexachloride (0.76 g) in tetrahydrofuran (20 mL) at −78° C. is treated with a 1.6 M solution of n-butyllithium in hexane (2.5 mL). The mixture is allowed to warm to ambient temperature over 20 minutes. A 13.8 mL portion of the resulting green solution is added to a solution of (4S,7R,8S,9R,13R,14S,16S)-13,14-epoxy-4,8-dihydroxy-2,6,10-trioxo-1,5,5,7,9,13-hexamethyl-16-(2-methylthiazole-4-yl)propen-2-yl)-1-aza-11-cyclohexadecene (370 mg) in 2 mL of tetrahydrofuran at ambient temperature. After 30 min, the reaction is cooled to 0° C. and treated with sat. $NaHCO_3$ (10 mL). The mixture is diluted with water and extracted with $CH_2Cl_2$. The extract is dried over $Na_2SO_4$, filtered, and evaporated. The product is purified by flash chromatography on $SiO_2$.

EXAMPLE 22

Liposomal Composition

This example describes liposomal compositions containing 9-oxo epothilone. A mixture of lipids and 9-oxo-epothilone D are dissolved in ethanol and the solution is dried as a thin film by rotation under reduced pressure. The resultant lipid film is hydrated by addition of the aqueous phase and the particle size of the epothilone-derivative containing liposomes is adjusted to the desired range. Preferably, the mean particle diameter is less than 10 microns, preferably from about 0.5 to about 4 microns. The particle size may be reduced to the desired level, for example, by using mills (e.g., air-jet mill, ball mill, or vibrator mill), microprecipitation, spray-drying, lyophillization, high-pressure homogenization, recrystrytallization from supercritical media, or by extruding an aqueous suspension of the liposomes through a series of membranes (e.g., polycarbonate membranes) having a selected uniform pore size. In one embodiment, the liposomal composition comprises: an inventive compound (1.00 mg); phosphatidylcholine (16.25 mg); cholesterol (3.75 mg); polyethyleneglycol derivatized distearyl phosphatidylethanolamine (5.00 mg); lactose (80.00 mg); citric acid (4.20 mg); tartaric acid (6.00 mg); NaOH (5.44 mg); water (up to 1 mL). In another embodiment, the liposomal composition comprises: an inventive compound (1.00 mg); phosphatidylcholine (19.80 mg); cholesterol (3.75 mg); distearyl phosphatidylcholine (1.45 mg); lactose (80.00 mg); citric acid (4.20 mg); tartaric acid (6.00 mg); NaOH (5.44 mg); water (up to 1 mL). In yet another embodiment, the liposomal composition comprises: an inventive compound (1.00 mg); 1-palmitoyl-2-oleyl-sn-glycero-3-phosphocholine (17.50 mg); 1-palmitoyl-2-oleyl-sn-glycero-3-phosphoglycerol, Na (7.5 mg); lactose (80. mg); citric acid(4.20 mg); tartaric acid (6.00 mg); NaOH (5.44 mg); water (up to 1 mL). Liposomal compositions containing other compounds of the present invention are prepared using conditions similar to those described above.

EXAMPLE 23

Polyglutamic Acid Conjugate

This example describes the preparation of a poly-glutamic acid-21-hydroxy-9-oxo-epothilone D conjugate. Poly(1-glutamic acid) ("PG") sodium salt (MW 34 K, Sigma, 0.35 g) is dissolved in water. The pH of the queous solution is adjusted to 2 using 0.2 M HCl. The precipitate is collected, dialyzed against distilled water, and lyophilized to yile 0.29 g of PG. To a solution of PG (75 mg, repeating unit FW 170, 0.44 mmol) in dry DMF (1.5 mL) is added 20 mg of 21-hydroxy-9-oxo-epothilone D, 15 mg of dicyclohexylcarbodiimide ("DCC") and a trace amount of dimethylaminopyridine. The reaction is allowed to proceed at room temperature for four hours or until completed as indicated by thin layer chromatography. The reaction mixture is poured into chloroform and the resulting precipitate is collected and dried in a vacuum to yield approximately 65 mg of PG-21-hydroxy-9-oxo-epothilone D conjugate. Changing the weight ratio of inventive compound to PG in the starting materials results in polymeric conjugates of various concentrations of 21-hydroxyl-10,11-dehydroepothilone D. Conjugates of other compounds of the present invention are prepared using conditions similar to those described above.

EXAMPLE 24

Intravenous Formulaion

This example describes an intravenous formuation of 9-oxo-epothilone D. The formulation contains 10 mg/mL of 9-oxo-epothilone D in a vehicle containing 30% propylene glycol, 20% Creomophor EL, and 50% ethanol. The vehicle is prepared by measuring ethanol (591.8 g) to a beaker containing a stir bar; adding Creomophor EL (315.0 g) to the solution and mixing for ten minutes; and then adding propylene glycol (466.2 g) to the solution and mixing for another ten minutes. 9-oxo-epothilone D (1 g) is added to a 1 L volumetric flask containing 400–600 mL of the vehicle and mixed for five minutes. After 10,11-dehydroepothilone D is in solution, the volume is brought to 1 L; allowed to mix for another ten minutes; and filtered through a 0.22 $\mu$m Millipore Millipak filter. The resulting solution is used to aseptically fill sterile 5 mL vials using a metered peristaltic pump to a targeted fill volume of 5.15 mL/vial. The filled vials are immediately stoppered and crimped.

The vial containing 10 mg/mL of 9-oxo-epothilone D is diluted in normal saline or 5% dextrose solution for administration to patients and administered in non-PVC, non-DEHP bags and administration sets. The product is infused over a one to six hour period to deliver the desired dose.

In one embodiment, the formulation is diluted twenty fold in sterile saline prior to intravenous infusion. The final infusion concentration is 0.5 mg/mL of the inventive compound, 1.5% propylene glycol, 1% Chremophor EL, and 2.5% ethanol which is infused over a one to six hour period to deliver the desired dose.

Intravenous formulations containing other compounds of the present invention may be prepared and used in a similar manner.

EXAMPLE 25

Pretreatment for Cremophor® Toxicity

This example describes a pretreatement regiment for for Cremophor® toxicity. Formulations of a compound of the invention that includes Cremophor® may cause toxicity in patients. Pretreatment with steroids can be used to prevent anaphylaxis. Any suitable corticosterioid or combination of corticosteroid with $H_1$ antagonists and/or $H_2$ antagonists may be used. In one embodiment, a subject is premedicated with an oral dose of 50 mg of diphenylhydramine and 300 mg of cimetidine one hour prior to treatment with the inventive compound in a Cremophor® containing formulation. In another embodiment, the subject is premedicated with an intravenous administration of 20 mg of dexamethasone at least one half hour prior to treatment with the inventive compound in a Cremophor® containing formulation. In another embodiment, the subject is premedicated with an intravenous administration of 50 mg of diphenylhydramine, 300 mg of cimetidine and 20 mg of dexamethasone at least one half hour prior to treatment with the inventive compound in a Cremophor® containing formulation. In yet another embodiment, the weight of the subject is taken into account and the subject is pretreated with an administration of diphenylhydramine (5 mg/kg, i.v.); cimetidine (5 mg/kg, i.v); and dexamethasone (1 mg/kg, i.m.) at least one half hour prior to the treatment with the inventive compound in a Cremophor® containing formulation.

All scientific and patent publications referenced herein are hereby incorporated by reference. The invention having now been described by way of written description and example, those of skill in the art will recognize that the invention can be practiced in a variety of embodiments, that the foregoing description and example is for purposes of illustration and not limitation of the following claims.

What is claimed is:

1. A method for isolating epothilone D from an epothilone D-producing *Myxococcus xanthus* cell, said method comprising (a) culturing said cell in the presence of methyl oleate;

(b) culturing said cell in the presence of XAD resin; and (c) eluting said epothilone from said XAD resin, thereby producing an eluate comprising epothilone.

2. The method of claim 1 further comprising a crystallization step in which epothilone D is crystallized from a binary solvent system in which water is the forcing solvent.

3. The method of claim 2 wherein the binary solvent system is ethanol and water.

4. A method for obtaining epothilone D from an epothilone D-producing cell, said method comprising (a) culturing said cell in the presence of XAD resin;

(b) eluting said epothilone from said XAD resin to obtain isolated epothilone D;

(c) subjecting said isolated epothilone D to further chromatography; and (d) crystallizing said isolated epothilone D from a binary solvent system in which water is the forcing solvent, thereby obtaining epothilone D that is more than 95% purified.

5. A method for obtaining epothilone D in crystalline form comprising crystallizing epothilone D from a binary solvent system in which water is the forcing solvent.

6. The method of claim 5 wherein the binary solvent system is ethanol and water.

7. The method of claim 6 wherein the epothilone D in crystalline form is more than 95% purified.

* * * * *

UNITED STATES PATENT AND TRADEMARK OFFICE

CERTIFICATE OF CORRECTION

PATENT NO. : 6,998,256 B2 
APPLICATION NO. : 09/957483
DATED : February 14, 2006
INVENTOR(S) : Robert L. Arslanian It is certified that error appears in the above-identified patent and that said Letters Patent is hereby corrected as shown below:

On The Title Page, Item (63), line 4, please correct “09/825,857” to read --09/825,876 --

Signed and Sealed this

Eighteenth Day of December, 2007

JON W. DUDAS

*Director of the United States Patent and Trademark Office*